(12) United States Patent
Chilkoti et al.

(10) Patent No.: US 11,649,275 B2
(45) Date of Patent: May 16, 2023

(54) DUAL AGONIST FUSION PROTEINS

(71) Applicant: Duke University, Durham, NC (US)

(72) Inventors: Ashutosh Chilkoti, Durham, NC (US); Caslin Gilroy, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 17/265,165

(22) PCT Filed: Aug. 2, 2019

(86) PCT No.: PCT/US2019/044911
§ 371 (c)(1),
(2) Date: Feb. 1, 2021

(87) PCT Pub. No.: WO2020/028806
PCT Pub. Date: Feb. 6, 2020

(65) Prior Publication Data
US 2021/0309722 A1    Oct. 7, 2021

Related U.S. Application Data

(60) Provisional application No. 62/713,752, filed on Aug. 2, 2018.

(51) Int. Cl.
| | | |
|---|---|---|
| *C07K 14/78* | (2006.01) | |
| *A61P 3/04* | (2006.01) | |
| *A61P 3/10* | (2006.01) | |
| *A61K 38/18* | (2006.01) | |
| *A61K 38/26* | (2006.01) | |
| *A61K 38/39* | (2006.01) | |
| *C07K 14/50* | (2006.01) | |
| *C07K 14/605* | (2006.01) | |

(52) U.S. Cl.
CPC .......... *C07K 14/78* (2013.01); *A61K 38/1825* (2013.01); *A61K 38/26* (2013.01); *A61K 38/39* (2013.01); *A61P 3/04* (2018.01); *A61P 3/10* (2018.01); *C07K 14/50* (2013.01); *C07K 14/605* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,415,732 A | 11/1983 | Caruthers et al. | |
| 4,458,066 A | 7/1984 | Caruthers et al. | |
| 4,500,707 A | 2/1985 | Caruthers et al. | |
| 4,554,101 A | 11/1985 | Hopp | |
| 4,668,777 A | 5/1987 | Caruthers et al. | |
| 4,973,679 A | 11/1990 | Caruthers et al. | |
| 4,976,734 A | 12/1990 | Urry et al. | |
| 5,153,319 A | 10/1992 | Caruthers et al. | |
| 5,250,516 A | 10/1993 | Urry | |
| 5,278,302 A | 1/1994 | Caruthers et al. | |
| 5,336,256 A | 8/1994 | Urry | |
| 5,453,496 A | 9/1995 | Caruthers et al. | |
| 5,534,408 A | 7/1996 | Green et al. | |
| 5,578,577 A | 11/1996 | Ching et al. | |
| 5,580,859 A | 12/1996 | Felgner et al. | |
| 5,602,244 A | 2/1997 | Caruthers et al. | |
| 5,676,646 A | 10/1997 | Hofmann et al. | |
| 5,679,647 A | 10/1997 | Carson et al. | |
| 5,702,359 A | 12/1997 | Hofmann et al. | |
| 5,703,055 A | 12/1997 | Felgner et al. | |
| 5,935,776 A | 8/1999 | Green et al. | |
| 6,068,650 A | 5/2000 | Hofmann et al. | |
| 6,096,020 A | 8/2000 | Hofmann | |
| 6,120,493 A | 9/2000 | Hofmann | |
| 6,150,148 A | 11/2000 | Nanda et al. | |
| 6,181,964 B1 | 1/2001 | Hofmann et al. | |
| 6,192,270 B1 | 2/2001 | Hofmann et al. | |
| 6,207,749 B1 | 3/2001 | Mayes et al. | |
| 6,208,893 B1 | 3/2001 | Hofmann | |
| 6,216,034 B1 | 4/2001 | Hofmann et al. | |
| 6,233,482 B1 | 5/2001 | Hofmann et al. | |
| 6,241,701 B1 | 6/2001 | Hofmann | |
| 6,245,515 B1 | 6/2001 | Vogelstein et al. | |
| 6,296,831 B1 | 10/2001 | Weller et al. | |
| 6,302,874 B1 | 10/2001 | Zhang et al. | |

(Continued)

FOREIGN PATENT DOCUMENTS

| | | | |
|---|---|---|---|
| AU | 2007265628 B2 | 12/2012 | |
| CA | 2327325 A1 | 11/1999 | |

(Continued)

OTHER PUBLICATIONS

Ahmed et al., "Preliminary Identification of Potential Vaccine Targets for the COVID-19 Coronavirus (SARS-CoV-2) Based on SARS-CoV Immunological Studies," Viruses, 2020, 12:254, 15 pages.
Amanat et al., "A serological assay to detect SARS-CoV-2 seroconversion in humans," Nat Med, 2020, 26(7): 1033-1036.
American Hospital Association, "AHA Hospital Statistics," 2020 edition. Available at: <https://www.aha.org/statistics/fast-facts-us-hospitals>.
Armbruster et al., "Limit of blank, limit of detection and limit of quantitation," Clin Biochem Rev, 2008, 29 Suppl 1: S49-52.
Arshavsky-Graham et al., "Lab-on-a-Chip Devices for Point-of-Care Medical Diagnostics," Advances in Biochemical Engineering/Biotechnology, 2020, 19 pages.

(Continued)

*Primary Examiner* — Maury A Audet
(74) *Attorney, Agent, or Firm* — Michael Best & Friedrich LLP

(57) ABSTRACT

Disclosed herein are fusion proteins including an elastin-like peptide domain, a GLP-1 receptor agonist domain attached to a N-terminal end of the ELP domain, and a FGF21 receptor agonist domain attached to the C-terminal end of the ELP domain. Also disclosed are methods of making the fusion proteins, compositions including a plurality of fusion proteins, and uses of the fusion proteins and compositions.

11 Claims, 40 Drawing Sheets

Specification includes a Sequence Listing.

(56) References Cited

U.S. PATENT DOCUMENTS

| | | |
|---|---|---|
| 6,413,587 B1 | 7/2002 | Hawker et al. |
| 6,512,060 B1 | 1/2003 | Matyjaszewski et al. |
| 6,541,580 B1 | 4/2003 | Matyjaszewski et al. |
| 6,623,950 B1 | 9/2003 | Osten et al. |
| 6,649,138 B2 | 11/2003 | Adams et al. |
| 6,660,247 B1 | 12/2003 | Gutowska et al. |
| 6,841,617 B2 | 1/2005 | Jeong et al. |
| 6,852,834 B2 | 2/2005 | Chilkoti |
| 6,869,588 B2 | 3/2005 | Weller et al. |
| 7,033,571 B2 | 4/2006 | Gutowska et al. |
| 7,087,244 B2 | 8/2006 | Jeong et al. |
| 7,300,922 B2 | 11/2007 | Sullenger et al. |
| 7,429,458 B2 | 9/2008 | Chilkoti |
| 7,531,524 B2 | 5/2009 | Rusconi |
| 7,664,545 B2 | 2/2010 | Westersten et al. |
| 7,674,882 B2 | 3/2010 | Kaplan et al. |
| 8,129,330 B2 | 3/2012 | Martinez et al. |
| 8,283,125 B2 | 10/2012 | Cebolla Ramirez et al. |
| 8,470,967 B2 | 6/2013 | Chilkoti et al. |
| 8,497,356 B2 | 7/2013 | Chilkoti et al. |
| 8,506,963 B2 | 8/2013 | Li et al. |
| 8,586,347 B2 | 11/2013 | Lochhead et al. |
| 8,841,414 B1 | 9/2014 | Raucher et al. |
| 8,912,310 B2 | 12/2014 | Chilkoti et al. |
| 8,937,153 B2 | 1/2015 | Abrahmsén et al. |
| 9,127,047 B2 | 9/2015 | Chilkoti |
| 9,132,178 B2 | 9/2015 | Philip |
| 9,138,743 B2 | 9/2015 | Yager et al. |
| 9,482,664 B2 | 11/2016 | Chilkoti et al. |
| 9,592,303 B2 | 3/2017 | Chilkoti et al. |
| 9,771,396 B2 | 9/2017 | Chilkoti et al. |
| 9,804,170 B2 | 10/2017 | Krishna et al. |
| 9,890,420 B2 | 2/2018 | Chilkoti et al. |
| 10,064,954 B2 | 9/2018 | Wu |
| 10,131,690 B2 | 11/2018 | Bonny et al. |
| 10,302,636 B2 | 5/2019 | Chilkoti et al. |
| 10,364,451 B2 | 7/2019 | Chilkoti et al. |
| 10,385,115 B2 | 8/2019 | Chilkoti et al. |
| 10,434,182 B2 | 10/2019 | Weng et al. |
| 2001/0034050 A1 | 10/2001 | Chilkoti |
| 2002/0052443 A1 | 5/2002 | Greenwald et al. |
| 2002/0146794 A1 | 10/2002 | Tomycz |
| 2003/0008308 A1 | 1/2003 | Enzelberger et al. |
| 2003/0138829 A1 | 1/2003 | Unger et al. |
| 2003/0175290 A1 | 9/2003 | Renner et al. |
| 2003/0185741 A1 | 10/2003 | Matyjaszewski et al. |
| 2003/0225251 A1 | 12/2003 | Sallberg et al. |
| 2003/0233675 A1 | 12/2003 | Cao et al. |
| 2004/0053976 A1 | 3/2004 | Martinez et al. |
| 2004/0101852 A1 | 5/2004 | Bennett et al. |
| 2004/0192072 A1 | 9/2004 | Snow et al. |
| 2005/0186214 A1 | 8/2005 | Liu et al. |
| 2005/0255554 A1 | 11/2005 | Chilkoti |
| 2005/0288229 A1 | 12/2005 | Sindrey et al. |
| 2006/0025524 A1 | 2/2006 | Schneider et al. |
| 2006/0034796 A1 | 2/2006 | Ashwell et al. |
| 2006/0051798 A1 | 3/2006 | Mirkin et al. |
| 2007/0087114 A1 | 4/2007 | Chilkoti et al. |
| 2007/0117173 A1 | 5/2007 | Levison et al. |
| 2008/0181861 A1 | 7/2008 | Jiang et al. |
| 2009/0098652 A1 | 4/2009 | Stupp et al. |
| 2009/0215194 A1 | 8/2009 | Magni et al. |
| 2010/0015070 A1 | 1/2010 | Bollschweiler et al. |
| 2010/0022455 A1* | 1/2010 | Chilkoti ............... A61K 38/26 514/18.8 |
| 2010/0048473 A1 | 2/2010 | Chaikof et al. |
| 2010/0120018 A1 | 5/2010 | Quake et al. |
| 2010/0241054 A1 | 9/2010 | Dacey et al. |
| 2010/0311059 A1 | 12/2010 | Didion et al. |
| 2010/0311669 A1 | 12/2010 | Greene et al. |
| 2010/0325765 P1 | 12/2010 | Pait et al. |
| 2011/0082283 A1 | 4/2011 | Dagher et al. |
| 2011/0119778 A1 | 5/2011 | Liss |
| 2011/0165557 A1 | 7/2011 | Ah et al. |
| 2011/0207673 A1 | 8/2011 | Chilkoti et al. |
| 2011/0248698 A1 | 10/2011 | Kikuchi et al. |
| 2011/0294189 A1 | 12/2011 | Chilkoti et al. |
| 2011/0303303 A1 | 12/2011 | Proper et al. |
| 2011/0305718 A1 | 12/2011 | Mugica et al. |
| 2012/0172298 A1 | 7/2012 | Andersen et al. |
| 2012/0208742 A1 | 8/2012 | Primiano et al. |
| 2013/0039927 A1 | 2/2013 | Dewhurst et al. |
| 2013/0079277 A1 | 3/2013 | Chilkoti |
| 2013/0079280 A1 | 3/2013 | Baca et al. |
| 2013/0096058 A1 | 4/2013 | Baca et al. |
| 2013/0102993 A1 | 4/2013 | Kim et al. |
| 2013/0130384 A1 | 5/2013 | Okamoto et al. |
| 2013/0157889 A1 | 6/2013 | Chilkoti et al. |
| 2013/0165389 A1 | 6/2013 | Schellenberger et al. |
| 2013/0172274 A1 | 7/2013 | Chilkoti |
| 2013/0197359 A1 | 8/2013 | Park et al. |
| 2013/0315823 A1 | 11/2013 | Trieu |
| 2013/0330335 A1 | 12/2013 | Bremel et al. |
| 2014/0024600 A1 | 1/2014 | Chilkoti et al. |
| 2014/0163201 A1 | 6/2014 | Winter et al. |
| 2014/0275227 A1 | 9/2014 | Hoge et al. |
| 2014/0294932 A1 | 10/2014 | Kim et al. |
| 2015/0094270 A1 | 4/2015 | Harris et al. |
| 2015/0099707 A1 | 4/2015 | Pastan et al. |
| 2015/0112022 A1 | 4/2015 | Chilkoti et al. |
| 2016/0017278 A1 | 1/2016 | Montclare et al. |
| 2016/0114053 A1 | 4/2016 | Chilkoti |
| 2016/0120952 A1 | 5/2016 | Chilkoti |
| 2016/0200787 A1 | 7/2016 | Matem et al. |
| 2016/0209356 A1 | 7/2016 | Herget et al. |
| 2016/0220727 A1 | 8/2016 | Lu et al. |
| 2016/0250165 A1 | 9/2016 | Sullenger et al. |
| 2016/0271262 A1 | 9/2016 | Lopez et al. |
| 2016/0303091 A1 | 10/2016 | Wang |
| 2016/0348147 A1 | 12/2016 | Lopez et al. |
| 2016/0355802 A1 | 12/2016 | Isaacs et al. |
| 2017/0088670 A1 | 3/2017 | Rowan et al. |
| 2017/0102357 A1 | 4/2017 | Liang et al. |
| 2017/0166621 A1 | 6/2017 | Boettcher et al. |
| 2017/0170142 A1 | 6/2017 | Edelstein et al. |
| 2017/0189545 A1 | 7/2017 | Lee et al. |
| 2017/0233714 A1 | 8/2017 | Chilkoti et al. |
| 2017/0239363 A1 | 8/2017 | Chilkoti et al. |
| 2017/0369651 A1 | 12/2017 | Cheng et al. |
| 2018/0135060 A1 | 5/2018 | Romero Ramos et al. |
| 2018/0161772 A1 | 6/2018 | Rammohan et al. |
| 2018/0171337 A1 | 6/2018 | O'Neill et al. |
| 2018/0200196 A1 | 7/2018 | Fahmy et al. |
| 2018/0217136 A1 | 8/2018 | Chilkoti et al. |
| 2018/0231469 A1 | 8/2018 | Gibbons et al. |
| 2018/0238864 A1 | 8/2018 | Burd et al. |
| 2018/0258157 A1 | 9/2018 | Chilkoti et al. |
| 2018/0326044 A1 | 11/2018 | Carter |
| 2018/0327752 A1 | 11/2018 | Pillay et al. |
| 2019/0016763 A1 | 1/2019 | Kitazawa et al. |
| 2019/0204309 A1 | 7/2019 | Gibbs |
| 2019/0285623 A1 | 9/2019 | Chilkoti et al. |
| 2019/0292549 A1 | 9/2019 | Zhang et al. |
| 2019/0345228 A1 | 11/2019 | Chilkoti et al. |
| 2020/0078313 A1 | 3/2020 | Roy et al. |
| 2020/0121809 A1 | 4/2020 | Hope et al. |
| 2020/0148724 A1 | 5/2020 | Chilkoti et al. |
| 2020/0163878 A1 | 5/2020 | Baumhof et al. |
| 2020/0181555 A1 | 6/2020 | Hinojosa et al. |
| 2021/0154143 A1 | 5/2021 | Chilkoti et al. |

FOREIGN PATENT DOCUMENTS

| | | |
|---|---|---|
| CA | 2423488 A1 | 4/2002 |
| CN | 104725628 B | 4/2018 |
| EP | 1670315 B1 | 4/2017 |
| EP | 2664340 B1 | 2/2020 |
| JP | 2014-156428 A | 8/2014 |
| JP | 2014-534265 A | 12/2014 |
| WO | WO1991/019813 A1 | 12/1991 |
| WO | WO2003/040165 A2 | 10/2002 |
| WO | WO2004/096124 A2 | 11/2004 |
| WO | WO2006/004778 A2 | 1/2006 |
| WO | 2006/110292 A2 | 10/2006 |

(56) References Cited

FOREIGN PATENT DOCUMENTS

| WO | WO2007/073486 A2 | 6/2007 |
|---|---|---|
| WO | WO2007/108013 A2 | 9/2007 |
| WO | WO2007/134245 A2 | 11/2007 |
| WO | WO2008/012543 A1 | 1/2008 |
| WO | WO2008/030968 A2 | 3/2008 |
| WO | WO2009/067584 A1 | 5/2009 |
| WO | WO2010/054699 A1 | 5/2010 |
| WO | WO2010/057154 A1 | 5/2010 |
| WO | WO2010/096422 A1 | 8/2010 |
| WO | WO2011/025572 A1 | 3/2011 |
| WO | WO2011/123813 A2 | 10/2011 |
| WO | 2012/162426 A1 | 11/2012 |
| WO | WO2013/049234 A2 | 4/2013 |
| WO | WO2013/065009 A1 | 5/2013 |
| WO | 2013/106715 A1 | 7/2013 |
| WO | WO2014/037373 A1 | 3/2014 |
| WO | WO2014/194244 A1 | 12/2014 |
| WO | 2015/011231 A1 | 1/2015 |
| WO | WO2015/130846 A2 | 9/2015 |
| WO | 2016/065300 A1 | 4/2016 |
| WO | WO2016/065273 A1 | 4/2016 |
| WO | WO2016/090103 A1 | 6/2016 |
| WO | WO2016/154530 A1 | 9/2016 |
| WO | WO2017/015132 A1 | 1/2017 |
| WO | WO2017/024182 A1 | 2/2017 |
| WO | WO2017/112825 A2 | 6/2017 |
| WO | WO2017/112826 A2 | 6/2017 |
| WO | WO 2017/192449 A1 * | 11/2017 |
| WO | WO2017/192449 A1 | 11/2017 |
| WO | WO2018/115401 A1 | 6/2018 |
| WO | WO2018/144854 A1 | 8/2018 |
| WO | 2019/103744 A1 | 5/2019 |
| WO | WO2019/147954 A1 | 8/2019 |
| WO | 2020/037214 A1 | 2/2020 |
| WO | 2020/160472 A1 | 8/2020 |
| WO | PCT/US2021/017809 | 2/2021 |

OTHER PUBLICATIONS

Atyeo et al., "Distinct Early Serological Signatures Track with SARS-CoV-2 Survival," Immunity, 2020, 53: 524-532.
Baraf et al., "Infusion-related reactions with pegloticase, a recombinant uricase for the treatment of chronic gout refractory to conventional therapy," J Clin Rheumatol, 2014, 20: 427-432.
Benn et al., "Physiology of Hyperuricemia and Urate-Lowering Treatments," Front Med (Lausanne), 2018, 5: 160, 28 pages.
Berry et al., "Development and characterisation of neutralising monoclonal antibody to the SARS-coronavirus," J Virol Methods, 2004, 120: 87-96.
Bryant et al., "Serology for SARS-CoV-2: Apprehensions, opportunities, and the path forward," Sci Immunol, 2020, 5: eabc6347, 4 pages.
Calabrese et al., "Frequency, distribution and immunologic nature of infusion reactions in subjects receiving pegloticase for chronic refractory gout," Arthritis Res Ther, 2017, 19: 191, 7 pages.
Caves et al., "Thermal inactivation of uricase (urate oxidase): mechanism and effects of additives," Biochemistry, 2013, 52: 497-507.
Chae et al., "Pharmacokinetic and pharmacodynamic evaluation of site-specific PEGylated glucagon-like peptide-1 analogs as flexible postprandial-glucose controllers," J Pharm Sci, 2009,98(4): 1556-1567.
Chen et al., "Real-world patterns of pegloticase use for treatment of gout: descriptive multidatabase cohort study," BMJ Open, 2020, 10: e041167, 6 pages.
Chen et al., "The influence of polymer topology on pharmacokinetics: differences between cyclic and linear PEGylated poly(acrylic acid) comb polymers," J Control Release, 2009, 140: 203-209.
Chu et al., "Molecular Diagnosis of a Novel Coronavirus (2019-nCoV) Causing an Outbreak of Pneumonia," Clin Chem, 2020, 66(4): 549-555.

Cong et al., "Nucleocapsid Protein Recruitment to Replication-Transcription Complexes Plays a Crucial Role in Coronaviral Life Cycle," J Virol, 2020, 94: e01925-19, 21 pages.
Crowther, "The ELISA guidebook," Methods Mol Biol, 2000, 149(III-IV): 1-413.
Dincer et al., "Multiplexed Point-of-Care Testing—xPOCT," Trends Biotechnol, 2017, 35(8): 728-742.
Dong et al., "An interactive web-based dashboard to track COVID-19 in real time," Lancet Infect Dis, 2020, 20: 533-534.
Dutta et al., "The Nucleocapsid Protein of SARS-CoV-2: a Target for Vaccine Development," J Virol, 2020, 94(13): e00647-20, 2 pages.
Ekladious et al., "Polymer-drug conjugate therapeutics: advances, insights and prospects," Nature Reviews Drug Discovery, 2019, 18: 273-294.
Fathallah et al., "Immunogenicity of Subcutaneously Administered Therapeutic Proteins—a Mechanistic Perspective," The AAPS Journal, 2013, 15(4): 897-900.
Fox et al., "Soluble polymer carriers for the treatment of cancer: the importance of molecular architecture," Acc Chem Res, 2009, 42(8): 1141-1151.
Garay et al., "Therapeutic perspectives on uricases for gout," Joint Bone Spine, 2012, 79: 237-242.
Harris et al., "Effect of pegylation on pharmaceuticals," Nature Reviews Drug Discovery, 2003, 2:214-221.
Heggestad et al., "In Pursuit of Zero 2.0: Recent Developments in Nonfouling Polymer Brushes for Immunoassays," Adv Mater, 2020, 32: e1903285.
Hermanson et al., "Peginesatide for the treatment of anemia due to chronic kidney disease—an unfulfilled promise," Expert Opin Drug Saf, 2016, 15(10): 1421-1426.
Hershfield et al., "Treating gout with pegloticase, a PEGylated urate oxidase, provides insight into the importance of uric acid as an antioxidant in vivo," Proc Natl Acad Sci USA, 2010, 107(32): 14351-14356.
Huang et al., "Clinical features of patients infected with 2019 novel coronavirus in Wuhan," China. Lancet, 2020, 395: 497-506.
Hucknall et al., "Simple Fabrication of Antibody Microarrays on Nonfouling Polymer Brushes with Femtomolar Sensitivity for Protein Analytes in Serum and Blood," Adv Mater, 2009, 21 (19): 1968-1971.
Jiang et al., "Neutralizing Antibodies against SARS-CoV-2 and Other Human Coronaviruses," Trends Immunol, 2020, 41(5): 355-359.
Joh et al., "Architectural Modification of Conformal PEG-Bottlebrush Coatings Minimizes Anti-PEG Antigenicity While Preserving Stealth Properties," Advanced Healthcare Materials, 2019, 8(8): 1801177, 27 pages.
Joh et al., "Inkjet-printed point-of-care immunoassay on a nanoscale polymer brush enables subpicomolar detection of analytes in blood," Proc Natl Acad Sci USA, 2017, 114: E7054-E7062.
Kang et al., "Crystal structure of SARS-CoV-2 nucleocapsid protein RNA binding domain reveals potential unique drug targeting sites," Acta Pharm Sin B, 2020, 10(7): 1228-1238.
Khailany et al., "Genomic characterization of a novel SARS-CoV-2," Gene Rep, 2020, 9: 100682, 6 pages.
Kozel et al., "Point-of-care testing for infectious diseases: past, present, and future," J Clin Microbiol, 2017, 55: 2313-2320.
Kozma et al., "Anti-PEG antibodies: Properties, formation, testing and role in adverse immune reactions to PEGylated nano-biopharmaceuticals," Adv Drug Deliv Rev, 2020, 154-155, 163-175.
Krammer et al., "Serology assays to manage COVID-19," Science, 2020, 368: 1060-1061.
Kuo et al., "Global epidemiology of gout: prevalence, incidence and risk factors," Nature Reviews Rheumatology, 2015, 11: 649-662.
Laing et al., "A dynamic COVID-19 immune signature includes associations with poor prognosis," Nat Med, 2020, 26:1623-1635.
Lieberman et al., "Comparison of Commercially Available and Laboratory-Developed Assays for In Vitro Detection of SARS-CoV-2 in Clinical Laboratories," J Clin Microbiol, 2020, 58(8):e00821-20.

(56) References Cited

OTHER PUBLICATIONS

Lipsitch et al., "Antibody testing will enhance the power and accuracy of COVID-19-prevention trials," Nat Med, 2020, 26: 818-819.

Lipsky et al., "Pegloticase immunogenicity: the relationship between efficacy and antibody development in patients treated for refractory chronic gout," Arthritis Res Ther, 2014, 16: R60.

Lisboa Bastos et al., "Diagnostic accuracy of serological tests for covid-19: systematic review and meta-analysis," BMJ, 2020, 370: m2516.

Liu et al., "High neutralizing antibody titer in intensive care unit patients with COVID-19," Emerg Microbes Infect, 2020, 9: 1664-1670.

Liu et al., "Semi-permeable coatings fabricated from comb-polymers efficiently protect proteins in vivo," Nature Communications, 2014, 5: 5526.

Liu et al., "The experiences of health-care providers during the COVID-19 crisis in China: a qualitative study," Lancet Glob Health, 2020, 8: e790-e798.

Lu et al., "Genomic characterisation and epidemiology of 2019 novel coronavirus: implications for virus origins and receptor binding," Lancet, 2020, 395: 565-574.

McAndrews et al., "Heterogeneous antibodies against SARS-CoV-2 spike receptor binding domain and nucleocapsid with implications for COVID-19 immunity," JCI Insight, 2020, 5(18):e142386, 14 pages.

McElvaney et al., "A linear prognostic score based on the ratio of interleukin-6 to interleukin-10 predicts outcomes in COVID-19," EBioMedicine, 2020, 61: 103026, 8 pages.

Mejía-Salazar et al., "Microfluidic Point-of-Care Devices: New Trends and Future Prospects for eHealth Diagnostics," Sensors, 2020, 20: 1951, 19 pages.

Miller et al., "Disease and healthcare burden of COVID-19 in the United States," Nat Med, 2020, 26: 1212-1217.

Nalla et al., "Comparative Performance of SARS-CoV-2 Detection Assays Using Seven Different Primer-Probe Sets and One Assay Kit," J Clin Microbiol, 2020, 58: e00557-20, 6 pages.

Norman et al., "Ultrasensitive high-resolution profiling of early seroconversion in patients with COVID-19," Nat Biomed Eng, 2020, 11 pages.

Nunn et al., "Crystal Structure of Tobacco Etch Virus Protease Shows the Protein C Terminus Bound within the Active Site," Journal of Molecular Biology, 2005, 350: 145-155.

Nyborg et al., "A Therapeutic Uricase with Reduced Immunogenicity Risk and Improved Development Properties," PLoS One, 2016, 11(12): e0167935, 23 pages.

Okba et al., "Severe Acute Respiratory Syndrome Coronavirus 2-Specific Antibody Responses in Coronavirus Disease Patients," Emerg Infect Dis, 2020, 26: 1478-1488.

Ozer et al., "Effect of Molecular Architecture on Cell Interactions and Stealth Properties of PEG," Biomacromolecules, 2017, 18: 2699-2710.

Pecoraro et al., "A systematic evaluation of immunoassay point-of-care testing to define impact on patients' outcomes," Ann Clin Biochem, 2017, 54(4): 420-431.

Ponti et al., "Biomarkers associated with COVID-19 disease progression," Crit Rev Clin Lab Sci, 2020, 57, 11 pages.

Posthuma-Trumpie et al., "Lateral flow (immuno)assay: its strengths, weaknesses, opportunities and threats. A literature survey," Anal Bioanal Chem, 2009, 393: 569-582.

Radzicka et al., "Comparing the Polrities of the Amino Acids: Side-Chain Distribution Coefficients between the Vapor Phase, Cyclohexane, 1-Octanol, and Neutral Aqueous Solution," Biochemistry, 1988, 27: 1664-1670.

Ravichandran et al., "Antibody signature induced by SARS-CoV-2 spike protein immunogens in rabbits," Sci Transl Med, 2020, 10.1126/scitranslmed.abc3539, 9 pages.

Rogers et al., "Isolation of potent SARS-CoV-2 neutralizing antibodies and protection from disease in a small animal model," Science, 2020, 369: 956-963.

Rosadas et al., "Testing for responses to the wrong SARS-CoV-2 antigen," Lancet, 2020, 396: e23.

Rothe et al., "Transmission of 2019-nCoV Infection from an Asymptomatic Contact in Germany," N Engl J Med, 2020, 382: 10, 2 pages.

Seow et al., "Longitudinal evaluation and decline of antibody responses in SARS-CoV-2 infection," medRxiv, 2020, 24 pages.

Sundy et al., "Efficacy and tolerability of pegloticase for the treatment of chronic gout in patients refractory to conventional treatment: two randomized controlled trials," Jama, 2011, 306(7): 711-720.

Sundy et al., "Pharmacokinetics and pharmacodynamics of intravenous PEGylated recombinant mammalian urate oxidase in patients with refractory gout," Arthritis Rheum, 2007, 56(3): 1021-1028.

Tang et al., "Laboratory Diagnosis of COVID-19: Current Issues and Challenges," J Clin Microbiol, 2020, 58: e00512-20, 9 pages.

Turner et al., "Challenges and Opportunities for the Subcutaneous Delivery of Therapeutic Proteins," Journal of Pharmaceutical Sciences, 2018, 107(5): 1247-1260.

U.S. FDA—Classify your medical devices. Updated as of: Feb. 7, 2020. Available at: <https://www.fda.gov/medical-devices/overview-device-regulation/classify-your-medical-device>.

U.S. FDA—In Vitro Diagnostics. Updated as of: Oct. 25, 2019. Available at: <https://www.fda.gov/medical-devices/products-and-medical-procedures/vitro-diagnostics>.

Vaninov, "In the eye of the COVID-19 cytokine storm," Nat Rev Immunol, 2020, 20: 277, 1 page.

Vashist et al., "Emerging Technologies for Next-Generation Point-of-Care Testing," Trends Biotechnol, 2015, 33(11): 692-705.

Verhoef et al., "Potential induction of anti-PEG antibodies and complement activation toward PEGylated therapeutics," Drug Discov Today, 2014, 19(12): 1945-1952.

Vugmeyster et al., "Pharmacokinetics and toxicology of therapeutic proteins: Advances and challenges," World J Biol Chem, 2012, 3(4): 73-92.

Waterboer et al., "Suppression of non-specific binding in serological Luminex assays," J Immunol Methods, 2006, 309: 200-204.

Weinhandl et al., "Relative safety of peginesatide and epoetin alfa," Pharmacoepidemiology and Drug Safety, 2014, 23(10): 1003-1011.

Whitman et al., "Evaluation of SARS-CoV-2 serology assays reveals a range of test performance," Nat Biotechnol, 2020, 38: 1174-1183.

Wiersinga et al., "Pathophysiology, Transmission, Diagnosis, and Treatment of Coronavirus Disease 2019 (COVID-19): A Review," JAMA, 2020, 324(8): 782-793.

Winter et al., "The important role of serology for COVID-19 control," Lancet Infect Dis, 2020, 20: 758-759.

Wölfel et al., "Virological assessment of hospitalized patients with COVID-2019," Nature, 2020, 581: 465-469.

Yang et al., "Analysis of Pre-existing IgG and IgM Antibodies against Polyethylene Glycol (PEG) in the General Population," Analytical Chemistry, 2016, 88(23): 11804-11812.

Yang et al., "Anti-PEG immunity: emergence, characteristics, and unaddressed questions," Wiley Interdiscip Rev Nanomed Nanobiotechnol, 2015, 7(5): 655-677.

Yang et al., "Plasma IP-10 and MCP-3 levels are highly associated with disease severity and predict the progression of COVID-19," J Allergy Clin Immunol, 2020, 146: 119-127.

Yang et al., "Uricases as therapeutic agents to treat refractory gout: Current states and future directions," Drug Dev Res, 2012, 73(2): 66-72.

Yong et al., "Connecting clusters of COVID-19: an epidemiological and serological investigation," Lancet Infect Dis, 2020, 20: 809-815.

Zhang et al., "Anti-PEG antibodies in the clinic: Current issues and beyond PEGylation," J Control Release, 2016, 244(Pt B): 184-193.

Zhang et al., "Impact of Large Aggregated Uricases and PEG Diol on Accelerated Blood Clearance of PEGylated Canine Uricase," PLoS ONE, 2012, 7(6): e39659.

Zhao et al., "Antibody responses to SARS-CoV-2 in patients of novel coronavirus disease 2019," Clin Infect Dis, 2020, 22 pages.

International Search Report and Written Opinion for Application No. PCT/US2021/020591 dated Oct. 7, 2021 (14 pages).

(56) References Cited

OTHER PUBLICATIONS

United States Patent Office Action for U.S. Appl. No. 16/614,282 dated Oct. 21, 2021 (14 pages).
United States Patent Office Action for U.S. Appl. No. 15/749,797 dated Nov. 29, 2021 (10 pages).
United States Patent Office Action for U.S. Appl. No. 16/477,229 dated Oct. 26, 2021 (10 pages).
AACR, "AACR Cancer Progress Report 2016," Clin Cancer Res, Oct. 2016, vol. 22, Issue 19, 143 pages.
Aaron et al., "Elastin as a Random-Network Elastomer—a Mechanical and Optical Analysis of Single Elastin Fibers," Biopolymers, 1981, 20(6): 1247-1260.
Abbaspourrad et al., "Controlling release from pH-responsive microcapsules," Langmuir, 2013, 29: 12697-12702.
Abbaspourrad et al., "Polymer microcapsules with programmable active release," J Am Chem Soc, 2013, 135: 7744-7750.
Abbruzzese et al., "A phase I clinical, plasma, and cellular pharmacology study of gemcitabine," J. Clin. Oncol. 1991, 3, 491-498.
Adams et al., "Safety and utilization of blood components as therapeutic delivery systems," Curr Pharm Biotechnol, 2003, 4(5): 275-82.
Adams et al., "Sustained release of antibiotics from injectable and thermally responsive polypeptide depots," J Biomed Mater Res B Appl Biomater, Jul. 2009, vol. 90B, Issue 1, pp. 67-74.
Adamska et al., "Pancreatic ductal adenocarcinoma: Current and evolving therapies," J Mol Sci, Jun. 2017, vol. 18, Issue 7, pp. 1338-1380.
Adiseshaiah et al., "Nanomedicine strategies to overcome the pathophysiological barriers of pancreatic cancer," Nat Rev Clin Oncol, Dec. 2016, vol. 13, Issue 12, pp. 750-765.
Agarwal et al., "One-step microfluidic generation of pre-hatching embryo-like core-shell microcapsules for miniaturized 3D culture of pluripotent stem cells," Lab Chip, 2013, 13: 4525-4533.
Aladini et al., "Chemical Synthesis and Characterization of Elastin-Like Polypeptides (ELPs) With Variable Guest Residues," J Pept Sci, May 2016, vol. 22, Issue 5, pp. 334-342.
Alarcon et al., "Exendin 4 controls insulin production in rat islet beta cells predominantly by potentiation of glucose-stimulated proinsulin biosynthesis at the translational level," Diabetologia, 2006, 49(12):2920-2929.
Albanese et al., "The effect of nanoparticle size, shape, and surface chemistry on biological systems," Annu. Rev. Biomed. Eng., Aug. 2012, vol. 14, pp. 1-16.
Alconcel et al., "FDA-approved poly(ethylene glycol)-protein conjugate drugs," Polym. Chem., vol. 2, Apr. 2011, Issue 7, pp. 1442-1448.
Allen et al., "Liposomal drug delivery systems: from concept to clinical applications," Adv Drug Deliv Rev, Elsevier, Jan. 2013, 65(1):36-48.
Alley et al., "Feasibility of drug screening with panels of human tumor cell lines using a microculture tetrazolium assay," Cancer Res., 1988, 48, 589-601.
Aluri et al., "Elastin-like peptide amphiphiles Form nanofibers with tunable length," Biomacromolecules, Sep. 2012, vol. 13, Issue 9, pp. 2645-2654.
American Diabetes Association, Standards of medical care in diabetes—2018. Diabetes Care, Jan. 2018, vol. 41, Supplement 1, pp. S1-S159.
Amiram et al., "A depot-forming glucagon-like peptide-1 fusion protein reduces blood glucose for five days with a single injection," J. Control. Release, Nov. 2013, vol. 172, Issue, pp. 144-151.
Amiram et al., "Evolution of translation machinery in recoded bacteria enables multi-site incorporation of nonstandard amino acids," Nat Biotechnol, 2015, 33: 1272-1279.
Amiram et al., "Injectable protease-operated depots of glucagon-like peptide-1 provide extended and tunable glucose control," Proc. Natl. Acad. Sci., Feb. 2013, vol. 110, Issue 8, pp. 2792-2797.
Andersen et al., "Extending Half-life by Indirect Targeting of the Neonatal Fc Receptor (FcRn) Using a Minimal Albumin Binding Domain," Journal of Biological Chemistry, Feb. 2011, vol. 286, Issue 7, pp. 5234-5241.
Anselmo et al., "Nanoparticles in the clinic, " Bioeng Transl Med, Jun. 2016, 1(1):10-29.
Antos et al., "Lipid Modification of Proteins through Sortase-Catalyzed Transpeptidation," J. Am. Chem. Soc., Dec. 2008, vol. 130, Issue 48, pp. 16338-16343.
Antos et al., "Site-Specific N- and C-Terminal Labeling of a Single Polypeptide Using Sortases of Different Specificity," J. Am. Chem. Soc., Aug. 2009, vol. 131, Issue 31, pp. 10800-10801.
Appleyard et al., "Multiplexed protein quantification with barcoded hydrogel microparticles," Anal Chem, 2011, 83: 193-199.
Arami et al., "In vivo delivery, pharmacokinetics, biodistribution and toxicity of iron oxide nanoparticles," Chem Soc Rev, Dec. 2015, 44(23):8576-8607.
Arias et al., "Superior preclinical efficacy of gemcitabine developed as chitosan nanoparticulate system," Biomacromolecules, Jan. 2011, vol. 12, Issue 1, pp. 97-104.
Armstrong et al., "Antibody against poly(ethylene glycol) adversely affects PEG-asparaginase therapy in acute lymphoblastic leukemia patients," Cancer, Jul. 2007, vol. 110, Issue 1, pp. 103-111.
Armstrong et al., "The Hydrodynamic Radii of Macromolecules and Their Effect on Red Blood Cell Aggregation," Biophys. J., 2004, 87, 4259-4270.
Arner et al., "FGF21 attenuates lipolysis in human adipocytes—a possible link to improved insulin sensitivity," FEBS Lett, May 2008, vol. 582, Issue 12, pp. 1725-1730.
Arnida et al., "Geometry and surface characteristics of gold nanoparticles influence their biodistribution and uptake by macrophages," Eur J Pharm Biopharm, Apr. 2011, vol. 77, Issue 3, pp. 417-423.
Asai et al., "Protein polymer hydrogels by in situ, rapid and reversible self-gelation," Biomaterials, Jul. 2012, vol. 33, Issue 21, pp. 5451-5458.
Astete et al., "Synthesis and characterization of PLGA nanoparticles," Journal of Biomaterials Science, Polymer Edition 2006, 17(3):247-289.
Atun et al., "Expanding global access to radiotherapy," Lancet Oncol, Sep. 2015, vol. 16, Issue 10, pp. 1153-1186.
Averick et al., "ATRP under biologically relevant conditions: grafting from a protein," ACS Macro. Lett., Jan. 2012, vol. 1, Issue 1, pp. 6-10.
Averick et al., "Protein-polymer hybrids: conducting ARGET ATRP from a genetically encoded cleavable ATRP initiator," Eur. Polym. J., Oct. 2013, vol. 49, Issue 10, pp. 2919-2924.
Awai et al., "Studies of the metabolism of I-131-labeled human transferrin," J. Lab. Clin. Med. 61, 1963, 363-396.
Awasthi et al., "Comparative benefits of Nab-paclitaxel over gemcitabine or polysorbate-based docetaxel in experimental pancreatic cancer," Carcinogenesis, Oct. 2013, vol. 34, Issue 10, pp. 2361-2369.
Awasthi et al., "Evaluation of combination treatment benefits of nab-paclitaxel in experimental pancreatic cancer," Journal of Clinical Oncology, 2012, 30, 170.
Axup et al., "Synthesis of site-specific antibody-drug conjugates using unnatural amino acids," Proc Natl Acad Sci USA, Feb. 2012, vol. 109, Issue 40, pp. 16101-16106.
Azhdarinia et al., "Regional radiochemotherapy using in situ hydrogel," Pharm Res., 2005, 22, 776-783.
Babu, "The contribution of intrinsically disordered regions to protein function, cellular complexity, and human disease," Biochem Soc Trans, Oct. 2016, 44(5):1185-1200.
Bache et al., "Investigating the accuracy of microstereotactic-body-radiotherapy utilizing anatomically accurate 3D printed rodent-morphic dosimeters," Medical Physics, Feb. 2015, vol. 42, Issue 2, pp. 846-855.
Badi, "Non-linear PEG-based thermoresponsive polymer systems," Progress in Polymer Science, Mar. 2017, vol. 66, pp. 54-79.
Bae et al., "Targeted drug delivery to tumors: myths, reality and possibility," J Control Release, Elsevier, Aug. 2011, 153(3):198-205.
Baggio et al., "A recombinant human glucagon-like peptide (GLP)-1-albumin protein (Albugon) mimics peptidergic activation of GLP-1 receptor-dependent pathways coupled with satiety, gastrointestinal motility, and glucose homeostasis," Diabetes 53, 2004, 2492-2500.
Baggio et al., "Biology of Incretins: GLP-1 and GIP," Gastroenterology, May 2007, vol. 132, Issue 6, pp. 2131-2157.

(56) References Cited

OTHER PUBLICATIONS

Bailey et al., "Genomic analyses identify molecular subtypes of pancreatic cancer," Nature, Mar. 2016, vol. 531, Issue 7592, pp. 47-52.
Bain et al., "Formation of monolayer films by the spontaneous assembly of organic thiols from solution onto gold," Journal of the American Chemical Society, 1989, 111: 321-335.
Balu et al., "An16-resilin: an advanced multi-stimuli-responsive resilin-mimetic protein polymer," Acta Biomater, Nov. 2014, 10:4768-4777.
Bamford et al., "The COSMIC (Catalogue of Somatic Mutations in Cancer) database and website," British Journal of Cancer, 2004, 91, 355-358.
Banani et al., "Biomolecular condensates: organizers of cellular biochemistry," Nat Rev Mol Cell Biol, May 2017, 18(5):285-298.
Banerjee et al., "Nanoparticles in cancer chemotherapy," Prog Mol Biol Transl Sci, Elsevier, Nov. 2011, 104:489-507.
Banga et al., "Parenteral controlled delivery and parmacokinetics of therapeutic peptides and proteins," (CRC Press, Boca Raton, FL, 2005).
Banjade et al., "Phase transitions of multivalent proteins can promote clustering of membrane receptors," Elife, Oct. 2014, 3:e04123.
Bansal et al., "PEGylation improves pharmacokinetic profile, liver uptake and efficacy of Interferon gamma in liver fibrosis," J. Control. Release, Sep. 2011, vol. 154, Issue 3, pp. 233-240.
Banskota et al., "Genetically encoded stealth nanoparticles of a zwitterionic polypeptide-paclitaxel conjugate have wider therapeutic window than Abraxane in multiple tumor models," Nano Lett, Mar. 2020, 20(4):2396-2409.
Barbuti et al., "Paclitaxel through the ages of anticancer therapy: Exploring its role in chemoresistance and radiation therapy," Cancers, Dec. 2015, vol. 7, Issue 4, pp. 2360-2371.
Barnett et al., "Normal tissue reactions to radiotherapy: towards tailoring treatment dose by genotype," Nat Rev Cancer, Feb. 2009, vol. 9, Issue 2, pp. 134-142.
Barton et al., "Estimating the demand for radiotherapy form the evidence: A review of changes from 2003 to 2012," Radiother Oncol, Jul. 2014, vol. 112, Issue 1, pp. 140-144.
Baskar et al., "Cancer and Radiation Therapy: Current Advances and Future Directions," Int. J. Med. Sci., Feb. 2012, vol. 9, Issue 3, pp. 193-199.
Bates et al., "Block copolymer thermodynamics: theory and experiment," Annu Rev. Phys. Chem., 1990, 41:525-57.
Bedford et al., "WW domain-mediated interactions reveal a spliceosome-associated protein that binds a third class of proline-rich motif: The proline glycine and methionine-rich motif," PNAS, 1998, 95: 10602-10607.
Beenken et al., "The FGF family: biology, pathophysiology and therapy," Nat Rev Drug Discov, Mar. 2009, vol. 8, Issue 3, pp. 235-253.
Begg et al., "Strategies to improve radiotherapy with targeted drugs," Nat Rev Cancer, Apr. 2011, vol. 11, Issue 4, pp. 239-253.
Bellucci et al., "A noncanonical function of sortase enables site-specific conjugation of small molecules to lysine residues in proteins," Angew. Chem. Int. Ed. 54, Jan. 2015, vol. 54, Issue 2, pp. 441-445.
Bellucci et al., "Three-in-One Chromatography-Free Purification, Tag Removal, and Site-Specific Modification of Recombinant Fusion Proteins Using Sortase A and Elastin-like Polypeptides," Angewandte Chemie International Edition, Mar. 2013, vol. 52, Issue 13, pp. 3703-3708.
Bender et al., "Synthesis, Crystallization, and Biological Evaluation of an Orally Active Prodrug of Gemcitabine," J. Med. Chem., Nov. 2009, vol. 52, Issue 22, pp. 6958-6961.
Berisio et al., "Imino Acids and Collagen Triple Helix Stability: Characterization of Collagen-like Polypeptides Containing Hyp-Hyp-Gly Seqeucne Repeats," JACS, 2004, 126: 11402-11403.
Bernacki et al., "Length-dependent aggregation of uninterrupted polyalanine peptides," Biochemistry, Sep. 2011, vol. 50, Issue 43, pp. 9200-9211.
Berndt et al., "Synthetic lipidation of peptides and amino acids: Monolayer structure and properties," J. Am. Chem. Soc., 1995, 117, 9515-9522.
Bessa et al., "Thermoresponsive self-assembled elastin-based nanoparticles for delivery of BMPs," Journal of Controlled Release, Mar. 2010, vol. 142, Issue 3, pp. 312-318.
Best, "Computational and theoretical advances in studies of intrinsically disordered proteins," Curr Opin Struct Biol, Feb. 2017, 42:147-154.
Bhattacharyya et al., "A paclitaxel-loaded recombinant polypeptide nanoparticle outperforms Abraxane in multiple murine cancer models," Nat. Commun., Aug. 2015, Issue 6, Article 7939, 30 pages.
Bhattacharyya et al., "Encapsulating a Hydrophilic Chemotherapeutic into Rod-Like Nanoparticles of a Genetically Encoded Asymmetric Triblock Polypeptide Improves its Efficacy," Advanced functional materials, Mar. 2017, vol. 27, Issue 12, Article 1605421, 9 pages.
Bidwell et al., "Development of elastin-like polypeptide for thermally targeted delivery of doxorubicin," Biochemical Pharmacology, Mar. 2007, vol. 73, Issue 5, pp. 620-631.
Binz et al., "Engineering novel binding proteins from nonimmunoglobulin domains," Nat Biotechnol, 2005, 23(10):1257-68.
Blanco et al., "Principles of nanoparticle design for overcoming biological barriers to drug delivery," Nat Biotechnol, Sep. 2015, 33(9):941-51.
Blasko et al., "Brachytherapy for carcinoma of the prostate: Techniques, patient selection, and clinical outcomes," Seminars in Radiation Oncology, 2002, 12, 81-94.
Blasko et al., "The role of external beam radiotherapy with I-125/Pd-103 brachytherapy for prostate carcinoma," Radiother Oncol, 2000, 57, 273-278.
Blasko et al., "Transperineal percutaneous iodine-125 implantation for prostatic carcinoma using transrectal ultrasound and template guidance," Endocurietherapy/Hyperthermia Oncology, 1987, 3, 131-139.
Bley et al., "Microtubule stabilising agents and ionising radiation: Multiple exploitable mechanisms for combined treatment," Eur J Cancer, Jan. 2013, vol. 49, Issue 1, pp. 245-253.
Bobo et al., "Nanoparticle-based medicines: a review of FDA-approved materials and clinical trials to date." Pharmaceutical research, Oct. 2016, vol. 33, Issue 10, pp. 2373-2387.
Bocci et al., "The pharmacological bases of the antiangiogenic activity of paclitaxel," Angiogenesis, Jul. 2013, vol. 16, Issue 3, pp. 481-492.
Bochicchio et al., "Investigating by CD the molecular mechanism of elasticity of elastomeric proteins," Chirality, Sep. 2008, vol. 20, Issue 9, pp. 985-994.
Boekhorst et al., "Genome-wide detection and analysis of cell wall-bound proteins with LPxTG-like sorting motifs," J. Bacteriol. 187, 2005, 4928-4934.
Boeynaems et al., "Protein Phase Separation: A New Phase in Cell Biology," Trends Cell Biol, Jun. 2018, 28(6):420-435.
Boeynaems et al., "Spontaneous driving forces give rise to protein-RNA condensates with coexisting phases and complex material properties," Proc Natl Acad Sci U S A, 2019, 116:7889-7898.
Boldt, "Use of albumin: an update," Br J. Anaesth., Mar. 2010, vol. 104, Issue 3, pp. 276-284.
Bond, "Exenatide (Byetta) as a novel treatment option for type 2 diabetes mellitus," Proc. (Bayl. Univ. Med. Cent.), Jul. 2006, vol. 19, Issue 3, pp. 281-284.
Bontempo et al., "Streptavidin as a macroinitiator for polymerization: in situ protein-polymer conjugate formation," J. Am. Chem. Soc., 2005, 6508-6509.
Borst et al., "The Therapeutic Antibody LM609 Selectively Inhibits Ligand Binding to Human αVβ3 Integrin via Steric Hindrance," Structure, Nov. 2017, 25(11):1732-1739.e5.
Bowditch et al., "Identification of a novel integrin binding site in fibronectin. Differential utilization by β3 integrins," Journal of Biological Chemistry, 1994, 269(14):10856-10863.
Boyer et al., "Well-Defined Protein-Polymer Conjugates via in Situ RAFT Polymerization," J. Am. Chem. Soc., Jun. 2007, vol. 129, Issue 22, pp. 7145-7154.

(56) References Cited

OTHER PUBLICATIONS

Branco et al., "Self-assembling materials for therapeutic delivery," Acta Biomaterialia, Mar. 2009, vol. 5, Issue 3, pp. 817-831.
Brangwynne et al., "Polymer physics of intracellular phase transitions," Nature Physics, Nov. 2015, 11(11):899-904.
Brannon-Peppas et al., "Nanoparticle and targeted systems for cancer therapy," Advanced Drug Delivery Reviews, Elsevier, Sep. 2012, 64(11):206-212.
Broome et al., "Expanding the utility of beta-galactosidase complementation: piece by piece," Mol Pharm, ACS Publications, Feb. 2010, 7(1):60-74.
Broyer et al., "Emerging synthetic approaches for protein-polymer conjugations," Chem. Commun., Feb. 2011, vol. 47, Issue 8, pp. 2212-2226.
Brusa et al., "Antitumor activity and pharmacokinetics of liposomes containing lipophilic gemcitabine prodrugs," Anticancer Res., Jan. 2007, vol. 27, Issue 1A, pp. 195-199.
Burchard, "Light Scattering Techniques," Physical techniques for the study of food biopolymers, 1994, 151-213.
Burke et al., "Multimodal nanoparticle imaging agents: design and applications," Philos Trans A Math Phys Eng Sci, Nov. 2017, 375:20170261.
Burnouf, "Modern plasma fractionation," Transfus. Med. Rev., Apr. 2007, vol. 21, Issue 2, pp. 101-117.
Buteau et al., "Glucagon-like peptide-1 prevents beta cell glucolipotoxicity," Diabetologia, 2004, 47(5):806-815.
Butler et al., "β-Cell Deficit and Increased β-Cell Apoptosis in Humans With Type 2 Diabetes," Diabetes, 2003, 52(1):102-110.
Cabral et al., "Accumulation of sub-100 nm polymeric micelles in poorly permeable tumours depends on size," Nature Nanotechnology, Oct. 2011, vol. 6, Issue 12, pp. 815-823.
Cabrera et al., "Automated, High-Throughput Assays for Evaluation of Human Pancreatic Islet Function," Cell Transplant, First published Nov. 2007, vol. 16, Issue 10, pp. 1039-1048.
Cabrera et al., "Glutamate Is a Positive Autocrine Signal for Glucagon Release," Cell Metab, Jun. 2008, vol. 7, Issue 6, pp. 545-554.
Cai et al., "Long-acting preparations of exenatide," Drug Des. Devel. Ther., Sep. 2013, vol. 7, pp. 963-970.
Caliceti et al., "Pharmacokinetic and biodistribution properties of poly(ethylene glycol)-protein conjugates," Adv. Drug Deliv. Rev, 2003, 55, 1261-1277.
Callahan et al., "Triple stimulus-responsive polypeptide nanoparticles that enhance intratumoral spatial distribution," Nano Letters, Mar. 2012, vol. 12, Issue 4, pp. 2165-2170.
Camilloni et al., "Determination of secondary structure populations in disordered states of proteins using nuclear magnetic resonance chemical shifts," Biochemistry, Feb. 2012, vol. 51, Issue 11, pp. 2224-2231.
Campbell et al., "Pegylated peptides V. Carboxy-terminal PEGlyted analogs of growth hormone-releasing factor (GRF) display enhanced duration of biological activity in vivo," J. Peptide Res., 1997, 49:527-537.
Cao et al., "Monitoring the effects of anti-angiogenesis on the radiation sensitivity of pancreatic cancer xenografts using dynamic contrast-enhanced computed tomography," Int J Radiation Oncol Biol Phys, Feb. 2014, vol. 88, Issue 2, pp. 412-418.
Cardenes et al., "Locally advanced pancreatic cancer: Current therapeutic approach," The Oncologist, Jun. 2006, vol. 11, Issue 6, pp. 612-623.
Carreiras et al., "Expression and localization of alpha v integrins and their ligand vitronectin in normal ovarian epithelium and in ovarian carcinoma," Gynecol Oncol, 1996, 62(2):260-7.
Carrico et al., "Introducing genetically encoded aldehydes into proteins," Nat Chem Biol, Jun. 2007, vol. 3, Issue 6, pp. 321-322.
Cataldo et al., "Radiation-induced crosslinking of collagen gelatin into a stable hydrogel," Journal of Radioanalytical and Nuclear Chemistry, Sep. 2008, vol. 275, Issue 1, pp. 125-131.

Centers for Disease Control and Prevention, "National Diabetes Statistics Report, 2017," Atlanta, GA: Centers for Disease Control and Prevention, US Department of Health and Human Services; 2017. Reviewed: Feb. 24, 2018.
Ceska et al., "A new and rapid method for the clinical determination of α-amylase activities in human serum and urine. Optimal conditions," Clinica Chimica Acta, 1969, 26, 437-444.
Cha et al., "Microfluidics-assisted fabrication of gelatin-silica core-shell microgels for injectable tissue constructs," Biomacromolecules, 2014, 15: 283-290.
Chakrabartty et al., "Stability of α-Helices," Adv Protein Chem, 1995, 46, 141-176.
Champion et al., "Particle shape: a new design parameter for micro- and nanoscale drug delivery carriers," J Control Release, Elsevier, Aug. 2007, 121(1-2):3-9.
Champion et al., "Role of particle size in phagocytosis of polymeric microspheres," Pharm Res, Srpinger, Mar. 2008, 25(8):1815-21.
Champion et al., "Role of target geometry in phagocytosis," Proc Natl Acad Sci U S A, The National Academy of Sciences of the USA, Mar. 2006, 103(13):4930-4.
Champion et al., "Shape induced inhibition of phagocytosis of polymer particles," Pharm Res, Springer, Jan. 2009, 26(1):244-9.
Chang et al., "Tumor-stroma interaction in orthotopic primary pancreatic cancer xenografts during hedgehog pathway inhibition," Int. J. Cancer, Jul. 2013, vol. 133, Issue 1, pp. 225-235.
Chapin et al., "Rapid microRNA profiling on encoded gel microparticles," Angew Chem Int Ed Engl, 2011, 50: 2289-2293.
Chatterjee et al., "Type 2 diabetes," The Lancet, Jun. 2017, vol. 389, Issue 10085, pp. 2239-2251.
Chaudhury et al., "The major histocompatibility complex-related Fc receptor for IgG (FcRn) binds albumin and prolongs its lifespan," J Exp Med, 2003, 197(3): p. 315-22.
Chen et al., "Anisotropic hydrogels fabricated with directional freezing and radiation-induced polymerization and crosslinking method," Materials Letters, Dec. 2012, vol. 89, pp. 104-107.
Chen et al., "Anti-hypervariable region antibody induced by a defined peptide: An approach for studying the structural correlates of idiotypes," PNAS, 1984, 81:1784-1788.
Chen et al., "Bioinspired Modular Synthesis of Elastin-Mimic Polymers To Probe the Mechanism of Elastin Elasticity," J. Am. Chem. Soc., Mar. 2010, vol. 132, Issue 13, pp. 4577-4579.
Chen et al., "Rheology of Soft Materials," Annual Review of Condensed Matter Physics, May 2010, vol. 1, pp. 301-322.
Chen et al., "Site-specific labeling of cell surface proteins with biophysical probes using biotin ligase," Nat Methods, 2005, 2(2):99-104.
Chen et al., "The use of self-adjuvanting nanofiber vaccines to elicit high-affinity B cell responses to peptide antigens without inflammation," Biomaterials, Nov. 2013, vol. 34, Issue 34, pp. 8776-8785.
Chen, "Small-molecule delivery by nanoparticles for anticancer therapy," Trends Mol Med, Cell Press, Dec. 2010, 16(12):594-602.
Chilkoti et al., "Design of thermally responsive, recombinant polypeptide carriers for targeted drug delivery," Advance Drug Delivery Reviews, 2002, 54:1093-1111.
Chilkoti et al., "Stimulus responsive elastin biopolymers: applications in medicine and biotechnology," Curr Opin Chem Biol, Dec. 2006, vol. 10, Issue 6, pp. 652-657.
Chilkoti et al., "Targeted drug delivery by thermally responsive polymers," Advanced Drug Delivery Reviews, 2002, 54:613-630.
Chin et al., "Addition of p-azido-l-phenylalanine to the genetic code of *Escherichia coli*," Journal of the American Chemical Society, 2002, 124: 9026-9027.
Chithrani et al., "Determining the size and shape dependence of gold nanoparticle uptake into mammalian cells," Nano Lett, Apr. 2006, vol. 6, Issue 4, pp. 662-668.
Chithrani et al., "Elucidating the mechanism of cellular uptake and removal of protein-coated gold nanoparticles of different sizes and shapes," Nano letters, ACS Publications, Jun. 2007, 7(6):1542-1550.
Chitkara et al., "Self-Assembling, Amphiphilic Polymer-Gemcitabine Conjugate Shows Enhanced Antitumor Efficacy Against Human Pancreatic Adenocarcinoma," Bioconjug. Chem., Jun. 2013, vol. 24, Issue 7, pp. 1161-1173.

(56) References Cited

OTHER PUBLICATIONS

Cho et al., "Effects of hofmeister anions on the phase transition temperature of elastin-like polypeptides," J. Phys. Chem. B., Nov. 2008, vol. 112, Issue 44, pp. 13765-13771.

Cho et al., "Hydrogen bonding of β-turn structure is stabilized in D(2)O," J Am Chem Soc, Oct. 2009, vol. 131, Issue 42, pp. 15188-15193.

Cho et al., "Therapeutic nanoparticles fordrug delivery in cancer," Clin. Cancer Res., Mar. 2008, vol. 14, Issue 5, pp. 1310-1316.

Chockalingam et al., "Design and application of stimulus-responsive peptide systems," Protein Engineering, Design & Selection, Apr. 2007, 20(4):155-161.

Choi et al., "Multiplexed detection of mRNA using porosity-tuned hydrogel microparticles," Anal Chem, 2012, 84: 9370-9378.

Choi et al., "Recent advances in engineering microparticles and their nascent utilization in biomedical delivery and diagnostic applications," Lab Chip, 2017, 17: 591-613.

Choi et al., "Renal Clearance of Nanoparticles," Nature biotechnology, Oct. 2007, vol. 25, Issue 10, pp. 1165-1170.

Chow et al., "Peptide-based biopolymers in biomedicine and biotechnology," Mater. Sci. Eng. R Reports, Jan. 2008, vol. 62, Issue 4, pp. 125-155.

Chow et al., "Ultra-High Expression of a Thermally Responsive Recombinant Fusion Protein in E. coli," Biotechnology Progress, Sep. 2006, vol. 22, Issue 3, pp. 638-646.

Choy et al., "Investigation of taxol as a potential radiation sensitizer," Cancer, 1993, 71, 3774-3778.

Christensen et al., "Fusion order controls expression level and activity of elastin-like polypeptide fusion proteins," Protein Science, Jul. 2009, vol. 18, Issue 7, pp. 1377-1387.

Christensen et al., "Predicting Transition Temperatures of Elastin-Like Polypeptide Fusion Proteins," Biomacromolecules, Mar. 2013, vol. 14, Issue 5, pp. 1514-1519.

Chu et al., "Controllable monodisperse multiple emulsions," Angew Chem Int Ed Engl, 2007, 46: 8970-8974.

Cid-Arregui et al., "Perspectives in the treatment of pancreatic adenocarcinoma," World Journal of Gastroenterology, Aug. 2015, vol. 21, Issue 31, pp. 9297-9316.

Ciezki et al., "Brachytherapy or surgery? A composite view," Oncology, Oct. 2009, vol. 23, Issue 11, pp. 960-964.

Cima, "AVMA Guidelines for the Euthanasia of Animal: 2013 Edition," Journal of the American Veterinary Medical Association, Jan. 2013, vol. 242, 102 pages.

Cirulis et al., "Viscoelastic properties and gelation of an elastin-like polypeptide," Journal of Rheology, Sep. 2009, vol. 53, Issue 5, pp. 1215-1228.

Clarke et al., "Tropoelastin massively associates during coacervation to form quantized protein spheres," Biochemistry, Jul. 2006, vol. 45, Issue 33, pp. 9989-9996.

Clavé et al., "Amylase, lipase, pancreatic isoamylase, and phospholipase A in diagnosis of acute pancreatitis," Clinical Chemistry, 1995, 41, 1129-1134.

Coin et al., "Solid-phase peptide synthesis: from standard procedures to the synthesis of difficult sequences," Nat. Protoc., Dec. 2007, vol. 2, Issue 12, 3247-3256.

Colomb et al., "Radiation-Convertible Polymers from Norbornenyl Derivatives. Crosslinking with Ionizing Radiation," Journal of Applied Polymer Science, 1970, 14, 1659-1670.

Conner et al., "Regulated portals of entry into the cell," Nature, 2003, 422(6927):37-44.

Conrad et al., "ELPylated anti-human TNF therapeutic single-domain antibodies for prevention of lethal septic shock," Plant Biotechnology Journal, Jan. 2011, vol. 9, Issue 1, pp. 22-31.

Coskun et al., "Fibroblast Growth Factor 21 Corrects Obesity in Mice," Endocrinology, Dec. 2008, vol. 149, Issue 12, pp. 6018-6027.

Costa et al., "Active Targeting of Cancer Cells by Nanobody Decorated Polypeptide Micelle with Bio-orthogonally Conjugated Drug," Nano letters, Dec. 2018, 19(1):247-254.

Costa et al., "Photo-crosslinkable unnatural amino acids enable facile synthesis of thermoresponsive nano- to microgels of intrinsically disordered polypeptides," Adv Mater, 2018, 30(5): 1704878.

Craik et al., "The future of peptide-based drugs," Chemical biology & drug design 81, Dec. 2013, vol. 81, Issue 1, pp. 136-147.

Cui et al., "Amino acid sequence in constitutionally isomeric tetrapeptide amphiphiles dictates architecture of one-dimensional nanostructures," J. Am. Chem. Soc., Aug. 2014, vol. 136, Issue 35, 12461-12468.

Cui et al., "Self-assembly of peptide amphiphiles: from molecules to nanostructures to biomaterials," Biopolymers, Jan. 2010, vol. 94, Issue 1, pp. 1-18.

Dai et al., "Versatile biomanufacturing through stimulus-responsive cell-material feedback," Nature chemical biology, Sep. 2019, 15(10):1017-1024.

Dalhaimer et al., "Single Molecule Visualization of Stable, Stiffness-Tunable, Flow-Conforming Worm Micelles," Macromolecules, 2003, 36(18):6873-6877.

Dalla Poza et al., "Targeting gemcitabine containing liposomes to CD44 expressing pancreatic adenocarcinoma cells causes an increase in the antitumoral activity," Biochim. Biophys. Acta, May 2013, vol. 1828, Issue 5, pp. 1396-1404.

Darling et al., "Viscoelastic properties of zonal articular chondrocytes measured by atomic force microscopy," Osteoarthritis Cartilage, 2006, 14: 571-579.

Darzynkiewicz et al., "DNA content measurement for DNA ploidy and cell cycle analysis," Current Protocols in Cytometry, 2001, 7.5.1-7.5.24.

Das et al., "Conformations of intrinsically disordered proteins are influenced by linear sequence distributions of oppositely charged residues," Proc Natl Acad Sci U S A, National Academy of Sciences, Aug. 2013, 110(33):13392-13397.

Dasgupta et al., "Isopeptide Ligation Catalyzed by Quintessential Sortase A: Mechanistic Cues From Cyclic and Branched Oligomers of Indolicidin," The Journal of Biological Chemistry, May 2011, vol. 286, No. 27, pp. 23996-24006, Supplemental Information.

Day et al., "A new glucagon and GLP-1 co-agonist eliminates obesity in rodents," Nat Chem Biol, Oct. 2009, 5:749.

De et al., "Temperature-Regulated Activity of Responsive Polymer-Protein Conjugates Prepared by Grafting—from via RAFT Polymerization," J. Am. Chem. Soc. Jul. 2008, 130, 11288-11289.

De Simone et al., "Accurate random coil chemical shifts from an analysis of loop regions in native states of proteins," J Am Chem Soc, Nov. 2009, 131, 16332-16333.

Deer et al., "Phenotype and genotype of pancreatic cancer cell lines," Pancreas, May 2010, 39, 425-435.

Dejana et al., "The role of adherens junctions and VE-cadherin in the control of vascular permeability," J Cell Sci, Jul. 2008, 121, 2115-2122.

Delaglio et al., "NMRPipe: A multidimensional spectral processing system based on UNIX pipes," Journal of Biomolecular NMR 6, 1995, 277-293.

DeLisser et al., "Vascular endothelial platelet endothelial cell adhesion molecule 1 (PECAM-1) regulates advanced metastatic progression," PNAS, Oct. 2010, 107, 18616-18621.

Dennis et al., "Albumin binding as a general strategy for improving the pharmacokinetics of proteins," J Biol Chem, 2002, 277(38): p. 35035-43.

Dennis et al., "Co-Translational Myristoylation Alters the Quaternary Structure of HIV-1 Nef in Solution," Proteins: Structure, Function, and Bioinformatics, 2005, 60:658-669.

Depp et al., "Native protein-initiated ATRP: A viable and potentially superior alternative to PEGylation for stabilizing biologies," Acta Biomater. Feb. 2009, 5, 560-569.

Deshayes et al., "Radium 223 dichloride for prostate cancer treatment," Drug Des Devel Ther, Sep. 2017, 11, 2643-2651.

DeYoung et al.,"Encapsulation of exenatide in poly-(D,L-lactide-co-glycolide) microspheres produced an investigational long-acting once-weekly formulation for type 2 diabetes," Diabetes Technol Ther, Nov. 2011, 13, 1145-1154.

Diana et al., "Prognostic role and correlation of CA9, CD31, CD68 and CD20 with the desmoplastic stroma in pancreatic ductal adenocarcinoma," Oncotarget, Nov. 2016, 7, 72819-72832.

(56) References Cited

OTHER PUBLICATIONS

Diehl et al., "A Good Practice Guide to the Administration of Substances and Removal of Blood Including Routes and Volumes," J Appl Toxicol, 2001, 21, 15-23.
Dignon et al., "Relation between single-molecule properties and phase behavior of intrinsically disordered proteins," Proc Natl Acad Sci U S A, Oct. 2018, 115(40):9929-9934.
Dignon et al., "Sequence determinants of protein phase behavior from a coarse-grained model," PLoS Comput Biol, Jan. 2018, 14(1):e1005941.
Ding et al., "Mechanism for the alpha-helix to beta-hairpin transition," Proteins, 2003, 53, 220-228.
Ding et al., "βKlotho Is Required for Fibroblast Growth Factor 21 Effects on Growth and Metabolism," Cell Metab, Sep. 2012, 16(3):387-393.
Donnelly et al., "DNA Vaccines," Ann. Rev. Immunol., 1997, 15, 617-648.
Dreher et al., "Evaluation of an elastin-like polypeptide-doxorubicin conjugate for cancer therapy," J. of Controlled Release, 2003, 91:31-43.
Dreher et al., "Temperature triggered self-assembly of polypeptides into multivalent spherical micelles," J. Am. Chem. Soc. Jan. 2008, 130, 687-694.
Dreher et al., "Thermal cycling enhances the accumulation of a temperature-sensitive biopolymer in solid tumors," Cancer Res, May 2007, 67, 4418-4424.
Dreher, M. R. Ph.D. Thesis, Duke University, Durham, NC, Apr. 2006.
Dreis et al., "Preparation, Characterisation and Maintenance of Drug Efficacy of Doxorubicin-Loaded Human Serum Albumin (HSA) Nanoparticles," Int. J. Pharm., Aug. 2007, 341, 207-214.
Drucker "Mechanisms of Action and Therapeutic Application of Glucagon-like Peptide-1," Cell Metab, Apr. 2018, 27(4):740-756.
Drucker et al., "The incretin system: glucagon-like peptide-1 receptor agonists and dipeptidyl peptidase-4 inhibitors in type 2 diabetes," Lancet 368, Nov. 2006, 1696-1705.
Drucker, "Glucagon-like peptides," Diabetes 47, 1998, 159-169.
Drucker, "Incretin action in the pancreas: potential promise, possible perils, and pathological pitfalls," Diabetes, Oct. 2013, 62, 3316-3323.
Du et al., "Endoscope-assisted brachytherapy for pancreatic cancer: From tumor killing to pain relief and drainage," Journal of interventional gastroenterology, Jan. 2011, 1, 23-27.
Du et al., "Tailor-made dual pH-sensitive polymer-doxorubicin nanoparticles for efficient anticancer drug delivery," J. Am. Chem. Soc., Oct. 2011, 133, 17560-17563.
Duan et al., "Fibronectin type III domain based monobody with high activity," Biochemistry, Oct. 2007 46(44):12656-12664.
Duan et al., "Improving the thermostability and catalytic efficiency of Bacillus deramificans pullulanase by site-directed mutagenesis," Appl Environ Microbiol, American Society for Microbiology, Jul. 2013, 79(13):4072-4077.
Dubey et al., "Development and evaluation of folate functionalized albumin nanoparticles for targeted delivery of gemcitabine," Int J Pharm., Aug. 2015, 492(1-2):80-91.
Ducreux et al., "Radiation plus docetaxel and cisplatin in locally advanced pancreatic carcinoma: A non-comparative randomized phase II trial," Digestive and Liver Disease, Oct. 2014, 46, 950-955.
Duke University, "Gemcitabine/Nab-Paclitaxel With HIGRT in Resectable Pancreatic Cancer," Clinical Trial NCT02318095 <https://clinicaltrials.gov/ct2/show/NCT02318095> Webpage accessed Jan. 11, 2017.
Duncan, "The dawning era of polymer therapeutics," Nature Reviews Drug Discovery, 2003, 2, 347-360.
Duncan, R. "Polymer conjugates as anticancer nanomedicines," Nat. Rev. Cancer, Sep. 2006, 6, 688-701.
Duronio et al., "Protein N-myristoylation in *Escherichia coli*: Reconstitution of a eukaryotic protein modification in bacteria," Proc. Natl. Acad. Sci. USA, 1990, vol. 87, pp. 1506-1510.
Dyrberg et al., "Peptide as Atigens," J. Exp. Med., 1986, 164:1344-1349.
Dzuricky et al., "Avidity and Cell Uptake of Integrin Targeting Polypeptide Micelles is Strongly Shape Dependent," Nano letters, Sep. 2019, 19(9):6124-6132.
Dzuricky et al., "The Convergence of Artificial Protein Polymers and Intrinsically Disordered Proteins," Biochemistry, May 2018, 57(17):2405-2414.
Egan et al., "The Insulinotropic Effect of Acute Exendin-4 Administered to Humans: Comparison of Nondiabetic State to Type 2 Diabetes," The Journal of Clinical Endocrinology & Metabolism, 2002, 87, 1282-1290.
Ehlerding et al., "Biodegradable and Renal Clearable Inorganic Nanoparticles," Adv Sci (Weinh), Feb. 2016, 3(2):1500223.
Eisenhaber et al., "Prediction of lipid posttranslational modifications and localization signals from protein sequences: Big-Π, NMT and PTS1," Nucleic Acids Res., 2003, 31, 3631-3634.
Eisenhauer et al., "New response evaluation criteria in solid tumours: Revised RECIST guideline (version 1.1)," Eur J Cancer, Jan. 2009, 45(2):228-247.
El-Assaad et al., "Saturated Fatty Acids Synergize with Elevated Glucose to Cause Pancreatic β-Cell Death," Endocrinology, 2003, 144(9):4154-4163.
Elbaum-Garfinkle et al., "The disordered P granule protein LAF-1 drives phase separation into droplets with tunable viscosity and dynamics," Proc Natl Acad Sci U S A, Jun. 2015, 112(23):7189-7194.
Ellis, "Macromolecular crowding: obvious but underappreciated," Trends Biochem. Sci., 2001, 26 (10), 597-604.
Elsabahy et al., "Design of polymeric nanoparticles for biomedical delivery applications," Chem Soc Rev, Royal Society of Chemistry, Apr. 2012, 41(7):2545-61.
Elvin et al., "Synthesis and properties of crosslinked recombinant pro-resilin," Nature, 2005, 437(7061):999-1002.
Elzoghby et al., "Implications of Protein- and Peptide-Based Nanoparticles as Potential Vehicles for Anticancer Drugs," Advances in Protein Chemistry and Structural Biology, Academic Press, Elsevier, Mar. 2015, Chapter Six, vol. 98, pp. 169-221.
Engin et al., "Thermoradiotherapy in the management of superficial malignant tumors," Clinical Cancer Research, 1995, 1, 139-145.
Erickson-Miller et al., "Differential toxicity of camptothecin, topotecan and 9-aminocamptothecin to human, canine, and murine myeloid progenitors (CFU-GM) in vitro," Cancer Chemother. Pharmacol., 1997, 39 (5), 467-472.
Etrych et al., "HPMA Copolymer Conjugates of Paclitaxe; and Docetaxel with pH-Controlled Drug Release," Molecular Pharmaceutics, Jun. 2010, 7(4):1015-1026.
Falk et al., "Hyperthermia in oncology," Int J Hyperthermia, 2001, 17, 1-18.
Farazi et al., "Structures of *Saccharomyces cerevisiae* N-myristoyltransferase with bound myristoylCoA and peptide provide insights about substrate recognition and catalysis," Biochemistry, 2001, 40, 6335-6343.
Farmer et al., "Conformational behavior of chemically reactive alanine-rich repetitive protein polymers," Biomacromolecules, 2005, 6, 1531-1539.
Farokhzad et al., "Targeted nanoparticle-aptamer bioconjugates for cancer chemotherapy in vivo," Proc Natl Acad Sci U S A, The National Academy of Sciences of the USA, Apr. 2006, 103(16):6315-20.
Feng et al., "Protein resistant surfaces: comparison of acrylate graft polymers bearing oligo-ethylene oxide and phosphorylcholine side chains," Biointerphases, Mar. 2006, 1 (1), 50.
Fernandez-Colino et al., "Amphiphilic Elastin-Like Block Co-Recombinamers Containing Leucine Zippers: Cooperative Interplay between Both Domains Results in Injectable and Stable Hydrogels," Biomacromolecules, Sep. 2015, 16, 3389-3398.
Finan et al., "A rationally designed monomeric peptide triagonist corrects obesity and diabetes in rodents," Nat Med, Jan. 2015, 21:27-36.
Finan et al., "Unimolecular Dual Incretins Maximize Metabolic Benefits in Rodents, Monkeys, and Humans," Sci Transl Med, Oct. 2013, 5(209):209ra151.

(56) References Cited

OTHER PUBLICATIONS

Fluegel et al., "Chain stiffness of elastin-like polypeptides," Biomacromolecules, Oct. 2010, 11, 3216-3218.
Fosgerau et al., "Peptide therapeutics: current status and future directions," Drug Discovery Today, Jan. 2015, 20, 122-128.
Franzmann et al., "Phase separation of a yeast prion protein promotes cellular fitness," Science, Jan. 2018, 359(6371):eaao5654.
Free et al., "A Phase 1, multi-center, randomized, double-blind, placebo controlled study to evaluate the safety/tolerability, pharmacokinetic and hemodynamic response following single ascending subcutaneous doses of PB1046 (Vasomera) in subjects with essential hypertension," Circulation, Mar. 2018, 130:A19112.
Friedman et al., "Directed Evolution to Low Nanomolar Affinity of a Tumor-Targeting Epidermal Growth Factor Receptor-Binding Affibody Molecule," J. Mol. Biol., Mar. 2008, 376, 1388-1402.
Frilling et al., "Recommendations for management of patients with neuroendocrine liver metastases," The lancet oncology, Jan. 2014, 15, e8-21.
Fu et al., "Nanoparticle Albumin—Bond (NAB) Technology is a Promising Method for Anti-Cancer Drug Delivery," Recent Patents on Anti-Cancer Drug Discovery, Nov. 2009. 4(3):262-272.
Fujiwara et al., "Modulating effect of the PI3-kinase inhibitor LY294002 on cisplatin in human pancreatic cancer cells," Journal of Experimental & Clinical Cancer Research, Nov. 2008, 27, 76.
Furgeson et al., "Structural optimization of a "smart" doxorubicin-polypeptide conjugate for thermally targeted delivery to solid tumors," Journal of Controlled Release, Jan. 2006, 110:362-369.
Furumoto et al., "Effect of coupling of albumin onto surface of PEG liposome on its In vivo disposition," International Journal of Pharmaceutics, Mar. 2007, 329(1-2): p. 110-116.
Gaberc-Porekar et al., "Obstacles and pitfalls in the PEGylation of therapeutic proteins," Curr. Opin. Drug Discov. Devel. 11, Mar. 2008, 242-250.
Gabizon et al., "Prolonged circulation time and enhanced accumulation in malignant exudates of doxorubicin encapsulated in poly-ethylene-glycol coated liposomes," Cancer Res., Feb. 1994, 54, 987-992.
Gaich et al., "The Effects of LY2405319, an FGF21 Analog, in Obese Human Subjects with Type 2 Diabetes," Cell Metab, Sep. 2013, 18(3):333-340.
Ganson et al., "Control of hyperuricemia in subjects with refractory gout, and induction of antibody against poly(ethylene glycol) (PEG), in a phase I trial of subcutaneous PEGylated urate oxidase," Arthritis Res. Ther. 8, Feb. 2006, R12-R22.
Ganson et al., "Pre-existing anti-polyethylene glycol antibody linked to first-exposure allergic reactions to pegnivacogin, a PEGylated RNA aptamer," J Allergy Clin Immunol, May 2016, 137(5): 1610-1613, e1617.
Gao et al., "In situ growth of a PEG-like polymer from the C terminus of an intein fusion protein improves pharmacokinetics and tumor accumulation" PNAS Early Edition, Jul. 2010, vol. 107, 1-6.
Gao et al., "In situ growth of a PEG-like polymer from the C terminus of an intein fusion protein improves pharmacokinetics and tumor accumulation," Proc. Natl. Acad. Sci., Sep. 2010, 107(38):16432-16437.
Gao et al., "In situ growth of a stoichiometric PEG-like conjugate at a protein's N-terminus with significantly improved pharmacokinetics," Proc. Natl. Acad. Sci., Sep. 2009, 15231-15236.
Gao, "Site-specific and in situ growth of stealth polymer conjugates of proteins with significally improved pharmacology," Journal of Controlled Release, Nov. 2013, 172(1):e116-e117.
Garanger et al., "Structural Evolution of a Stimulus-Responsive Diblock Polypeptide Micelle by Temperature Tunable Compaction of its Core," Macromolecules, Sep. 2015, 48, 6617-6627.
Garay et al., "Antibodies against polyethylene glycol in healthy subjects and in patients treated with PEG-conjugated agents," Expert Opinion. Drug Deliv. 9, Nov. 2012, 1319-1323.
Garcia Quiroz et al., "Syntax of Phase Transition Peptide Polymers with LCST and UCST Behavior," Jan. 1, 2013, Retrieved from the Internet: URL:https://dukespace.lib.duke.edu/dspace/bitstream/handle/10161/7256/GarciaQuirozduke0066D 11972.pdf?sequence=1 &isAllowed=y.
Gauthier et al., "Peptide/protein-polymer conjugates: synthetic strategies and design concepts," Chem. Commun., Jul. 2008, 2591-2611.
Ge et al., "Self-Cleavable Stimulus Responsive Tags for Protein Purification without Chromatography" J. Am. Chem. Soc., 2005, 127: 11228-11229.
Genbank Accession NM_001182082.1 (Mar. 2017).
Geng et al., Shape effects of filaments versus spherical particles in flow and drug delivery, Nat Nanotechnol, Nature Research, Apr. 2007, 2(4):249-55.
Ghoorchian et al., "Molecular architecture influences the thermally induced aggregation behavior of elastin-like polypeptides," Biomacromolecules, Oct. 2011, 12, 4022-4029.
Gianni et al., "Nonlinear pharmacokinetics and metabolism of paclitaxel and its pharmacokinetic/pharmacodynamic relationships in humans," J. Clin. Oncol., 1995, 13 (1), 180-190.
Giberti et al., "Radical retropubic prostatectomy versus brachytherapy for low-risk prostatic cancer: a prospective study," World J Urol, Oct. 2009, 27, 607-612.
Gibson et al., "Enzymatic assembly of DNA molecules up to several hundred kilobases," Nat Methods, May 2009, 6, 343-345.
Gilbreth et al., "Structural insights for engineering binding proteins based on non-antibody scaffolds," Curr Opin Struct Biol, Elsevier, Jun. 2012, 22(4):413-20.
Gillies et al., "Dendrimers and dendritic polymers in drug delivery," Drug Discovery Today, 2005, 10(1):35-43.
Gilroy et al., "Fusion of fibroblast growth factor 21 to a thermally responsive biopolymer forms an injectable depot with sustained anti-diabetic action," J Control Release, May 2018, 277:154-164.
Glassman et al., "Toughening of Thermoresponsive Arrested Networks of Elastin-Like Polypeptides To Engineer Cytocompatible Tissue Scaffolds," Biomacromolecules, Feb. 2016, 17, 415-426.
Gluck et al., "Single Vector System for Efficient N-myristoylation of Recombinant Proteins in *E. coli*," Plos One, Apr. 2010, 5(4) e100881.
Göke et al., "Exendin-4 is a high potency agonis and truncated exendin-(9-39)-amide an antagonist at the glucagon-like peptide 1-(7-36)-amide receptor of insulin-secreting b-cells," J. Biol. Chem. 268, 1993, 19650-19655.
Goldsmith et al., "Enzyme engineering: reaching the maximal catalytic efficiency peak," Curr Opin Struct Biol, Dec. 2017, 47:140-150.
Gordon et al., "Protein N-myristoylation," J. Biol. Chem., 1991, 266, 8647-8650.
Gosline et al., "Elastic proteins: biological roles and mechanical properties," Philos Trans R Soc Lond B Biol Sci, 2002, 357, 121-132.
Gottlieb et al., "NMR chemical shifts of common laboratory solvents as trace impurities," J. Org. Chem., 1997, 62, 7512-7515.
Goutelle et al., "The Hill equation: a review of its capabilities in pharmacological modelling. Fundam.," Clin. Pharmacol. Dec. 22, 2008, 633-648.
Graff et al., "Theoretical analysis of antibody targeting of tumor spheroids: importance of dosage for penetration, and affinity for retention," Cancer Research, 2003, 63(6):1288-1296.
Gratton et al., "The effect of particle design on cellular internalization pathways," Proc Natl Acad Sci U S A, The National Academy of Sciences of the USA, Aug. 2008, 105(33):11613-8.
Greco et al., "The search for synergy: a critical review from a response surface perspective," Pharmacological Reviews, 1995, 24, 331-385.
Green et al., "Abraxane®, a novel Cremophor®-free, albumin-bound particle form of paclitaxel for the treatment of advanced non-small-cell lung cancer," Annals of Oncology, Aug. 2006, 17, 1263-1268.
Green et al., "Novel dipeptidyl peptidase IV resistant analogues of glucagon-like peptide-1 (7-36)amide have preserved biological activities in vitro conferring improved glucose-lowering action in vivo" J. of Mol. Endocrin., 2003, 31(3): 529-540.
Greenfield, "Using circular dichroism spectra to estimate protein secondary structure," Nat. Protoc., Dec. 2006, 1(6):2876-90.

(56) References Cited

OTHER PUBLICATIONS

Griffin et al., "Accelerated wound healing by injectable microporous gel scaffolds assembled from annealed building blocks," Nat Mater, 2015, 14: 737-744.
Grimm et al., "Advances in Brachytherapy," Reviews in Urology, 2004, 6, S37-S48.
Grover et al., "Protein-Polymer Conjugates: Synthetic Approaches by Controlled Radical Polymerizations & Interesting Applications", Curr Opin Chem Bioi., Dec. 2010; 14(6): 818-827.
Gu et al., "Enzymatic Synthesis of Nucleobase-Modified Single-Stranded DNA Offers Turnable Resistance to Nuclease Degradation," Biomacromolecules, Jul. 2018, 19, 3525-3535.
Gu et al., "Photocontrolled micellar aggregation of amphiphilic DNA-azobenzene conjugates," Colloids Surfaces B: Biointerfaces, Nov. 2015, 135, 126-132.
Gu et al., "Precise engineering of targeted nanoparticles by using self-assembled biointegrated block copolymers," Proc Natl Acad Sci U S A, The National Academy of Sciences of the USA, Feb. 2008, 105(7):2586-91.
Güngör et al., "Pancreatic cancer," British Journal of Pharmacology, Jan. 2014, 171, 849-858.
Guo et al., "Nanoparticles escaping RES and endosome: challenges for siRNA delivery for cancer therapy," J. Nanomaterials, Aug. 2011, 2011: 1-12.
Gustafsson, "Nonlinear structured-illumination microscopy: widefield fluorescence imaging with theoretically unlimited resolution," Proc Natl Acad Sci U S A, 2005, 102, 13081-13086.
Gustafsson, "Surpassing the lateral resolution limit by a factor of two using structured illumination microscopy," Short Communication. Journal of Microscopy, 2000, 198, 82-87.
Guzman et al., "Leiodermatolide, a novel marine natural product, has potent cytotoxic and antimitotic activity against cancer cells, appears to affect microtubule dynamics, and exhibits antitumor activity," Int. J. Cancer, Nov. 2016, 139, 2116-2126.
Ha et al., "Immunoglobulin Fc Heterodimer Platform Technology: From Design to Applications in Therapeutic Antibodies and Proteins," Front Immunol, Oct. 2016, 7(394) (in English).
Haider et al., "Genetically engineered polymers: Status and prospects for controlled release," J. Control. Release, 2004, 95, 1-26.
Halozyme Therapeutics, "PEGPH20 Plus Nab-Paclitaxel Plus Gemcitabine Compared With Nab-Paclitaxel Plus Gemcitabine in Subjects With Stage IV Untreated Pancreatic Cancer (HALO-109-202)," Clinical Trial NCT01839487 <https://clinicaltrials.gov/ct2/show/study/NCT01839487> Accessed May 29, 2018.
Hamada et al., "Novel therapeutic strategies targeting tumor-stromal interactions in pancreatic cancer," Frontiers in Physiology, Nov. 2013, vol. 4, Article 331, 7 pages.
Hamidi et al., "Pharmacokinetic Consequences of Pegylation," Drug Deliv., Dec. 2006, 13, 399-409.
Hamley, "Self-assembly of amphiphilic peptides," Soft Matter, Feb. 2011, 7, 4122.
Hampp et al., "Use of Antidiabetic Drugs in the U.S., 2003-2012," Diabetes Care, May 2014, 37:1367-1374.
Han et al., "Survival of patients with advanced pancreatic cancer after iodine[125] seeds implantation brachytherapy: A meta-analysis," Medicine, Feb. 2017, 96, e5719.
Harmon et al., "A Model for Hysteresis Observed in Phase Transitions of Thermally Responsive Intrinsically Disordered Protein Polymers," Biophysical Journal, Feb. 2017, 112(3):207a.
Harries et al., "Nanoparticle Albumin-Bound Paclitaxel for Metastatic Breast Cancer," J. Clin. Oncol., 2005, 23(31):7768-7771.
Harris et al., "Pegylation," Clinical Pharmacokinetics, 2001, 40(7):539-551.
Hart et al., "Attenuation of FGF signalling in mouse β-cells leads to diabetes," Nature, 2000, 408:864.
Hartgerink et al., "Self-assembly and mineralization of peptide-amphiphile nanofibers," Science, 2001, 294, 1684-8.
Hassouneh et al., "Elastin-like Polypeptide Diblock Copolymers Self-Assemble into Weak Micelles," Macromolecules, Jun. 2015, 48, 4183-4195.
Hassouneh et al., "Elastin-Like Polypeptides as a Purification Tag for Recombinant Proteins," Curr Protoc Protein Sci., Aug. 2010, Chapter 6. Unit 6.11. 10.1002/0471140864.ps0611s61.
Hassouneh et al., "Fusions of elastin-like polypeptides to pharmaceutical proteins," Methods Enzymol., Jan. 2012, 502, 215-37.
Hassouneh et al., "Unexpected Multivalent Display of Proteins by Temperature Triggered Self-assembly of Elastin-like Polypeptide Block Copolymers," Biomacromolecules, Apr. 2012, vol. 13, Issue 4, pp. 1598-1605.
Hathout et al., "Analysis of seed loss and pulmonary seed migration in patients treated with virtual needle guidance and robotic seed delivery," American journal of clinical oncology, Oct. 2011, 34, 449-453.
He et al., "Comparative genomics of elastin: Sequence analysis of a highly repetitive protein," Matrix Biology, Sep. 2007, 26:524-540.
He et al., "Improving protein resistance of α-Al2O3 membranes by modification with POEGMA brushes," Applied Surface Science, Nov. 2011, 258(3):1038-1044.
Heagerty et al., Biometrics, "Time-dependent ROC curves for censored survival data and a diagnostic marker," Jun. 2000, 56(2):337-44.
Heal et al., "N-Myristoyltransferase-mediated protein labelling in vivo," Org. Biomol. Chem., Aug. 2008, 6(13):2308-2315.
Heal et al., "Site-specific N-terminal labelling of proteins in vitro and in vivo using N-myristoyl transferase and bioorthogonal ligation chemistry," Chem. Commun., Jan. 2008, 3, 480-482.
Heredia et al., "In Situ Preparation of Protein—"Smart" Polymer Conjugates with Retention of Bioactivity," J. Am. Chem. Soc. Jan. 2006, 127, 16955-16960.
Herrero-Vanrell et al., "Self-assembled particles of an elastin-like polymer as vehicles for controlled drug release," J Control Release, 2005, 102, 113-122.
Hershfield et al., "Induced and pre-existing anti-polyethylene glycol antibody in a trial of every 3-week dosing of pegloticase for refractory gout, including in organ transplant recipients," Arthritis Res. Ther. Mar. 16, 2014, R63.
Hidalgo, "Pancreatic Cancer," N Engl J Med, Apr. 2010, 362, 1605-1617.
Hingorani et al., "Phase 1b Study of PEGylated Recombinant Human Hyaluronidase and Gemcitabine in Patients with Advanced Pancreatic Cancer," Clinical Cancer Research, Jun. 2016, 22, 2848-2854.
Ho et al., "Chemoenzymatic Labeling of Proteins for Imaging in Bacterial Cells," J. Am. Chem. Soc., Nov. 2016, 138(46):15098-15101.
Ho et al., "Internal radiation therapy for patients with primary or metastatic hepatic cancer: a review," Cancer, 1998, 83, 1894-1907.
Hober et al., "Protein A chromatography for antibody purification," Journal of Chromatography B 848, Mar. 2007, pp. 40-47.
Hochkoeppler, "Expanding the landscape of recombinant protein production in *Escherichia coli*," Biotechnol. Lett., Dec. 2013, 35, 1971-1981.
Hofmann et al., "A kinetic study on the enzymatic hydrolysis of fluoresceindiacetate and fluorescein-di-β-D-galactopyranoside," Analytical biochemistry, 1983, 131(1):180-186.
Holehouse et al., "CIDER: Classification of Intrinsically Disordered Ensemble Regions," Biophysical Journal, Feb. 2015, vol. 108, Issue 2, Supplement 1, p. 228a.
Holehouse et al.,"Functional Implications of Intracellular Phase Transitions," Biochemistry, May 2018, 57(17):2415-2423.
Holm et al., "Transperineal [125]iodine seed implantation in prostatic cancer guided by transrectal ultrasonography," The Journal of urology, 2002, 167, 985-988.
Hopp et al., "The effects of affinity and valency of an albumin-binding domain (ABD) on the half-life of a single-chain diabody-ABD fusion protein," Protein Engineering Design and Selection, Sep. 2010, 23(11): p. 827-834.
Hortobágyi, "Anthracyclines in the Treatment of Cancer," Drugs, 1997, vol. 54, No. 4, pp. 1-7.
Howell et al., "The MIRD Perspective 1999," J Nucl Med, 1999, 40, 3S-10S.

(56) References Cited

OTHER PUBLICATIONS

Hruby et al., "New bioerodable thermoresponsive polymers for possible radiotherapeutic applications," Journal of Controlled Release, May 2007, 119, 25-33.
Hruby et al., "Thermoresponsive polymeric radionuclide delivery system—an injectable brachytherapy," Eur J Pharm Sci., Feb. 2011, 42, 484-488.
Hrycushko et al., "Direct intratumoral infusion of liposome encapsulated rhenium radionuclides for cancer therapy: effects of non-uniform intratumoral dose distribution," Med Phys, Mar. 2011, 38, 1339-1347.
Hu et al., "Design of tumor-homing and pH-responsive polypeptide-doxorubicin nanoparticles with enhanced anticancer efficacy and reduced side effects," Chemical Communications, Jun. 2015, 51, 11405-11408.
Hu et al., "Nanografting De Novo Proteins onto Gold Surfaces," Langmuir, 2005, vol. 21:9103-9109.
Huang et al., "Photodynamic Therapy Synergizes with Irinotecan to Overcome Compensatory Mechanisms and Improve Treatment Outcomes in Pancreatic Cancer," Cancer Research, Mar. 2016, 76, 1066-1077.
Huber et al., "Designer amphiphilic proteins as building blocks for the intracellular formation of organelle-like compartments," Nat Mater, Jan. 2015, 14(1):125-132.
Huotari et al., "Endosome maturation," EMBO J, Aug. 2011, 30 (17), 3481-3500.
Hutter et al., "Calibration of atomic-force microscope tips," Review of Scientific Instruments, 1993, 64: 1868-1873.
Hwang et al., "Caprolactonic poloxamer analog: PEG-PCL-PEG," Biomacromolecules, 2005, 6, 885-890.
Hwang et al., "Differentially degradable janus particles for controlled release applications," Macromol Rapid Commun, 2012, 33: 1178-1183.
Hwang et al., "Gene therapy for primary and metastatic pancreatic cancer with intraperitoneal retroviral vector bearing the wild-type p53 gene," Surgery, 1998, 124, 143-151.
Ibrahim et al., "Phase I and pharmacokinetic study of ABI-007, a Cremophor-free, protein-stabilized, nanoparticle formulation of paclitaxel," Clin. Cancer Res., 2002, 8 (5), 1038-1044.
Ilangovan et al., "Structure of sortase, the transpeptidase that anchors proteins to the cell wall of *Staphylococcus aureus*," Proc. Natl. Acad. Sci. 98, 2001, 6056-6061.
Inostroza-Brito et al., "Co-assembly, spatiotemporal control and morphogenesis of a hybrid protein-peptide system," Nat. Chem., Nov. 2015, 7, 1-8.
Ishida et al., "Accelerated blood clearance (ABC) phenomenon upon repeated injection of PEGylated liposomes," International Journal of Pharmaceutics, May 2008, 354(1-2):56-62.
Ito et al., "Impaired negative feedback suppression of bile acid synthesis in mice lacking βKlotho," J Clin Invest, 2005, 115(8):2202-2208.
Ito et al., "In vivo antitumor effect of the mTOR inhibitor CCI-779 and gemcitabine in xenograft models of human pancreatic cancer," International Journal of Cancer, May 2006, 118, 2337-2343.
Jacob et al., "Human phagocytes employ the myeloperoxidase-hydrogen peroxide system to synthesize dityrosine, trityrosine, pulcherosine, and isodityrosine by a tyrosyl radical-dependent pathway," J. Biol. Chem., 1996, 271, 19950-19956.
Jain, "Barriers to Drug-Delivery in Solid Tumors," Sci Am, 1994, 271, 58-65.
Jakubowski et al., "Activators regenerated by electron transfer for atom-transfer radical polymerization of (meth)acrylates and related block copolymers," Angew. Chem. Int. Ed., Jun. 2006, 4482-4486.
Janes et al., "Chitosan nanoparticles as delivery systems for doxorubicin," J. Control Release, 2001, 73, 255-267.
Jang et al., "Engineering Globular Protein Vesicles through Tunable Self-Assembly of Recombinant Fusion Proteins," Small, 2017, 13(36): 1700399.
Jenkins et al., In vivo monitoring of tumor relapse and metastasis using bioluminescent PC-3M-luc-C6 cells in murine models of human prostate cancer. Clinical & Experimental Metastasis, 2003, 20, 745-756.
Ji et al., "RGD-conjugated albumin nanoparticles as a novel delivery vehicle in pancreatic cancer therapy," Cancer Biology & Therapy, Feb. 2012, 13, 206-215.
Jia et al., "Preparation, physicochemical characterization and cytotoxicity in vitro of gemcitabine-loaded PEG-PDLLA nanovesicles," World J. Gastroenterol., Feb. 2010, 16(8):1008-1013.
Jiang et al., "Nanoparticle-mediated cellular response is size-dependent," Nat Nanotechnol, Nature Research, Mar. 2008, 3(3):145-50.
Jiang et al., "The internal structure of self-assembled peptide amphiphiles nanofibers," Soft Matter, Feb. 2007, 3, 454.
Jin et al., "Protein-resistant polyurethane prepared by surface-initiated atom transfer radical graft polymerization (ATRgP) of water-soluble polymers: effects of main chain and side chain lengths of grafts," Colloids and surfaces. B, Biointerfaces, Apr. 2009, 70 (1), 53-9.
Johansson et al., "Structure, Specificity, and Mode of Interaction for Bacterial Albumin-binding Modules," J. Biol. Chem. 2002, 277 (10), 8114-8120.
Johansson et al., "The GA module, a mobile albumin-binding bacterial domain, adopts a three-helix-bundle structure," FEBS Lett, 1995, 374(2): 257-261.
Johnson et al., "Fibroblast Growth Factor 21 Reduces the Severity of Cerulein-Induced Pancreatitis in Mice," Gastroenterology, Nov. 2009, 137(5):1795-1804.
Jokerst et al., "Nanoparticle PEGylation for imaging and therapy," Nanomedicine (Lond), Future Medicine, Jun. 2011, 6(4):715-28.
Jonsson et al., "Engineering of a femtomolar affinity binding protein to human serum albumin," Protein Engineering Design and Selection, Aug. 2008, 21(8): 515-527.
Junutula et al., "Site-specific conjugation of a cytotoxic drug to an antibody improves the therapeutic index," Nat Biotechnol, Aug. 2008, 26(8):925-932.
Jurney et al., "Unique size and shape-dependent uptake behaviors of non-spherical nanoparticles by endothelial cells due to a shearing flow," J Control Release, Jan. 2017, 245:170-176.
Kaighn et al., "Establishment and characterization of a human prostatic carcinoma cell line (PC-3)," Investigative urology, 1979, 17, 16-23.
Kaitin et al., "Pharmaceutical innovation in the 21st century: new drug approvals in the first decade, 2000-2009," Clin Pharmacol Ther, Feb. 2011, 89, 183-188.
Kamaly et al., "Targeted polymeric therapeutic nanoparticles: design, development and clinical translation," Chem Soc Rev, Royal Society of Chemistry, Apr. 2012, 41(7):2971-3010.
Kamisawa et al., "Pancreatic cancer," Lancet, Jul. 2016, 388, 73-85.
Kanoski et al., "The role of nausea in food intake and body weight suppression by peripheral GLP-1 receptor agonists, exendin-4 and liraglutide," Neuropharmacology 62, Apr. 2012, 1916-1927.
Kanyama et al., "Usefulness of Repeated Direct Intratumoral Gene Transfer Using Hemagglutinating Virus of Japan-Liposome Method for Cytosine Deaminase Suicide Gene Therapy," Cancer Research, 2001, 61, 14-18.
Karagoz et al., "Polymerization-Induced Self-Assembly (PISA)—control over the morphology of nanoparticles for drug delivery applications," Polym. Chem., Jan. 2014, 5(2):350-355.
Karamanolis et al., "Increased expression of VEGF and CD31 in postradiation rectal tissue: implications for radiation proctitis," Mediators Inflamm, May 2013, 515048.
Karperien, A. FracLac for Image J, version 2.5 <http://rsb.info.nih.gov/ij/plugins/fraclac/FLHelp/Introduction.htm> 1999-2012.
Kaspar et al., "Future directions for peptide therapeutics development," Drug Discovery Today, Sep. 2013, 18, 807-817.
Katakura, "Nuclear Data Sheets for A=125," Nuclear Data Sheets, Mar. 2011, 112, 495-705.
Kataoka et al., "Block copolymer micelles for drug delivery: Design, characterization and biological significance," Advanced Drug Delivery Reviews, 2001, 47:113-131.

(56) References Cited

OTHER PUBLICATIONS

Kato et al., "Acidic extracellular microenvironment and cancer," Cancer Cell Int, Sep. 2013, 13, 89, 8 pages.

Katti et al., "Amino acid repeat patterns in protein sequences: Their diversity and structural-functional implications," Protein Science, 2000, 9: 1203-1209.

Keefe et al., "Poly(zwitterionic)protein conjugates offer increased stability without sacrificing binding affinity or bioactivity," Nat Chem, Jan. 2012, 4(1):59-63.

Keller et al., "Empirical Statistical Model To Estimate the Accuracy of Peptide Identifications Made by MS/MS and Database Search," Anal. Chem. 2002, 74, 5383-5392.

Kelly et al., "How to study proteins by circular dichroism," Biochim. Byophys. Acta—Proteins Proteomics, 2005, 1751(2):119-39.

Kelly et al., "Shape-specific, monodisperse nano-molding of protein particles," J Am Chem Soc, ACS Publications, Apr. 2008, 130(16):5438-9.

Kesharwani et al., "Dendrimer as nanocarrier for drug delivery," Progress in Polymer Science, Feb. 2014, 39(2):268-307.

Keten et al., "Nanoconfinement controls stiffness, strength and mechanical toughness of β-sheet crystals in silk," Nat Mater, Mar. 2010, 9, 359-367.

Khademhosseini et al., "Micromolding of photocrosslinkable hyaluronic acid for cell encapsulation and entrapment," J Biomed Mater Res A, 2006, 79: 522-532.

Khandare et al., "Polymer-drug conjugates: Progress in polymeric drugs," Prog. Polym. Sci., 2005, vol. 31, pp. 359-397.

Khanna et al., "The dog as a cancer model," Nat. Biotechnol., Sep. 2006, 24, 1065-1066.

Kharitonenkov et al., "FGF-21 as a novel metabolic regulator," J Clin Invest, 2005, 115(6):1627-1635.

Kharitonenkov et al., "FGF21 Revolutions: Recent Advances Illuminating FGF21 Biology and Medicinal Properties," Trends Endocrinol Metab, Nov. 2015, 26(11):608-617.

Kharitonenkov et al., "Fibroblast growth factor 21 night watch: advances and uncertainties in the field," J Intern Med, Nov. 2016, 281(3):233-246.

Kharitonenkov et al., "Inventing new medicines: The FGF21 story," Mol Metab, Jun. 2014, 3(3):221-229.

Khazov et al., "Nuclear Data Sheets for A=131," Nuclear Data Sheets, 2006, 107, 2715-2930.

Khoo et al., "Activation of mitogen-activating protein kinase by glucose is not required for insulin secretion," Proc Natl Acad Sci USA, 1997, 94(11):5599-5604.

Khoo et al., "Regulation of Insulin Gene Transcription by ERK1 and ERK2 in Pancreatic β Cells," J Biol Chem, 2003, 278(35):32969-32977.

Kim et al., "Effects of Once-Weekly Dosing of a Long-Acting Release Formulation of Exenatide on Glucose Control and Body Weight in Subjects With Type 2 Diabetes," Diabetes Care, Jun. 2007, 30, 1487-93.

Kim et al., "Generation of core-shell microcapsules with three-dimensional focusing device for efficient formation of cell spheroid," Lab Chip, 2011, 11: 246-252.

Kim et al., "Recombinant elastin-mimetic biomaterials: Emerging applications in medicine," Adv Drug Deliv Rev, Dec. 2010, 62, 1468-1478.

Kim et al., "Site-Specific PEGylated Exendin-4 Modified with a High Molecular Weight Trimeric PEG Reduces Steric Hindrance and Increases Type 2 Antidiabetic Therapeutic Effects," Bioconjugate Chem., Nov. 2012, 23, 2214-2220.

Kim et al., "Ultrasensitive Carbon nanotube-based biosensors using antibody-binding fragments," Analytical Biochemistry, Jul. 2008, 381, 193-198.

Knop et al., "Poly(ethylene glycol) in Drug Delivery: Pros and Cons as Well as Potential Alternatives," Angewandte Chemie International Edition, Aug. 2010, 49(36):6288-6308.

Knudsen, "Glucagon-like Peptide-1: The Basis of a New Class of Treatment for Type 2 Diabetes" J. Med. Chem, 2004, 47: 4128-4134.

Kobashigawa et al., "Attachment Of An NMR-Invisible Solubility Enhancement Tag Using A Sortase-Mediated Protein Ligation Method," J Biomol NMR. Mar. 2009, vol. 43, No. 3; pp. 145-150.

Kobayashi et al., "Summary of recombinant human serum albumin development," Biologicals, Mar. 2006, 34(1): 55-59.

Koehler et al., "Albumin affinity tags increase peptide half-life In vivo," Bioorganic & Medicinal Chemistry Letters, 2002, 12(20): 2883-2886.

Kontos et al., "Drug development: longer-lived proteins," Chemical Society Reviews, Feb. 2012, 41(7):2686-2695.

Koong et al., "Phase II study to assess the efficacy of conventionally fractionated radiotherapy followed by a stereotactic radiosurgery boost in patients with locally advanced pancreatic cancer," Int J Radiation Oncol Biol Phys, 2005, 63, 320-323.

Kothare et al., "Pharmacokinetics, pharmacodynamics, tolerability, and safety of exenatide in Japanese patients with type 2 diabetes mellitus," J. Clin. Pharmacol. 48, Jan. 2009, 1389-1399.

Kowalczyk et al., "Elastin-like Polypeptides as a Promising Family of Genetically-Engineered Protein Based Polymers," World Journal of Microbiology and Biotechnology, Springer, Apr. 2014, 30(8):2141-2152.

Kramer et al., "Quantitative Side-Chain Modifications of Methionine-Containing Elastin-Like Polypeptides as a Versatile Tool to Tune Their Properties," ACS Macro Lett., Nov. 2015, 4(11):1283-1286.

Kraulis et al., "The serum albumin-binding domain of streptococcal protein G is a three-helical bundle: a heteronuclear NMR study," FEBS letters, 1996, 378(2): p. 190-194.

Krause et al., "Structure and function of claudins," Biochmica et Biophysica Acta, Mar. 2008, 1778, 631-645.

Krempien et al., "Neoadjuvant chemoradiation in patients with pancreatic adenocarcinoma," HPB (Oxford), Feb. 2006, 8(1):22-28.

Kruger et al., "Analysis of the Substrate Specificity of the *Staphylococcus aureus* Sortase Transpeptidase SrtA†," Biochemistry, 2004, 43, 1541-1551.

Kulkarni et al., "Bioorthogonal Chemoenzymatic Functionalization of Calmodulin for Bioconjugation Applications," Bioconjug. Chem., Oct. 2015, 26(10):2153-2160.

Kulkarni et al., "Design of lipid nanoparticles for in vitro and in vivo delivery of plasmid DNA," Nanomedicine, May 2017, 13(4):1377-1387.

Kulkarni et al., "Selective functionalization of the protein N terminus with N-myristoyl transferase for bioconjugation in cell lysate," ChemBioChem, Oct. 2013, 14, 1958-1962.

Kumar et al., "N-Terminal Region of the Catalytic Domain of Human N-Myristoyltransferase 1 Acts as an Inhibitory Module," PLoS One, May 2015, 10(5):e0127661.

Kupelian et al., "Radical prostatectomy, external beam radiotherapy <72 Gy, external beam radiotherapy > or =72 Gy, permanent seed implantation, or combined seeds/external beam radiotherapy for stage T1-T2 prostate cancer," International journal of radiation oncology, biology, physics, 2004, 58, 25-33.

Kurosu et al., "Tissue-specific Expression of βKlotho and Fibroblast Growth Factor (FGF) Receptor Isoforms Determines Metabolic Activity of FGF19 and FGF21," J Biol Chem, Sep. 2007, 282(37):26687-26695.

Kyte et al., "A Simple Method for Displaying the Hydropathic Character of a Protein," J. Mol. Biol., 1982, 157:105-132.

Labelle et al., "Vascular endothelial cadherin promotes breast cancer progression via transforming growth factor β signaling," Cancer Res. Mar. 2008, 68, 1388-1397.

Lacroix et al., "Elucidating the folding problem of alpha-helices: local motifs, long-range electrostatics, ionic-strength dependence and prediction of NMR parameters," J Mol Biol, 1998, 284, 173-191.

Langer et al., "Designing materials for biology and medicine," Nature, 2004, 428, 487-92.

Laybutt et al., "Endoplasmic reticulum stress contributes to beta cell apoptosis in type 2 diabetes," Diabetologia, Apr. 2007, 50(4):752-763.

Le Droumaguet et al., "Recent advances in the design of bioconjugates from controlled/living radical polymerization," Polym. Chem. Jan. 2010, 1, 563-598.

(56) References Cited

OTHER PUBLICATIONS

Le Meins et al., "Hybrid polymer/lipid vesicles: State of the art and future perspectives," Mater. Today, Oct. 2013, 16, 397-402.
Leader et al., "Protein therapeutics: a summary and pharmacological classification," Nat. Rev. Drug Discov. Jan. 7, 2008, 21-39.
Lee et al., "Atomistic molecular dynamics simulations of peptide amphiphile self-assembly into cylindrical nanofibers," J. Am. Chem. Soc., Feb. 2011, 133, 3677-3683.
Lee et al., "Immunohistochemical analysis of claudin expression in pancreatic cystic tumors," Oncology Reports, Apr. 2011, 25(4): 971-978.
Lee et al., "In vivo bioluminescent imaging of irradiated orthotopic pancreatic cancer xenografts in nonobese diabetic-severe combined immunodeficient mice: a novel method for targeting and assaying efficacy of ionizing radiation," Transl. Oncol., Jun. 2010, 3, 153-159.
Lee et al., "Mechanical properties of cross-linked syntheti elastomeric polypentapeptides," Macromolecules, 2001, 34, 5968-5974.
Lee et al., "Nanoparticle-Delivered Chemotherapy: Old Drugs in New Packages." Oncology (Williston Park, NY) 31.3 (Mar. 2017): 198-208.
Lee et al., "Phase transition and elasticity of protein-based hydrogels," J. Biomater. Sci. Polymer Edn, 2001, 12, 229-242.
Lee et al., "Polymersomes for drug delivery: design, formation and characterization," J Control Release, Elsevier, Jul. 2012, 161(2):473-83.
Lee et al., "Structures of β-klotho reveal a 'zip code'-like mechanism for endocrine FGF signaling," Nature, Jan. 2018, 553:501-505.
Lee et al., "Theranostic nanoparticles with controlled release of gemcitabine for targeted therapy and MRI of pancreatic cancer," ACS Nano, Mar. 2013, 7(3):2078-2089.
Leibowitz et al., "Glucose-Regulated Proinsulin Gene Expression Is Required for Adequate Insulin Production during Chronic Glucose Exposure," Endocrinology, 2002, 143(9):3214-3220.
Lele et al., "Synthesis of uniform protein-polymer conjugates," Biomacromolecules 6, 2005, 3380-3387.
Lennen et al., "Membrane Stresses Induced by Overproduction of Free Fatty Acids in *Escherichia coli*," Appl Environ Microb., Nov. 2011, 77(22):8114-28.
Leung et al., "Bio-Click Chemistry: Enzymatic Functionalization of PEGylated Capsules for Targeting Applications**," Angew. Chem. Int. Ed. Jul. 2012, 51, 7132-7136.
Levine et al., "Thioflavine T interaction with synthetic Alzheimer's disease beta-amyloid peptides: detection of amyloid aggregation in solution," Protein Sci., 1993, 2, 404-10.
Levy et al., "Novel Exenatide Analogs with Peptidic Albumin Binding Domains: Potent Anti-Diabetic Agents with Extended Duration of Action," PLoS ONE, Feb. 2014, 9(2): e87704, 9 pages.
Lewis et al., "Use of digitized video microscopy with a fluorogenic enzyme substrate to demonstrate cell- and compartment-specific gene expression in *Salmonella enteritidis* and Bacillus subtilis," Molecular microbiology, 1994, 13:655-662.
Li et al., "Elastin is an essential determinant of arterial morphogenesis," Nature, 1998, 393, 276-280.
Li et al., "FGF21 Is Not a Major Mediator for Bone Homeostasis or Metabolic Actions of PPARα and PPARγ Agonists," J Bone Miner Res, Apr. 2017, 32(4):834-845.
Li et al., "Molecular description of the LCST behavior of an elastin-like polypeptide," Biomacromolecules, Aug. 2014, 15, 3522-3530.
Li et al., "Nanoparticles Evading The Reticuloendothelial System: Role of The Supported Bilayer," Biochim. Biophys. Acta, Oct. 2009, 1788 (10), 2259-2266.
Li et al., "Pancreatic cancer," Lancet, 2004, 363, 1049-1057.
Li et al., "Phase transitions in the assembly of multivalent signalling proteins," Nature, Nature Research, Mar. 2012, 483(7389):336-340.
Li et al., "Prediction of solvent-induced morphological changes of polyelectrolyte diblock copolymer micelles," Soft Matter, Nov. 2015, 11(42): 8236-45.
Li et al., "Protein adsorption on oligo(ethylene glycol)-terminated alkanethiolate self-assembled monolayers: The molecular basis for nonfouling behavior," The journal of physical chemistry. B, 2005, 109 (7), 2934-41.
Li et al., "Temperature-Triggered Phase Separation of a Hydrophilic Resilin-Like Polypeptide," Macramol. Rapid Commun., Jan. 2015, 36(1):90-95.
Li et al., "Tunable Assembly of Protein-Microdomains in Living Vertebrate Embryos," Advanced Biosystems, Oct. 2018, 2(10):1800112.
Liao et al., "Removal of N-terminal methionine from recombinant proteins by engineered *E. coli* methionine aminopeptidase," Prot. Sci. 13, 2004, 1802-1810.
Liechty et al., "Polymers for Drug Delivery Systems," Annual review of chemical and biomolecular engineering, Aug. 2010, 1:149-173.
Lillie et al., "The viscoelastic basis for the tensile strength of elastin," Int J Biol Macromol, 2002, 30, 119-127.
Lim et al., "Improved Non-Chromatographic Purification of a Recombinant Protein by Cationic Elastin-like Polypeptides" Biomacromolecules, May 2007, 8(5): 1417-1424.
Lim et al., "In situ cross-linking of elastin-like polypeptide block copolymers fortissue repair," Biomacromolecules, Feb. 2008, 9, 222-230.
Lim et al., "In vivo post-translational modifications of recombinant mussel adhesive protein in insect cells," Biotechnol. Prog., Sep.-Oct. 2011, 27(5):1390-1396.
Lin et al., "Adiponectin Mediates the Metabolic Effects of FGF21 on Glucose Homeostasis and Insulin Sensitivity in Mice," Cell Metab, May 2013, 17(5):779-789.
Lin et al., "Formation and Maturation of Phase-Separated Liquid Droplets by RNA-Binding Proteins," Mol Cell, Oct. 2015, 60(2):208-219.
Lin et al., "Functional expression of a biologically active fragment of soluble gp130 as an ELP-fusion protein in transgenic plants: purification via inverse transition cycling," Biochem J, Sep. 2006, 398(3):577-583.
Lin et al., "Intrinsically disordered sequences enable modulation of protein phase separation through distributed tyrosine motifs," J Biol Chem, Nov. 2017, 292(46):19110-19120.
Lin et al., "Phase Separation and Single-Chain Compactness of Charged Disordered Proteins Are Strongly Correlated," Biophys J, May 2017, 112(10):2043-2046.
Lin et al., "Sequence-Specific Polyampholyte Phase Separation in Membraneless Organelles," Phys Rev Lett, Oct. 2016, 117(17):178101.
Lin et al., "Statistical properties of the traditional algorithm-based designs for phase I cancer clinical trials," Biostatistics, 2001, 2(2):203-215.
Lin et al., "Utility of immunohistochemistry in the pancreatobiliary tract," Arch Pathol Lab Med, Jan. 2015, 139, 24-38.
Linder et al., "Lipid Modifications of G Protein Subunits," J. Biol. Chem., 1991, 266(7):4654-4659.
Ling et al., "Protein thioester synthesis enabled by sortase," J. Am Chem Soc, Jul. 2012, 134(26):10749-10752.
Liong et al., "Multifunctional inorganic nanoparticles for imaging, targeting, and drug delivery," ACS Nano, ACS Publications, May 2008, 2(5):889-96.
Litiere et al., "RECIST—learning from the past to build the future," Nat Rev Clin Oncol, Mar. 2017, 14, 187-192.
Liu et al., "Brachytherapy using injectable seeds that are self-assembled from genetically encoded polypeptides in situ," Cancer Res, Nov. 2012, 72, 5956-5965.
Liu et al., "Hydrophobic modifications of cationic polymers for gene delivery," Prog. in Polym. Sci., Sep. 2010, 35, 1144-1162.
Liu et al., "In Situ Formation of Protein-Polymer Conjugates through Reversible Addition Fragmentation Chain Transfer Polymerization**," Angew. Chem. Int. Ed. Apr. 2007, 46, 3099-3103.
Liu et al., "Injectable intratumoral depot of thermally responsive polypeptide-radionuclide conjugates delays tumor progression in a mouse model," J. Control Release, May 2010, 144(1):2-9.
Liu et al., "Integrin $\alpha_v\beta_3$-Targeted Cancer Therapy," Drug Dev Res, Wiley, Sep. 2008, 69(6):329-339.

(56) References Cited

OTHER PUBLICATIONS

Liu et al., "Tracking the in vivo fate of recombinant polypeptides by isotopic labeling," Journal of Controlled Release, Sep. 2006, 114, 184-192.
Liu et al., "Tumor accumulation, degradation and pharmacokinetics of elastin-like polypeptides in nude mice," Journal of Controlled Release, Nov. 2006, 116, 170-178.
Liu, L. et al., "Monodisperse core-shell chitosan microcapsules for pH-responsive burst release of hydrophobic drugs," Soft Matter, 2011, 7: 4821-4827.
Livingstone, "Theoretical property predictions. Curr Top Med Chem FIELD Full Journal Title: Current topics in medicinal chemistry," Curr. Top. Med. Chem. 2003, 3, 1171-1192.
Loh et al., "Utilising inorganic nanocarriers for gene delivery," Biomater Sci, Jan. 2016, 4(1):70-86.
LoPresti et al., "Polymersomes: nature inspired nanometer sized compartments," Journal of Materials Chemistry, RSC Publishing, Jun. 2009, 19(22):3576-3590.
Lovshin et al., "Incretin-based therapies for type 2 diabetes mellitus," Nat. Rev. Endocrinol. 5, Jun. 2009, 262-269.
Ludden, "Nonlinear pharmacokinetics: clinical Implications," Clin. Pharmacokinet., 1991, 20 (6), 429-446.
Luginbuhl et al., "One-week glucose control via zero-order release kinetics from an injectable depot of glucagon-like peptide-1 fused to a thermosensitive biopolymer," Nat. Biomed. Eng. 1, Jun. 2017, Article No. 0078.
Luginbuhl et al., "Recombinant Synthesis of Hybrid Lipid-Peptide Polymer Fusions that Self-Assemble and Encapsulate Hydrophobic Drugs," Angew Chem Int Ed Engl., Nov. 2017, 56(45):13979-13984.
Lukyanov et al., "Micelles From Lipid Derivatives of Water-Soluble Polymers as Delivery Systems for Poorly Soluble Drugs," Adv. Drug Deliver. Rev., 2004, 56(9):1273-1289.
Lukyanov et al., "Tumor-targeted liposomes: doxorubicin-loaded long-circulating liposomes modified with anti-cancer antibody," J Control Release, 2004, 100(1):135-44.
Lund et al., "Phase II study of gemcitabine (2',2'-difluorodeoxycytidine) in previously treated ovarian cancer patients," J. Natl. Cancer. Inst. 1994, 86(20):1530-1533.
Luo et al., "Noncovalent Modulation of the Inverse Temperature Transition and Self-Assembly of Elastin-b-Collagen-like Peptide Bioconjugates," J Am Chem Soc, Dec. 2015, 137, 15362-15365.
Lutz et al., "About the Phase Transitions in Aqueous Solutions of Thermoresponsive Copolymers and Hydrogels Based on 2-(2-methoxyethoxy)ethyl Methacrylate and Oligo(ethylene glycol) Methacrylate," Macromolecules, Mar. 2007, 40, 2503-2508.
Lutz et al., "Preparation of Ideal PEG Analogues with a Tunable Thermosensitivity by Controlled Radical Copolymerization of 2-(2-Methoxyethoxy)ethyl Methacrylate and Oligo(ethylene glycol) Methacrylate," Macromolecules, Jan. 2006, 39, 893-896.
Lyons et al., "Comparisons of Recombinant Resilin-like Proteins: Repetitive Domains Are Sufficient to Confer Resilin-like Properties," Biomacromolecules, ACS Publications, Oct. 2009, 10(11):3009-3014.
Lyons et al., "Design and facile production of recombinant resilin-like polypeptides: Gene construction and a rapid protein purification method," Protein Engineering Design & Selection, Oxford university Press, Jan. 2007, 20(1):25-32.
Ma et al., "Core-shell hydrogel microcapsules for improved islets encapsulation," Adv Healthc Mater, 2013, 2:667-672.
Ma et al., "Non-fouling" oligo(ethylene glycol)-functionalized polymer brushes synthesized by surface-initiated atom transfer radical polymerization, Advanced Materials 2004, 16 (4), 338.
Ma et al., "Protein-resistant polymer coatings on silicon oxide by surface-initiated atom transfer radical polymerization," Langmuir: the ACS journal of surfaces and colloids, Mar. 2006, 22 (8), 3751-6.
Ma et al., "Surface-Initiated Atom Transfer Radical Polymerization of Oligo(ethylene glycol) Methyl Methacrylate from a Mixed Self-Assembled Monolayer on Gold," Advanced Functional Materials, Mar. 2006, 16 (5), 640-648.

MacEwan et al., "Applications of elastin-like polypeptides in drug delivery," Journal of Controlled Release, Sep. 2014, 190: p. 314-330.
MacEwan et al., "Controlled apoptosis by a thermally toggled nanoscale amplifier of cellular uptake," Nano Letters, Apr. 2014, 14, 2058-2064.
MacEwan et al., "Digital switching of local arginine density in a genetically encoded self-assembled polypeptide nanoparticle controls cellular uptake," Nano Lett., Jun. 2012, 12, 3322-3328.
MacEwan et al., "Elastin-like polypeptides: Biomedical applications of tunable biopolymers," Biopolymers, Jan. 2010, 94, 60-77.
MacEwan et al., "Non-chromatographic Purification of Recombinant Elastin-like Polypeptides and their Fusions with Peptides and Proteins from *Escherichia coli*," Jun. 2014, 88, p. e51583.
MacEwan et al., "Phase Behavior and Self-Assembly of Perfectly Sequence-Defined and Monodisperse Multiblock Copolypeptides," Biomacromolecules, Jan. 2017, 18(2):599-609.
Mack et al., "Antiobesity action of peripheral exenatide (exendin-4) in rodents: effects on food intake, body weight, metabolic status and side-effect measures," Int. J. Obes. Sep. 30, 2006, 1332-1340.
MacKay et al., "Self-assembling chimeric polypeptide-doxorubicin conjugate nanoparticles the abolish tumors after single injection," Nat Mater, Dec. 2009, 8(12):993-999.
Maeda et al., "Tumor vascular permeability and the EPR effect in macromolecular therapeutics: a review," J. Control. Release, Mar. 2000, 65(1-2)271-284.
Maeda et al., "Tumoritropic and lymphotropic principles of macromolecular drugs," Critical reviews in therapeutic drug carrier systems, 1989, 6(3):193-210.
Maeda, "The enhanced permeability and retention (EPR) effect in tumor vasculature: the key role of tumor-selective macromolecular drug targeting," Advances in Enzyme Regulation, 2001, 41(1):189-207.
Magnusson et al., "In Situ Growth of Side-Chain PEG Polymers from Functionalized Human Growth Hormone—A New Technique for Preparation of Enhanced Protein-Polymer Conjugates," Bioconjugate Chem. Mar. 21, 2010, 671-678.
Magnusson et al., "Ion-Sensitive "Isothermal" Responsive Polymers Prepared in Water," Journal of the American Chemical Society, Aug. 2008, 130, 10852-10853.
Maitra et al., "Pancreatic Cancer," Annu Rev Pathol Mech Dis, Feb. 2008, 3, 157-188.
Malam et al., "Liposomes and nanoparticles: nanosized vehicles fordrug delivery in cancer," Trends Pharmacol Sci, Cell Press, Nov. 2009, 30(11):592-9.
Malik et al., "Recent advances in protein and peptide drug delivery systems," Curr. Drug Deliv. 2, Apr. 2007, 141-151.
Manders et al., "Dynamics of three-dimensional replication patterns during the S-phase, analysed by double labelling of DNA and confocal microscopy," Journal of cell science, 1992, 103(Pt 3):857-862.
Mann et al., "Proteomic analysis of post-translational modifications," Nat. Biotechnol., 2003, 21, 255-61.
Manzoor et al., "Overcoming limitations in nanoparticle drug delivery: triggered, intravascular release to improve drug penetration into tumors," Cancer Res, Nov. 2012, 72, 5566-5575.
Mao et al., "DNA repair by nonhomologous end joining and homologous recombination during cell cycle in human cells," Cell cycle, Sep. 2008, 7, 2902-2906.
Mao et al., "Net charge per residue modulates conformational ensembles of intrinsically disordered proteins," Proc Natl Acad Sci U S A, 2010, 107(18):8183-8188.
Mao et al., "Sortase-mediated protein ligation: a new method for protein engineering," J. Am. Chem. Soc., 2004, 126(9):2670-2671.
Maraffini et al., "Sortases and the art of anchoring proteins to the envelopes of Gram-positive bacteria," Microbiol Mol Biol Rev, Mar. 2006, 70(1):192-221.
Mariam et al., "Albumin corona on nanoparticles—a strategic approach in drug delivery," Drug Deliv., Oct. 2016, 23 (8), 2668-2676.
Marr et al., "Effect of Temperature on the Composition of Fatty Acids in *Escherichia coli*," J Bacteriol., 1962, 84(6):1260-7.

(56) References Cited

OTHER PUBLICATIONS

Marten et al., "A randomized multicentre phase II trial comparing adjuvant therapy in patients with interferon alpha-2b and 5-FU alone or in combination with either external radiation treatment and cisplatin (CapRI) or radiation alone regarding event-free survival—CapRI-2," BMC Cancer, Feb. 2009, 9, 1-8.
Maskarinec et al., "Protein engineering approaches to biomaterials design," Curr. Opin. Biotechnol., 2005, 16, 422-426.
Masood, "Polymeric nanoparticles for targeted drug delivery system for cancer therapy," Mater Sci Eng C Mater Biol Appl, Mar. 2016, 60:569-578.
Massey et al., "Self-Assembly of a Novel Organometallic-Inorganic Block Copolymer in Solution and the Solid State: Nonintrusive Observation of Novel Wormlike Poly(ferrocenyldimethylsilane)-b-Poly(dimethylsiloxane) Micelles," J. Am. Chem. Soc. 1998, 120(37):9533-9540.
Mastria et al., "Doxorubicin-conjugated polypeptide nanoparticles inhibit metastasis in two murine models of carcinoma," J Control Release, Jun. 2015, 208:52-8.
Mastria et al., "Nanoparticle formulation improves doxorubicin efficacy by enhancing host antitumor immunity," J Control Release, Jan. 2018, 269:364-373.
Matsumura et al., "A new concept for macromolecular therapeutics in cancer chemotherapy: mechanism of tumoritropic accumulation of proteins and the antitumor agent smancs," Cancer Res. 1986, 46, 6387-6392.
Matsumura, "Cancer stromal targeting (CAST) therapy," Advanced Drug Delivery Reviews, Jun. 2012, 64, 710-719.
Matsunaga et al., "Molding cell beads for rapid construction of macroscopic 3D tissue architecture," Adv Mater, 2011, 23: H90-94.
Matthews et al., "Pharmacodynamics, Pharmacokinetics, Safety, and Tolerability of Albiglutide, a Long-Acting Glucagon-Like Peptide-1 Mimetic, in Patients with Type 2 Diabetes," J Clin Endocrinol Metab, Dec. 2008, 93(12):4810-4817.
Matyjaszewski et al., "Atom transfer radical polymerization," Chem. Rev. 101, Sep. 2001, 2921-2990.
Matyjaszewski et al., "Macromolecular engineering by atom transfer radical polymerization," J. Am. Chem. Soc. 136, 2014, 6513-6533.
Maurer-Stroh et al., "N-terminal N-myristoylation of proteins: prediction of substrate proteins from amino acid sequence" J Mol Biol., 2002, 317(4):541-557.
Maurer-Stroh et al., "N-terminal N-myristoylation of proteins: Refinement of the sequence motif and its taxon-specific differences," J Mol Biol., 2002, 317(4):523-540.
Mayo et al., "Cell Adhesion Promoting Peptide GVKGDKGNPGWPGAP from the Collagen Type IV Triple Helix: Cis/Trans Proline-Induced Multiple 1H NMR Conformations and Evidence for a KG/PG Multiple Turn Repeat Motif in the All-Trans proline State," Biochemistry, 1991, 30: 8251-8267.
McConkey et al., "Molecular Characterization of Pancreatic Cancer Cell Lines," Pancreatic Cancer, Jan. 2010, 457-469.
McDaniel et al., "A unified model for de novo design of elastin-like polypeptides with tunable inverse transition temperatures," Biomacromolecules, Aug. 2013, 14(8):2866-2872.
McDaniel et al., "Actively targeting solid tumours with thermoresponsive drug delivery systems that respond to mild hyperthermia," Int J Hyperthermia, Aug. 2013, 29, 501-510.
McDaniel et al., "Doxorubicin-conjugated chimeric polypeptide nanoparticles that respond to mild hyperthermia," Control. Release, May 2012, 159 (3), 362-367.
McDaniel et al., "Drug delivery to solid tumors by elastin-like polypeptides," Adc. Drug Deliver. Rev., Dec. 2010, 62(15):1456-1467.
McDaniel et al., "Noncanonical Self-Assembly of Highly Asymmetric Genetically Encoded Polypeptide Amphiphiles into Cylindrical Micelles," Nano Lett., Sep. 2014, 14(11):6590-6598.
McDaniel et al., "Rational design of "heat seeking" drug loaded polypeptide nanoparticles that thermally target solid tumors," Nano Letters, Apr. 2014, 14, 2890-2895.
McDaniel et al., "Recursive Directional Ligation by Plasmid Reconstruction Allows Rapid and Seamless Cloning of Oligomeric Genes," Biomacromolecules, Feb. 2010, 11(4):944-952.
McDaniel et al., "Self-assembly of thermally responsive nanoparticles of a genetically encoded peptide polymer by drug conjugation," Chem. Int. Ed. Feb. 2013, 52, 1683-1687.
McDaniel, "Assembly of Highly Asymmetric Genetically-Encoded Amphiphiles for Thermally Targeted Delivery of Therapeutics," Dissertation, 2013, 295 pages, Published Mar. 1, 2014.
McHale et al., "Synthesis and in vitro evaluation of enzymatically cross-linked elastin-like polypeptide gels for cartilaginous tissue repair," Tissue Eng., 2005, 11, 1768-1779.
McIlhinney et al., "Characterization of a polyhistidine-tagged form of human myristoyl-CoA: protein N-myristoyltransferase produced in *Escherichia coli*," European Journal of Biochemistry, 1994, 222(1):137-146.
McKenzie et al., "Multivalent Binding of a Ligand-Coated Particle: Role of Shape, Size, and Ligand Heterogeneity," Biophys J, Apr. 2018, 114(8):1830-1846.
Meier et al., "Determination of Optimal Sample Size for Quantification of β-Cell Area, Amyloid Area and β-Cell Apoptosis in Isolated Islets," J Histochem Cytochem, Aug. 2015, 63(8):663-673.
Mejuch et al., "Synthesis of lipidated proteins," Bioconjug. Chem. Jul. 27, 2016, 1771-1783.
Meng et al., "Stimuli-responsive polymersomes for programmed drug delivery," Biomacromolecules, ACS Publications, Feb. 2009, 10(2):197-209.
Merkel et al., "Using mechanobiological mimicry of red blood cells to extend circulation times of hydrogel microparticles," Proc Natl Acad Sci U S A, The National Academy of Sciences of the USA, Jan. 2011, 108(2):586-91.
Mero et al., "Transglutaminase-mediated PEGylation of proteins: direct identification of the sites protein medification by mass spectrometry using a novel monodisperse PEG," Bioconjug Chem, Feb. 2009, 20(2):384-389.
Merriam Webster Dictionary, "Plurality," <https://www.merriam-webster.com/dictionary/plurality> webpage accessed Jun. 25, 2020.
Merrick et al., "Seed fixity in the prostate/periprostatic region following brachytherapy," International journal of radiation oncology, biology, physics, 2000, 46, 215-220.
Meyer et al., "Drug targeting using thermally responsive polymers and local hyperthermia," Journal of Controlled Release, 2001, 74, 213-224.
Meyer et al., "Genetically Encoded Synthesis of Protein-Based Polymers with Precisely Specified Molecular Weight and Sequence by Recursive Directional Ligation: Examples from the Elastin-like Polypeptide System," Biomacromolecules, 2002, 3:357-367.
Meyer et al., "Purification of recombinant proteins by fusion with thermally-responsive polypeptide," Nat. Biotechnol., 1999, 17(11):1112-1115.
Meyer et al., "Quantification of the effects of chain length and concentration on the thermal behavior of elastin-like polypeptides," Biomacromolecules, 2004, 5(3):846-51.
Meyer et al., "Targeting a Genetically Engineered Elastin-Like Polypeptide to Solid Tumors by Local Hyperthermia," Cancer Res., 2001, 61(4):1548-1554.
Miao et al., "Sequence and domain arrangements influence mechanical properties of elastin-like polymeric elastomers," Biopolymers, Jun. 2013, 99, 392-407.
Miao et al., "Structural determinants of cross-linking and hydrophobic domains for self-assembly of elastin-like polypeptides," Biochemistry, 2005, 44, 14367-14375.
Michl et al., "Current concepts and novel targets in advanced pancreatic cancer," Gut, Jan. 2013, 62, 317-326.
Micsonai et al. "Accurate secondary structure prediction and fold recognition for circular dichroism spectroscopy," Proc Natl Acad Sci U S A, Jun. 2015, 112, E3095-3103.
Milenic et al., "Antibody-targeted radiation cancer therapy," Nature Reviews Drug Discovery, 2004, 3, 488-498.
Miller et al., "Solubilized, Spaced Polyalanines: A Context-Free System for Determining Amino Acid α-Helix Propensities," Journal of the American Chemical Society, 2002, 124, 945-962.

(56) References Cited

OTHER PUBLICATIONS

Mitragotri et al., "Physical approaches to biomaterial design," J. Nat Mater, Nature Publishing Group, Jan. 2009, 8(1):15-23.
Miyata et al., "Polymeric micelles for nano-scale drug delivery," Reaction & Functional Polymers, Mar. 2011, 71, 227-234.
Mjelle et al., "Cell cycle regulation of human DNA repair and chromatin remodeling genes," DNA Repair, Jun. 2015, 30, 53-67.
Modery et al., "Heteromultivalent liposomal nanoconstructs for enhanced targeting and shear-stable binding to active platelets for site-selective vascular drug delivery," Biomaterials, Elsevier, Dec. 2011, 32(35):9504-9514.
Molliex et al., "Phase separation by low complexity domains promotes stress granule assembly and drives pathological fibrillization," Cell, Sep. 2015, 163(1):123-133.
Moosmann et al., "Alpha complementation of LacZ in mammalian cells," Nucleic Acids Res, 1996, 24(6):1171-1172.
Morgan et al., "The combination of epidermal growth factor receptor inhibitors with gemcitabine and radiation in pancreatic cancer," Clin Cancer Res, Aug. 2008, 14, 5142-5149.
Mosbach et al., "Formation of proinsulin by immobilized Bacillus subtilis," Nature, 1983, 302, 543-545.
Mozhdehi et al., "Genetically Encoded Cholesterol-Modified Polypeptides," Journal of the American Chemical Society, Jan. 2019, 141(2):945-951.
Mozhdehi et al., "Genetically encoded lipid-polypeptide hybrid biomaterials that exhibit temperature-triggered hierarchical self-assembly," Nature chemistry, May 2018, 10(5):496-505.
Mu et al., "FGF21 Analogs of Sustained Action Enabled by Orthogonal Biosynthesis Demonstrate Enhanced Antidiabetic Pharmacology in Rodents," Diabetes, Feb. 2012, 61(2):505-512.
Muiznieks et al., "Modulated growth, stability and interactions of liquid-like coacervate assemblies of elastin," Matrix Biology 36, Jun. 2014, pp. 39-50.
Muiznieks et al., "Proline periodicity modulates the self-assembly properties of elastin-like polypeptides," J Biol Chem, The American Society for Biochemistry and Molecular Biology, Inc, Dec. 2010, 285(51):39779-39789.
Muiznieks et al., "Structural changes and facilitated association of tropoelastin," Archives of Biochemistry and Biophysics, 2003, 410, 317-323.
Muñoz et al., "Elucidating the folding problem of helical peptides using empirical parameters," Nature Structural Biology, 1994, 1, 399-409.
Muñoz et al., "Elucidating the Folding Problem of Helical Peptides using Empirical Parameters. II†. Helix Macrodipole Effects and Rational Modification of the Helical Content of Natural Peptides," Journal of Molecular Biology, 1995, 245, 275-296.
Muñoz et al., "Elucidating the folding problem of helical peptides using empirical parameters. III. Temperature and pH dependence," J Mol Biol, 1995, 245, 297-308.
Muralidharan et al., "Protein Ligation: an Enabling Technology for the Biophysical Analysis of Proteins," Nature Methods, Jun. 2006, vol. 3, No. 6, pp. 429-438.
Muro, "Challenges in design and characterization of ligand-targeted drug delivery systems," J Control Release, Elsevier, Dec. 2012, 164(2):125-37.
Murphy et al., "A dosimetric model of duodenal toxicity after stereotactic body radiotherapy for pancreatic cancer," Int J Radiation Oncology Biol Phys, Dec. 2010, 78, 1420-1426.
Na et al., "Thermoresponsive pore structure of biopolymer microspheres for a smart drug carrier," Langmuir, Jun. 2010, 26, 11165-11169.
Nagarsekar et al., "Genetically Engineered Polymers for Drug Delivery," Journal of Drug Targeting, 1999, 7(1):11-32.
Nahire et al., "Multifunctional Polymersomes for Cytosolic Delivery of Gemcitabine and Doxorubicin to Cancer Cells," Biomaterials, Aug. 2014, 35(24):6482-6497.
Nairn et al., "A Synthetic Resilin Is Largely Unstructured," Biophysical Journal, Oct. 2008, vol. 95 3358-3365.

Nakaoka et al., "Prolongation of the serum half-life period of superoxide dismutase by poly(ethylene glycol) modification," Journal of Controlled Release, 1997, 46(3):253-261.
Nanoprecision Medical, "Pipeline, Type II Diabetes," <http://www.nanoprecisionmedical.com/pipeline/diabetes> webpage available as early as Aug. 2018.
Napier et al., "Nanoparticle drug delivery platform," Journal of Macromolecular Science, Part C: Polymer Reviews, Taylor & Francis Group, LLC, Aug. 2007, 47(3):321-327.
National Institute of Mental Health, "Methods and Welfare Considerations in Behavioral Research with Animals: Report of a National Institutes of Health Workshop," NIH Publication No. 02-54083, Washington, DC: U.S. Government Printing Office. (Mar. 2002).
Nauck "Glucagon-like Peptide 1 (GLP-1) in the Treatment of Diabetes," Horm Metab Res, 2004, 36(11/12):852-858 (in English).
Nayeem et al., "Engineering enzymes for improved catalytic efficiency: a computational study of site mutagenesis in epothilone-B hydroxylase," Protein Eng Des Sel, Oxford Academy, Apr. 2009, 22(4):257-266.
Neidigh et al., "Exendin-4 and glucagon-like-peptide-q: NMR structural comparisons in the solution and micelle-associated states," Biochemistry 40, 2001, 13188-13200.
Nettles et al., "Applications of elastin-like polypeptides in tissue engineering," Adv Drug Deliv Rev, Dec. 2010, 62, 1479-1485.
Nettles et al., "In situ crosslinking elastin-like polypeptide gels for application to articular cartilage repair in a goat osteochondral defect model," Tissue Eng Part A, Jul. 2008, 14, 1133-1140.
Newcomb et al., "Advances in cryogenic transmission electron microscopy for the characterization of dynamic self-assembling nanostructures," Current Opinion in Colloid and Interface Science, Dec. 2012, 17, 350-359.
Newton et al., "Commissioning a small-field biological irradiator using point, 2D, and 3D dosimetry techniques," Medical Physics, Dec. 2011, 38, 6754-6762.
Ni et al., "Engineering of inorganic nanoparticles as magnetic resonance imaging contrast agents," Chem Soc Rev, Nov. 2017, 46(23):7438-7468.
Nichols et al., "Claudin 4 protein expression in primary and metastatic pancreatic cancer," Am J Clin Pathol, 2004, 121, 226-230.
Nicolas et al., "Fluorescently tagged polymer bioconjugates from protein derived macroinitiators," Chem. Commun. Jan. 2007, 45, 4697-4699.
Nie, "Understanding and overcoming major barriers in cancer nanomedicine," Nanomedicine (Lond) Jun. 2010, 5 (4), 523-528.
Nielsen, "Incretin mimetics and DPP-IV inhibitors for the treatment of type 2 diabetes," Drug Discov. Today 10, 2005, 703-710.
Nies et al., "Fibroblast Growth Factor Signaling in Metabolic Regulation," Front Endocrinol, Jan. 2016, 6(193) (in English).
Nilvebrant et al., "The albumin-binding domain as a scaffold for protein engineering," Computational and Structural Biotechnology Journal, Mar. 2013, 6: e201303009, 8 pages.
Niu et al., "The role of adhesion molecules, αvβ3, αvβ5 and their ligands in the tumor cell and endothelial cell adhesion," Eur J Cancer Prev, Wolters Kluwer, Dec. 2007, 16(6):517-27.
Nott et al., "Phase transition of a disordered nuage protein generates environmentally responsive membraneless organelles," Mol Cell, Mar. 2015, 57(5):936-947.
Nucci et al., "The therapeutic value of poly(ethylene glycol)-modified proteins," Adv. Drug Deliv. Rev., 1991, 6(2):133-151.
Nuhn et al., "Secondary structure formation and LCST behavior of short elastin-like peptides," Biomacromolecules, Sep. 2008, 9, 2755-2763.
O'Day et al., "Therapeutic Protein-polymer Conjugates: Advancing beyond PEGylation," J. Am. Chem. Soc., Sep. 2014, vol. 136, pp. 14323-14332.
Ogawara et al., "Pre-coating with serum albumin reduces receptor-mediated hepatic disposition of polystyrene nanosphere: implications for rational design of nanoparticles," Journal of Controlled Release, 2004, 100(3): 451-455.

(56) References Cited

OTHER PUBLICATIONS

Oh et al., "The development of microgels/nanogels for drug delivery applications," Progress in Polymer Science, 2008, 33(4): 448-477.
Olafsen et al., "Covalent disulfide-linked anti-CEA diabody allows site-specific conjugation and radiolabeling for tumor targeting applications," Protein Engineering, Design & Selection, 2004, 17(1):21-27.
Ortega et al., "Hydrodynamic properties of rodlike and dislike particles in dilute solution," The Journal of Chemical Physics, 2003, 119(18):9914-9919.
Ortony et al., "Internal dynamics of a supramolecular nanofibre," Nat. Mater., Aug. 2014, 13, 1-5.
Ozer et al., "Site-Specific and Stoichiometric Stealth Polymer Conjugates of Therapeutic Peptides and Proteins," Bioconjug Chem, Mar. 2017, 28(3):713-723.
Pace et al., "How to measure and predict the molar absorption coefficient of a protein" Protein Science 1995, 4: 2411-2423.
Pagani et al., "International guidelines for management of metastatic breast cancer: can metastatic breast cancer be cured?," Journal of the National Cancer Institute, Apr. 2010, 102, 456-463.
Pak et al., "Sequence Determinants of Intracellular Phase Separation by Complex Coacervation of a Disordered Protein," Mol Cell, Jul. 2016, 63(1):72-85.
Palmerston Mendes et al., "Dendrimers as Nanocarriers for Nucleic Acid and Drug Delivery in Cancer Therapy," Molecules, Aug. 2017, 22(9):1401.
Palta et al., "Interim Acute Toxicity Analysis and Surgical Outcomes of Neoadjuvant Gemcitabine/nab-Paclitaxel and Hypofractionated Image Guided Intensity Modulated Radiation Therapy in Resectable and Borderline Resectable Pancreatic Cancer (ANCHOR) Study," International Journal of Radiation Oncology • Biology • Physics, Oct. 2016, 96, S204-S205.
Palva et al., "Secretion of interferon by Bacillus subtilis," Gene, 1983, 22, 229-235.
Panda et al., "Stop-flow lithography to generate cell-laden microgel particles," Lab Chip, 2008, 8: 1056-1061.
Pang et al., "A Modular Method for the High-Yield Synthesis of Site-Specific Protein-Polymer Therapeutics," Angew Chem Int Ed Engl, Jul. 2016, 55, 10296-10300.
Paolino et al., "Folate-targeted supramolecular vesicular aggregates as a new frontier for effective anticancer treatment in in vivo model," Eur. J. Pharm. Biopharm., Jun. 2012, 82(1):94-102.
Paolino et al., "Gemcitabine-loaded PEGylated unilamellar liposomes vs Gemzar: biodistribution, pharmacokinetic features and in vivo antitumor activity," J. Control. Release Jun. 2010, 144(2):144-150.
Paoloni et al., "Translation of new cancer treatments from pet dogs to humans," Nat. Rev. Cancer Feb. 2008, 8 (2), 147-156.
Papa et al., "PEGylated Liposomal Gemcitabine: Insights Into a Potential Breast Cancer Therapeutic," Cell Oncol. (Dordr), Oct. 2013, 36(6):449-457.
Paramonov et al., "Self-assembly of peptide-amphiphile nanofibers: The roles of hydrogen bonding and amphiphilic packing," J. Am. Chem. Soc., May 2006, 128, 7291-7298.
Pardridge, "The blood-brain barrier: bottleneck in brain drug development," NeuroRx, 2005, 2(1):3-14.
Park et al., "Exendin-4 and exercise improve hepatic glucose homeostasis by promoting insulin signaling in diabetic rats," Metabolism, Jan. 2010, 59, 123-133.
Park et al., "Formulation optimization and in vivo proof-of-concept study of thermosensitive liposomes balanced by phospholipid, elastin-like polypeptide, and cholesterol," PLoS One, Jul. 2014, 9: e103116, 13 pages.
Park et al., "Protein stitchery: Design of a protein for selective binding to a specific DNA sequence," PNAS, 1992, vol. 89:9094-9096.
Parker et al., "Antibody mimics based on human fibronectin type three domain engineered for thermostability and high-affinity binding to vascular endothelial growth factor receptor two," Protein Eng Des Sel, 2005, 18(9):435-44.

Parkes et al. "Discovery and development of exenatide: the first antidiabetic agent to leverage the multiple benefits of the incretin hormone, GLP-1," Expert Opinion. Drug Deliv., Feb. 2013, 8(2):219-244.
Parveen et al., "Nanomedicine," Clinical Pharmacokinetics, Oct. 2006, 45(10):965-988.
Pastuszka et al., "A tunable and reversible platform for the intracellular formation of genetically engineered protein microdomains," Biomacromolecules, ACS Publications, Oct. 2012, 13(11):3439-3444.
Patil et al., "Cellular delivery of doxorubicin via pH-controlled hydrazone linkage using multifunctional nano vehicle based on poly(beta-l-malic acid)," Int J Mol Sci, Sep. 2012, 13, 11681-11693.
Paulsen et al., "Optofluidic fabrication for 3D-shaped particles," Nat Commun, 2015, 6: 6976.
Peeler et al., "Genetically encoded initiator for polymer growth from proteins," J. Am. Chem. Soc. 132, Oct. 2010, 13575-13577.
Peng et al., "Length-dependent prediction of protein intrinsic disorder," BMC Bioinformatics, Springer Nature, Apr. 2006, 7:208.
Peters, "Serum albumin," Adv. Protein Chem. 37, 1985, 161-245.
Petitdemange et al., "Tuning Thermoresponsive Properties of Cationic Elastin-like Polypeptides by Varying Counterions and Side-Chains," Bioconjug. Chem., May 2017, 28(5):1403-1412.
Petros et al., "Strategies in the design of nanoparticles for therapeutic applications," Nat Rev Drug Discov, Nature Research, Aug. 2010, 9(8):615-27.
Phan et al., "Temperature-responsive self-assembly of charged and uncharged hydroxyethylcellulose-graft-poly(N-isopropylacrylamide) copolymer in aqueous solution," Colloid Polym. Sci., Apr. 2011, 289 (9), 993-1003.
Pinkas et al., "Tunable, post-translational hydroxylation of collagen domains in *Escherichia coli*," ACS Chem. Biol., Apr. 2011, 6(4):320-324.
Pliarchopoulou et al., "Pancreatic cancer: Current and future treatment strategies," Cancer Treatment Reviews, Aug. 2009, 35, 431-436.
Poitout et al., "Glucolipotoxicity: Fuel Excess and β-Cell Dysfunction," Endocr Rev, May 2008, 29(3):351-366.
Pometun et al., "Quantitative observation of backbone disorder in native elastin," J Biol Chem, 2004, 279, 7982-7987.
Popp et al., "Site-specific labeling via sortase-mediated transpeptidation," Curr. Protoc. Protein Sci. 56, Apr. 2009, 15.13.1-15.13.9.
Popp et al., "Sortase-Catalyzed Transformations That Improve The Properties Of Cytokines," PNAS, Feb. 2011, vol. 108, No. 8, pp. 3169-3174.
Potters et al., "12-year outcomes following permanent prostate brachytherapy in patients with clinically localized prostate cancer," The Journal of urology, 2005, 173, 1562-1566.
Potters et al., "Monotherapy for stage T1-T2 prostate cancer: radical prostatectomy, external beam radiotherapy, or permanent seed implantation," Radiotherapy and oncology: journal of the European Society for Therapeutic Radiology and Oncology, 2004, 71, 29-33.
Potters et al., "Potency after permanent prostate brachytherapy for localized prostate cancer," International journal of radiation oncology, biology, physics, 2001, 50(5): 1235-1242.
Potthoff et al., "Endocrine fibroblast growth factors 15/19 and 21: from feast to famine," Genes Dev, Feb. 2012, 26(4):312-324.
Prestwich et al., "Beta dose point kernels for radionuclides of potential use in radioimmunotherapy," J Nucl Med, 1989, 30, 1036-1046.
Privratsky et al., "PECAM-1: regulatorof endothelial junctional integrity," Cell Tissue Res, Mar. 2014, 355, 607-619.
Prostate Seed Center, "Brachytherapy seed pre-plan rendering," <http://www.prostateseedcenter.com/dynamics-of-brachytherapy> webpage available as early as Aug. 30, 2012.
Provenzano et al., "Enzymatic targeting of the stroma ablates physical barriers to treatment of pancreatic ductal adenocarcinoma," Cancer cell, Mar. 2012, 21, 418-429.
Provenzano et al., "Hyaluronan, fluid pressure, and stromal resistance in pancreas cancer," Br J Cancer, Jan. 2013, 108, 1-8.
Pulaski et al., "Mouse 4T1 breast tumor model," Curr. Protoc. Immunol., 2001, Chapter 20, Unit 20.2.

(56) References Cited

OTHER PUBLICATIONS

Qamar et al., "FUS Phase Separation Is Modulated by a Molecular Chaperone and Methylation of Arginine Cation-pi Interactions," Cell, Apr. 2018, 173(3):720-734.e15.
Qi et al., "A brush-polymer conjugate of exendin-4 reduces blood glucose for up to five days and eliminates poly(ethylene glycol) antigenicity," Nat Biomed Eng, Nov. 2016, 1:0002.
Qi et al., Dataset for A brush-polymer conjugate of exendin-4 reduces blood glucose for up to five days and eliminates poly(ethylene glycol) antigenicity. Figshare, Nov. 2016, <http://dx.doi.org/10.6084/m9.figshare.3976761>.
Qi et al., "Growing polymers from peptides and proteins: a biomedical perspective," Polym. Chem., Jan. 2014, 5(2):266-276.
Qi et al., "Protein-polymer conjugation—moving beyond PEGylation," Curr. Opin. Chem. Biol. Oct. 28, 2015, 181-193.
Qi et al., "Sortase-catalyzed initiator attachment enables high yield growth of a stealth polymer from the C terminus of a protein," Macromol. Rapid Commun., Aug. 2013, 34(15):1256-1260.
Qiu et al., "Development of Orthotopic Pancreatic Tumor Mouse Models," Methods Mol Biol, Jan. 2013, 980: 215-223.
Qiu et al., "Polymer Architecture and Drug Delivery," Pharmaceutical Research, Feb. 2006, 23(1):1-30.
Quarmby et al., "Irradiation induces upregulation of CD31 in human endothelial cells," Arterioscler Thromb Vasc Biol, 1999, 19, 588-597.
Quarmby et al., "Radiation-induced normal tissue injury: role of adhesion molecules in leukocyte-endothelial cell interactions," Int J Cancer, 1999, 82, 385-395.
Quiroz et al., "Intrinsically disordered proteins access a range of hysteretic phase separation behaviors," Scientific advances, Oct. 2019, 5(10):eaax5177.
Quiroz et al., "Sequence heuristics to encode phase behaviour in intrinsically disordered protein polymers," Nat. Mater., Nov. 2015, 14(11):1164-1171.
Rabotyagova et al., "Protein-based block copolymers," Biomacromolecules, Feb. 2011, 12(2): 269-289.
Radivojac et al., "Intrinsic Disorder and Functional Proteomics," Biophysical Journal, Mar. 2007, vol. 92, Issue 5, pp. 1439-1456.
Ragupathi et al., "Abstract A73: Antitumor activity of MVT-5873, a monoclonal antibody targeting sialyl Lewisa, alone and in combination with gemcitabine/nab-paclitaxel in a BxPC3 human pancreatic cancer xenograft model," Cancer Research, Dec. 2016, 76.
Rankine et al., "Investigating end-to-end accuracy of image guided radiation treatment delivery using a micro-irradiator," Physics in Medicine and Biology, Nov. 2013, 58(21): 7791-7801.
Rao et al., "Synthetic nanoparticles camouflaged with biometric erythrocyte membranes for reduced reticuloendothelial system uptake," Nanotechnology, Jan. 2016, 27 (8), 85106, 9 pages.
Rapaka et al., "Coacervation of Sequential Polypeptide Models of Tropoelastin," Int J Peptide Protein Res, 1978, 11: 97-108.
Ratner et al., "Radiation-grafted hydrogels for biomaterial applications as studied by the ESCA technique," Journal of Applied Polymer Science, 1978, 22, 643-664.
Ratner, "A pore way to heal and regenerate: 21st century thinking on biocompatibility," Regen Biomater, Feb. 2016, 3(2):107-110.
Rauscher et al. "Proline and Glycine Control Protein Self-Organization into Elastomeric or Amyloid Fibrils," Structure, Nov. 2006, 14(11):1667-1676.
Ravikumar et al., "Mimicking adhesive functionalities of blood platelets using ligand-decorated liposomes," Bioconjugate chemistry, ACS Publications, May 2012, 23(6):1266-1275.
Ray et al., "Aptamer-mediated delivery of chemotherapy to pancreatic cancer cells." Nucleic acid therapeutics, Oct. 2012, 22(5): 295-305.
Regier et al., American Heart Association 2014 Scientific Sessions, May 2015, vol. 7, pp. 299-303.
Reguera et al., "Thermal Behavior and Kinetic Analysis of the Chain Unfolding and Refolding and of the Concomitant Nonpolar Solvation and Desolvation of Two Elastin-like Polymers," Macromolecules, 2003, 36, 8470-8476.
Ren et al., "Mesenchymal stem cell-mediated immunosuppression occurs via concerted action of chemokines and nitric oxide," Cell Stem Cell, Feb. 2008, 2(2): p. 141-150.
Resh, "Covalent Lipid Modifications of Proteins," Curr Biol., May 2013, 23(10): R431-R435.
Ribeiro et al., "Influence of the amino-acid sequence on the inverse temperature transition of elastin-like polypeptides," Biophysical Journal, Jul. 2009, 97(1):312-320.
Richards et al., "Engineered fibronectin type III domain with a RGDWE sequence binds with enhanced affinity and specificity to human $\alpha v\beta 3$ integrin," J Mol Biol, 2003, 326(5):1475-1488.
Richards et al., "Man's best friend: what can pet dogs teach us about non-Hodgkin lymphoma?" Inmunol Rev., Jan. 2015, 263 (1): 173-191.
Riddles et al., "Ellman's reagent: 5,5'-dithiobis(2-nitrobenzoic acid)—a reexamination," Anal Biochem. 1979, 94(1):75-81.
Riedel et al., "Engineered glucagon-like peptide-1-producing hepatocytes lower plasma glucose levels in mice," Am J Physiol Endocrinol Metab, Apr. 2009, 296(4):E936-E944.
Rincon et al., "Biocompatibility of elastin-like polymer poly(VPAVG) microparticles: in vitro and in vivo studies," Journal of Biomedical Materials Research, 2005, 78A, 343-351.
Rios-Doria et al., "Doxil synergizes with cancer immunotherapies to enhance antitumor responses in syngeneic mouse models," Neoplasia, Aug. 2015, 17(8):661-670.
Ritcher et al., "Antibodies against polyethylene glycol produced in animals by immunization with monomethoxy polyethylene glycol modified proteins," Int. Arch. Allergy Appl. Immunol. 70, 1983, 124-131.
Ritcher et al., "Polyethylene glycol reactive antibodies in man: titer distribution in allergic patients treated with monomethoxy polyethylene glycol modified allergens or placebo, and in healthy blood donors," Int. Arch. Allergy Appl. Immunol. 74, 1984, 36-39.
Rivory et al., "Effects of lipophilicity and protein binding on the hepatocellular uptake and hepatic disposition of two anthracyclines, doxorubicin and iododoxorubicin," Cancer Chemother Pharmacol, 1996, 38(5):439-445.
Roberts et al., "Elastin-like polypeptides as models of intrinsically disordered proteins," FEBS Lett., Sep. 2015, 589, 2477-2486.
Roberts et al., "Injectable tissue integrating networks from recombinant polypeptides with tunable order," Nature Materials, 2018, 17(12): 1154-1163.
Robinet et al. "Elastin-derived peptides enhance angiogenesis by promoting endothelial cell migration and tubulogenesis through upregulation of MT1-MMP," J. Cell Science, 2005, 118:343-356.
Rodriguez-Cabello et al., "Elastin-like polypeptides in drug delivery," Adv Drug Deliv Rev, 2016, 97: 85-100.
Rodriguez-Diaz et al., "Alpha cells secrete acetylcholine as a non-neuronal paracrine signal priming beta cell function in humans," Nat Med, Jun. 2011, 17:888-892.
Rolland et al., "Direct fabrication and harvesting of monodisperse, shape-specific nanobiomaterials," J Am Chem Soc, 2005, 127(28):10096-100.
Römer et al., "The elaborate structure of spider silk: structure and function of a natural high performance fiber," Prion, Nov. 2008, 2(4):154-161.
Roopenian et al., "FcRn: the neonatal Fc receptor comes of age," Nat. Rev. Immunol., Sep. 2007, vol. 7, No. 9, 715-725.
Rosenberg et al., "Present and future innovations in radiation oncology," Surg Oncol Clin N Am, Jul. 2013, 22(3):599-618.
Rosenholm et al., "Towards multifunctional, targeted drug delivery systems using mesoporous silica nanoparticles—opportunities & challenges," Nanoscale, Royal Society of Chemistry, Oct. 2010, 2(10):1870-83.
Rösler et al., "Advanced drug delivery devices via self-assembly of amphiphilic block copolymers," Advanced Drug Delivery Reviews, 2001, 53:95-108.
Rozak et al., "G148-GA3: a streptococcal virulence module with atypical thermodynamics of folding optimally binds human serum albumin at physiological temperatures," Biochim Biophys Acta, 2005, 1753(2): p. 226-33.
Ruiz van Haperen et al., "Regulation of phosphorylation of deoxycytidine and 2',2'-difluorodeoxycytidine (gemcitabine); effects

(56) References Cited

OTHER PUBLICATIONS of cytidine 5'-triphosphate and uridine 5'-triphosphate in relation to chemosensitivity for 2',2'-difluorodeoxycytidine," Biochem. Pharmacol. 1996, 51(7):911-908.
Russo et al., "The role of neoadjuvant therapy in pancreatic cancer: a review," Future Oncol, Mar. 2016, 12(5):669-685.
Ryerson et al., "Annual report to the nation on the status of cancer, 1975-2012, featuring the Increasing incidence of liver cancer," Cancer, May 2016, 122(9): 1312-1337.
Ryu et al., "Elastin-like polypeptide for improved drug delivery for anticancer therapy: preclinical studies and future applications," Expert Opinion on Drug Delivery, Informa Healthcare, Oct. 2014, 12(4):653-667.
Saba et al., "A Comparative Oncology Study of Iniparib Defines Its Pharmacokinetic Profile and Biological Activity in a Naturally-Occurring Canine Cancer Model," PLoS One, Feb. 2016, 11(2): 1-11.
Safran et al., "Gemcitabine, paclitaxel, and radiation for locally advanced pancreatic cancer: A phase I trial," Int J Radiation Oncology Biol Phys, 2002, 54, 137-141.
Sagle et al., "Investigating the hydrogen-bonding model of urea denaturation," J Am Chem Soc, Jun. 2009, 131(26): 9304-9310.
Saifer et al., "Selectivity of binding of PEGs and PEG-like oligomers to anti-PEG antibodies induced by methoxyPEG-proteins," Molecular Immunology, Feb. 2014, 57(2):236-246.
Sandler et al., "Gemcitabine: Single-Agent and Combination Therapy in Non-Small Cell Lung Cancer," Oncologist 1999, 4(3)241-251.
Sanna et al., "Targeted therapy using nanotechnology: focus on cancer," Int J Nanomedicine, Jan. 2014, 9:467-83.
Schaal et al., "Biopolymer β-brachytherapy delivered with concomitant paclitaxel outperforms traditional x-ray radiation to include complete regression in multiple pancreatic tumor xenograft models through synergistic modulation of the tumor microenvironment," Poster #5831, 2018.
Schaal et al., "Injectable polypeptide micelles that form radiation crosslinked hydrogels in situ for intratumoral radiotherapy," Journal of Controlled Release, Apr. 2016, 228, 58-66.
Schellenberg et al., "Gemcitabine chemotherapy and single-fraction stereotactic body radiotherapy for locally advanced pancreatic cancer," Int J Radiation Oncol Biol Phys,Nov. 2008, 72(3): 678-686.
Schellenberg et al., "Single-fraction stereotactic body radiation therapy and sequential gemcitabine for the treatment of locally advanced pancreatic cancer," Int J Radiation Oncology Biol Phys, Sep. 2011, 81(1): 181-188.
Schellenberger et al., "A recombinant polypeptide extends the in vivo half-life of peptides and proteins in a tunable manner," Nat. Biotechnol., Dec. 2009, 27(12):1186-1188.
Schlaff et al., "Bringing the heavy: carbon ion therapy in the radiobiological clinical context," Radiation Oncology, Mar. 2014, 9, Article 88, 1-18.
Schneider et al., "NIH Image to ImageJ: 25 years of image analysis," Nature Methods, Jul. 2012, 9(7): 671-675.
Schnell et al., "Expression of integrin αvβ3 in gliomas correlates with tumor grade and is not restricted to tumor vasculature," Brain Pathol, International Society of Neuropathology, Aug. 2008, 18(3):378-86.
Schwendeman et al., "Injectable controlled release depots for large molecules," J Control Release, Sep. 2014, 190, 240-253.
Senin et al., "N-Myristoylation of recoverin enhances its efficiency as an inhibitor of rhodopsin kinase," Febs. Lett., 1995, 376, 87-90.
Senior et al., "Val-Gly-Val-Ala-Pro-Gly, a Repeating Peptide in Elastin, Is Chemotactic for Fibroblasts and Monocytes," The Journal of Cell Biology, 1984, 99: 870-874.
Serrano et al., "An infrared spectroscopic study of the conformational transition of elastin-like polypeptides," Biophys. J., Oct. 2007, 93(7):2429-2435.
Shadwick, "Mechanical design in arteries," J Exp Biol, 1999, 202, 3305-3313.

Shang et al., "pH-Dependent Protein Conformational Changes in Albumin:Gold Nanoparticle Bioconjugates: A Spectroscopic Study," Langmuir, Feb. 2007, 23 (5), 2714-2721.
Shao et al., "Super-resolution 3D microscopy of live whole cells using structured illumination," Nat Methods, Oct. 2011, 8(12): 1044-1046.
Sharma et al., "Dendrimer nanoarchitectures for cancer diagnosis and anticancer drug delivery," Drug Discov Today, Feb. 2017, 22(2):314-326.
Sharma et al., "PLGA-based nanoparticles: A new paradigm in biomedical applications," TrAC Trends in Analytical Chemistry, Jun. 2016, 80:30-40.
Sharma et al., "Polymer particle shape independently influences binding and internalization by macrophages," Journal of Controlled Release, Elsevier, Nov. 2010, 147(3):408-412.
Shen et al., "Conjugation site modulates the in vivo stability and thearpeutic activity of antibody-drug conjugates," Nat Biotechnol, Jan. 2012, 30(2):184-189.
Sheparovych et al., "Stimuli-Responsive Properties of Peptide-Based Copolymers Studied via Directional Growth of Self-Assembled Patterns on Solid Substrate," Biomacromolecules, Jul. 2009, 10:1955-1961.
Sherman et al., "Next-Generation PEGylation Enables Reduced Immunoreactivity of PEG-Protein Conjugates," Drug and Development & Delivery, Jun. 2012, vol. 12, No. 5, 36-42.
Sherman et al., "Role of the Methoxy Group in Immune Responses to mPEG-Protein Conjugates," Bioconjugate Chemistry, Mar. 2012, 23(3): 485-499.
Shi et al., "Cell adhesion on a POEGMA-modified topographical surface," Langmuir: the ACS journal of surfaces and colloids, Dec. 2012, 28 (49), 17011-8.
Shi et al., "Triggered sorting and co-assembly of genetically engineered protein microdomains in the cytoplasm," Adv Mater, Wiley, Jan. 2014, 26(3):449-454.
Shimoboji et al., "Temperature-Induced Switching of Enzyme Activity with Smart Polymer-Enzyme Conjugates," Bioconjugate Chem. 2003, 14, 517-525.
Shin et al., "Liquid phase condensation in cell physiology and disease," Science, Sep. 2017, 357(6357):eaaf4382.
Shusharina et al., "Micelles of Diblock Copolymers with Charged and Neutral Blocks: Scaling and Mean-Field Lattice Approaches," Macromolecules, 2000, 33(10): 3892-3901.
Sickmeier et al., "DisProt: the Database of Disordered Proteins," Nucleic Acids Res, Oxford Academy, Jan. 2007, 35:D786-793.
Siegel et al., "Absorbed fractions for electrons and beta particles in spheres of various sizes," J Nucl Med, 1994, 35, 152-156.
Siegwart et al., "ATRP In The Design Of Functional Materials For Biomedical Applications," Prog Polymer Science, Jan. 2012, vol. 37, No. 1, pp. 18-37.
Silberstein et al., "The SNM Practice Guideline for Therapy of Thyroid Disease with $^{131}$I, 3.0," J Nucl Med, Jul. 2012, 53, 1-19.
Silva et al., "Selective differentiation of neural progenitor cells by high-epitope density nanofibers," Science, 2004, 303, 1352-5.
Simakova et al., "Aqueous ARGET ATRP," Macromolecules, Aug. 2012, 45(16):6371-6379.
Simnick et al., "In vivo tumor targeting by a NGR-decorated micelle of a recombinant diblock copolypeptide," J Control Release, Oct. 2011, 155(2): 144-151.
Simnick et al., "Morphing low-affinity ligands into high-avidity nanoparticles by thermally triggered self-assembly of a genetically encoded polymer," ACS Nano, Apr. 2010, 4(4):2217-2227.
Simon et al., "Engineered Ribonucleoprotein Granules Inhibit Translation in Protocells," Molecular cell, Jul. 2019, 75(1):66-75.
Simon et al., "Programming molecular self-assembly of intrinsically disordered proteins containing sequences of low complexity," Nat Chem, Jun. 2017, 9(6):509-515.
Singhal et al., "Fibroblast Growth Factor 21 (FGF21) Protects against High Fat Diet Induced Inflammation and Islet Hyperplasia in Pancreas," PLoS One, Feb. 2016, 11(2):e0148252.
Sisson et al., "Radiation safety in the treatment of patients with thyroid diseases by radioiodine 131I: practice recommendations of the American Thyroid Association," Thyroid, Apr. 2011, 21(4):335-346.

(56) References Cited

OTHER PUBLICATIONS

Skerra, "Alternative non-antibody scaffolds for molecular recognition," Curr Opin Biotechnol, Elsevier, Aug. 2007, 18(4):295-304.
Smith et al., "The Role of Beta Cell Glucagon-like Peptide-1 Signaling in Glucose Regulation and Response to Diabetes Drugs," Cell Metab, Jun. 2014, 19(6):1050-1057.
Smits et al., "Elastin-Like Polypeptide Based Nanoparticled: Design Rationale Toward Nanomedicine," Macromolecular Bioscience, Macromolecular Journals, Jan. 2015, 15(1):36-51.
Sonawane et al., "Hydrazo linkages in pH responsive drug delivery systems," European Journal Pharmaceutical Sciences, Mar. 2017, 99, 45-65.
Song et al., "Budding-like division of all-aqueous emulsion droplets modulated by networks of protein nanofibrils," Nat Commun, 2018, 9: 2110.
Sorkin et al., "Signal transduction and endocytosis: close encounters of many kinds," Nat Rev Mol Cell Biol, 2002, 3(8):600-614.
Sousa et al., "Production of a polar fish antimicrobial peptide in *Escherichia coli* using an ELP-intein tag," J Biotechnol, Sep. 2016, 234:83-89.
Srinivas et al., "Aptamer-functionalized microgel particles for protein detection," Anal Chem, 2011, 83: 9138-9145.
Sriraman et al., "Barriers to drug delivery in solid tumors," Tissue Barriers, Jul. 2014, 2(3): 2-10.
Stanislaus et al., "A Novel Fc-FGF21 With Improved Resistance to Proteolysis, Increased Affinity Toward β-Klotho, and Enhanced Efficacy in Mice and Cynomolgus Monkeys," Endocrinology, May 2017, 158(5):1314-1327.
Stefl et al., "RNA sequence-and shape-dependent recognition by proteins in the ribonucleoprotein particle" EMBO reports (2005) 6(1):33-38.
Steichen et al., "A Review of Current Nanoparticle and Targeting Moieties for the Delivery of Cancer Therapeutics," Eur J Pharm Sci, Elsevier, Feb. 2013, 48(3):416-27.
Stock et al., "Penile erectile function after permanent raioactive seed implantation for treatment of prostate cancer," The Journal of urology, 2001, 165, 436-439.
Stork et al., "A novel tri-functional antibody fusion protein with improved pharmacokinetic properties generated by fusing a bispecific single-chain diabody with an albumin-binding domain from streptococcal protein G," Protein Engineering Design and Selection, Nov. 2007, 20(11): p. 569-576.
Strohmaier et al., "Comparison of $^{60}$Co and $^{192}$Ir sources in HDR brachytherapy," J Contemp Brachyther, Dec. 2011, 3(4): 199-208.
Strulson et al., "RNA catalysis through compartmentalization," Nat Chem, Nature Publishing Group, Nov. 2012, 4(11):941-946.
Stutz et al., "Seed loss through the urinary tract after prostate brachytherapy: examining the role of cystoscopy and urine straining post implant," Medical physics, 2003, 30, 2695-2698.
Sugyo et al., "Evaluation of efficacy of radioimmunotherapy with 90Y-labeled fully human anti-transferring receptor monoclonal antibody in pancreatic cancer mouse models," PLoS One, Apr. 2015, 10, 1-17.
Suk et al., "PEGylation as a Strategy for Improving Nanoparticle-Based Drug and Gene Delivery," Adv Drug Deliv Rev, Apr. 2016, 99(Pt A):28-51.
Sumerlin, "Proteins as Initiators of Controlled Radical Polymerization: Grafting-from via ATRP and RAFT," ACS Macro Lett. Jan. 2012, 1(1): 141-145.
Sun et al., "Autofluorescence Imaging of Living Pancreatic Islets Reveals Fibroblast Growth Factor-21 (FGF21)-Induced Metabolism," Biophys J, Dec. 2012, 103(11):2379-2388.
Sun et al., "Contributions of the extracellular and cytoplasmic domains of platelet-endothelial cell adhesion molecule-1 (PECAM-1/CD31) in regulating cell-cell localization," J. Cell Sci., 2000, 113, 1459-1469.
Sun et al., "Efficacy and safety of the hypoxia-activated prodrug TH-302 in combination with gemcitabine and nab-paclitaxel in human tumor xenograft models of pancreatic cancer," Cancer Biology & Therapy, Feb. 2015, 16(3): 438-449.
Sun et al., "EUS-guided interstitial brachytherapy of the pancreas: a feasibility study," Gastrointestinal Endoscopy, 2005, 62, 775-779.
Sun et al., "On the Thermally Reversible Dynamic Hydration Behavior of Oligo(ethylene glycol) Methacrylate-Based Polymers in Water," Macromolecules, Jan. 2013, 46(1): 236-246.
Sunamura et al., "Gene Therapy for Pancreatic Cancer Targeting the Genomic Alterations of Tumor Suppressor Genes using Replication-selective Oncolytic Adenovirus," Human Cell, 2002, 15, 138-150.
Surwit et al., Diet-induced type II diabetes in C57BL/6J mice, Diabetes 37, 1988, 1163-1167.
Sussman et al., "Porous implants modulate healing and induce shifts in local macrophage polarization in the foreign body reaction," Ann Biomed Eng, Jul. 2014, 42(7): 1508-1516.
Swee et al., "Sortase-mediated modification of αDEC205 affords optimization of antigen presentation and immunization against a set of viral epitopes," Proc Natl Acad Sci USA, Jan. 2013, 110(4):1428-1433.
Swers et al., Multivalent Scaffold Proteins as Superagonists of TRAIL Receptor 2-Induced Apoptosis, Mol Cancer Ther, Jul. 2013, 12(7): 1235-1244.
Swider et al., "Customizing Poly(lactic-Co-Glycolic Acid) Particles for Biomedical Applications," Acta Biomater, Jun. 2018, 73:38-51.
Takalkar et al., "Radium-223 dichloride bone-targeted alpha particle therapy for hormone-refractory breast cancer metastatic to bone," Exp Hematol Oncol, Sep. 2014, 8, Article No. 23.
Talelli et al., "Core-Crosslinked Polymeric Micelles: Principles, Preparation, Biomedical Applications and Clinical Translation," Nano Today, Feb. 2015, 10(1):93-117.
Tallarida, "Quantitative methods for assessing drug synergism," Genes & Cancer, Nov. 2011, 2(11): 1003-1008.
Talukdar et al., "A Long-Acting FGF21 Molecule, PF-05231023, Decreases Body Weight and Improves Lipid Profile in Non-human Primates and Type 2 Diabetic Subjects," Cell Metab, Mar. 2016, 23(3):427-440.
Tamburro et al., "Dissection of human tropoelastin: exon-by-exon chemical synthesis and related conformational studies," Biochemistry, 2003, 42, 13347-13362.
Tamburro et al., "Localizing alpha-helices in human tropoelastin: assembly of the elastin "puzzle"," Biochemistry, Aug. 2006, 45(31): 9518-9530.
Tan et al., "Characterization of a new primary human pancreatic tumor line," Cancer investigation, 1986, 4, 15-23.
Tang et al., "Combinatorial codon scrambling enables scalable gene synthesis and amplification of repetitive proteins," Nature Mater., Apr. 2016, 15(4): 419-424.
Tang et al., "Enzymatic Polymerization of High Molecular Weight DNA Amphiphiles That Self-Assemble into Star-Like Micelles," Advanced Materials, Feb. 2014, 26(19): 3050-3054.
Tang et al., "High-Molecular-Weight Polynucleotides by Transferase-Catalyzed Living Chain-Growth Polycondensation," Angew. Chem., Jun. 2017, 56(24): 6778-6782.
Tang et al., "Identification of PECAM-1 in solid tumor cells and its potential involvement in tumor cell adhesion to endothelium," J. Biol. Chem., 1993, 268, 22883-22894.
Tantakitti et al., "Energy landscapes and functions of supramolecular systems," Nat. Mater., Apr. 2016, 15(4): 469-476.
Tedja et al., "Effect of TiO2 nanoparticle surface functionalization on protein adsorption, cellular uptake and cytotoxicity: the attachment of PEG comb polymers using catalytic chain transfer and thiol-ene chemistry," Polymer Chemistry, Oct. 2012, 3 (10), 2743-2751.
Teicher, "In vivo/ex vivo and in situ assays used in cancer research: a brief review," Toxicol. Pathol., Jan. 2009, 37 (1), 114-122.
Thakor et al., "Clinically Approved Nanoparticle Imaging Agents," J Nucl Med, Oct. 2016, 57(12):1833-1837.
Theillet et al., "The alphabet of intrinsic disorder: I. Act like a Pro: On the abundance and roles of proline residues in intrinsically disordered proteins," Intrinsically Disord Proteins, Taylor & Francis, Apr. 2013, 1(1):e24360.
Therasse et al., "New guidelines to evaluate the response to treatment in solid tumors," J Natl Cancer Inst, 2000, 92, 205-216.

(56) References Cited

OTHER PUBLICATIONS

Thorens et al., "Cloning and functional expression of the human islet GLP-1 receptor: demonstration that Exendin-4 Is an agonist and Exendin-(9-39) an antagonist of the receptor," Diabetes 42, 1993, 1678-1682.
Tomiyama et al., "Relevant use of Klotho in FGF19 subfamily signaling system in vivo," Proc Natl Acad Sci USA, Jan. 2010, 107(4):1666-71.
Tompa et al., "Fuzzy complexes: polymorphism and structural disorder in protein-protein interactions," Trends Biochem Sci, Jan. 2008, 33(1): 2-8.
Tong et al., "Protein Modification with Amphiphilic Block Copoly(2-oxazoline)s as a New Platform for Enhanced Cellular Delivery," Mol. Pharm., Aug. 2010, vol. 7, No. 4, pp. 984-992.
Ton-That et al., "Assembly of pili on the surface of Corynebacterium diptheriae," 2003, 50(4):1429-1438.
Ton-That et al., "Purification and characterization of sortase, the transpeptide that cleaves surface proteins of Staphylococcus aureus and the LPXTG motif," Proc Natl Acad Sci USA, 1999, 96(22):12424-12429.
Torchilin, "Recent advances with liposomes as pharmaceutical carriers," Nature Rev. Drug Discov. 2005, 4(2):145-160.
Towler et al., "Purification and Characterization of Yeast Myristoyl-Coa—Protein N-Myristoyltransferase," P Natl Acad Sci USA, 1987, 84(9):2708-12.
Trabbic-Carlson et al., "Effect of protein fusion on the transition temperature of an environmentally responsive elastin-like polypeptide: a role for surface hydrophobicity?," Protein Engineering Design and Selection, 2004, 17(1): 57-66.
Trabbic-Carlson et al., "Expression and purification of recombinant proteins from Escherichia coli: Comparison of an elastin-like polypeptide fusion with an oligohistidine fusion" Protein Science, 2004, 13: 3274-3284.
Trakul et al., "Stereotactic body radiotherapy in the treatment of pancreatic cancer," Semin Radiat Oncol, Apr. 2014, 24(2): 140-147.
Trieu et al., "P0157 Preclinical evaluation of NBN-paclitaxel in pancreatic cancer xenograft models," Eur J Cancer, May 2014, 50(4): e53.
Triola et al., "Chemical biology of lipidated proteins," ACS Chemical Biology, Jan. 2012, 7(1): 87-99.
Troyanskaya et al., "Nonparametric methods for identifying differentially expressed genes in microarray data," Bioinformatics, 2002, 18(11):1454-61.
Truong et al., "Polymeric filomicelles and nanoworms: two decades of synthesis and application," Polymer Chemistry, Jun. 2016, 7(26):4295-4312.
Truong et al., "The Importance of Nanoparticle Shape in Cancer Drug Delivery," Expert Opin Drug Deliv, Jan. 2015, 12(1):129-42.
Truong, et al., "The effect of hydration on molecular chain mobility and the viscoelastic behavior of resilin-mimetic protein-based hydrogels," Biomaterials, Elsevier, Nov. 2011, 32(33):8462-73.
Tsarevsky et al., "Deactivation efficiency and degree of control over polymerization in ATRP in protic solvents," Macromolecules 37, 2004, 9768-9778.
Tschöp et al., "Unimolecular Polypharmacy for Treatment of Diabetes and Obesity," Cell Metab, Jul. 2016, 24(1):51-62.
Tsuda et al., "Monodisperse cell-encapsulating peptide microgel beads for 3D cell culture," Langmuir, 2010, 26: 2645-2649.
Tsume et al., "The development of orally administrate gemcitabine prodrugs with D-enantiomer amino acids: Enhanced membrane permeability and enzymatic stability," Eur. J. Pharm. Biopharm., Apr. 2014, 86(3):514-523.
Tu et al., "Stages in tropoelastin coalescence during synthetic elastin hydrogel formation," Micron, Apr. 2010, 41(3): 268-272.
Turunen et al., "Paclitaxel Succinate Analogs: Anionic Introduction as a Strategy to Impart Blood Brain Barrier Permeability," Bioorg Med Chem Lett, Nov. 2008, 18(22):5971-5974.
Tward et al., "Survival of men with clinically localized prostate cancer treated with prostatectomy, brachytherapy, or no definitive treatment: impact of age at diagnosis," Cancer, Oct. 2006, 107(10): 2392-2400.
Uchida et al., "Potential of adenovirus-mediated REIC/Dkk-3 gene therapy for use in the treatment of pancreatic cancer," Journal of Gastroenterology and Hepatology, Apr. 2014, 29(5): 973-983.
Urry et al., "Calculation of distorted circular dichroism curves for poly-L-glutamic acid suspensions," Arch Biochem Biophys, 1970, 137, 214-221.
Urry et al., "Coacervation of solubilized elastin effects a notable conformational change," Nature, 1969, 222, 795-796.
Urry et al., "Differential scatter of left and right circularly polarized light by optically active particulate systems," Proc Natl Acad Sci U S A, 1970, 65, 845-852.
Urry et al., "Distortions in circular dichroism patterns of particulate (or membranous) systems," Arch Biochem Biophys, 1968, 128, 802-807.
Urry et al., "Elastic protein-based polymers in soft tissue augmentation and generation," J. Biomater. Sci. Polym. Ed., 1998, 9, 1015-1048.
Urry et al., "Hydrophobicity Scale for Proteins Based on InverseTemperature Transitions," Biopolymers, 1992, 32:1243-1250.
Urry et al., "Physical chemistry of biological free energy transduction as demonstrated by elastic protein-based polymers," J. of Phys. Chem. B., 1997, 101, 11007-11028.
Urry et al., "Temperature dependence of length of elastin and its polypentapeptide," Biochem Biophys Res Commun, 1986, 141, 749-755.
Urry et al., "Temperature of polypeptide inverse temperature transition depends on mean residue hydrophobicity," J. Am. Chem. Soc., 1991, 113(11):4346-4348.
Urry, "Free energy transduction in polypeptides and proteins based on inverse temperature transitions," Prog Biophys Mol Biol, Jan. 1992, 57(1):23-57.
Urry, "Protein elasticity based on conformations of sequential polypeptides: The biological elastic fiber," J Protein Chemistry, 1984, 3, 403-436.
Utada et al., "Monodisperse double emulsions generated from a microcapillary device," Science, 2005, 308: 537-541.
Uversky et al., "Intrinsically disordered proteins as crucial constituents of cellular aqueous two phase systems and coacervates," FEBS Lett, Jan. 2015, 589(1):15-22.
Uversky et al., "Understanding protein non-folding," Biochim Biophys Acta, Elsevier, Jun. 2010, 1804(6):1231-1264.
Uversky, "Protein intrinsic disorder-based liquid-liquid phase transitions in biological systems: Complex coacervates and membraneless organelles," Adv Colloid Interface Sci, 2017, 239: 97-114.
Valkenburg et al., "Targeting the tumour stroma to improve cancer therapy," Nature Reviews Clinical Oncology, Jun. 2018, 15, 366-381.
Van der Lee et al., "Classification of intrinsically disordered regions and proteins," Chem Rev, Jul. 2014, 114(13): 6589-6631.
Van Roey et al., "Short linear motifs: ubiquitous and functionally diverse protein interaction modules directing cell regulation," Chem Rev, Jul. 2014, 114(13): 6733-6778.
Van Roy, "Beyond E-cadherin: roles of other cadherin superfamily members in cancer," Nat Rev Cancer, Feb. 2014, 14(2): 121-134.
Vasey et al., "Phase I clinical and Pharmacokinetic study of PK1 (N-(2-Hydroxypropyl)methacrylamide Copolymer Doxorubicin): First member of a New Class of Chemotherapeutic Agents-Drugs-Polymer Conjugates" Clinical Cancer Research, 1999, 5:83-94.
Vazquez-Lombardi et al., "Challenges and Opportunities for Non-Antibody Scaffold Drugs," Drug Discov Today, Oct. 2015, 20(10):1271-83.
Vega et al., "Targeting Doxorubicin to Epidermal Growth Factor Receptors by Site-Specific Conjugation of C225 to Poly(L-Glutamic Acid) through a Polyethylene Glycol Spacer," Pharmaceutical Research, 2003, 20(5):826-832.
Venkataraman et al., "The Effects of Polymeric Nanostructure Shape on Drug Delivery," Adv Drug Deliv Rev, Elsevier, Nov. 2011, 63(14-15):1228-46.

(56) References Cited

OTHER PUBLICATIONS

Verma et al., "Effect of surface properties on nanoparticle-cell interactions," Small, Wiley, Jan. 2010, 6(1):12-21.
Veronese et al., "PEGylation, successful approach to drug delivery," Drug Discovery Today, 2005, 10(21):1451-1458.
Veronese, "Peptide and protein PEGylation: a review of problems and solutions," Biomaterials 22, 2001, 405-417.
Vicini et al., "An interinstitutional and interspecialty comparison of treatment outcome data for patients with prostate carcinoma based on predefined prognostic categories and minimum follow-up," Cancer, 2002, 95, 2126-2135.
Viegas et al., "Polyoxazoline: Chemistry, properties and applications," Bioconjugate Chem., May 2011, 22(5): 976-986.
Vlieghe et al., "Synthetic therapeutic peptides: science and market," Drug Discovery Today, Jan. 2010, 15(1-2): 40-56.
Voelker et al., "Alteration of the specificity and regulation of fatty acid synthesis of *Escherichia coli* by expression of a plant medium-chain acyl-acyl carrier protein thioesterase," J Bacteriol., 1994, 176(23):7320-7.
Volkova et al., "Anthracycline Cardiotoxicity: Prevalence, Pathogenesis and Treatment," Curr. Cardiol. Rev., Nov. 2011, vol. 7, No. 4, pp. 214-220.
Volodkin et al., "One-Step Formulation of Protein Microparticles with Tailored Properties: Hard Templating at Soft Conditions," Advanced Functional Materials, 2012, 22: 1914-1922.
Von Roemeling et al., "Breaking Down the Barriers to Precision Cancer Nanomedicine," Trends Biotechnol, Feb. 2017, 35(2):159-171.
Vonarbourg et al., "Evaluation of pegylated lipid nanocapsules versus complement system activation and macrophage uptake," J Biomed Mater Res A, Wiley, Sep. 2006, 78(3):620-8.
Vrhovski et al., "Biochemistry of tropoelastin," Eur J Biochem, 1998, 258, 1-18.
Vrhovski et al., "Coacervation Characteristics of Recombinant Human Tropoelastin," European Journal of Biochemistry, 1997, 250(1):92-98.
Vrignaud et al., "Strategies for the nanoencapsulation of hydrophilic molecules in polymer-based nanoparticles," Biomaterials, Nov. 2011, 32(33):8593-8604.
Walczak, "Death Receptor-Ligand Systems in Cancer, Cell Death, and Inflammation," Cold Spring Harb. Perspect. Biol., May 2013, 5(5): a008698.
Wali et al., "Measuring Death of Pancreatic Beta Cells in Response to Stress and Cytotoxic T Cells," Methods in Molecular Biology, Mar. 2015, 1292:165-176.
Walsh et al., "Post-translational modifications in the context of therapeutic proteins," Nat. Biotechnol., Oct. 2006, 24(10): 1241-1252.
Walsh et al., "Posttranslationale Proteinmodifikation: die Chemie der Proteomdiversifizierung," Angew Chem, 2005, 117, 7508-7539.
Walsh et al., "Protein posttranslational modifications: The chemistry of proteome diversifications," Angew. Chem. Int. Ed., 2005, 44, 7342-7372.
Wang et al., "A Molecular Grammar Governing the Driving Forces for Phase Separation of Prion-like RNA Binding Proteins," Cell, Jul. 2018, 174(3):688-699.e616.
Wang et al., "Enhanced Tumor Delivery of Gemcitabine via PEG-DSPE/TPGS Mixed Micelles," Mol. Pharm., Apr. 2014, 11(4): 1140-1150.
Wang et al., "Extending Half Life of H-Ferritin Nanoparticle by Fusing Albumin Binding Domain for Doxorubicin Encapsulation," Biomacromolecules, Mar. 2018, 19(3):773-781.
Wang et al., "Functional polymeric microparticles engineered from controllable microfluidic emulsions," Acc Chem Res, 2014, 47: 373-384.
Wang et al., "More effective nanomedicines through particle design," Small, Wiley, Jul. 2011, 7(14):1919-31.
Wang et al., "Nanoparticle delivery of cancer drugs," Annu Rev Med, Annual Reviews, Feb. 2012, 63:185-98.
Wang et al., "Quantitative Mapping of the Spatial Distribution of Nanoparticles in Endo-Lysosomes by Local pH," Nano Lett., Feb. 2017, 17(2): 1226-1232.
Wang et al., "Size and dynamics of caveolae studied using nanoparticles in living endothelial cells," ACS nano, Dec. 2009, 3(12): p. 4110-4116.
Wang et al., "Stimuli-responsive Dendrimers in Drug Delivery," Biomater Sci, Mar. 2016, 4(3):375-90.
Wang et al., "The Weak Link: Optimization of the Ligand-Nanoparticle Interface To Enhance Cancer Cell Targeting by Polymer Micelles," Nano Lett Oct. 2017, 17(10):5995-6005.
Waterman et al., "Edema associated with I-125 or Pd-103 prostate brachytherapy and its impact on post-implant dosimetry: an analysis based on serial CT acquisition," International journal of radiation oncology, biology, physics, 1998, 41, 1069-1077.
Wechsel et al., "Renal Cell Carcinoma: Immunohistological Investigation of Expression of the Integrin $\alpha v\beta 3$," Anticancer research, 1999, 19(2C):1529-1532.
Wei et al., "Anticancer drug nanomicelles formed by self-assembling amphiphilic dendrimer to combat cancer drug resistance," Proceedings of the National Academy of Sciences of the United States of America, Mar. 2015, 112(10): 2978-2983.
Wei et al., "Fibroblast growth factor 21 promotes bone loss by potentiating the effects of peroxisome proliferator-activated receptor $\gamma$," Proc Natl Acad Sci USA, Feb. 2012, 109(8):3143-3148.
Weis et al., "$\alpha$V Integrins in Angiogenesis and Cancer," Cold Spring Harb Perspect Med, Cold Spring Harbor Laboratory Press, Sep. 2011, 1(1):a006478.
Weitzhandler et al., "Micellar Self-Assembly of Recombinant Resilin-/Elastin-Like Block Copolypeptides," Biomacromolecules, Aug. 2017, 18(8):2419-2426.
Wendt et al., "DNA-mediated Folding and Assembly of MyoD-E47 Heterodimers," Journal of Biol. Chem., 1998, 273(10):5735-5743.
Wente et al., "Fibroblast Growth Factor-21 Improves Pancreatic $\beta$-Cell Function and Survival by Activation of Extracellular Signal-Regulated Kinase 1/2 and Akt Signaling Pathways," Diabetes, Sep. 2006, 55(9):2470-2478.
Werle et al., "Strategies to improve plasma half life time of peptide and protein drugs," Amino Acids 30, Jun. 2006, 30(4):351-367.
Wienkers et al., "Predicting in vivo drug interactions from in vitro drug discovery data," Nat. Rev. Drug. Discov. 2005, 4(10):825-833.
Wilkins et al., "Hydrodynamic Radii of Native and Denatured Proteins Measured by Pulse Field Gradient NMR Techniques," Biochemistry, 1999, 38(50):16424-16431.
Williams et al., "Targeted radionuclide therapy," Medical Physics, Jul. 2008, 35(7): 3062-3068.
Williamson et al., "Efficient N-terminal labeling of proteins by use of sortase," Angew Chem Int ed Engl, Sep. 2012, 51(37):9377-9380.
Wimley et al., "Experimentally determined hydrophobicity scale for proteins at membrane interfaces," Nature Structural & Molecular Biology, 1996, 3(10):842-848.
Winzell et al., "The high-fat diet-fed mouse: a model for studying mechanisms and treatment of impaired glucose tolerance and type 2 diabetes," Diabetes 53, 2004, S215-S219.
Wold, "In vivo chemical modification of proteins," Annu. Rev. Med., 1981, 50, 783-814.
Wood et al., "Experiences Using Chloramine-T and 1,3,4,6-Tetrachloro-3-Alpha,6-Alpha-Diphenylglycoluril (Iodogen) for Radioiodination of Materials for Radioimmunoassay," J Clin Chem Clin Bio, 1981, 19, 1051-1056.
Wright et al., "Intrinsically disordered proteins in cellular signalling and regulation," Nat Rev Mol Cell Biol, Jan. 2015, 16(1):18-29.
Wright et al., "Self-assembly of block copolymers derived from elastin-mimetic polypeptide sequences," Advanced Drug Delivery Reviews, 2002, 54, 1057-1073.
Wright et al., "Thermoplastic elastomer hydrogels via self-assembly of an elastin-mimetic triblock polypeptide," Advanced Functional Materials, 2002, 12, 149-154.
Wu et al., "Site-specific chemical modification of recombinant proteins produced in mammalian cells by using the genetically encoded aldehyde tag," Proc Natl Acad Sci USA, Mar. 2009, 106(9):3000-3005.

(56) References Cited

OTHER PUBLICATIONS

Wu et al., "Sortase A-Catalyzed Transpeptidation of Glycosylphosphatidylinositol Derivatives for Chemoenzymatic Synthesis of GPI-Anchored Proteins," J. Am. Chem. Soc., Feb. 2010, 132(5): 1567-1571.
Wust et al., "Hyperthermia in combined treatment of cancer," The Lancet Oncology, 2002, 3, 487-497.
Xavier et al., "HPLC Method for the Dosage of Paclitaxel in Copaiba Oil: Development, Validation, Application to the Determination of the Solubility and Partition Coefficients," Chromatographia, Apr. 2016, 79(7-8): 405-412.
Xia et al., "Tunable self-assembly of genetically engineered silk—elastin-like protein polymers," Biomacromolecules, Nov. 2011, 12(11): 3844-3850.
Xie et al., "The Effect of Shape on Cellular Uptake of Gold Nanoparticles in the Forms of Stars, Rods, and Triangles," Sci Rep, Jun. 2017, 7(1):3827.
Xiong et al., "Engineering of amphiphilic block copolymers for polymeric micellar drug and gene delivery," J Control Release, Elsevier, Oct. 2011, 155(2):248-61.
Xu et al., "A quality by design (QbD) case study on liposomes containing hydrophilic API: II. Screening of critical variables, and establishment of design space at laboratory scale," Int. J. Pharm., Feb. 2012, 423(2):543-553.
Xu et al., "Downregulation of GLP-1 and GIP Receptor Expression by Hyperglycemia," Diabetes, Jun. 2007, 56(6):1551-58.
Xu et al., "Exendin-4 stimulates both beta-cell replication and neogenesis, resulting in increased beta-cell mass and improved glucose tolerance in diabetic rats," Diabetes 48, 1999, 2270-2276.
Xu et al., "Fibroblast Growth Factor 21 Reverses Hepatic Steatosis, Increases Energy Expenditure, and Improves Insulin Sensitivity in Diet-Induced Obese Mice," Diabetes, Jan. 2009, 58(1):250-259.
Xu et al., "Genetically engineered block copolymers: influence of the length and structure of the coiled-coil blocks on hydrogel self-assembly," Pharm Res, Mar. 2008, 25, 674-682.
Xu et al., "Inorganic nanoparticles as carriers for efficient cellular delivery," Chemical Engineering Science, Elsevier, Feb. 2006, 61(3):1027-1040.
Xu et al., "Role of pancreatic stellate cells in pancreatic cancer metastasis," Am J of Pathology, Nov. 2010, 177(5): 2585-2596.
Xu et al., "Self-assembly behavior of peptide amphiphiles (PAs) with different length of hydrophobic alkyl tails," Colloids Surfaces B Biointerfaces, Nov. 2010, 81(1): 329-335.
Yamamoto et al., "ATRP Synthesis of Thermally Responsive Molecular Brushes from Oligo(ethylene oxide) Methacrylates," Macromolecules, Dec. 2007, 40(26): 9348-9353.
Yang et al., "Long Term Exendin-4 Treatment Reduces Food Intake and Body Weight and Alters Expression of Brain Homeostatic and Reward Markers," Endocrinology, Sep. 2014, 155(9): 3473-3483.
Yang et al., "Poly(carboxybetaine) nanomaterials enable long circulation and prevent polymer-specific antibody production," Nano Today, Feb. 2014, 9(1):10-16.
Yates et al., "Contemporary management of patients with high-risk non-muscle-invasive bladder cancer who fail intravesical BCG therapy," World journal of urology, May 2011, 29(4): 415-422.
Yeh et al., "Micromolding of shape-controlled, harvestable cell-laden hydrogels," Biomaterials, 2006, 27: 5391-5398.
Yeo et al., "Coacervation of tropoelastin," Adv Colloid Interface Sci, Sep. 2011, 167(1-2): 94-103.
Yokoe et al., "Albumin-conjugated PEG liposome enhances tumor distribution of liposomal doxorubicin in rats," International Journal of Pharmaceutics, May 2008, 353(1-2): 28-34.
Yoo et al., "A systemic Small RNA Signaling System in Plants" The Plant Cell (2004) vol. 16, pp. 1979-2000.
Yoo et al., "Biodegradable Nanoparticles Containing Doxorubicin-Plga Conjugate for Sustained Release," Pharm. Res., 1999, 16(7):1114-1118.
Youn et al., "Evaluation of therapeutic potentials of site-specific PEGylated glucagon-like peptide-1 isomers as a type 2 anti-diabetic treatment: Insulinotropic activity, glucose-stabilizing capability, and proteolytic stability" Biochem. Pharmacol, 2007, 73: 84-93.
Youn et al., "High-yield production of biologically active mono-PEGylated salmon calcitonin by site-specific PEGylation," J. Control. Release, Feb. 2007, 117(3):371-379.
Yousefpour et al., "Co-opting biology to deliver drugs," Biotechnol Bioeng, Sep. 2014, 111(9): p. 1699-1716.
Yousefpour et al., "Genetically Encoding Albumin Binding into Chemotherapeutic-loaded Polypeptide Nanoparticles Enhances Their Antitumor Efficacy," Nano Lett., Dec. 2018, 18(12): 7784-7793.
Yu et al., "Effectiveness and security of CT-guided percutaneous implantation of (125)I seeds in pancreatic carcinoma," The British journal of radiology, Jul. 2014, 87(1039): 20130642, 7 pages.
Yusta et al., "GLP-1 receptor activation improves β cell function and survival following induction of endoplasmic reticulum stress," Cell Metab, Nov. 2006, 4(5):391-406.
Zhang et al., "A self-assembly pathway to aligned monodomain gels," Nat. Mater., Jul. 2010, 9(7): 594-601.
Zhang et al., "In Depth Analysis on the Unusual Multistep Aggregation Process of Oligo(ethylene glycol) Methacrylate-Based Polymers in Water," Macromolecules, Jul. 2014, 47(14): 4728-4737.
Zhang et al., "Nanoparticles in medicine: therapeutic applications and developments," Clin. Pharmacol. Ther., May 2008, 83(5):761-769.
Zhang et al., "Novel agents for pancreatic ductal adenocarcinoma: emerging therapeutics and future directions," Jounral of Hematology & Oncology, Jan. 2018, 11:14, 17 pages.
Zhang et al., "Sensitive and Quantitative Detection of Anti-Poly(ethylene glycol) (PEG) Antibodies by Methoxy-PEG-Coated Surface Plasmon Resonance Sensors," Anal Chem, Aug. 2017, 89(16): 8217-8222.
Zhang et al., "Shape Effects of Nanoparticles Conjugated with Cell-Penetrating Peptides (HIV Tat PTD) on CHO Cell Uptake," Bioconjugate Chem, Sep. 2008, 19(9):1880-1887.
Zhao et al., "A new Bliss Independence model to analyze drug combination data," J Biomol Screen, Jun. 2014, 19(5): 817-821.
Zhao et al., "Cellular uptake, intracellular trafficking, and cytotoxicity of nanomaterials," Small, Wiley, May 2011, 7(10):1322-37.
Zhao et al., "Fluorescence probe techniques used to study micelle formation in water-soluble block copolymers," Langmuir 1990, 6(2):514-516.
Zhao et al., "Tumor αvβ3 Integrin Is a Therapeutic Target for Breast Cancer Bone Metastases," Cancer Res, AACR Publications, Jun. 2007, 67(12):5821-30.
Zimm, "Apparatus and Methods for Measurement and Interpretation of the Angular Variation of Light Scattering; Preliminary Results on Polystyrene Solutions," J. Chem. Phys. 1948, 16, 1099-1116.
Zini et al., "Contemporary management of adrenocortical carcinoma," European urology, Nov. 2011, 60(5): 1055-1065.
Zong et al., "Crystal structures of Staphylococcus aureus sortase A and its substrate complex," J. Biol. Chem. 279, 2004, 31383-31389.
Zununi Vahed et al., "Targeted cancer drug delivery with aptamer-functionalized polymeric nanoparticles," Journal of drug targeting, Mar. 2019, 27(3):292-299.
International Search Report and Written Opinion for Application No. PCT/US2008/084159 dated Feb. 27, 2009 (8 pages).
International Search Report and Written Opinion for Application No. PCT/US2016/024202 dated Aug. 26, 2016 (9 pages).
International Search Report and Written Opinion for Application No. PCT/US2016/045655 dated Dec. 2, 2016 (13 pages).
International Search Report and Written Opinion for Application No. PCT/US2016/068141 dated Jul. 19, 2017 (12 pages).
International Search Report and Written Opinion for Application No. PCT/US2016/068142 dated Jul. 19, 2017 (12 pages).
International Search Report and Written Opinion for Application No. PCT/US2018/032785 dated Sep. 25, 2018 (16 pages).
International Search Report and Written Opinion for Application No. PCT/US2017/035530 dated Aug. 23, 2017 (13 pages).
International Search Report and Written Opinion for Application No. PCT/US2017/052887 dated Jan. 26, 2018 (20 pages).
International Search Report and Written Opinion for Application No. PCT/US2017/051661 dated Jan. 2, 2018 (12 pages).

(56) References Cited

OTHER PUBLICATIONS

International Search Report and Written Opinion for Application No. PCT/US2018/013611 dated May 30, 2018 (18 pages).
International Search Report and Written Opinion for Application No. PCT/US2018/040409 dated Nov. 5, 2018 (16 pages).
International Search Report and Written Opinion for Application No. PCT/US2019/015176 dated Jun. 3, 2019 (12 pages).
International Search Report and Written Opinion for Application No. PCT/US2019/023583 dated Jul. 5, 2019 (10 pages).
International Search Report and Written Opinion for Application No. PCT/US2019/030022 dated Jul. 25, 2019 (8 pages).
International Search Report and Written Opinion for Application No. PCT/US2019/044911 dated Dec. 10, 2019 (11 pages).
International Search Report and Written Opinion for Application No. PCT/US2019/050077 dated Jan. 27, 2020 (19 pages).
International Search Report and Written Opinion for Application No. PCT/US2019/061144 dated May 21, 2020 (15 pages).
United States Patent Office Action for U.S. Appl. No. 13/904,836 dated Mar. 27, 2014 (10 pages).
United States Patent Office Notice of Allowance for U.S. Appl. No. 13/904,836 dated Jul. 30, 2014 (6 pages).
United States Patent Office Action for U.S. Appl. No. 13/942,037 dated Jan. 15, 2016 (19 pages).
United States Patent Office Action for U.S. Appl. No. 13/942,037 dated Jun. 4, 2015 (33 pages).
United States Patent Office Action for U.S. Appl. No. 13/942,037 dated Nov. 28, 2016 (22 pages).
United States Patent Office Action for U.S. Appl. No. 13/942,037 dated Feb. 9, 2018 (29 pages).
United States Patent Office Notice of Allowance for U.S. Appl. No. 13/245,459 dated Feb. 27, 2013 (13 pages).
United States Patent Office Action for U.S. Appl. No. 14/572,391 dated Oct. 26, 2016 (11 pages).
United States Patent Office Notice of Allowance for U.S. Appl. No. 14/572,391 dated Jun. 16, 2017 (10 pages).
United States Patent Office Action for U.S. Appl. No. 15/387,536 dated Sep. 27, 2018 (11 pages).
United States Patent Office Action for U.S. Appl. No. 15/387,540 dated Sep. 27, 2018 (12 pages).
United States Patent Office Action for U.S. Appl. No. 15/561,799 dated Dec. 27, 2018 (8 pages).
United States Patent Office Notice of Allowance for U.S. Appl. No. 15/387,536 dated Mar. 13, 2019 (13 pages).
United States Patent Office Notice of Allowance for U.S. Appl. No. 15/561,799 dated Apr. 2, 2019 (6 pages).
United States Patent Office Notice of Allowance for U.S. Appl. No. 15/387,540 dated Apr. 17, 2019 (9 pages).
United States Patent Office Action for U.S. Appl. No. 16/058,924 dated Nov. 26, 2019 (23 pages).
United States Patent Office Action for U.S. Appl. No. 16/064,424 dated Apr. 22, 2020 (18 pages).
United States Patent Office Action for U.S. Appl. No. 16/064,425 dated Apr. 22, 2020 (18 pages).
United States Patent Office Action for U.S. Appl. No. 16/058,924 dated Jul. 6, 2020 (51 pages).
United States Patent Office Action for U.S. Appl. No. 15/749,797 dated May 11, 2020 (14 pages).
United States Patent Office Action for U.S. Appl. No. 15/749,797 dated Oct. 20, 2020 (16 pages).
United States Patent Office Action for U.S. Appl. No. 16/335,734 dated Nov. 20, 2020 (15 pages).
United States Patent Office Action for U.S. Appl. No. 16/525,374 dated Dec. 7, 2020 (9 pages).
United States Patent Office Action for U.S. Appl. No. 16/305,696 dated Jan. 28, 2021 (15 pages).
United States Patent Office Notice of Allowance for U.S. Appl. No. 16/332,865 dated Apr. 2, 2021 (10 pages).
United States Patent Office Action for U.S. Appl. No. 16/477,229 dated Apr. 12, 2021 (14 pages).

Alghoul et al., "The effect of hyaluronan hydrogel on fat graft survival," Aesthet Surg J, 2012, 32: 622-633.
American Society of Plastic Surgeons, "2017 Plastic Surgery Statistics Report," Oct. 2018, 25 pages.
Balaji, "Subdermal fat grafting for Parry-Romberg syndrome," Ann Maxillofac Surg, 2014, 4: 55-59.
Banyard et al., "Preparation, Characterization, and Clinical Implications of Human Decellularized Adipose Tissue Extracellular Matrix (hDAM): A Comprehensive Review," Aesthet Surg J, 2016, 36: 349-357.
Bennett et al., "Association of Fat Grafting With Patient-Reported Outcomes in Postmastectomy Breast Reconstruction," JAMA Surg, 2017, 152: 944-950.
Brzezienski et al., "Autologous Fat Grafting to the Breast Using REVOLVE System to Reduce Clinical Costs," Ann Plast Surg, 2016, 77: 286-289.
Chang et al., "Thermoprecipitation of Glutathione S-Transferase by Glutathione-Poly(N-isopropylacrylamide) Prepared by RAFT Polymerization," Macromolecular Rapid Communications, Oct. 2010, 31: 1691-1695.
De Leon-Rodriguez et al., "Multifunctional thermoresponsive designer peptide hydrogels," Acta Biomaterialia, 2017, 47: 40-49.
Eom et al., "The number of operations required for completing breast reconstruction," Plast Reconstr Surg Glob Open, 2012, 2: e242.
Frandsen et al., "Recombinant protein-based polymers for advanced drug delivery," Chem Soc Rev, 2012, 41: 2696-2706.
Gabriel et al., "Fat grafting and breast reconstruction: tips for ensuring predictability," Gland Surg, 2015, 4: 232-243.
Gylbert, "Applanation tonometry for the evaluation of breast compressibility," Scand J Plast Reconstr Surg Hand Surg, 1989, 23: 223-229.
Hess et al., "Graphene Transistors for Multifunctional Polymer Brushes for Biosensing Applications," Applied Materials & Interfaces, 2014, 6: 9705-9710.
Hsu et al., "Fat grafting's past, present, and future: why adipose tissue is emerging as a critical link to the advancement of regenerative medicine," Aesthet Surg J, 2015, 32: 892-899.
Hwang et al., "Synthesis and Characterization of Polystyrene Brushes for Organic Thin Film Transistors," Journal of Nanoscience and Nanotechnology, 2012, 12: 4137-4141.
Kronowitz et al., "Delayed-Immediate Breast Reconstruction," Plastic and Reconstructive Surgery, 2004, 113: 1617-1628.
Minteer et al., "Fat Grafting for Pedal Fat Pad Atrophy in a 2-Year, Prospective, Randomized, Crossover, Single-Center Clinical Trial," Plast Reconstr Surg, 2018, 142: 862e-871e.
Pan et al., "A Pig Model for the Histological Analysis of Adipocytes after Co-injections of Autologous Fat with Fillers," International Journal of Surgery & Surgical Techniques, 2016, 2: 7 pages.
Park et al., "Polymer Brush As a Facile Dielectric Surface Treatment for High-Performance, Stable, Soluble Acene-Based Transistors," Chemistry of Materials, 2010, 22: 5377-5382.
Rasmussen et al., "A Novel Porcine Model for Future Studies of Cell-enriched Fat Grafting," Plast Reconstr Surg Glob Open, 2018, 6: e1735.
Roca et al., "Autologous Fat Grafting for Treatment of Breast Implant Capsular Contracture: A Study in Pigs," Aesthet Surg J, 2014, 34: 769-775.
Sandberg et al., "The Structure of the Elastic Fiber: An Overview," The Journal of Investigative Dermatology, 1982, 79(S1): 128s-132s.
Simonacci et al., "Procedure, applications, and outcomes of autologous fat grafting," Ann Med Surg (Lond), 2017, 20: 49-60.
Strong et al., "The Current State of Fat Grafting: A Review of Harvesting, Processing, and Injection Techniques," Plast Reconstr Surg, 2015, 136: 897-912.
Tamburro et al., "Fractal aspects of elastin supramolecular organization," J Biomol Struct Dyn, 1995, 12: 1161-1172.
Toshima et al., "Three-dimensional architecture of elastin and collagen fiber networks in the human and rat lung," Arch Histol Cytol, 2004, 67: 31-40.
UniProtKB—P15214 (GST_PROMI) acessed online at <https://www.uniprot.org/uniprot/P152146/> on Jun. 8, 2021, 7 pages.

(56) References Cited

OTHER PUBLICATIONS

Wang et al., "Pigs Can Be Used as a Large Animal Model for Autologous Fat Grafting," Ophthalmic Plast Reconstr Surg, 2016, 32: 73-74.
Wu et al., "An injectable adipose matrix for soft-tissue reconstruction," Plast Reconstr Surg, 2012, 129: 1247-1257.
United States Patent Office Action for U.S. Appl. No. 15/749,797 dated May 12, 2021 (19 pages).
United States Patent Office Notice of Allowance for U.S. Appl. No. 16/332,865 dated May 17, 2021 (5 pages).
United States Patent Office Notice of Allowance for U.S. Appl. No. 16/335,734 dated Jun. 16, 2021 (9 pages).
United States Patent Office Action for U.S. Appl. No. 16/305,696 dated Jun. 22, 2021 (20 pages).
Nikolic et al., "Structural basis for the recognition of LDL-receptor family members by VSV glycoprotein," Nature Communications, 2018, 9: 1029, 12 pages.
International Search Report and Written Opinion for Application No. PCT/US2021/020589 dated Jul. 15, 2021 (21 pages).
International Search Report and Written Opinion for Application No. PCT/US2021/017809 dated Jul. 22, 2021 (20 pages).
International Search Report and Written Opinion for Application No. PCT/US2021/046833 dated Nov. 8, 2021 (13 pages).
International Search Report and Written Opinion for Application No. PCT/US2021/035823 dated Dec. 8, 2021 (16 pages).
United States Patent Office Action for U.S. Appl. No. 16/927,982 dated Jan. 6, 2022 (6 pages).
United States Patent Office Action for U.S. Appl. No. 16/964,832 dated Jan. 19, 2022 (12 pages).
United States Patent Office Action for U.S. Appl. No. 16/625,899 dated Dec. 15, 2021 (12 pages).
Chan et al., "A randomized, repeat-dose, pharmacodynamic and safety study of an antidote-controlled factor IXa inhibitor," J Thromb Haemost, 2008, 6(5): 789-796.
Chan et al., "Phase 1b randomized study of antidote-controlled modulation of factor IXa activity in patients with stable coronary artery disease," Circulation, 2008, 117(22): 2865-2874.
Chappell et al., "Computational design of small transcription activating RNAs for versatile and dynamic gene regulation," Nat Commun, 2017, 8(1): 1051.
Chappell et al., "Creating small transcription activating RNAs," Nat Chem Biol, 2015, 11(3): 214-220.
Chase et al., "Single-Stranded DNA Binding Proteins Required for DNA Replication," Ann. Rev. Biochem., 1986, 55: 103-136.
Cohen et al., "First clinical application of an actively reversible direct factor IXa inhibitor as an anticoagulation strategy in patients undergoing percutaneous coronary intervention," Circulation, 2010, 122(6): 614-622.
Dale et al., "Direct covalent mercuration of nucleotides and polynucleotides," Biochemistry, 1975, 14(11): 2447-2457.
Davis et al., "Antibodies and the RNA World: A Role for Low-molecular-weight Effectors in Biochemical Evolution," RNA World, 1993, Chapter 8, p. 185-204.
Dyke et al., "First-in-human experience of an antidote-controlled anticoagulant using RNA aptamer technology: a phase 1a pharmacodynamic evaluation of a drug-antidote pair for the controlled regulation of factor IXa activity," Circulation, 2006, 114(23): 2490-2497.
Eichhorn et al., "Interactions of metal ions with polynucleotides and related compounds. XII. The relative effect of various metal ions on DNA helicity," J. Am. Chem. Soc, 1968, 90: 7323-7328.
Ganesan et al., "Lipid Nanoparticles: Different Preparation Techniques, Characterization, Hurdles, and Strategies for the Production of Solid Lipid Nanoparticles and Nanostructured Lipid Carriers for Oral Drug Delivery," Sustain. Chem. Pharm., 2017, 6: 37-56.
Gold et al., "Aptamers and the RNA World, Past and Present," Cold Spring Harbor Perspect. Biol., 2012, 4: a003582, 9 pages.
Heus, "RNA aptamers," Nat Struct Biol, 1997, 4(8): 597-600.
Hucknall et al., "Simple Fabrication of Antibody Microarrays on Nonfouling Polymer Brushes with Femtomolar Sensitivity for Protein Analytes in Serum and Blood," Adv Mater, 2009, 21: 1968-1971.
Hwang et al., "Inhibition of gene expression in human cells through small molecule-RNA interactions," Proc. Natl. Acad. Sci. USA, 1999, 96(23): 12997-13002.
Keefe et al., "Aptamers as therapeutics," Nature Reviews Drug Discovery, 2010, 9: 537-550.
Korte et al., "Short activated partial thromboplastin times are related to increased thrombin generation and an increased risk for thromboembolism," Am J Clin Pathol, 2000, 113(1): 123-127.
Li et al., "Ferric Chloride-induced Murine Thrombosis Models," J. Vis. Exp., 2016, 115: e54479, 12 pages.
Lincoff et al., "Effect of the REG1 anticoagulation system versus bivalirudin on outcomes after percutaneous coronary intervention (REGULATE-PCI): a randomised clinical trial," Lancet, 2016, 387(10016): 349-356.
Lippard et al., "Platinum complexes: probes of polynucleotide structure and antitumor drugs," Acc. Chem. Res., 1978, 11(5): 211-217.
Maier et al., "From selection hits to clinical leads: progress in aptamer discovery," Mol. Ther. Methods Clin. Dev., 2016, 3: 16014, 10 pages.
McManus et al., "Gene silencing in mammals by small interfering RNAs," Nat Rev Genet, 2002, 3(10): 737-747.
Moreno et al., "Anti-PEG Antibodies Inhibit the Anticoagulant Activity of PEGylated Aptamers," Cell Chem Biol, 2019, 26(5): 634-644.e3.
Nimjee et al., "Aptamers as Therapeutics," Annu Rev Pharmacol Toxicol, 2017, 57: 61-79.
Pisal et al., "Delivery of therapeutic proteins," Journal of Pharmaceutical Sciences, 2010, 99(6): 2557-2575.
Povsic et al., "A Phase 2, randomized, partially blinded, active-controlled study assessing the efficacy and safety of variable anticoagulation reversal using the REG1 system in patients with acute coronary syndromes: results of the RADAR trial," Eur Heart J, 2013, 34(31): 2481-2489.
Povsic et al., "Pre-existing anti-PEG antibodies are associated with severe immediate allergic reactions to pegnivacogin, a PEGylated aptamer," J Allergy Clin Immunol, 2016, 138(6): 1712-1715.
Purtell et al., "Isoelectric point of albumin: effect on renal handling of albumin," Kidney Int, 1979, 16(3): 366-376.
Richter et al., "Mechanistic determinants of biotherapeutics absorption following SC administration," AAPS J, 2012, 14(3): 559-570.
Rinaldi et al., "Antisense oligonucleotides: the next frontier for treatment of neurological disorders," Nat Rev Neurol, 2018, 14(1): 9-21.
Rusconi et al., "Antidote-mediated control of an anticoagulant aptamer in vivo," Nat Biotechnol, 2004, 22(11): 1423-1428.
Rusconi et al., "RNA aptamers as reversible antagonists of coagulation factor IXa," Nature, 2002, 19(6902): 90-94.
Shu et al., "GISAID: Global initiative on sharing all influenza data—from vision to reality," Euro Surveill 22, 2017, 22(13): 30494, 3 pages.
Smith et al., "Coronaviruses lacking exoribonuclease activity are susceptible to lethal mutagenesis: evidence for proofreading and potential therapeutics," PLoS Pathog, 2013, 9: e1003565, 11 pages.
Tuerk et al., "Systematic evolution of ligands by exponential enrichment: RNA ligands to bacteriophage T4 DNA polymerase," Science, 1990, 249(4968): 505-510.
Werstuck et al., "Controlling gene expression in living cells through small molecule-RNA interactions," Science, 1998, 282(5387): 296-298.
Woodruff et al., "Modulation of the Coagulation Cascade Using Aptamers," Arterioscler Thromb Vasc Biol, 2015, 35(10): 2083-2091.
Yamaoka et al., "Distribution and tissue uptake of poly(ethylene glycol) with different molecular weights after intravenous administration to mice," Journal of Pharmaceutical Sciences, 1994, 83(4): 601-606.

(56) References Cited

OTHER PUBLICATIONS

Yizhi et al., "A brush-polymer/exendin-4 conjugate reduces blood glucose levels for up to five days and eliminates poly(ethylene glycol) antigenicity," Nature Biomedical Engineering, 2016, 1(1): 0002.
Zhou et al., "Aptamers as targeted therapeutics: current potential and challenges," Nat Rev Drug Discov, 2017, 16(3): 181-202.
Gilroy et al., "Sustained release of a GLP-1 and FGF21 dual agonist from an injectable depot protects mice from obesity and hyperglycemia," Science Advances, 2020, 6(35): eaaz9890, 12 pages.
European Patent Office Extended Search Report for Application No. 19844008.3 dated Apr. 8, 2022 (14 pages).
United States Patent Office Notice of Allowance for U.S. Appl. No. 15/749,797 dated Mar. 16, 2022 (6 pages).
United States Patent Office Action for U.S. Appl. No. 16/477,229 dated Mar. 3, 2022 (10 pages).
Ren et al., "Stimulus-Responsive Polymer Prodrugs," Progress in Chemistry, 2013, 25(5): 10 pages.
United States Patent Office Action for U.S. Appl. No. 16/614,282 dated Apr. 27, 2022 (15 pages).
United States Patent Office Notice of Allowance for U.S. Appl. No. 16/305,696 dated May 23, 2022 (10 pages).
United States Patent Office Notice of Allowance for U.S. Appl. No. 16/305,696 dated Jun. 10, 2022 (4 pages).
United States Patent Office Notice of Allowance for U.S. Appl. No. 15/749,797 dated Jun. 2, 2022 (6 pages).
United States Patent Office Action for U.S. Appl. No. 16/477,229 dated Jun. 13, 2022 (11 pages).
Da Pieve Chiara et al., "Modification of Thiol Functionalized Aptamers by Conjugation of Synthetic Polymers," Bioconjugate Chemistry, 2009, 1(1): 169-174.
International Search Report and Written Opinion for Application No. PCT2022/023158 dated Jun. 21, 2022 (7 pages).
International Search Report and Written Opinion for Application No. PCT/US2022/017349 dated Jun. 3, 2022 (20 pages).
United States Patent Office Action for U.S. Appl. No. 16/964,832 dated Jul. 14, 2022 (6 pages).
United States Patent Office Notice of Allowance for U.S. Appl. No. 16/927,982 dated Jul. 15, 2022 (8 pages).
United States Patent Office Notice of Allowance for U.S. Appl. No. 16/614,282 dated Aug. 23, 2022 (7 pages).
U.S. Appl. No. 13/245,459, filed Sep. 26, 2011, U.S. Pat. No. 8,470,967, Jun. 25, 2013.
U.S. Appl. No. 13/904,836, filed May 29, 2013, U.S. Pat. No. 8,912,310, Dec. 16, 2014.
U.S. Appl. No. 14/572,391, filed Dec. 16, 2014, U.S. Pat. No. 9,771,396, Jun. 25, 2013.
U.S. Appl. No. 15/679,751, filed Aug. 17, 2017, 2018/0037609, Feb. 8, 2018.
U.S. Appl. No. 62/138,847, filed Mar. 26, 2015.
PCT/US2016/024202, filed Mar. 25, 2016, WO2016/154530, Sep. 26, 2016.
U.S. Appl. No. 15/561,799, filed Sep. 26, 2017, U.S. Pat. No. 10,385,115, Aug. 20, 2019.
U.S. Appl. No. 16/525,374, filed Jul. 29, 2019, 2019/0345228, Nov. 14, 2019.
U.S. Appl. No. 62/399,123, filed Sep. 23, 2016.
PCT/US2017/052887, Sep. 22, 2017, WO2018/057847, Mar. 29, 2018.
U.S. Appl. No. 16/335,734, filed Mar. 22, 2019, 2020/0017557, Jan. 16, 2020.
U.S. Appl. No. 13/942,037, filed Jul. 15, 2015, 2014/0024600, Jan. 23, 2014.
U.S. Appl. No. 16/058,924, filed Aug. 8, 2018, 2019/0023743, Jan. 24, 2019.
U.S. Appl. No. 62/270,401, filed Dec. 21, 2015.
U.S. Appl. No. 62/310,534, filed Mar. 18, 2016.
U.S. Appl. No. 62/329,800, filed Apr. 29, 2016.
U.S. Appl. No. 62/407,403, filed Oct. 12, 2016.
PCT/US2016/068141, Dec. 21, 2016, WO2017/112825, Jun. 29, 2017.
PCT/US2016/068142, Dec. 21, 2016, WO2017/112826, Jun. 29, 2017.
U.S. Appl. No. 15/387,536, filed Dec. 21, 2016, U.S. Pat. No. 10,364,451, Jul. 30, 2019.
U.S. Appl. No. 15/387,540, filed Dec. 21, 2016, U.S. Pat. No. 10,392,611, Aug. 27, 2019.
U.S. Appl. No. 16/064,424, filed Jun. 20, 2018, 2019/0015520, Jan. 17, 2019.
U.S. Appl. No. 16/064,425, filed Sep. 12, 2016, 2018/0369399, Dec. 27, 2018.
U.S. Appl. No. 62/506,593, filed May 15, 2017.
U.S. Appl. No. 62/534,442, filed Jul. 19, 2017.
U.S. Appl. No. 62/544,720, filed Aug. 11, 2017.
U.S. Appl. No. 62/545,313, filed Aug. 14, 2017.
PCT/US20168/032785, May 15, 2018, WO2018/213320, Nov. 22, 2018.
U.S. Appl. No. 16/614,282, filed Nov. 15, 2019.
U.S. Appl. No. 62/200,726, filed Aug. 4, 2015.
PCT/US2016/045655, Aug. 4, 2016, WO2017/024182, Feb. 9, 2017.
U.S. Appl. No. 15/749,797, filed Feb. 2, 2018, 2018/0228908, Aug. 16, 2018.
U.S. Appl. No. 62/394,662, filed Sep. 14, 2016.
PCT/US2017/051661, Sep. 14, 2017, WO2018/053201, Mar. 22, 2018.
U.S. Appl. No. 16/332,865, filed Mar. 13, 2019, 2020/0164082, May 28, 2020.
U.S. Appl. No. 62/445,504, filed Jan. 12, 2017.
U.S. Appl. No. 62/479,977, filed Mar. 31, 2017.
PCT/US2018/013611, Jan. 12, 2018, WO2018/132732, Jul. 19, 2018.
U.S. Appl. No. 16/477,229, filed Jul. 11, 2019, 2019/0328662, Oct. 31, 2019.
U.S. Appl. No. 62/527,836, filed Jun. 30, 2017.
U.S. Appl. No. 62/534,019, filed Jul. 18, 2017.
PCT/US2018/040409, Jun. 29, 2018, WO2019/006374, Jan. 3, 2019.
U.S. Appl. No. 16/625,899, filed Dec. 23, 2019, 2020/0148724, May 14, 2020.
U.S. Appl. No. 62/343,926, filed Jun. 1, 2016.
U.S. Appl. No. 62/414,877, filed Oct. 31, 2016.
PCT/US2017/035530, Jun. 1, 2017, WO2017/210476, Dec. 7, 2018.
U.S. Appl. No. 16/305,696, filed Nov. 29, 2018, 2020/0378916, Dec. 3, 2020.
U.S. Appl. No. 62/728,582, filed Sep. 7, 2018.
PCT/US2019/050077, Sep. 6, 2019, WO2020/051541, Mar. 12, 2020.
U.S. Appl. No. 62/767,736, filed Nov. 15, 2018.
PCT/US2019/061144, Nov. 13, 2019, WO2020/102324, May 22, 2020.
U.S. Appl. No. 62/622,249, filed Jan. 26, 2018.
PCT/US2019/015176, Jan. 25, 2019, WO2019/147954, Aug. 1, 2019.
U.S. Appl. No. 16/964,832, filed Jul. 24, 2020.
U.S. Appl. No. 62/647,199, filed Mar. 23, 2018.
PCT/US2019/023583, Mar. 22, 2019, WO2019/183476, Sep. 26, 2019.
U.S. Appl. No. 62/664,512, filed Apr. 30, 2018.
PCT/US2019/030022, Apr. 30, 2019, WO2019/213150, Nov. 7, 2019.
U.S. Appl. No. 17/051,202, filed Oct. 28, 2020.
U.S. Appl. No. 62/700,939, filed Jul. 20, 2018.
U.S. Appl. No. 62/873,306, filed Jul. 12, 2019.
U.S. Appl. No. 16/927,982, filed Jul. 13, 2020, 2021/0009999, Jan. 14, 2021.
U.S. Appl. No. 62/985,174, filed Mar. 4, 2020.
U.S. Appl. No. 62/985,179, filed Mar. 4, 2020.
U.S. Appl. No. 62/898,353, filed Sep. 12, 2019.

(56) References Cited

OTHER PUBLICATIONS

U.S. Appl. No. 17/015,315, filed Sep. 9, 2020, 2021/0046188, Feb. 18, 2021.
U.S. Appl. No. 62/975,479, filed Feb. 12, 2020.

* cited by examiner

DUAL AGONIST FUSION PROTEINS

CROSS-REFERENCE TO RELATED APPLICATIONS

This patent application is the U.S. national stage entry, under 35 U.S.C. § 371, of International Application Number PCT/US2019/044911, filed Aug. 2, 2019, which claims priority to U.S. Provisional Application No. 62/713,752, filed Aug. 2, 2018, the entire contents of each of which are hereby incorporated by reference.

SEQUENCE LISTING

The sequence listing is filed with the application in electronic format only and is incorporated by reference herein. The sequence listing text file "028193-9331-WO01_As_Filed_Sequence_Listing.txt" was created on Aug. 2, 2019, and is 81,600 bytes in size.

BACKGROUND

Over 30 million people in the United States have diabetes, with the number of diagnosed individuals growing rapidly, and obesity serving as a major risk factor. Type 2 diabetes mellitus (T2D) accounts for most new cases and is characterized by a state of insulin resistance and impaired ability to maintain glucose homeostasis. Treatment beyond lifestyle changes generally begins with oral anti-diabetic agents, however these medicines have only transitory benefit as the progressive nature of T2D requires therapeutic intensification ultimately including insulin within 5-10 years for many. Moreover, many current treatments, including insulin, are frequently accompanied by weight gain. Thus, there is a pressing need for the development of drugs or drug combinations that maximize glycemic control while promoting weight loss.

SUMMARY

In one aspect, disclosed are fusion proteins comprising an elastin-like polypeptide (ELP) domain; a GLP-1 receptor agonist domain attached to a N-terminal end of the ELP domain; and a FGF21 receptor agonist domain attached to a C-terminal end of the ELP domain.

In another aspect, disclosed are compositions comprising a plurality of fusion proteins as disclosed herein, wherein the plurality of fusion proteins assemble into an aggregate above the $T_t$ of the fusion protein.

In another aspect, disclosed are methods of treating a metabolic disease in a subject in need thereof, the method comprising administering to the subject an effective amount of the composition as disclosed herein.

In another aspect, disclosed are methods of synthesizing a dual agonist fusion protein, the method comprising transforming a bacteria with a recombinant expression vector comprising a first polynucleotide encoding the fusion protein as disclosed herein; and culturing the transformed bacteria to express the fusion protein.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 3 is a series of plots showing that recombinant GLP1-ELP-FGF21 fusion proteins have dual agonism and lower critical solution temperature (LCST) phase behavior. (FIG. 3C) The optical density at 350 nm of GLP1-ELP-FGF21 at the indicated concentration in PBS, was measured as a function of temperature, with temperature ramped at a rate of 1° C./min. (FIG. 3D) Turbidity vs. temperature scans were repeated as in (FIG. 3C) for the indicated concentrations (n=3). $T_t$s were defined as the temperature corresponding to the 50% maximum optical density and are plotted as a function of fusion protein concentration. The horizontal dashed line indicates the approximate temperature of the subcutaneous (s.c.) space in a mouse. (FIG. 3E) A turbidity scan was repeated for GLP1-ELP-FGF21 at an injection-relevant concentration (150 μM), with the temperature ramped up to 37° C., and then down to 20° C.

FIG. 5 is a set of plots showing that GLP1-ELP-FGF21 dual agonist fusion proteins have potent and sustained effects on glycemia and body weight.

FIG. 6 is a series of plots showing production and in vitro characterization of single agonist ELP fusion controls. (FIG. 6B and FIG. 6C) The optical density at 350 nm measured as a function of temperature for GLP1-ELP (FIG. 6B) or a 1:1 mixture of GLP1-ELP and ELP-FGF21 (FIG. 6C). Dilutions were prepared in PBS, with the 1:1 mixture consisting of the indicated concentration of each respective fusion protein. Temperature was ramped at a rate of 1° C./min. (FIG. 6D and FIG. 6E) Turbidity vs. temperature scans were repeated as in (FIG. 6B and FIG. 6C) for the indicated concentrations (n=3). Tts were measured as the temperature corresponding to the 50% maximum optical density and plotted as a function of concentration. The horizontal dashed line indicates the approximate temperature of the s.c. space in a mouse. (FIG. 6F and FIG. 6G) Turbidity scans were repeated for GLP1-ELP and the 1:1 mixture at injection-relevant concentrations (200 μM and 100 μM, respectively), ramping up to 37° C., then down to 20° C.

FIG. 8 is a series of plots showing raw body weight and % HbA1c values for chronic dual agonist treatment study. 6-week-old db-db mice (n=6-7) were treated weekly for 4 weeks with GLP1-ELP-FGF21, GLP1-ELP, ELP-FGF21, a 1:1 mixture of GLP1-ELP and ELP-FGF21, or PBS vehicle. Drugs were administered s.c. at 1000 nmol/kg (or 1000 nmol/kg of each in the drug mixture).

FIG. 9 is a series of plots showing acute and chronic GLP1-ELP-FGF21 dual agonist performance. 6-week-old db/db mice (n=6-7) were treated weekly for 4 weeks with GLP1-ELP-FGF21, GLP1-ELP, ELP-FGF21, a 1:1 mixture of GLP1-ELP and ELP-FGF21, or PBS vehicle. Fusion proteins were administered s.c. at 1000 nmol/kg (or 1000 nmol/kg of each in the drug mixture).

DETAILED DESCRIPTION

Figure 1:
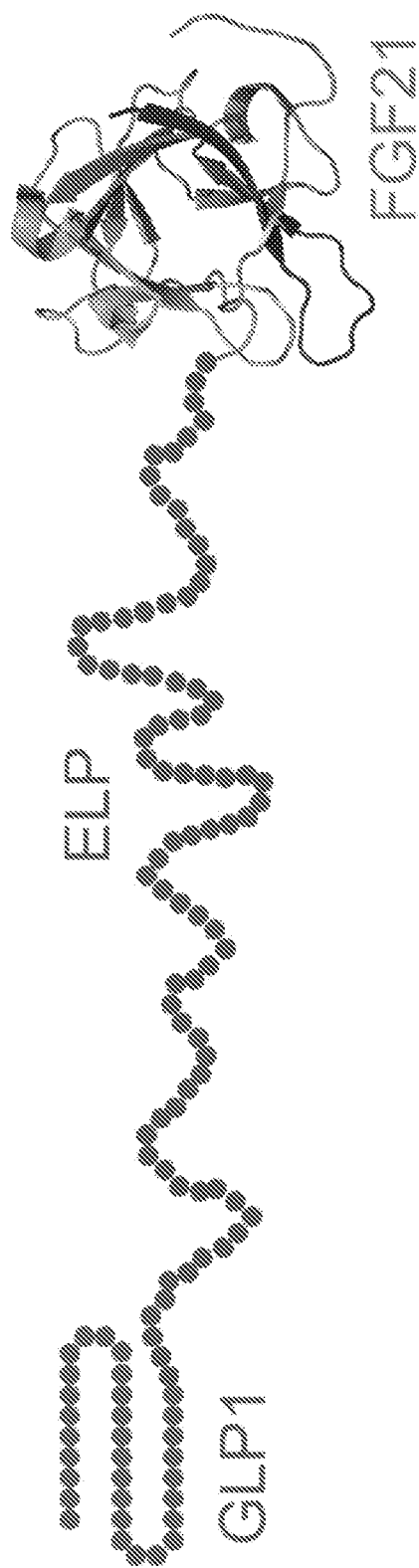
FIG. 1 is a schematic of a dual agonist fusion protein.

It has been found that GLP-1 and FGF21 can each (1) promote insulin production in the pi-cell; and (2) can exert cytoprotective effects on β-cells through pathways that appear to converge. Disclosed herein are fusion proteins that incorporate GLP-1 and FGF21 into a unimolecular drug that can provide synergistic effects at the cellular level, and can translate to superior efficacy in vivo when compared to a GLP1/FGF21 drug mixture.

1. Definitions

Unless otherwise defined, all technical and scientific terms used herein have the same meaning as commonly understood by one of ordinary skill in the art. In case of conflict, the present document, including definitions, will control. Preferred methods and materials are described below, although methods and materials similar or equivalent to those described herein can be used in practice or testing of the present invention. All publications, patent applications, patents and other references mentioned herein are incorporated by reference in their entirety. The materials, methods, and examples disclosed herein are illustrative only and not intended to be limiting.

The terms "comprise(s)," "include(s)," "having," "has," "can," "contain(s)," and variants thereof, as used herein, are intended to be open-ended transitional phrases, terms, or words that do not preclude the possibility of additional acts or structures. The singular forms "a," "and" and "the" include plural references unless the context clearly dictates otherwise. The present disclosure also contemplates other embodiments "comprising," "consisting of" and "consisting essentially of," the embodiments or elements presented herein, whether explicitly set forth or not.

The modifier "about" used in connection with a quantity is inclusive of the stated value and has the meaning dictated by the context (for example, it includes at least the degree of error associated with the measurement of the particular quantity). The modifier "about" should also be considered as disclosing the range defined by the absolute values of the two endpoints. For example, the expression "from about 2 to about 4" also discloses the range "from 2 to 4." The term "about" may refer to plus or minus 10% of the indicated number. For example, "about 10%" may indicate a range of 9% to 11%, and "about 1" may mean from 0.9-1.1. Other meanings of "about" may be apparent from the context, such as rounding off, so, for example "about 1" may also mean from 0.5 to 1.4.

For the recitation of numeric ranges herein, each intervening number there between with the same degree of precision is explicitly contemplated. For example, for the range of 6-9, the numbers 7 and 8 are contemplated in addition to 6 and 9, and for the range 6.0-7.0, the number 6.0, 6.1, 6.2, 6.3, 6.4, 6.5, 6.6, 6.7, 6.8, 6.9, and 7.0 are explicitly contemplated.

The term "agonist," as used herein refers to a polypeptide-based entity that binds to a receptor and activates the receptor to produce a biological response. An "antagonist" blocks or inhibits the action or signaling of the agonist. An "inverse agonist" causes an action opposite to that of the agonist. The activities of agonists, antagonists, and inverse agonists may be determined in vitro, in situ, in vivo, or a combination thereof.

The term "amino acid" as used herein refers to naturally occurring and non-natural synthetic amino acids, as well as amino acid analogs and amino acid mimetics that function in a manner similar to the naturally occurring amino acids. Naturally occurring amino acids are those encoded by the genetic code. Amino acids can be referred to herein by either their commonly known three-letter symbols or by the one-letter symbols recommended by the IUPAC-IUB Biochemical Nomenclature Commission.

The term "biologically active agent," as used herein, refers to a substance that can act on a cell, virus, tissue, organ, organism, or the like, to create a change in the functioning of the cell, virus, tissue, organ, or organism. Examples of a biologically active agent include, but are not limited to, drugs, pharmaceuticals, anti-microbial agents, cells, proteins, and nucleic acids. A biologically active agent is capable of treating and/or ameliorating a condition or disease, or one or more symptoms thereof, in a subject. Biologically active agents of the present disclosure also include prodrug forms of the agent.

The term "C-terminal end," as used herein refers to a fragment of a polypeptide that begins at any amino acid in the C-terminal half of the polypeptide and ends at the last amino acid of the polypeptide. For example, the C-terminal end of SEQ ID NO:19 begins at any amino acid from about amino acid 300 to about amino acid 590 of SEQ ID NO:19 and ends at amino acid 600 of SEQ ID NO:19.

The term "C-terminus," as used herein refers to the last amino acid of a polypeptide.

The term "effective amount" or "therapeutically effective amount," as used herein refers to an amount sufficient to effect beneficial or desirable biological and/or clinical results.

The term "expression vector," as used herein indicates a plasmid, a virus or another medium, known in the art, into which a nucleic acid sequence for encoding a desired protein can be inserted or introduced.

The term "fusion," as used herein refers to a single protein or polypeptide that is produced by joining two or more originally separate genes into a single gene.

The term "host cell," as used herein is a cell that is susceptible to transformation, transfection, transduction, conjugation, and the like with a nucleic acid construct or expression vector. Host cells can be derived from plants, bacteria, yeast, fungi, insects, animals, etc. In some embodiments, the host cell includes *Escherichia coli*.

The term "metabolic disease," as used herein refers to a cluster of conditions, such as increased blood pressure, high blood sugar, excess body fat, and abnormal cholesterol or triglyceride levels—that can occur together or individually, increasing the risk of, e.g., heart disease, stroke and diabetes. Examples include, but are not limited to, type 1 diabetes mellitus, type 2 diabetes mellitus, postprandial hyperglycemia, overweight, obesity, metabolic syndrome, gestational diabetes, pancreatitis, dyslipidemia, nonalcoholic fatty liver disease (NAFLD), nonalcoholic steatohepatitis (NASH), insulin resistance, hyperinsulinemia, glucose intolerance, and hyperglycemia.

The term "N-terminal end," as used herein refers to a fragment of a polypeptide that begins at the first amino acid of the polypeptide and ends at any amino acid in the N-terminal half of the polypeptide. For example, the N-terminal end of SEQ ID NO:19 is from amino acid 1 of SEQ ID NO:19 to any amino acid from about amino acid 10 to amino acid 300 of SEQ ID NO:19.

The term "N-terminus," as used herein refers to the first amino acid of a polypeptide.

The term "peptide," as used herein, refers to a linked sequence of two or more amino acids linked by peptide bonds.

The term "subject," "patient," or "organism," as used herein, includes humans and mammals (e.g., mice, rats, pigs, cats, dogs, and horses). Typical subjects of the present disclosure may include mammals, particularly primates, and especially humans. For veterinary applications, suitable subjects may include, for example, livestock such as cattle, sheep, goats, cows, swine, and the like; poultry such as chickens, ducks, geese, turkeys, and the like, as well as domesticated animals particularly pets such as dogs and cats. For diagnostic or research applications, suitable subjects may include mammals, such as rodents (e.g., mice, rats, hamsters), rabbits, primates, and swine such as inbred pigs and the like.

The term "treatment" or "treating," as used herein when referring to protection of a subject from a disease, means preventing, suppressing, repressing, ameliorating, or completely eliminating the disease. Preventing the disease involves administering a composition of the present disclosure to a subject prior to onset of the disease. Suppressing the disease involves administering a composition of the present disclosure to a subject after induction of the disease but before its clinical appearance. Repressing or ameliorating the disease involves administering a composition of the present disclosure to a subject after clinical appearance of the disease.

The term "variant," as used herein refers to a peptide or polypeptide that differs in amino acid sequence by the insertion, deletion, or conservative substitution of amino acids, but retain at least one biological activity. Representative examples of "biological activity" include the ability to be bound by a specific antibody or polypeptide or to bind to its specific receptor. Variant can mean a substantially identical sequence. Variant can mean a functional fragment thereof. Variant can also mean a polypeptide with an amino acid sequence that is substantially identical to a referenced polypeptide with an amino acid sequence that retains at least one biological activity. A conservative substitution of an amino acid, i.e., replacing an amino acid with a different amino acid of similar properties (e.g., hydrophilicity, degree and distribution of charged regions) is recognized in the art as typically involving a minor change.

A variant can be a polynucleotide sequence that is substantially identical over the full length of the full gene sequence or a fragment thereof. The polynucleotide sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the gene sequence or a fragment thereof. A variant can be an amino acid sequence that is substantially identical over the full length of the amino acid sequence or fragment thereof. The amino acid sequence can be 80%, 81%, 82%, 83%, 84%, 85%, 86%, 87%, 88%, 89%, 90%, 91%, 92%, 93%, 94%, 95%, 96%, 97%, 98%, 99%, or 100% identical over the full length of the amino acid sequence or a fragment thereof.

2. Dual Agonist Fusion Proteins

Disclosed herein are dual agonist fusion proteins that comprise an elastin-like polypeptide (ELP) domain, a glucagon-like peptide-1 (GLP-1) receptor agonist domain, and a fibroblast growth factor 21 (FGF21) receptor agonist domain. The dual agonist fusion protein (also referred to as fusion protein herein) has a linear architecture where the GLP-1 receptor agonist domain is attached to a N-terminal end of the ELP domain, and the FGF21 receptor agonist domain is attached to a C-terminal end of the ELP domain. Accordingly, the ELP domain is positioned in between the GLP-1 receptor agonist domain and the FGF21 receptor agonist domain. The linear architecture of the fusion protein can allow each of the receptor agonist domains to interact with their target receptors.

The disclosed fusion proteins have a phase transition at a transition temperature ($T_t$) due to the presence of the ELP domain. "Phase transition" or "transition" refers to the aggregation of fusion proteins, which occurs sharply and in some instances reversibly at a specific temperature. The phase transitioning ability and $T_t$ of the fusion protein can be analyzed via a UV-Vis spectrophotometer and other techniques known within the art. Below the $T_t$, for example, the fusion protein may be highly soluble. Upon heating above the transition temperature, for example, the fusion protein may hydrophobically collapse and aggregate, forming a separate, phase. The $T_t$ of the fusion protein may be dependent on the $T_t$ of the ELP domain alone (e.g., unattached to the receptor agonist domains). An aggregate of fusion proteins may have a varying size. The aggregate may be, for example, nanoscale aggregates, micron-sized aggregates, or macroscale aggregates. In some embodiments, at a temperature above the $T_t$, the aggregate has a diameter or length of about 100 nm to about 1 cm.

The fusion protein may have a $T_t$ of about 20° C. to about 40° C., such as about 25° C. to about 37° C., about 26° C. to about 35° C., or about 27° C. to about 32° C. The fusion protein may have a $T_t$ greater than 20° C., greater than 21° C., greater than 22° C., greater than 23° C., greater than 24° C., or greater than 25° C. The fusion protein may have a $T_t$ less than 40° C., less than 39° C., less than 38° C., less than 37° C., less than 36° C., or less than 35° C.

The fusion protein may undergo phase transition at varying concentrations. For example, the fusion protein may phase transition at a concentration of about 5 µM to about 1 M, such as about 10 µM to about 500 µM, about 15 µM to about 250 µM, about 20 µM to about 150 µM, or about 25 µM to about 100 µM. In some embodiments, the fusion protein phase transitions at a concentration that is suitable for administration to a subject.

In addition, phase transition behavior may enable purification of the fusion protein using inverse transition cycling, thereby eliminating the need for chromatography. "Inverse transition cycling" refers to a protein purification method for polypeptides having phase transition behavior, and the method may involve the use of the fusion protein's reversible phase transition behavior to cycle the solution through soluble and insoluble phases, thereby removing contaminants and eliminating the need for chromatography.

The dual agonist fusion protein can have a varying molecular weight. The molecular weight of the fusion protein can be measured by SDS-PAGE analysis, or other techniques known within the art. The fusion protein may have a molecular weight of about 50 kDa to about 100 kDa, such as about 55 kDa to about 95 kDa, about 60 kDa to about 85 kDa, about 65 kDa to about 80 kDa, or about 65 kDa to about 100 kDa. In some embodiments, the fusion protein has a molecular weight of greater than 50 kDa, greater than 55 kDa, greater than 60 kDa, or greater than 65 kDa. In some embodiments, the fusion protein has a molecular weight of less than 100 kDa, less than 95 kDa, less than 90 kDa, less than 85 kDa, or less than 80 kDa.

In some embodiments, the fusion protein comprises an amino acid sequence selected from the group consisting of (SEQ ID NO:15), (SEQ ID NO:17), (SEQ ID NO:18), (SEQ ID NO:23), (SEQ ID NO:24) and variants thereof. In some embodiments, the fusion protein comprises an amino acid sequence selected from the group consisting of (SEQ ID NO:15), (SEQ ID NO:17), (SEQ ID NO:18), (SEQ ID NO:23), and (SEQ ID NO:24).

In some embodiments, the fusion protein comprises an amino acid sequence selected from the group consisting of (SEQ ID NO:15), (SEQ ID NO:17), (SEQ ID NO:18), and variants thereof. In some embodiments, the fusion protein comprises an amino acid sequence selected from the group consisting of (SEQ ID NO:15), (SEQ ID NO:17), and (SEQ ID NO:18). In some embodiments, the fusion protein is (SEQ ID NO:15), (SEQ ID NO:17), or (SEQ ID NO:18).

A. Elastin-Like Polypeptide Domain

The ELP domain is a thermally responsive polypeptide that can instill phase transition properties to the fusion proteins. For example, the ELP domain has its own independent $T_t$, which can be the same or different from that of the fusion protein. The $T_t$ of the ELP domain, the fusion protein, or both can be adjusted by varying the amino acid sequence of the ELP domain, by varying the length of the ELP domain, or a combination thereof. In addition, the ELP domain is an unstructured polypeptide lacking secondary structure, which can provide a flexible linker between the two different receptor agonist domains.

The unattached ELP domain (e.g., not attached to either receptor agonist domain) may have a $T_t$ of about 20° C. to about 40° C., such as about 25° C. to about 37° C., about 26° C. to about 35° C., or about 27° C. to about 32° C. The unattached ELP domain may have a $T_t$ greater than 20° C., greater than 21° C., greater than 22° C., greater than 23° C., greater than 24° C., or greater than 25° C. The unattached ELP domain may have a $T_t$ less than 40° C., less than 39° C., less than 38° C., less than 37° C., less than 36° C., or less than 35° C.

The ELP domain can comprise a pentapeptide repeat sequence (VPGXG)$_n$(SEQ ID NO:1), wherein X is any amino acid except proline and n is an integer greater than or equal to 1. In some embodiments, n is 2 to 200, 80 to 160, or 100 to 140. In some embodiments, n is 60, 120, or 180. In some embodiments, n is 120. In some embodiments, X is valine, alanine, leucine, or a combination thereof. Embodiments that include a combination of valine, alanine, and/or leucine can include these amino acids at varying ratios. For example, X may be a ratio of valine:alanine of 1:0 to 10:1. In some embodiments, X is a ratio of valine:alanine of 4:1. In some embodiments, the ELP domain comprises (SEQ ID NO:19). In some embodiments, the ELP domain is (SEQ ID NO:19).

B. GLP-1 Receptor Agonist Domain

GLP-1 receptor agonists refer to a class of agonists based on an endogenous ligand-receptor system that can mediate action of GLP-1. GLP1 is a 31-amino acid endogenous peptide released from the intestines post-prandially that can enhance glucose-stimulated insulin secretion from the pancreas. When administered as a drug, GLP1 receptor (GLP1R) agonists can improve long-term glycemic control as measured by glycated hemoglobin (HbA1c), can promote satiety and weight loss, and can improve O-cell function. Furthermore, the insulinotropic effects of GLP1R agonists may decrease when glucose levels drop below a certain level, which can reduce the risk of hypoglycemia. Accordingly, the GLP-1 receptor agonist domain can be used to target multiple aspects of metabolic diseases, such as type 2 diabetes.

In some embodiments, the GLP-1 receptor agonist domain comprises an amino acid sequence selected from the group consisting of:

```
                                           (SEQ ID NO: 2)
AAHGEGTFTSDVSSYLEEQAAKEFIAWLVKGA;

(SEQ ID NO: 3)
GAHGEGTFTSDVSSYLEEQAAKEFIAWLVKGA;

(SEQ ID NO: 4)
HGEGTFTSDVSSYLEEQAAKEFIAWLVKGA,
``` and variants thereof.

In some embodiments, the GLP-1 receptor agonist domain comprises an amino acid sequence selected from the group consisting of: (SEQ ID NO:2); (SEQ ID NO:3); and (SEQ ID NO:4).

The GLP-1 receptor agonist domain is located at the N-terminal end of the ELP domain in order to allow the N-terminal end of the GLP-1 receptor agonist domain to interact with its target. In some embodiments, the GLP-1 receptor agonist domain is attached to the N-terminus of the ELP domain.

C. FGF21 Receptor Agonist Domain

FGF21 refers to a metabolic hormone that can target the liver, pancreas, and/or adipose tissues to regulate insulin resistance and lipid metabolism. Accordingly, the FGF21 receptor agonist domain can be used to target multiple aspects of metabolic diseases, such as type 2 diabetes. In some embodiments, the FGF21 receptor agonist domain comprises an amino acid sequence selected from the group consisting of:

```
                                           (SEQ ID NO: 5)
AYPIPDSSPLLQFGGQVRQRYLYTDDDQDTEAHLEIREDGTVVGAAHRS

PESLLELKALKPGVIQILGVKASRFLCQQPDGALYGSPHFDPEACSFRE

RLLEDGYNVYQSEAHGLPLRLPQKDSPNQDATSWGPVRFLPMPGLLHEP

QDQAGFLPPEPPDVGSSDPLSMVEGSQGRSPSYAS;

(SEQ ID NO: 6)
AYPIPDSSPLLQFGGQVRQRYLYTDDDQDTEAHLEIREDGTVVGAAHRS

PESLLELKALKPGVIQILGVKASRFLCQQPDGALYGSPHFDPEACSFRE

LLLEDGYNVYQSEAHGLPLRLPQKDSPNQDATSWGPVRFLPMPGLLHEP

QDQAGFLPPEPPDVGSSDPLSMVEPLQGRSPSYAS;

(SEQ ID NO: 7)
HPIPDSSPLLQFGGQVRQRYLYTDDAQQTEAHLEIREDGTVGGAADQSP

ESLLQLKALKPGVIQILGVKTSRFLCQRPDGALYGSLHFDPEACSFRER

LLEDGYNVYQSEAHGLPLHLPGNKSPHRDPAPRGPARFLPLPGLPPALP

EPPGILAPQPPDVGSSDPLSMVGGSQGRSPSYAS;

(SEQ ID NO: 8)
HPIPDSSPLLQFGGQVRQRYLYTDDAQQTEAHLEIREDGTVGGAADQSP

ESLLQLKALKPGVIQILGVKTSRFLCQRPDGALYGSLHFDPEACSFREL

LLEDGYNVYQSEAHGLPLHLPGNKSPHRDPAPRGPARFLPLPGLPPALP

EPPGILAPQPPDVGSSDPLSMVGPSQGRSPSYAS,
``` and variants thereof.

In some embodiments, the FGF21 receptor agonist domain comprises an amino acid sequence selected from the group consisting of: (SEQ ID NO:5), (SEQ ID NO:6), (SEQ ID NO:7), and (SEQ ID NO:8).

The FGF21 receptor agonist domain is located at the C-terminal end of the ELP domain in order to allow the C-terminal end of the FGF21 receptor agonist domain to interact with its target. In some embodiments, the FGF21 receptor agonist domain is attached to the C-terminus of the ELP domain.

3. Methods of Making the Dual Agonist Fusion Protein

Also disclosed are methods of making the dual agonist fusion proteins. The method can include transforming a bacteria with a recombinant expression vector comprising a first polynucleotide encoding disclosed fusion proteins, and culturing the transformed bacteria to express the disclosed fusion proteins. The culturing temperature of the bacteria can affect the yield of the fusion protein. In some embodiments, culturing is done at less than 37° C. In some embodiments, culturing is done at about 10° C. to less than 37° C.

The first polynucleotide may also encode an alanine-alanine or a glycine-alanine leader sequence attached to the N-terminal end of the fusion protein, which can be cleaved off by, e.g., DPP4 during culturing and/or purification. The polynucleotide encoding the fusion protein can also be adapted to provide higher yields of the fusion protein. For example, the expression vector can further comprise a second polynucleotide encoding a translation initiation domain attached to the N-terminal end of the fusion protein. In some embodiments, the translation initiation domain is attached to the N-terminus of the fusion protein. The translation initiation domain can include a leader sequence and a protease cleavage site, where the protease cleavage site is located between the leader sequence and the fusion protein. In some embodiments, the translation initiation domain comprises MSKGPGENLYFQGA (SEQ ID NO:20). In some embodiments, the translation initiation domain is (SEQ ID NO:20).

A. Polynucleotides

Further provided are polynucleotides encoding the fusion proteins detailed herein. A vector may include the polynucleotide (e.g., first polynucleotide) encoding the fusion proteins detailed herein. To obtain expression of a polypeptide, one may subclone the polynucleotide encoding the polypeptide into an expression vector that contains a promoter to direct transcription, a transcription/translation terminator, and if for a nucleic acid encoding a protein, a ribosome binding site for translational initiation. An example of a vector is pet24. Suitable bacterial promoters are well known in the art. Further provided is a host cell transformed or transfected with an expression vector comprising a polynucleotide encoding a fusion protein as detailed herein. Bacterial expression systems for expressing the protein are available in, e.g., *E. coli, Bacillus* sp., and *Salmonella* (Paiva et al., *Gene* 1983, 22, 229-235; Mosbach et al., *Nature* 1983, 302, 543-545), which is incorporated by reference herein in its entirety. Kits for such expression systems are commercially available. Eukaryotic expression systems for mammalian cells, yeast, and insect cells are well known in the art and are also commercially available. Retroviral expression systems can also be used in the present disclosure.

4. Uses of the Dual Agonist Fusion Proteins

A. Compositions

Also disclosed are uses of the dual agonist fusion proteins. As mentioned above, the fusion protein has temperature dependent phase transition behavior. This can be used advantageously for drug delivery applications. For example, phase transition behavior may be used to form drug depots within a tissue of a subject for controlled release of the fusion protein. Accordingly, disclosed herein are compositions comprising a plurality of fusion proteins, wherein the plurality of fusion proteins assemble into an aggregate above the $T_t$ of the fusion protein. In addition, the composition can further comprise a biologically active agent that can be encapsulated upon the plurality of fusion proteins forming an aggregate. Examples of biologically active agents include, but are not limited to, insulin, sulfonylurea, thiazolidinediones. DPP-4 inhibitors, SGLT2 inhibitors, metformin. PPAR agonists, farnesoid X receptor agonists, and glucose-dependent insulinotropic polypeptide. In some embodiments the biologically active agent is selected from the group consisting of insulin, sulfonylurea, thiazolidinediones, DPP-4 inhibitors, SGLT2 inhibitors, metformin, PPAR agonists, farnesoid X receptor agonists, glucose-dependent insulinotropic polypeptide, and a combination thereof.

i. Administration

The composition comprising the plurality of fusion proteins can be formulated for administration in accordance with standard techniques known to those skilled in the pharmaceutical art. The composition may be prepared for administration to a subject and used in, e.g., methods of treating metabolic diseases as discussed below. Such compositions comprising the fusion protein can be administered in dosages and by techniques well known to those skilled in the medical arts taking into consideration such factors as the age, sex, weight, and condition of the particular subject, and the route of administration.

The composition comprising the plurality of fusion proteins can be administered prophylactically or therapeutically. In prophylactic administration, the compositions can be administered in an amount sufficient to induce a response. In therapeutic applications, the compositions can be administered to a subject in need thereof in an amount sufficient to elicit a therapeutic effect. An amount adequate to accomplish this is referred to as "therapeutically effective dose." Amounts effective for this use will depend on, e.g., the particular composition of the fusion protein regimen administered, the manner of administration, the stage and severity of the disease, the general state of health of the patient, and the judgment of the prescribing physician.

An effective amount of the composition comprising the plurality of fusion proteins as described herein may be given in one dose, but is not restricted to one dose. The administration can be two, three, four, five, six, seven, eight, nine, ten, eleven, twelve, thirteen, fourteen, fifteen, sixteen, seventeen, eighteen, nineteen, twenty, or more, administrations of the composition. Where there is more than one administration in the disclosed methods, the administrations can be spaced by time intervals of one minute, two minutes, three, four, five, six, seven, eight, nine, ten, or more minutes, by intervals of about one hour, two hours, three, four, five, six, seven, eight, nine, ten, 11, 12, 13, 14, 15, 16, 17, 18, 19, 20, 21, 22, 23, 24 hours, and so on. The administrations can also be spaced by time intervals of one day, two days, three days, four days, five days, six days, seven days, eight days, nine days, ten days, 11 days, 12 days, 13 days, 14 days, 15 days, 16 days, 17 days, 18 days, 19 days, 20 days, 21 days, or combinations thereof. The administration of the composition is not limited to dosing intervals that are spaced equally in time, but encompass doses at non-equal intervals, such as a priming schedule of administration at 1 day, 4 days, 7 days, or 25 days.

A dosing schedule of, for example, once/week, twice/week, three times/week, four times/week, five times/week, six times/week, seven times/week, once every two weeks, once every three weeks, once every four weeks, once every five weeks, and the like, is available for the composition. The dosing schedules can encompass dosing for a total period of time, for example, one week, two weeks, three weeks, four weeks, five weeks, six weeks, two months, three months, four months, five months, six months, seven months, eight months, nine months, ten months, eleven months, or twelve months.

Provided are cycles of the above dosing schedules. The cycle can be repeated about, e.g., every seven days; every 14 days; every 21 days; every 28 days; every 35 days; every 42 days; every 49 days; every 56 days; every 63 days; every 70 days; and the like. An interval of non-dosing can occur between a cycle, where the interval can be about, e.g., seven days; 14 days; 21 days; 28 days; 35 days; 42 days; 49 days; 56 days; 63 days; 70 days; and the like.

The composition comprising the plurality of fusion proteins may further include a pharmaceutically acceptable carrier. As used herein, "pharmaceutical acceptable carrier" refers to a physiologically acceptable diluent including, but not limited to water, phosphate buffered saline, or saline. Acceptable carriers, excipients, or stabilizers are nontoxic to subjects at the dosages and concentrations employed, and can include buffers such as phosphate, citrate, and other organic acids; antioxidants including ascorbic acid, BHA, and BHT; low molecular weight (less than about 10 residues) polypeptides; proteins, such as serum albumin, gelatin or immunoglobulins; hydrophilic polymers, such as polyvinylpyrrolidone, amino acids such as glycine, glutamine, asparagine, arginine, or lysine; monosaccharides, disaccharides, and other carbohydrates including glucose, mannose, or dextrins; chelating agents such as EDTA; sugar alcohols such as mannitol or sorbitol; salt-forming counter-ions such as sodium; and/or nonionic surfactants such as Tween, Pluronics, or PEG. The compositions including a pharmaceutically acceptable carrier optionally may be sterile. The compositions may be frozen or lyophilized for storage and reconstituted in a suitable sterile carrier prior to use. The compositions having a pharmaceutically acceptable carrier can be generated in accordance with conventional techniques described in, e.g., *Remington: The Science and Practice of Pharmacy*, 21st Edition, Lippincott Williams & Wilkins, Philadelphia, Pa. (2001), which is incorporated by reference herein in its entirety.

The composition comprising the plurality of fusion proteins can be administered by methods known in the art as described in Donnelly et al. (*Ann. Rev. Immunol.* 1997, 13, 617-648); Felgner et al. (U.S. Pat. No. 5,580,859, issued Dec. 3, 1996); Felgner (U.S. Pat. No. 5,703,055, issued Dec. 30, 1997); and Carson et al. (U.S. Pat. No. 5,679,647, issued Oct. 21, 1997), all of which are incorporated by reference herein in their entirety. The composition comprising the plurality of fusion proteins can be delivered via a variety of routes. Typical delivery routes include parenteral administration, e.g., intradermal, intramuscular or subcutaneous delivery. Other routes include oral administration, intranasal, intravaginal, transdermal, intravenous, intraarterial, intratumoral, intraperitoneal, and epidermal routes. In some embodiments, the composition is administered intraperitoneally or subcutaneously to the subject.

The composition comprising the plurality of fusion proteins according to the present disclosure may also be administered with one or more additional drugs/compounds. Methods for co-administration with an additional drug/compound are well known in the art (Hardman, et al. (eds.) (2001) Goodman and Gilman's The Pharmacological Basis of Therapeutics, 10th ed., McGraw-Hill, New York, N.Y.; Poole and Peterson (eds.) (2001) Pharmacotherapeutics for Advanced Practice: A Practical Approach, Lippincott, Williams & Wilkins, Phila., Pa.; Chabner and Longo (eds.) (2001) Cancer Chemotherapy and Biotherapy, Lippincott, Williams & Wilkins, Phila., Pa.), all of which are incorporated by reference herein in their entirety.

B. Methods of Treating Metabolic Diseases

Also disclosed herein are methods of treating metabolic diseases using the compositions and fusion proteins. The method of treating a metabolic disease in a subject in need thereof can include administering to the subject an effective amount of the composition comprising the plurality of fusion proteins. The above description of the fusion protein and compositions thereof can also be applied to the methods of treating metabolic diseases.

Examples of metabolic diseases include, but are not limited to, obesity, type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia. In some embodiments, the metabolic disease is selected from the group consisting of obesity, type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, and a combination thereof. In some embodiments, the metabolic disease is type 2 diabetes mellitus.

As mentioned above, the composition can comprise a plurality of fusion proteins that can form an aggregate above the $T_t$ of the fusion proteins. For example, when the fusion protein has a $T_t$ below body temperature, it can form an aggregate upon administration to the subject. The aggregate formation can allow the fusion protein to be released over an extended period of time, such as for about 12 hours to about 1 year following administration. In some embodiments, the composition releases the fusion protein following administration for greater than 1 day, greater than 3 days, greater than 10 days, greater than 1 month, or greater than 6 months. In some embodiments, the composition releases the fusion protein following administration for less than 1 year, less than 9 months, less than 6 months, less than 1 month, or less than 2 weeks. In some embodiments, the composition releases the fusion protein following administration for greater than 3 days.

The fusion protein and compositions thereof can be used advantageously in the treatment of metabolic diseases, such as type 2 diabetes mellitus. For example, administration of the composition can result in the subject having at least one of decreased blood glucose level, decreased body fat, increased insulin production, decreased hemoglobin A1c values, decreased circulating fatty acids, decreased liver fat content, decreased liver inflammation, and/or decreased liver fibrosis compared to a subject not receiving the administration of the composition. In some embodiments, the administration of the composition can result in the subject having an about 10% to about 90% decrease in blood glucose levels compared to a subject not receiving the administration of the composition. The decrease in blood glucose levels can be over a course of 1 to 7 days following administration. In some embodiments, the administration of the composition can result in the subject having an about 1% to about 25% decrease in body fat compared to a subject not receiving the administration of the composition. The decrease in body fat can be measured within 1 to 7 days following administration.

The above description for administration of the fusion proteins, aggregates thereof, and compositions thereof can also be applied to the methods of treating metabolic diseases.

5. Examples

Example 1

Expression of Dual Agonist Fusion Proteins

Materials & Methods

Expression Vector Synthesis: The nucleotide sequence encoding the 182 amino acid murine wild type FGF21 protein, minus the signal peptide, was codon optimized for *E. coli* expression and ligated into a pET-24a+ vector modified for seamless fusion of genes. Point mutations for amino acid substitutions L99R, P172G, and L173S were introduced to enhance protein stability, and the mutated Fgf2 gene was fused at the 5' end to a gene encoding an ELP, following a previously reported seamless cloning strategy. The ELP of 120 repeats of a (Val-Pro-Gly-$X_{aa}$-Gly) pentapeptide—where $X_{aa}$ signifies a 4:1 ratio of Val:Ala—and the final vector encoded the polypeptide fusion "ELP-FGF21."

The analog included GLP-1 (7-37) with A8G, G22E, R36A amino acid substitutions, as well as an AA leader at the N terminus to enable activation through cleavage by Dipeptidyl-Peptidase 4 (DPP4). Following a similar process as for Fgf21, the nucleotide sequence encoding the resulting 32 amino acid GLP-1 peptide was codon optimized for *E. coli* expression, ligated into the modified pET-24a+ vector, and fused at the 3' end to the gene encoding the ELP described above. The final vector encoded the polypeptide fusion "GLP1-ELP."

For synthesis of the vector encoding the GLP-1/FGF21 dual agonist drug, the gene encoding GLP1-ELP was fused at the 3' end to the mutated Fgf21 gene following a seamless cloning strategy (McDaniel, J. R., J. A. MacKay, F. G. Quiroz, and A. Chilkoti, *Recursive Directional Ligation by Plasmid Reconstruction Allows Rapid and Seamless Cloning of Oligomeric Genes*. Biomacromolecules, 2010. 11(4): p. 944-952, which is incorporated by reference in its entirety), and the final vector encoded the polypeptide fusion referred to as "GLP1-ELP-FGF21."

Protein Expression & Purification: The GLP1 analog includes GLP1 (7-37) with A8G, G22E, R36A amino acid substitutions, as well as an AA leader at the N terminus to enable activation through cleavage by DPP4. Following a similar process as described for assembling the ELP-FGF21-encoding vector, the nucleotide sequence encoding the 32 amino acid GLP1 peptide was codon optimized for *E. coli* expression, ligated into the modified pET-24a+ vector, and fused at the 3' end to a gene encoding an ELP. The resulting vector encoded a GLP1-ELP polypeptide fusion, with the ELP varying depending on (VPGX$_{aa}$G) pentapeptide repeats and the $X_{aa}$ guest residue composition. The gene encoding each GLP1-ELP construct was then fused at the 3' end to the mutated Fgf21 gene. The final vector encoded the polypeptide fusions referred to as "GLP1-ELP-FGF21."

GLP1-ELP-FGF21-encoding expression vectors were transformed into either SHuffle cells or Ultra BL21 (DE3) cells. Expression and purification were carried out as described for ELP$_{100\%Val,60}$-FGF21 with the following exception: pre- and post-induction temperatures were experimentally varied. The final purified fusion products were visualized on Coomassie-stained SDS-PAGE gels. For production of the GLP1-ELP$_{40\%Ala,160}$ control, the ELP-encoding expression vector was transformed into Ultra BL21 (DE3) cells and expression and ITC purification were carried out.

A starter culture containing 50 mL of 55 g/L terrific broth (TB) plus 250 µM kanamycin was inoculated and grown overnight at 37° C. with orbital shaking at 250 rpm. The starter culture was centrifuged, resuspended in TB, and used to inoculate three 1-L volumes of TB plus kanamycin in 6 L Erlenmeyer flasks. The flasks were cultured at 30° C. with orbital shaking at 200 rpm until they reached an OD$_{600}$ of 2.0. Protein expression was then induced by addition of 250 µM IPTG. The culturing temperature was reduced to 16° C., and growth was allowed to proceed for an additional 18 h.

Bacterial cultures were centrifuged at 4° C. for 10 min at 3365 rcf and resuspended in cold PBS. Cell membranes were disrupted via sonication (Q500 sonicator, QSonica, Newtown, Conn.), and pulsed at 10 s on and 40 s off for a total sonication time of 90 s. DNA was precipitated by addition of 10% polyethylenimine, and cell lysates were separated into soluble and insoluble fractions by centrifugation at 4° C. for 10 min at 23,645 rcf. The soluble fraction was brought to room temperature, and the ELP fusion protein was purified from solution by ITC. In this process, the phase transition of the ELP fusion protein was triggered by addition of 0.2 M $(NH_4)_2SO_4$, producing a turbid suspension due to coacervation of the ELP fusion. The suspension was centrifuged at 25° C. for 15 min at 23,426 rcf; this step is referred to as a "hot spin." The supernatant was discarded and the pellet was resolubilized in PBS at 4° C. with 25 rpm gentle rotation (R4045 Roto-Bot Programmable Rotator, Benchmark Scientific, Sayreville, N.J.). The resulting solution was centrifuged at 4° C. for 5 min at 18,407 rcf to pellet insoluble contaminants, and the supernatant was reserved; this step is referred to as a "cold spin."

The ITC process was repeated by warming the solution to room temperature, adding $(NH_4)_2SO_4$ to trigger the phase transition, centrifuging at 25° C. for 8 min at 18,407 rcf to pellet the ELP fusion protein, resolubilizing the pellet in PBS at 4° C. with gentle rotation, and centrifuging at 4° C. for 5 min at 18,407 rcf. Three total rounds of ITC were necessary to isolate the fusion from contaminants, and final products were visualized on a Coomassie- or CuCl$_2$-stained SDS-PAGE gel.

Results

The GLP1/FGF21 dual agonist was designed as a head-to-tail polypeptide fusion protein, with GLP1 located at the N terminus and FGF21 at the C terminus (FIG. 1). This orientation provided GLP1 a solvent-exposed N terminus and FGF21 an exposed C terminus, both important for activating their respective receptors, while the linear architecture enabled facile synthesis and scale-up in a bacterial expression system. Between GLP1 and FGF21 was fused an ELP to serve a two-fold role as both a linker and a circulation-enhancing scaffold. GLP1-ELP-FGF21 fusions employed mutations in FGF21 to promote protein stability and amino acid substitutions in GLP1 to stabilize the alpha helix and protect from proteolytic cleavage. GLP1 also incorporated a di-alanine leader to facilitate recombinant expression before endogenous removal by DPP4 to expose an active N terminus. A library of dual agonist constructs was assembled in which the ELP varied in length and composition (Table 1)—with the goal of producing fusion proteins of variable $T_t$s to allow for identification of constructs with optimal properties for in vivo depot formation.

Expression yields of GLP1-ELP-FGF21 fusions were poor (Table 1). We have observed that recombinant expression of fusion proteins with GLP1 at the N terminus have low yields at reduced culturing temperatures (<37° C.). However, reduced temperatures are important when expressing fusion proteins incorporating FGF21 to promote proper protein folding. Thus, we were left with the option of varying the ELP composition and the bacterial strain and testing resulting expression levels. The best yields were observed for the GLP1-ELP-FGF21 fusion incorporating ELP$_{20\%Ala,120}$. GLP1-ELP$_{20\%Ala,120}$-FGF21 was produced in SHuffle cells at reduced culturing temperatures and purified by the non-chromatographic ITC purification method. A 72 kDa band associated with the full-length fusion product was visible by SDS-PAGE throughout the purification process, and ITC purification alone was sufficient to isolate the dual agonist from contaminants.

was separated from GLP1 by a single alanine. Cleavage by TEV protease should thereby leave a GA leader, which will then serve as a substrate for cleavage by DPP4. Oligonucleotides encoding the GLP1 with the N-terminal leader were codon optimized for *E. coli* expression, annealed, and ligated into the modified pET-24a+ vector. The gene encoding Leader-GLP1 was fused at the 3' end to the gene encoding ELP$_{20\%Ala,120}$-FGF21 following the previously reported seamless cloning strategy, and the final vector encoded the polypeptide fusion "Leader-GLP1-ELP$_{20\%Ala,120}$-FGF21"- or simply "Leader-GLP-ELP-FGF21".

Protein expression and purification: Leader-GLP1-ELP-FGF21 was expressed and purified as described for leaderless GLP1-ELP-FGF21, however Leader-GLP1-ELP-FGF21 was resuspended after its final round of ITC in TEV protease reaction buffer, substituting 3 mM glutathione for

TABLE 1

GLP1-ELP-FGF21 construct compositions, culturing conditions, and associated expression yields.

| Construct name | (VPGX$_{aa}$G) repeats | X$_{aa}$ composition | E. coli strain | Temperature (pre/post induction) | Yield (mg/L) |
|---|---|---|---|---|---|
| GLP1-ELP$_{20\% Ala, 120}$-FGF21 | 120 | 20% alanine, 80% valine | Shuffle | 25° C./16° C. | 3-5 |
| GLP1-ELP$_{20\% Ala, 120}$-FGF21 | 120 | 20% alanine, 80% valine | Shuffle | 37° C./30° C. | <1 |
| GLP1-ELP$_{20\% Ala, 120}$-FGF21 | 120 | 20% alanine, 80% valine | BL21 | 25° C./16° C. | <1 |
| GLP1-ELP$_{20\% Ala, 80}$-FGF21 | 80 | 20% alanine, 80% valine | Shuffle | 25° C./16° C. | <1 |
| GLP1-ELP$_{100\% Val, 120}$-FGF21 | 120 | 0% alanine, 100% valine | Shuffle | 25° C./16° C. | 1-3 |
| GLP1-ELP$_{100\% Val, 60}$-FGF21 | 60 | 0% alanine, 100% valine | Shuffle | 25° C./16° C. | 1-3 |
| GLP1-ELP$_{30\% Ala, 80}$-FGF21 | 80 | 30% alanine, 70% valine | Shuffle | 25° C./16° C. | <1 |
| GLP1-ELP$_{30\% Ala, 80}$-FGF21 | 80 | 30% alanine, 70% valine | BL21 | 25° C./16° C. | 0 |
| GLP1-ELP$_{50\% Ala, 120}$-FGF21 | 120 | 50% alanine, 50% valine | Shuffle | 25° C./16° C. | 0 |
| GLP1-ELP$_{40\% Ala, 160}$-FGF21 | 160 | 40% alanine, 60% valine | Shuffle | 25° C./16° C. | <1 |

GLP1 expresses on a wide variety of ELPs, however expression yields of GLP1-ELP are universally lower compared to ELP-FGF21. GLP1-ELP yields are further diminished at the reduced culturing temperatures necessary for proper FGF21 folding. Meanwhile, ELP-FGF21 expresses in large quantities, but only with a selective number of ELPs. Thus, GLP1-ELP-FGF21 expressed best on one ELP and in very small quantities. Nevertheless, a full-length dual agonist fusion protein was produced recombinantly and purified by ITC. GLP1-ELP$_{20\%Ala,120}$-FGF21 was capable of potently activating both the GLP1 and FGF21 receptors, therefore exhibiting dual agonism in vitro.

Example 2

Increasing GLP1-ELP-FGF21 Expression Yields

Materials & Methods

Expression vector synthesis: The GLP1 analog consisted of GLP1 (7-37) with A8G, G22E, R36A amino acid substitutions. A leader was added to the N terminus of GLP1 comprised of an expression-enhancing sequence (MSKGPG) (SEQ ID NO:21) followed by a TEV protease cleavage sequence (ENLYFQG) (SEQ ID NO:22), which dithiothreitol. The final fusion product was visualized on a CuCl$_2$-stained SDS-PAGE gel. Conventional GLP1-ELP-FGF21 (expressed without a translation-enhancing leader) and GLP1-ELP were produced as described above.

Removal of the translation-enhancing sequence: Leader-GLP1-ELP-FGF21 was incubated for 16 h at 4° C. with TEV protease (Sigma) at a 1:100 protease:Leader-GLP1-ELP-FGF21 mass ratio. After the reaction, the phase transition of the ELP was triggered by addition of 0.2 M (NH$_4$)$_2$SO$_4$ and the resulting suspension containing immiscible GLP1-ELP-FGF21, as well as miscible cleaved Leader and TEV protease was centrifuged 15 min at 25° C. The pellet containing GLP1-ELP-FGF21 was resuspended in PBS.

cAMP production assay: Following removal of the Leader from GLP1-ELP-FGF21, GLP1 in vitro activity was measured through the cell-based assay described herein. As with fusions employing the previous GLP1 analog version, the dual agonist was first incubated overnight at 4° C. with DPP4 at a 1:500 DPP4:GLP1 molar ratio to expose an active N terminus. This time, however, the intended cleavage substrate was a GA leader instead of the AA leader. Cells were treated with serial dilutions of GLP1-ELP-FGF21 (after removal of the expression-enhancing sequence), conventional GLP1-ELP-FGF21 (expressed without a translation-enhancing leader), GLP1-ELP, or native human GLP1 (7-37) (ProSpec) and resulting luminescence was measured as previously described. Data were fit to a three-parameter dose-response curve to determine $EC_{50}$s.

Results

Design and production of expression-enhanced GLP1-ELP-FGF21: A vector was assembled that encoded the dual agonist along with a leader sequence that served three purposes: 1) enhance expression, 2) allow for removal of the expression enhancer by protease cleavage, and 3) allow for removal of the protease cleavage scar by endogenous DPP4.

Expression of the dual agonist was robustly enhanced by addition of the MSKGPG leader sequence. A 73 kDa band associated with Leader-GLP1-ELP-FGF21 was visible in the bacterial cell lysate and persisted in the soluble fractions, with final protein yields surpassing 50 mg/L following ITC purification.

Figure 2:
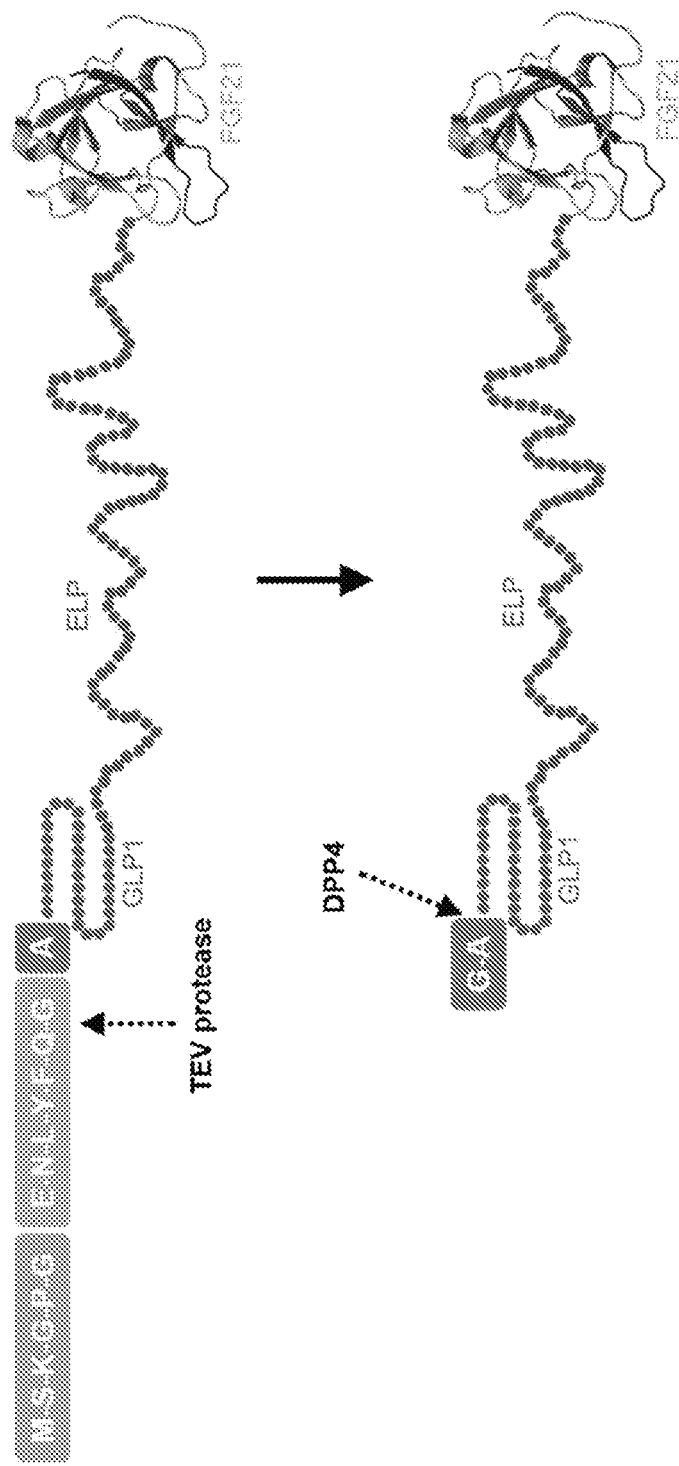
FIG. 2 is a schematic for improving bacterial expression of dual agonist fusion proteins.

Expression-enhanced GLP1-ELP-FGF21 is partially active: Approximately 4 mg purified Leader-GLP1-ELP-FGF21 was reacted with TEV protease overnight for removal of all leader sequence residues except for glycine-alanine (FIG. 2). The ELP phase change was then triggered by addition of salt, and the dual agonist was spun out of the reaction and resuspended. Leader-GLP1-ELP-FGF21 was then incubated overnight with DPP4 for removal of the last two residues to expose the N-terminal histidine on GLP1, and GLP1R agonism was assayed in vitro. As observed previously, fusion of GLP1 to an ELP or to ELP-FGF21 increased the $EC_{50}$~10-fold (3.1±0.5 µM compared to 29.5±5.0 µM for GLP1-ELP$_{20\%Ala,120}$ and 23.9±5.7 µM for conventionally expressed dual agonist). Unfortunately, the incorporation and removal of an expression-enhancing leader increased the dual agonist $EC_{50}$ yet an additional order of magnitude (212±46 pM), suggesting incomplete leader removal.

Described here was a proof-of-concept study to investigate the possibility of improving dual agonist yields. We were successful in robustly increasing expression, with product yields increasing from 5 to 50 mg/L, which is a quite meaningful difference in the field of recombinant protein production. With optimization, we should be able to increase the efficiency of leader sequence removal to restore full GLP1 receptor binding capability. One disadvantage of this design is that both cleaved and uncleaved Leader-GLP1-ELP-FGF21 are spun out of solution and retained after the reaction. Thus, any dual agonist that failed to successfully react with TEV protease—and is therefore incapable of binding the GLP1R—will be carried downstream to the DPP4 reaction and the GLP1 activity assay where it will manifest as an increase in $EC_{50}$. The TEV protease reaction must therefore be optimized for near 100% cleavage efficiency, which will require experimenting with different ratios of protease:Leader-GLP1-ELP-FGF21. It should be noted that the TEV protease employed in this pilot study may have been only partially functional.

Example 3

In Vitro Characterization of Dual Agonist Fusion Proteins

Materials & Methods

Endotoxin purification and testing: All proteins were endotoxin-purified using Acrodisc Units (Pall Corporation, Port Washington, N.Y.), and resulting endotoxin levels were tested using the Endosafe Nexgen-PTS spectrophotometer (Charles River Laboratories, Wilmington, Mass.).

ERK phosphorylation assay: For quantitative evaluation of FGF21 in vitro activity, a HEK293 cell line was previously generated that stably expresses murine β-Klotho and FGF receptor 1 and thereby enables FGF21-mediated ERK1/2 phosphorylation. Cells were seeded at $5\times10^4$ cells/cm$^2$ and adhered overnight. After serum starvation for 6 h, cells were treated with serial dilutions of FGF21-containing fusion proteins or native mouse FGF21 (ProSpec-Tany, East Brunswick, N.J.) for 5 min. Cells were lysed and assessed for phospho-ERK1/2 and total ERK1/2 content using the AlphaLISA Surefire Ultra Assay Kits (PerkinElmer) and the EnSpire Alpha Plate Reader (PerkinElmer). Phospho-ERK1/2 was normalized to total ERK1/2 and fit to a three-parameter dose-response curve to determine $EC_{50}$s using GraphPad Prism 8 software (La Jolla, Calif.).

cAMP production assay: GLP-1 in vitro activity was quantified by a cell-based assay that utilizes a HEK293 cell line that stably expresses the GLP-1R and a cAMP-inducible luciferase reporter. Cells were seeded at $1\times10^5$ cells/cm$^2$ into 96 well plates and adhered overnight. Concurrently, GLP-1-containing fusions were incubated overnight at 4° C. with DPP4 (ProSpec) at a 1:500 DPP4:GLP-1 molar ratio to cleave the AA leader and expose the active N terminus of GLP-1. In the morning, cell media was replaced with induction buffer (129 mM NaCl, 4.8 mM KCl, 1.2 mM MgSO$_4$, 1.2 mM KH$_2$PO$_4$, 2.5 mM CaCl$_2$, 5 mM NaHCO$_3$, 10 mM HEPES, 0.5% BSA, and 50 µM 3-isobutyl-1-methylxanthine). Cells were treated with serial dilutions of GLP-1-containing fusion proteins or native human GLP-1 (7-37) (ProSpec) in induction buffer for 5 h, at which point supernatants were removed and replaced with Bright-Glo (Promega, Madison, Wis.). Luminescence of the supernatant samples were measured on a Victor X3 Plate Reader (Perkin Elmer) and normalized to zero drug treatment control wells. Data were fit to a three-parameter dose-response curve to determine $EC_{50}$s using GraphPad Prism 8 software.

Phase behavior characterization: The lower critical solution temperature (LCST) phase transition behavior of ELP fusion proteins was evaluated by monitoring the OD$_{350}$ of solutions in PBS as a function of temperature on a Cary 300 UV-visible spectrophotometer equipped with a multicell thermoelectric temperature controller (Agilent Technologies, Santa Clara, Calif.). Heating and cooling were set to a rate of 1° C./min. The $T_t$ was defined as the temperature at which the optical density reached 50% of its maximal value.

Results

Figure 3A:
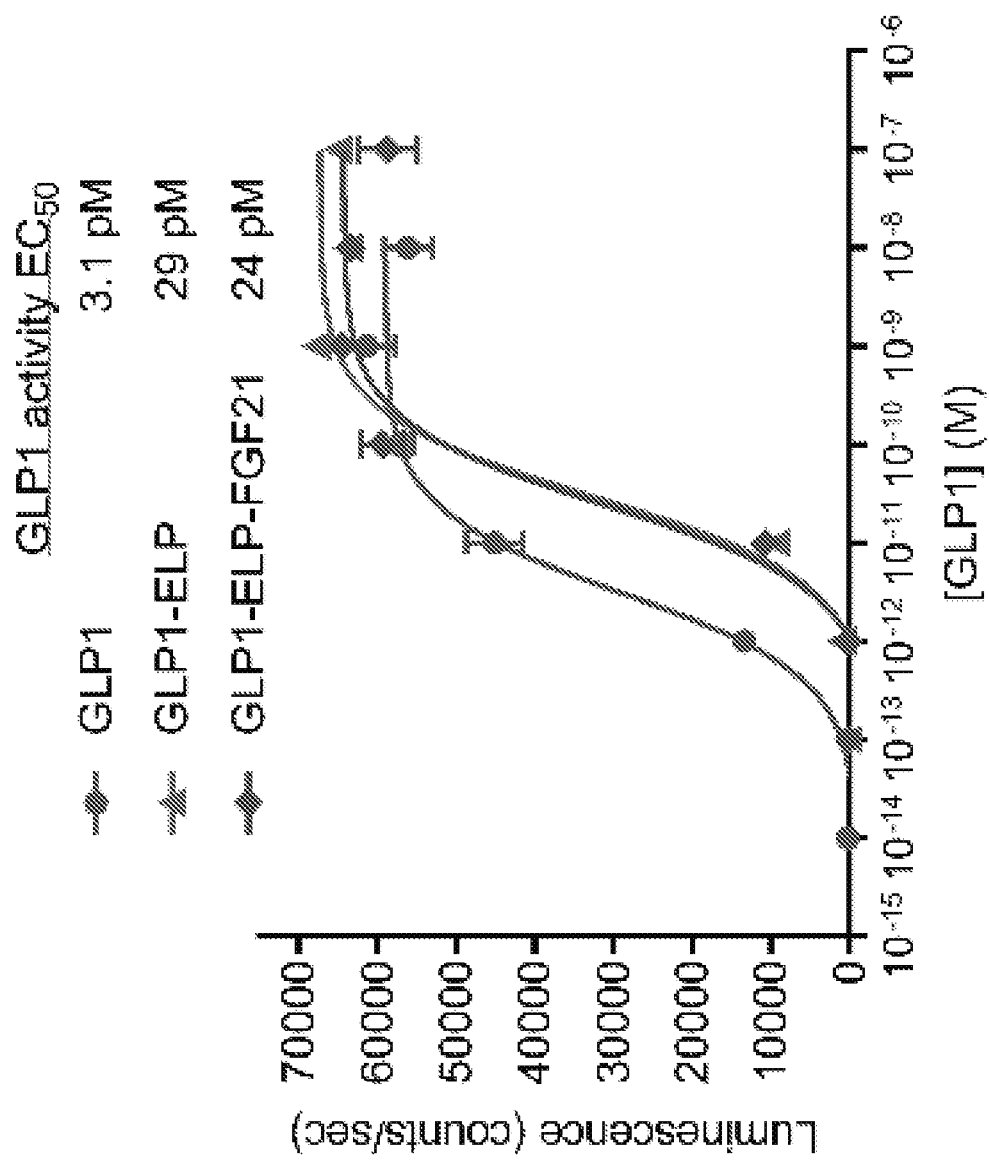
(FIG. 3A and FIG. 3B) In vitro GLP-1 and FGF21 activity assays for GLP1-ELP-FGF21. GLP-1R agonism (FIG. 3A) was measured by quantifying cAMP production in HEK293 cells stably expressing the GLP-1R and a cAMP-inducible luciferase reporter. Cells were stimulated 5 h with GLP1-ELP-FGF21, the GLP1-ELP single agonist control, or native GLP-1. FGF21 receptor agonism (FIG. 3B) was measured by quantifying ERK1/2 phosphorylation in HEK293 cells stably expressing FGFR1 and βKlotho, and normalizing phospho-ERK1/2 to total ERK1/2. Cells were stimulated 5 min with GLP1-ELP-FGF21, the ELP-FGF21 single agonist control, or native FGF21. Data are presented as mean±SEM, n=3.
Figure 3B:
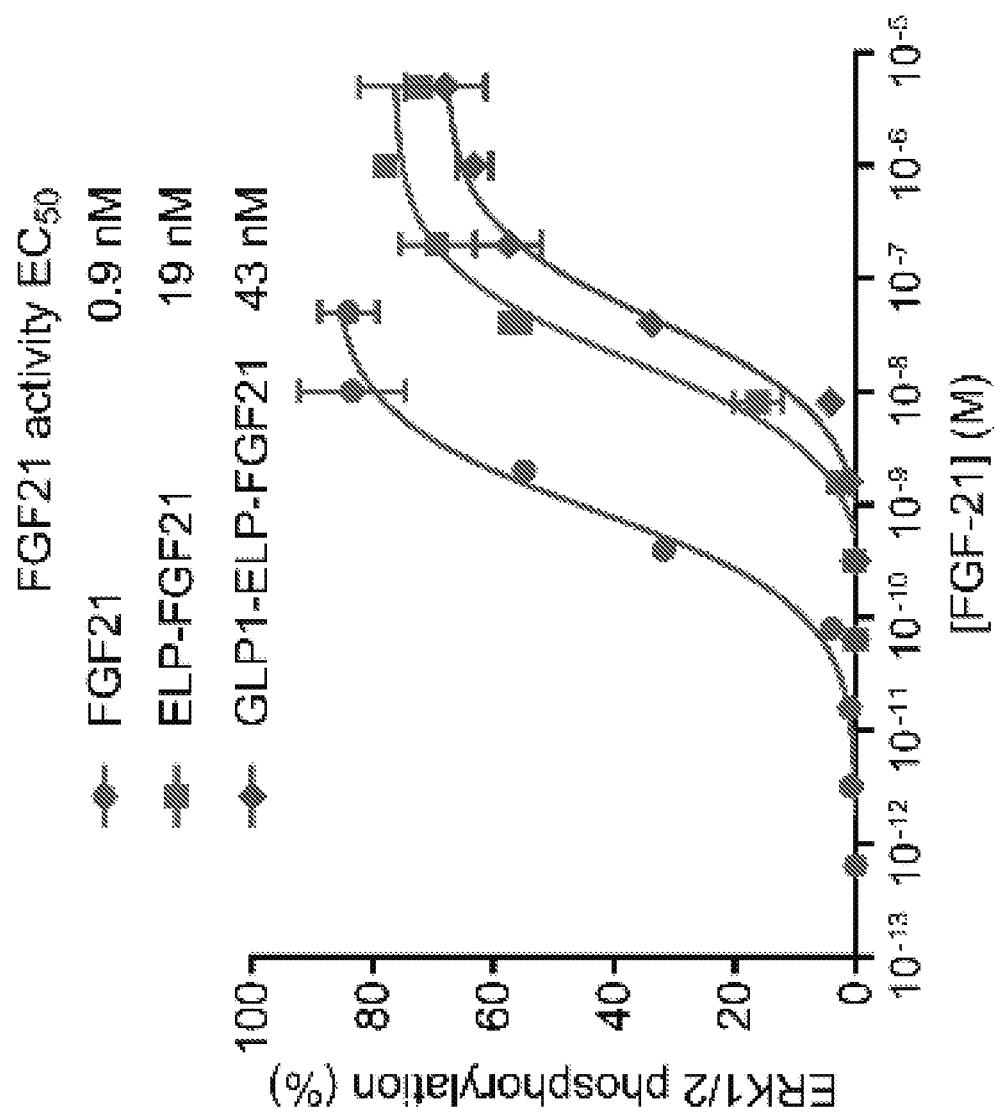
Figure 11:
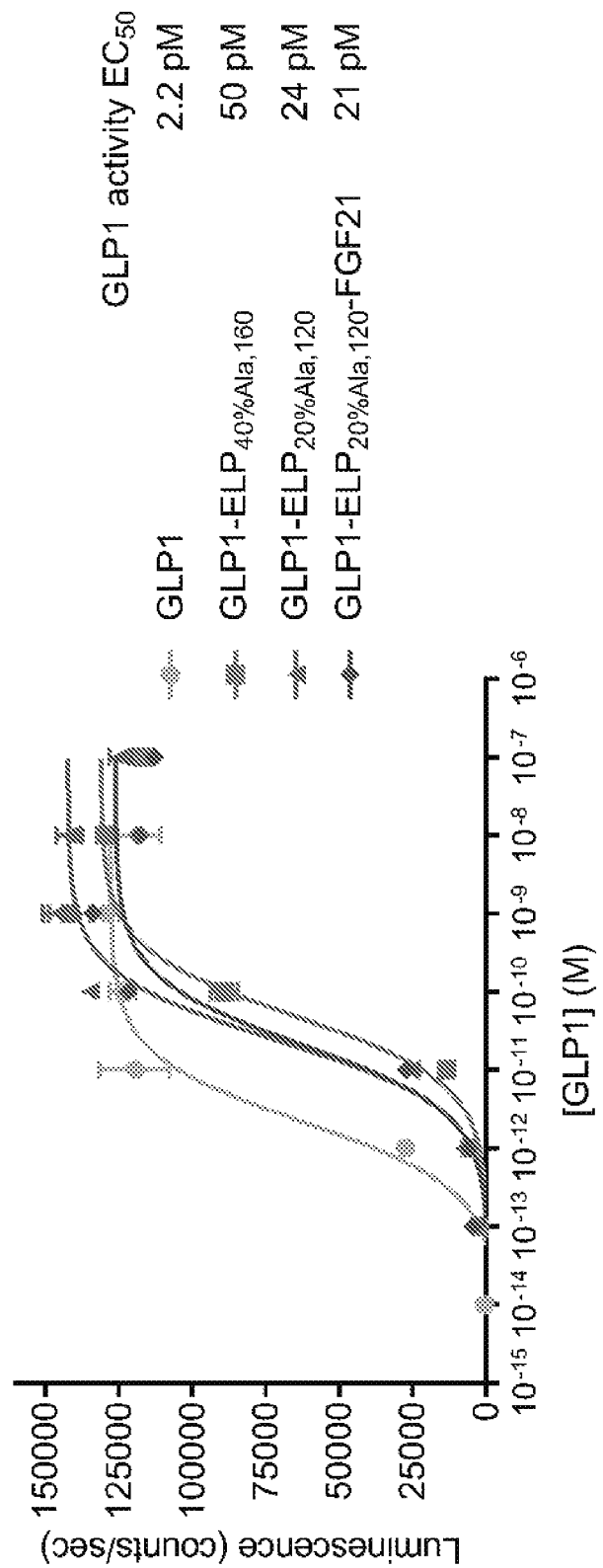
FIG. 11 is a plot of in vitro activity of GLP1-ELP single agonist control at the GLP1R. GLP1-ELP$_{20\%Ala,120}$ incorporates an ELP of 120 VPGX$_{aa}$G pentapeptide repeats with a 2:8 ratio of alanine:valine at the X$_{aa}$ residue, which matches the ELP employed in the GLP1-ELP-FGF21 dual agonist. GLP1-ELP$_{40\%Ala,160}$ incorporates an ELP of 160 VPGX$_{aa}$G repeats with a 4:6 ratio of alanine:valine at the X residue. GLP1R agonism was measured by quantifying cAMP production following 5 h stimulation of HEK293 cells stably expressing the GLP1R and a cAMP-inducible luciferase reporter. Data are presented as means±SEM, n=3. $EC_{50}$s were determined by fitting a three-parameter dose-response curve.

GLP1-ELP-FGF21 has dual agonism at the GLP-1 and FGF21 receptors: The half maximal effective concentration ($EC_{50}$) for the FGF21 and GLP-1 dual agonist components were measured using in vitro activity assays in cells stably expressing either the GLP-1R or the FGF21 receptor complex. Fusion of GLP-1 to an ELP increased GLP-1R $EC_{50}$ approximately ten-fold (FIG. 3A), while the GLP-1R $EC_{50}$ of GLP1-ELP-FGF21 (23.9±5.7 µM) was not different from that of GLP1-ELP (29.5±5.0 µM). Fusion of FGF21 to an ELP increased the FGF21 receptor $EC_{50}$ approximately twenty-fold (FIG. 3B). The dual agonist had a marginally greater FGF21 receptor $EC_{50}$ (43.2±8.4 nM) compared to ELP-FGF21 (18.8±4.5 nM), but this difference was not statistically significant (p>0.05). Together, these data demonstrate that simultaneous presentation of GLP-1 and FGF21 on an ELP does not significantly impact the activity of each drug. See also FIG. 11 for agonist activity.

Figure 3C:
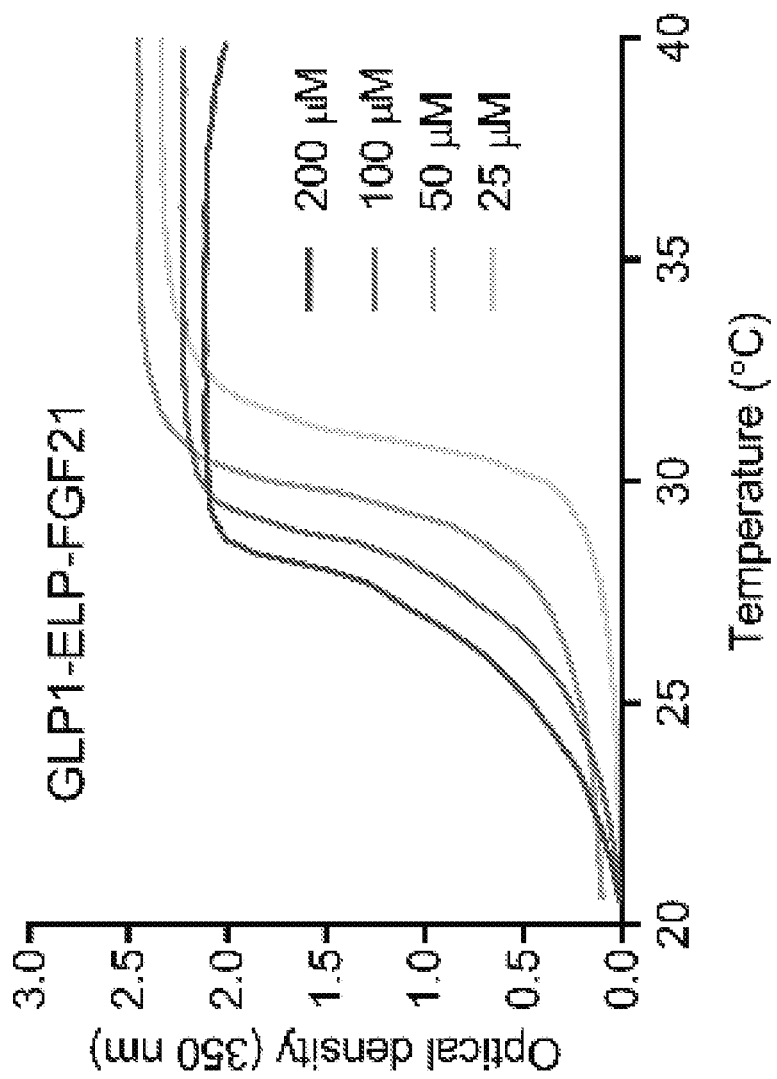
(FIG. 3C, FIG. 3D, and FIG. 3E) LCST phase transition behavior of GLP1-ELP-FGF21.
Figure 3D:
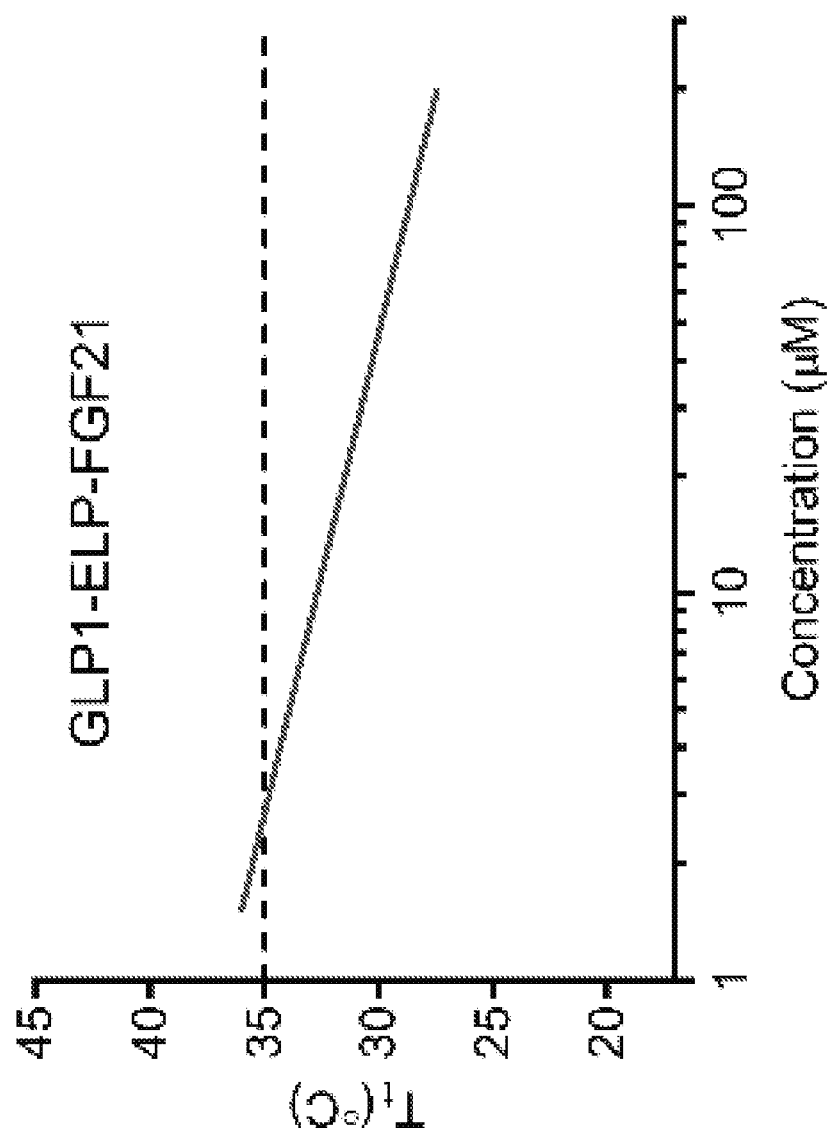
Figure 3E:
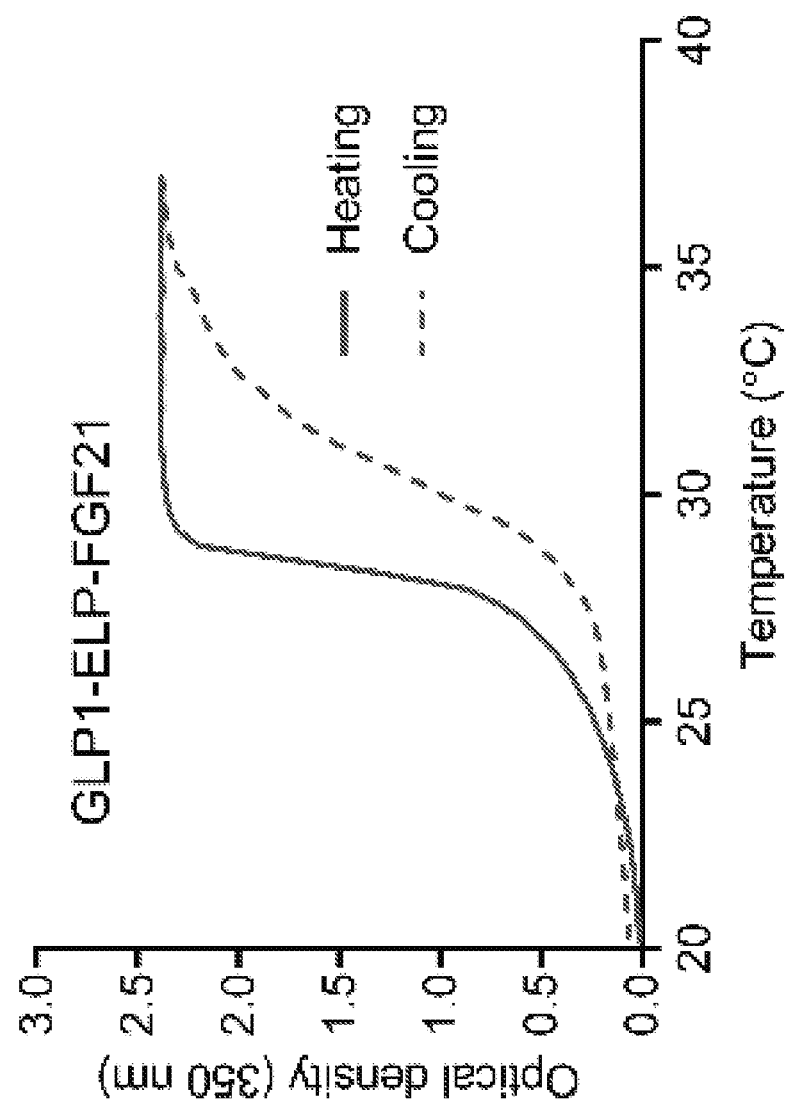

Phase transition behavior of GLP1-ELP-FGF21 is suitable for depot formation: The LCST phase transition behavior of the GLP1-ELP-FGF21 fusion was evaluated by monitoring the optical density of a fusion protein solution as a function of temperature, defining the $T_t$ as the temperature at which the solution becomes turbid. A target $T_t$ range between 27° C. and 32° C. was chosen to be suitable for depot formation—triggered by body heat—with ELP-drug release kinetics appropriate for once weekly dosing. An ELP fusion with a $T_t<27°$ C. forms an excessively stable coacervate that exhibits poor drug absorption, while a fusion with a $T_t$ near 35° C. (the temperature of the s.c. space) exhibits a bolus-like release profile. GLP1-ELP-FGF21 was confirmed to have LCST phase change behavior, with a $T_t$ between 27 and 29° C. at the injection-relevant concentration range of 100-200 µM (FIG. 3C). The $T_t$ was concentration-dependent (FIG. 3D), and the dual agonist phase change behavior was reversible (FIG. 3E). The reversibility and inverse dependence of $T_t$ on fusion protein concentration are attributes to the controlled release capabilities of ELP-based drug depots: as fusion unimers at the depot margin are diluted, their $T_t$ rises above body temperature, thereby reversing the LCST phase transition and allowing release of ELP-drug molecules from the coacervate.

Example 4

In Vivo Characterization of Dual Agonist Fusion Proteins

Materials & Methods

Animals: In vivo studies were conducted in accordance with the AAALAC-accredited Duke Institutional Animal Care and Use Committee. 5-week-old B6.BKS(D)-Lepr$^{db}$/J ("db/db") male mice were purchased from Jackson Laboratory (Bar Harbor, Me.) and maintained on a 12 h/12 h light/dark cycle with ad libitum access to food (LabDiet 5053) and water. Animals were group-housed and allowed 1-week acclimation before stratification into control and treatment groups based on baseline ambient blood glucose levels and body weights.

ELP fusion treatments: ELP fusion proteins were administered at 150-200 µM concentration via injection into the subcutaneous (s.c.) space on the hind flank. Animals received either a single s.c. injection for short-term studies or weekly s.c. injections for chronic studies. The "1:1 mixture" treatment group received a single injection containing an equimolar mixture of GLP1-ELP and ELP-FGF21, with the indicated dose referring to the dose of each respective fusion in the mixture. Vehicle control refers to PBS.

Ambient blood glucose measurements: Blood glucose levels were measured from a tail vein puncture with an AlphaTRAK 2 Blood Glucose Meter (Zoetis, Parsippany-Troy Hills, N.J.) every 24 h, 1-2 h following onset of the light cycle. Data are presented as either raw values, or as a magnitude change from a mean baseline established from three independent measurements collected prior to treatment. Areas under the curve (AUCs) were calculated with GraphPad Prism 8 software using the trapezoidal rule and setting a Y=0 baseline. Treatment group AUCs were normalized to the vehicle-treated group where indicated.

Glucose tolerance test: Animals were fasted at the onset of the light cycle for 5 h with ad libitum access to water, then injected via intraperitoneal (i.p.) with 0.75 g/kg D-glucose. Blood glucose levels were measured from a tail snip with a Contour Blood Glucose Meter (Bayer, Leverkusen, Germany) at t=0 (before glucose injection), 10, 20, 30, 60, 90, and 120 min. AUCs were calculated as described for ambient blood glucose measurements.

Extended fast blood glucose measurements: Animals were fasted for 16 h starting at 4:00 PM with ad libitum access to water, after which blood glucose levels were measured from the tail vein as described for ambient blood glucose measurements.

Blood parameters: 50 µL blood samples were collected from the tail veins following a 6 h fast using Microvette EDTA coated tubes (Sarstedt), which were placed on ice until centrifugation at 5000 rcf at 4° C. for 15 min. Plasma supernatants were stored at −80° C. until time of assay. Plasma insulin levels were quantified using the Mercodia Mouse Insulin ELISA, according to the manufacturers' instructions. Percent glycosylated hemoglobin (% HbA1c) was measured from whole blood using a DCA Vantage Analyzer (Siemens).

Food Intake: For food intake studies, animals were group-housed 4 per cage, and food pellets were weighed every 1-2 days. Total cage food intake was calculated for each time increment, averaged per animal, and summed over the course of the study to yield a cumulative food intake per mouse. N=8 treatment groups were divided into 2 cages, allowing for an n=2 food intake standard error calculation.

Pharmacokinetic studies: Tyrosine residues on GLP1-ELP, ELP-FGF21, or GLP1-ELP-FGF21 fusion proteins were reacted with Na$^{125}$I radionuclide (Perkin Elmer) using Pierce Pre-Coated Iodination Tubes (Thermo Fisher Scientific) and the indirect method for iodination. Radiolabeled protein was purified from unreacted radionuclide with Zeba Spin Desalting Columns (Thermo Fisher Scientific). Activities of radiolabeled constructs were measured with an Atomlab 400 Dose Calibrator (Biodex, Shirley, N.Y.) and correlated to protein concentration. Mice received a single s.c. injection of radiolabeled fusion, and 10 µL blood samples were collected at frequent time points from the tail vein and stored at room temperature until radioactivity quantification. Sample counts were measured at the end of the study on a Wallac Wizard 1480 Automatic Gamma Counter (Perkin Elmer). An activity vs. count standard curve was used to convert sample counts to activities, and subsequently to moles of drug.

Pharmacokinetic analysis: The maximum serum concentration ($C_{max}$) was recorded as observed, as well as time to reach $C_{max}$ ($t_{max}$). AUC was estimated utilizing a serum concentration of 0 nM at time zero and extrapolated to 16 days post-administration based on a linear regression curve fit to the terminal portion of the log serum concentration vs. time curve. Absorption half-life ($t_{1/2,\ abs}$) was estimated from the slope of the linear regression curve. When a drug administered at an extravascular site yields a terminal half-life greater than that resulting from an i.v. bolus, the terminal half-life reflects the absorption half-life.

Statistical analyses (used throughout the Examples): Data are presented as means±SEM. Data were analyzed by one-way ANOVA followed by Dunnett's multiple comparisons tests, or by two-way repeated measures ANOVA followed by Dunnett's tests. In vitro $EC_{50}$s were compared by one-way ANOVA followed by Tukey's tests.

Results

GLP1-ELP and ELP-FGF21 co-treatment has potent weight-lowering effects: To test our hypothesis that GLP-1 and FGF21 act at least additively to control glycemia and inhibit weight gain, we carried out a short-term pilot study comparing a combination treatment of long-acting GLP-1 and FGF21 analogs to each respective single-drug treatment. ELPs are repetitive peptide polymers characterized by a (VPGX$_{aa}$G)$_n$ sequence, where "X$_{aa}$" is any amino acid besides proline, and "n" is the number of repeats. A notable feature of ELPs is their reversible lower critical solution temperature (LCST) phase behavior in aqueous media. ELPs have a distinct and tunable "transition temperature" (T$_t$); below the T$_t$ they are miscible in water, and above the T$_t$ they form a water-immiscible coacervate, and their thermal responsiveness is retained when genetically fused to a peptide or protein drug. By manipulating the T$_t$—via choice of the X$_{aa}$ residue and the molecular weight—an ELP-drug fusion can be designed to form an immiscible depot under the skin that steadily releases ELP fusions into systemic circulation. GLP1-ELP and ELP-FGF21 fusions are active in vitro and form subcutaneous (s.c.) depots capable of blood glucose-lowering effects for at least 5 days in diabetic mice following a single injection.

Figure 4A:
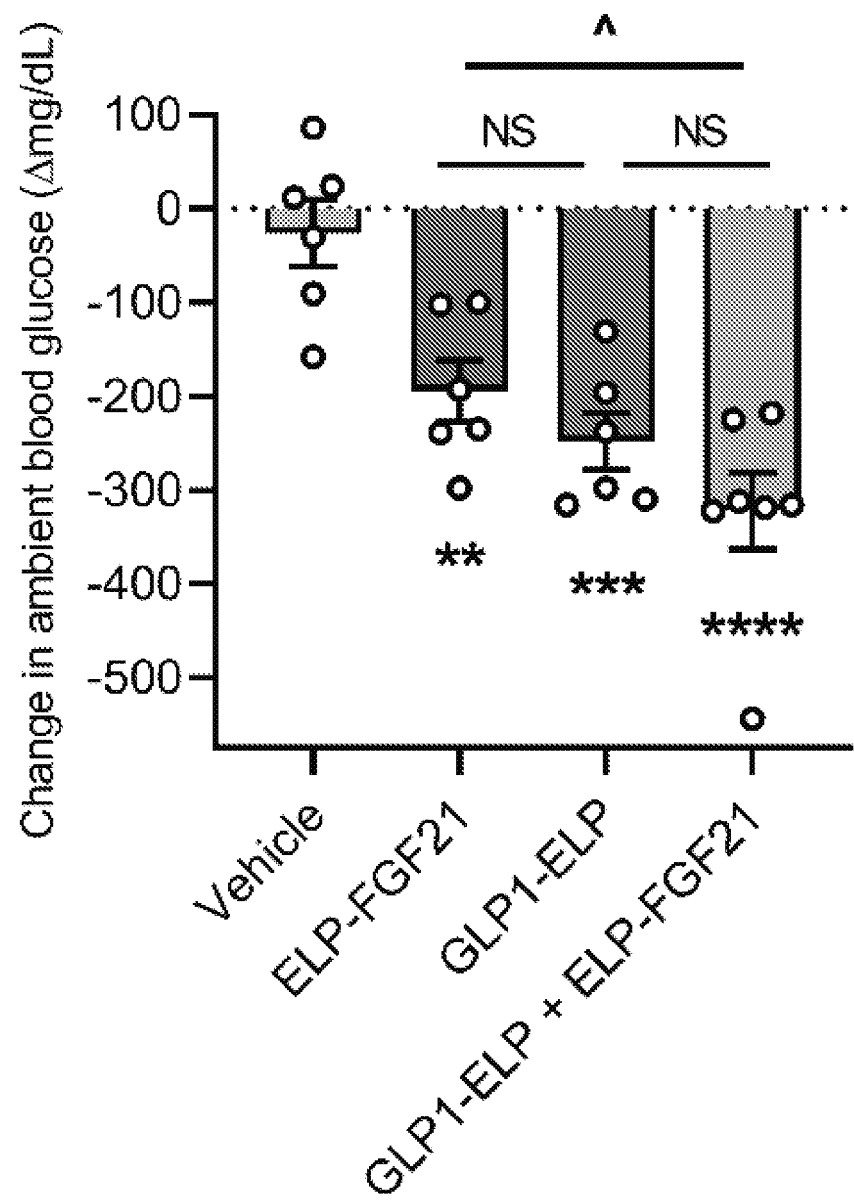
FIG. 4 is a set of plots showing that GLP-1 and FGF21 co-treatment can augment the blood glucose-lowering and weight gain-inhibiting effects of single drug treatment. 6-week-old db/db mice (n=6-7) were injected s.c. with 1000 nmol/kg ELP-FGF21, 1000 nmol/kg GLP1-ELP, or 1000 nmol/kg each of GLP1-ELP and ELP-FGF21. Ambient blood glucose levels (FIG. 4A) and body weights (FIG. 4B) were measured 48 h post-injection and reported as a magnitude change from pre-treatment baseline and a % change from pre-injection weight. Data are presented as mean±SEM; *=treatment compared to vehicle; ^=comparisons between treatments; */^=p<005; /^^=p<0.01; */^^^=p<0.001; ****/^^^^=p<0.0001; NS=not significant.
Figure 4B:
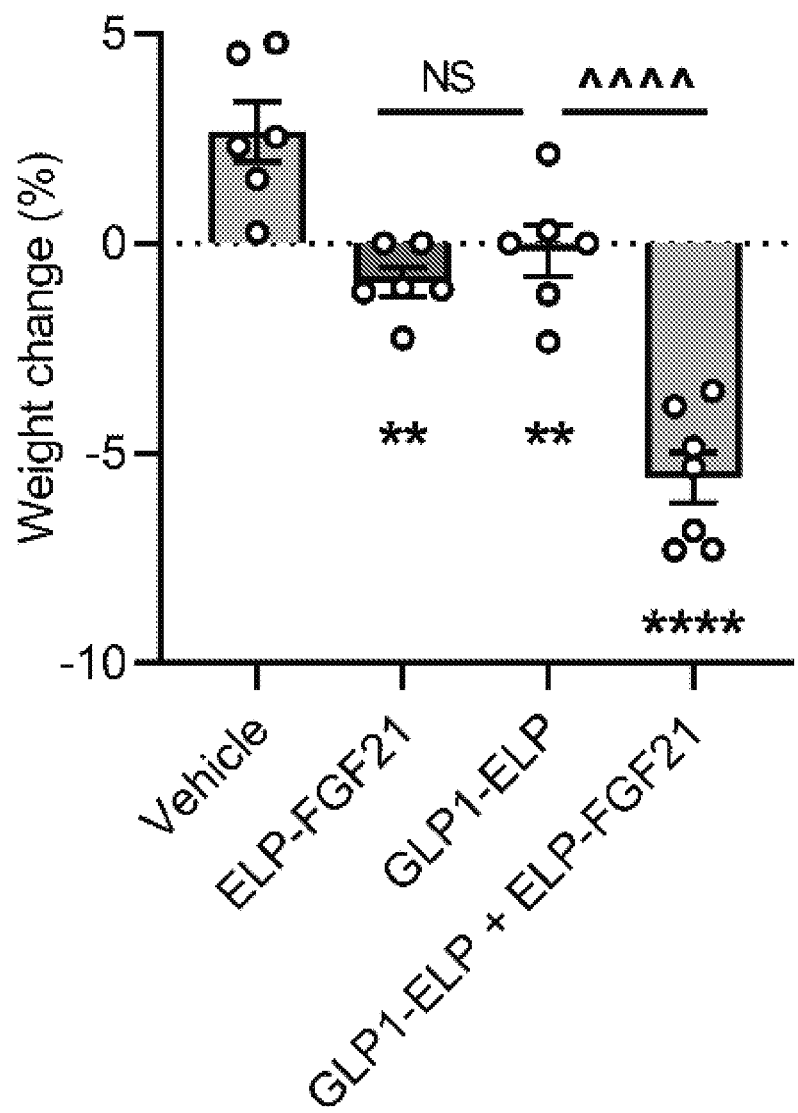

Db/db mice were injected s.c. with GLP1-ELP, ELP-FGF21, an equimolar mixture of the two drugs, or vehicle control. Ambient blood glucose levels and body weights were measured 48 h post-injection and reported as a change from pre-injection baseline. All treatments significantly reduced blood glucose levels compared to vehicle, while combination treatment resulted in blood glucose levels that trended even lower than each respective single drug (FIG. 4A). Treatment with ELP-FGF21 or GLP1-ELP effectively inhibited weight gain (−0.9±0.3% and −0.2±0.6%) compared to vehicle-treated mice, who gained 2.7±0.7% body weight in 48 h (FIG. 4B). In contrast, mice treated with the ELP-FGF21+GLP1-ELP drug combination exhibited a robust 5.6±0.6% reduction in body weight (FIG. 4B). Together these data suggest that GLP-1 and FGF21 act at least additively to induce weight loss—and possibly to improve glycemic control—in diabetic mice.

Figure 5A:
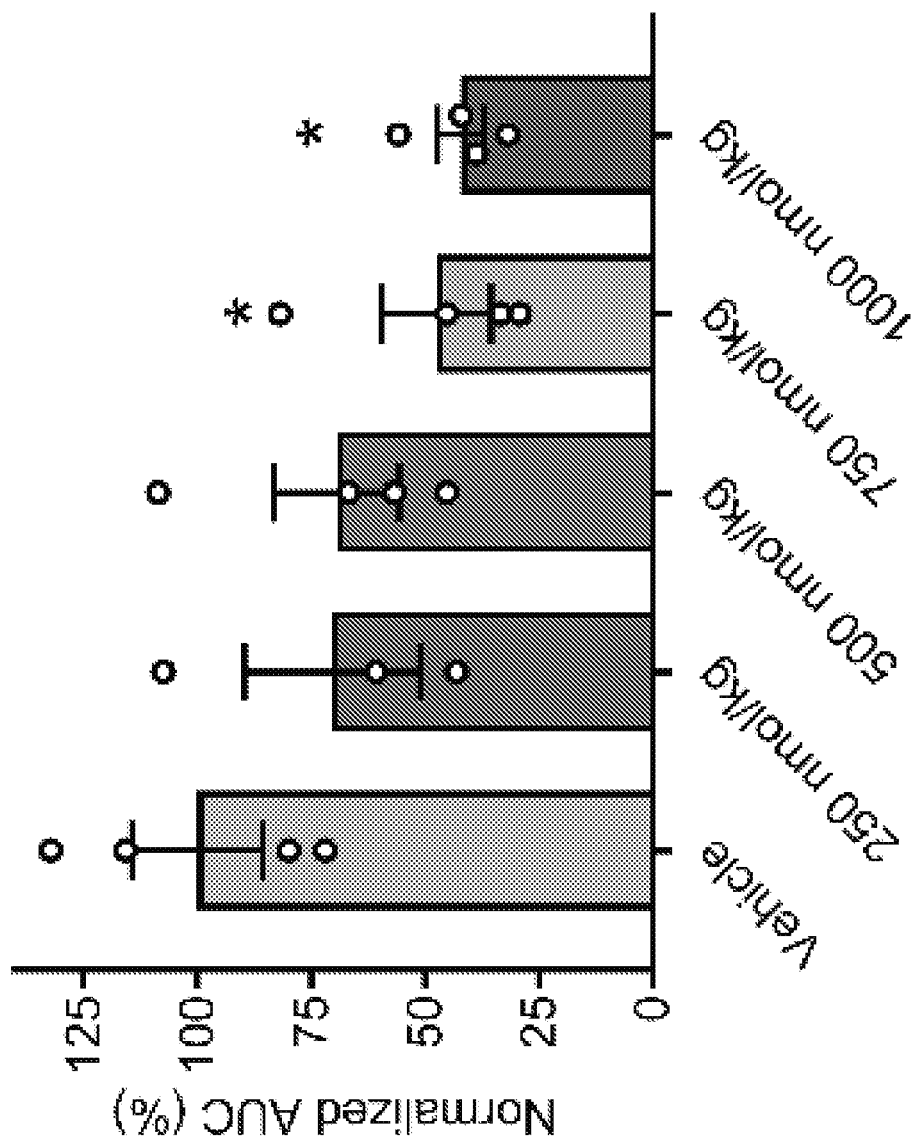
(FIG. 5A, FIG. 5B, FIG. 5C, and FIG. 5D) 6-week-old db/db mice (n=3-4) received a single s.c. injection of GLP1-ELP-FGF21 at the indicated dose or vehicle. Ambient blood glucose levels were measured every 24 h until animals returned to baseline levels and are reported as blood glucose vs. time AUC or raw values (FIG. 5A and FIG. 5B). Body weights were recorded daily and are reported as a % change from pre-injection weight over time (FIG. 5C) or on day 7 post-injection (FIG. 5D).
Figure 5B:
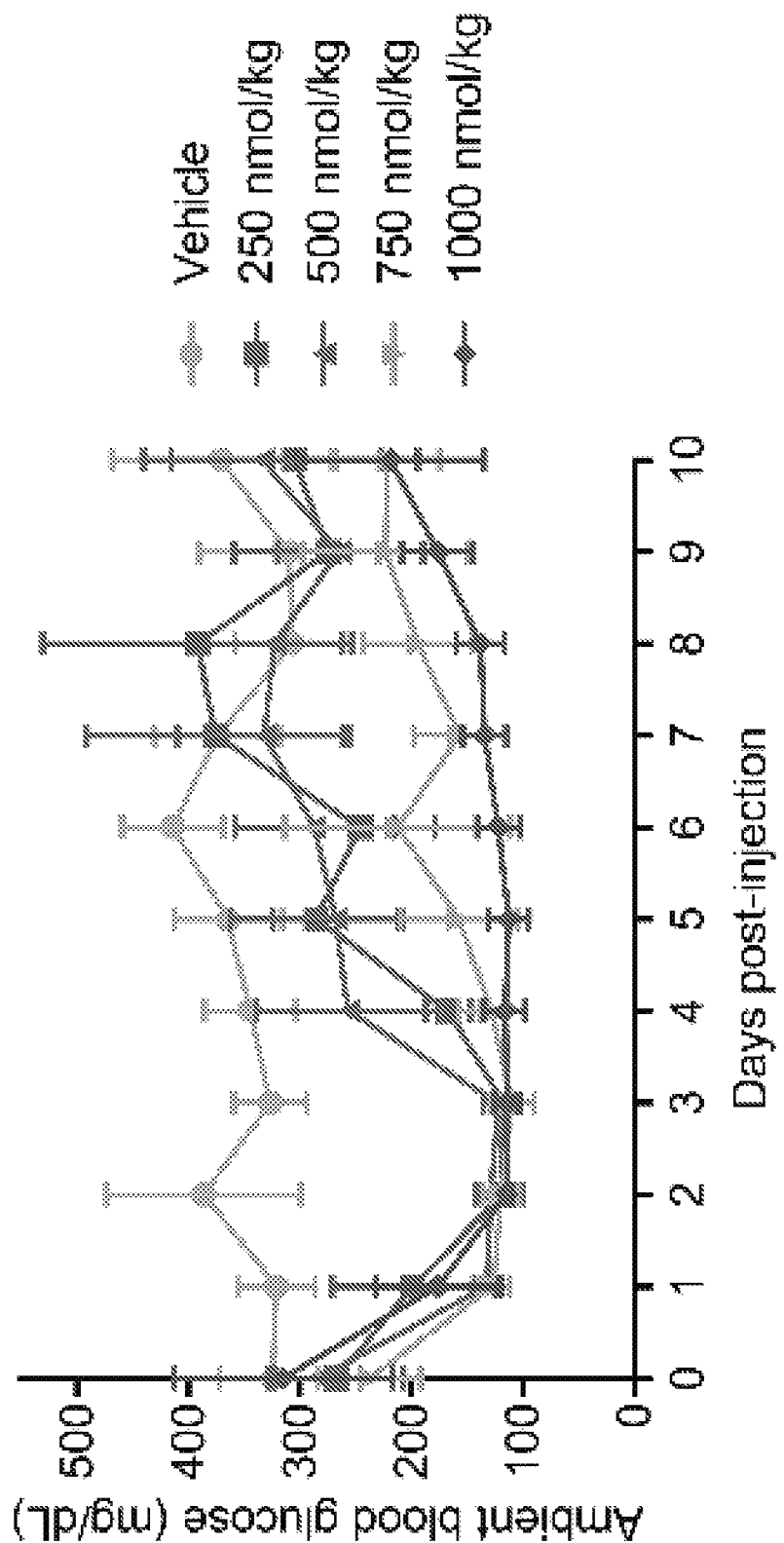
Figure 5C:
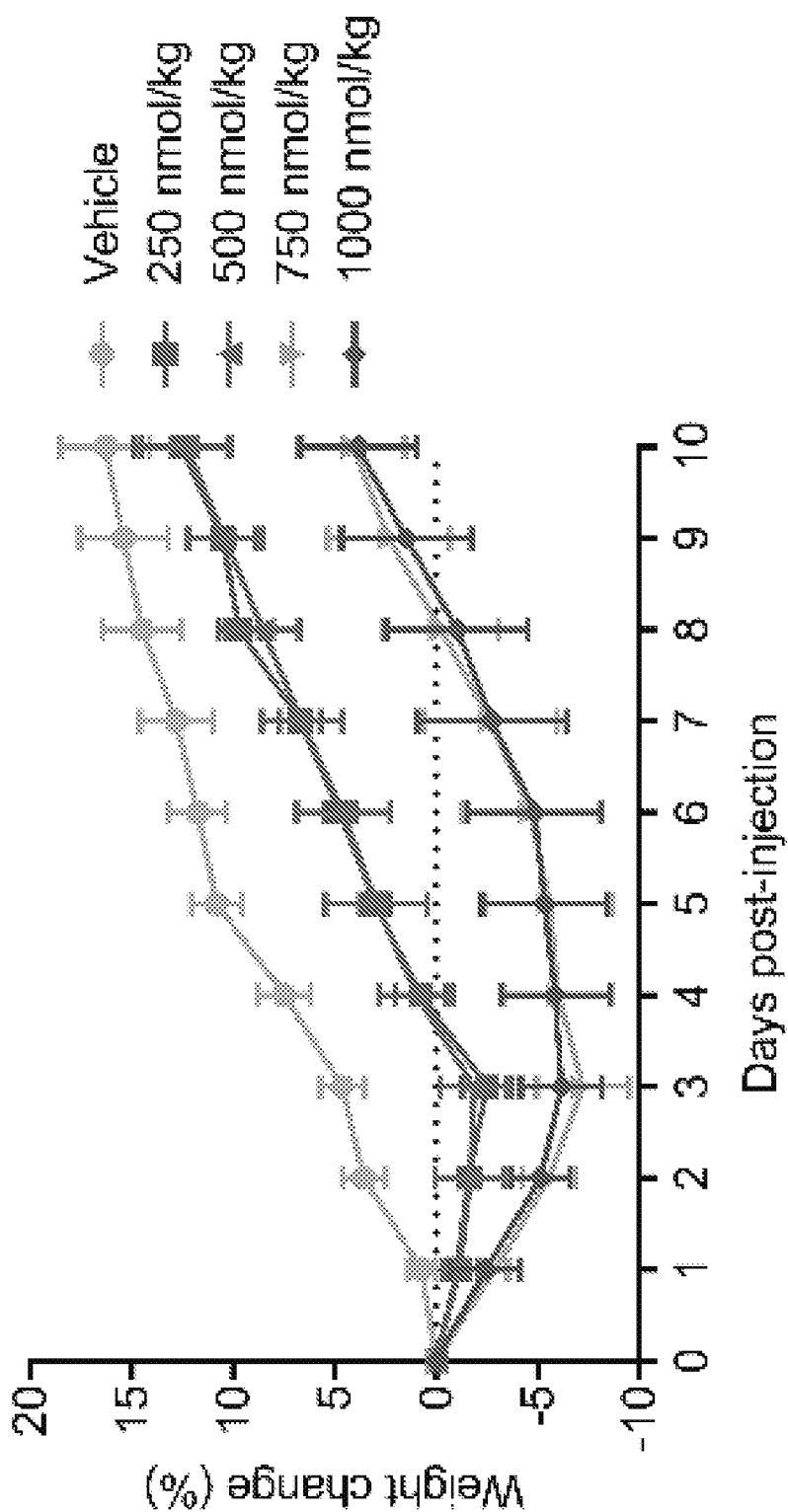
Figure 5D:
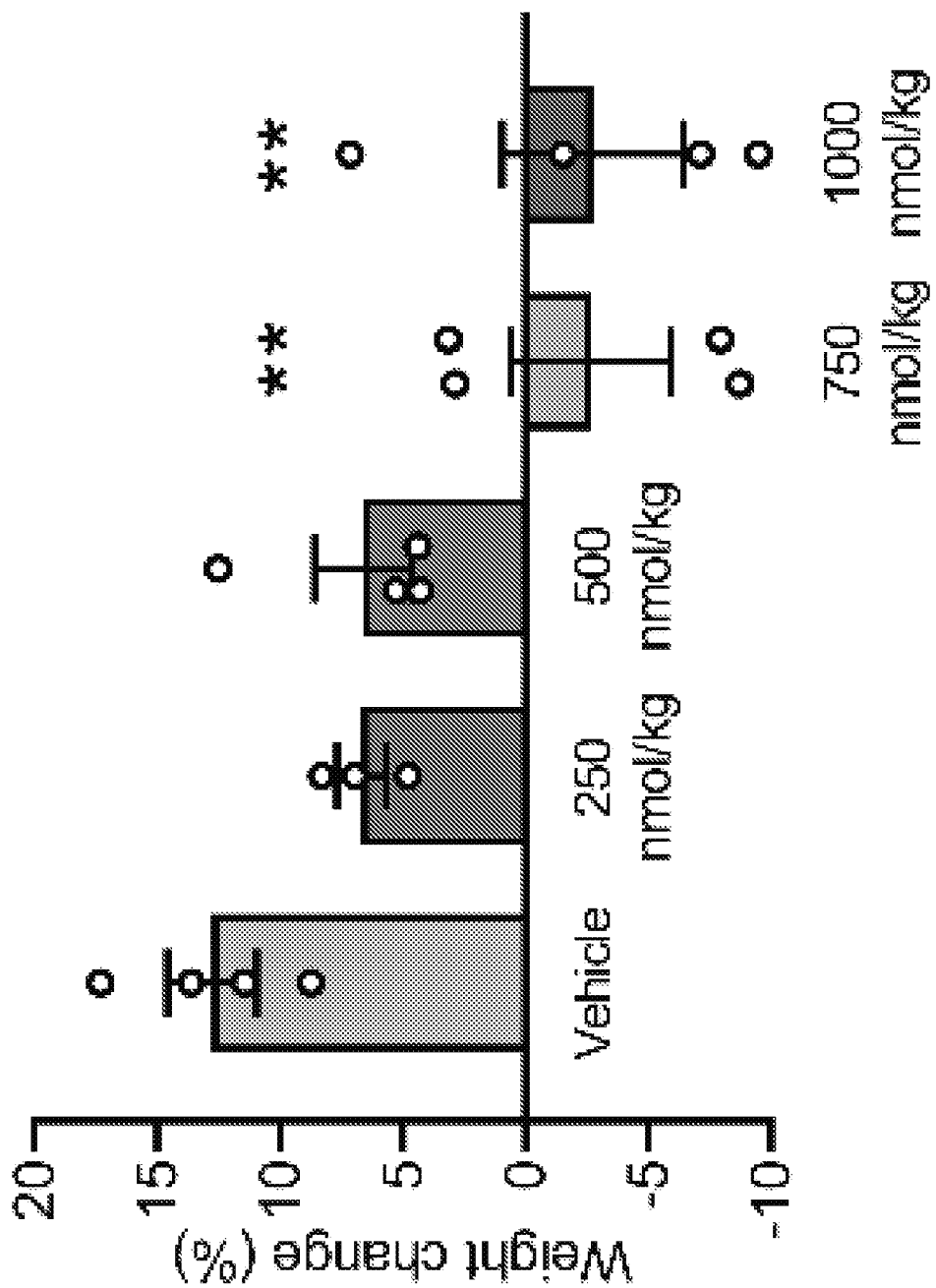

A GLP1-ELP-FGF21 dual agonist fusion protein has sustained dose-dependent effects on body weight and glycemia: The dual agonist drug was tested for efficacy in diabetic mice. The db/db mouse model was selected due to its extreme degree of hyperglycemia paired with obesity, as high baseline body weight and glycemic levels would provide a larger window to identify potentially additive effects of dual agonism. Mice were treated with either a single GLP1-ELP-FGF21 s.c. injection at the indicated dose, or vehicle. Ambient blood glucose levels were measured daily, until all cohorts returned to baseline levels. Significant reductions in blood glucose vs. time AUC were observed at the two highest doses tested (750 nmol/kg and 1000 nmol/kg) (FIG. 5A), however, raw blood glucose vs. time data revealed that it was not effect size but rather effect duration that increased in a dose-dependent manner (FIG. 5B). All doses reduced blood glucose levels from >300 mg/dL to <150 mg/dL (FIG. 5B), with effects persisting 4 days at the lowest dose (250 nmol/kg), and 8 days at the highest dose tested (1000 nmol/kg) (FIG. 5B). Compared to vehicle control, all tested doses of GLP1-ELP-FGF21 had an inhibitory effect on weight gain, while the two highest doses tested induced weight loss—reducing body weights by up to 7.2±2.3% (FIG. 5C). On day 7 post-treatment, a net weight loss effect persisted in the 750 and 1000 nmol/kg groups (−2.6±3.3% and −2.7±3.7%, respectively) (FIG. 5D).

Figure 5E:
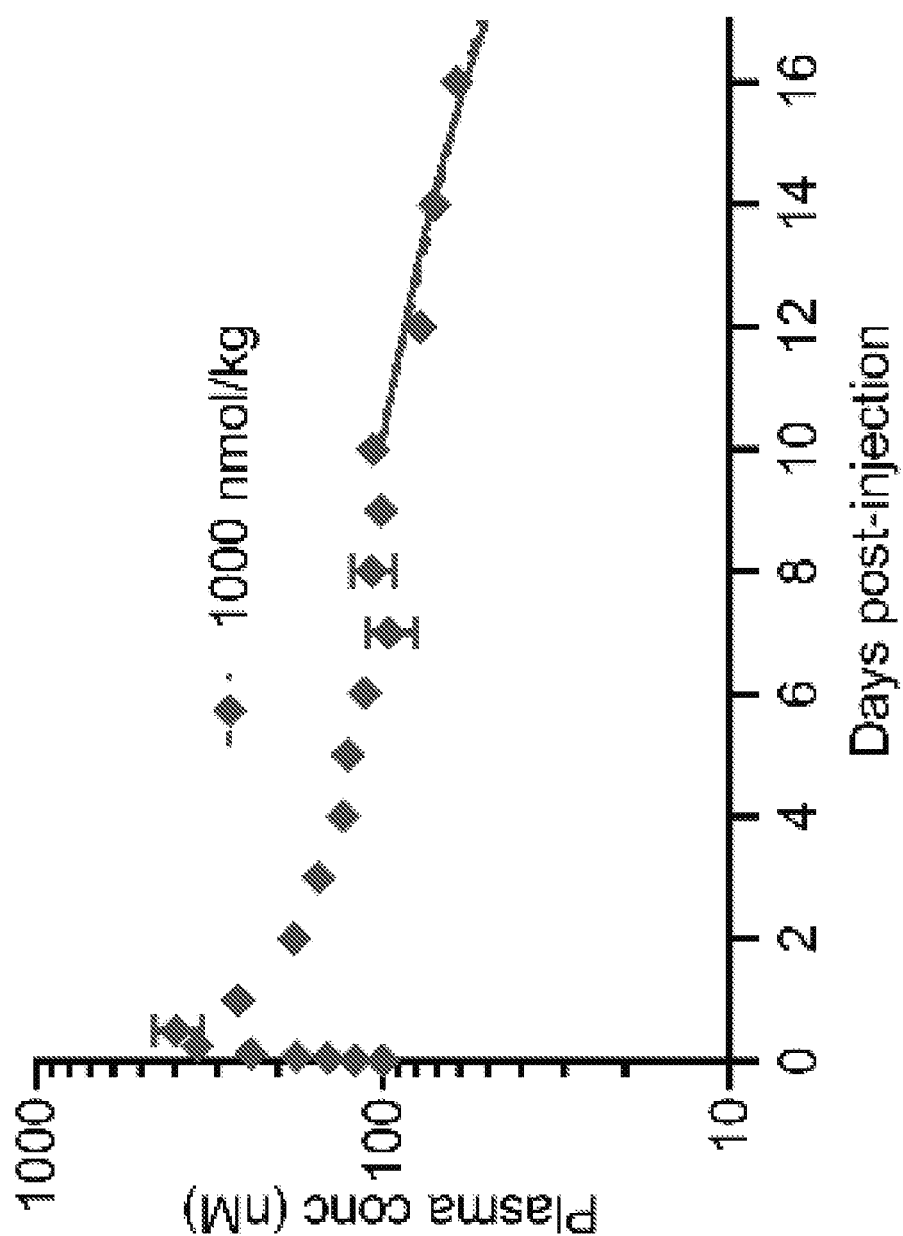
(FIG. 5E) 1000 nmol/kg GLP1-ELP-FGF21 was administered s.c. to 6-week-old db/db mice (n=4) as a radiolabeled protein, blood samples were collected at indicated time points following injection, and plasma gamma counts were correlated to fusion protein concentration. Regression curves were fit to the terminal portion of the data set, and data could be described by either a first-order (dotted) or a zero-order (solid) elimination model. Data are presented as mean±SEM, *=p<0.05, **=p<0.01.

To confirm that sustained efficacy was a result of prolonged drug in circulation—as is observed when an ELP depot forms at the site of injection—plasma drug levels were measured over time following a single s.c. injection of GLP1-ELP-FGF21 to db/db mice. Aside from a modest burst release in the first 24 h, plasma drug levels remained steady near 100 nM out to day 10 (FIG. 5E), at which point drug levels decreased at a rate consistent with first-order elimination. When a linear regression curve was fit to the terminal portion of the data (Table 2), the absorption half-life was calculated to be 7.6±1.1 days (Table 3). Interestingly, the data were described nearly as well by a zero-order elimination model ($R^2$=0.81) as by a first-order model ($R^2$=0.85) (Table 2). When pharmacokinetic data were analyzed alongside the 1000 nmol/kg blood glucose vs. time efficacy data (FIG. 5B), 100 nM appeared to be the minimal therapeutic concentration, as blood glucose levels returned to baseline in the same time frame that serum drug levels dropped below 100 nM (on or after day 10).

In summary, treatment of obese and hyperglycemic mice with a GLP-1/FGF21 dual agonist drug had potent and sustained effects on body weights and ambient blood glucose levels. A single injection was sufficient to maintain therapeutic drug levels and protect mice from hyperglycemia and weight gain for >7 days, demonstrating the suitability of a GLP1-ELP-FGF21 depot for a once-weekly dosing scheme. A dose of 1000 nmol/kg was identified as yielding a maximal therapeutic effect and selected for further evaluation.

A GLP1-ELP-FGF21 dual agonist confers greater glycemic control compared to a long-acting GLP-1 RA: To elucidate the relative contribution of GLP-1 and FGF21 to the potent in vivo effects of the dual agonist, we next compared GLP1-ELP-FGF21 with the GLP1-ELP and ELP-FGF21 single agonist monotherapies. An equimolar mixture of GLP1-ELP and ELP-FGF21 was included to understand the impact of incorporating both drugs into a single molecule.

Figure 6A:
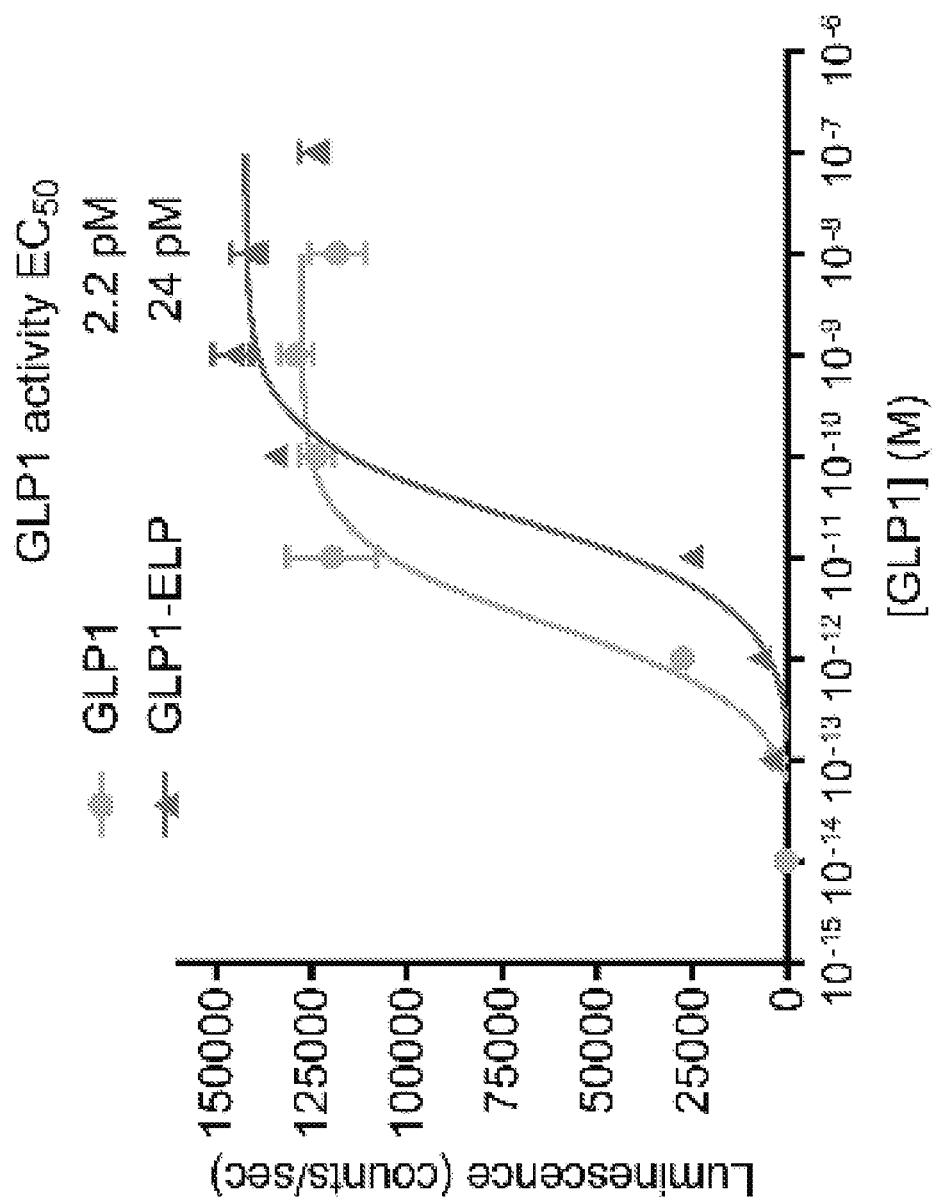
(FIG. 6A) In vitro activity assay evaluating the $EC_{50}$ of GLP1-ELP fusion protein at the GLP-1R. GLP-1R agonism was measured by quantifying cAMP production following 5 h stimulation of HEK293 cells stably expressing the GLP-1R and a cAMP-inducible luciferase reporter. Data are presented as mean±SEM n=3.
Figure 6B:
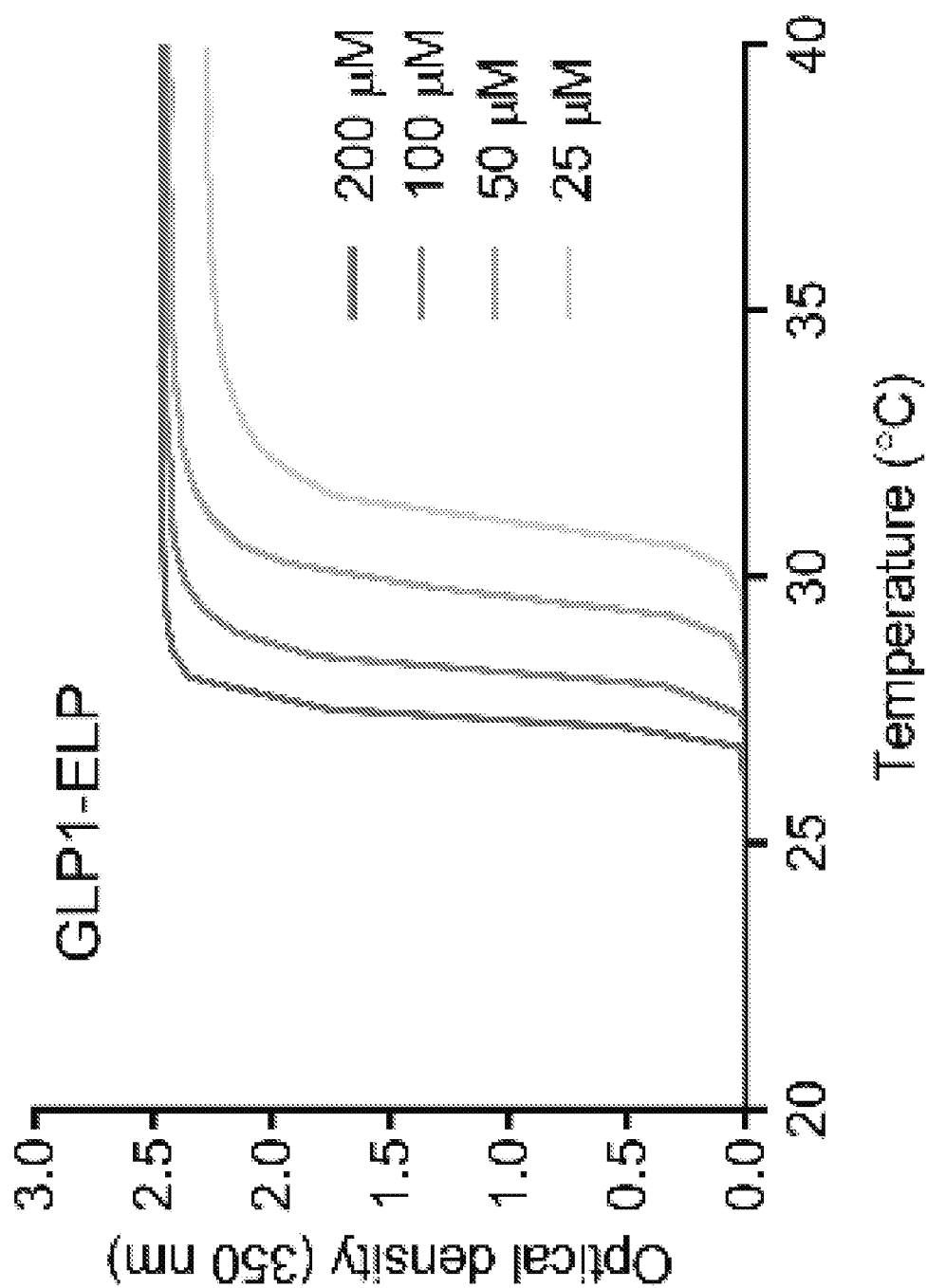
(FIG. 6B, FIG. 6C, FIG. 6D, FIG. 6E, FIG. 6F, and FIG. 6G) LCST phase transition behavior of single agonist ELP fusion proteins.
Figure 6C:
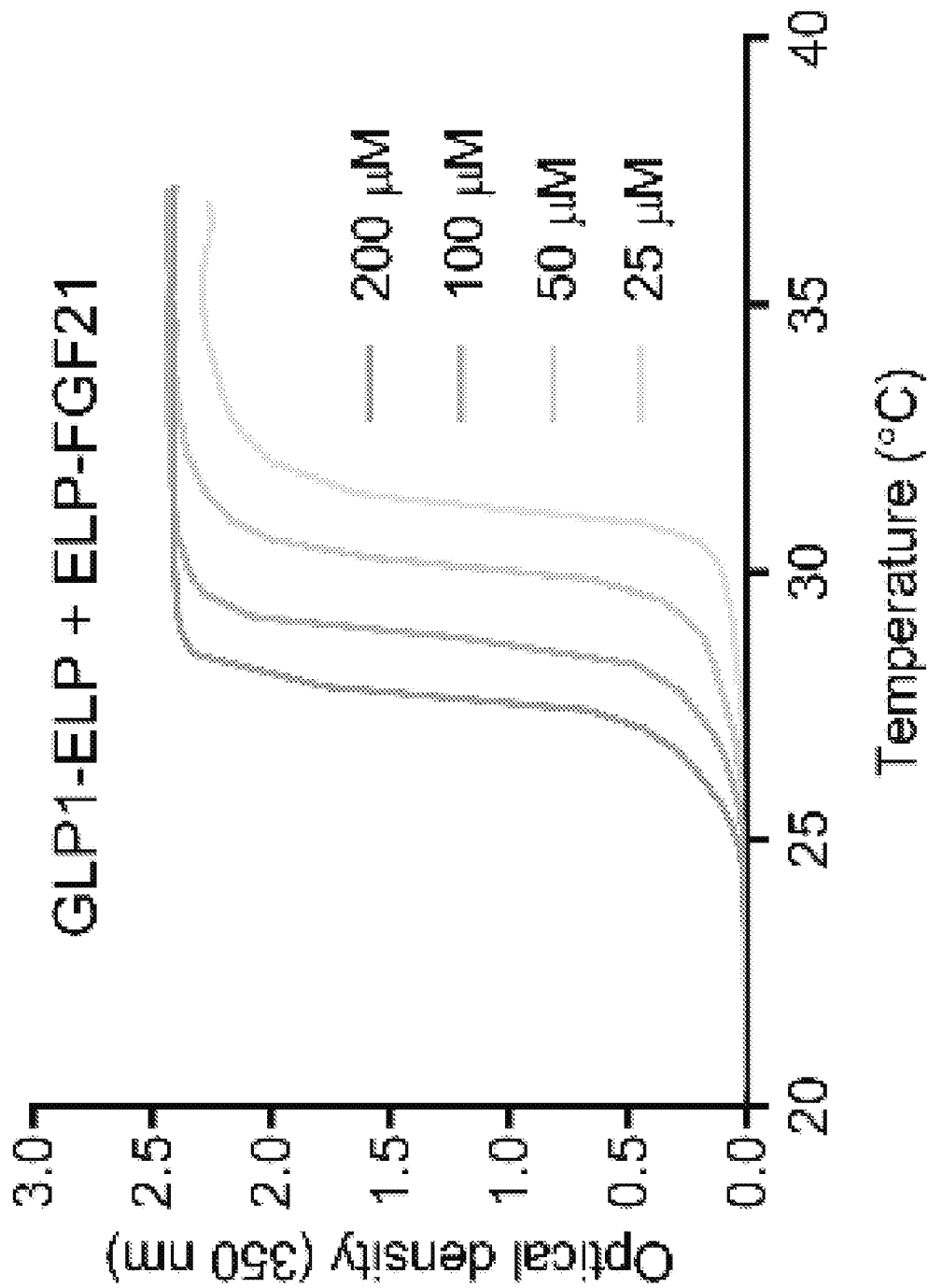
Figure 6D:
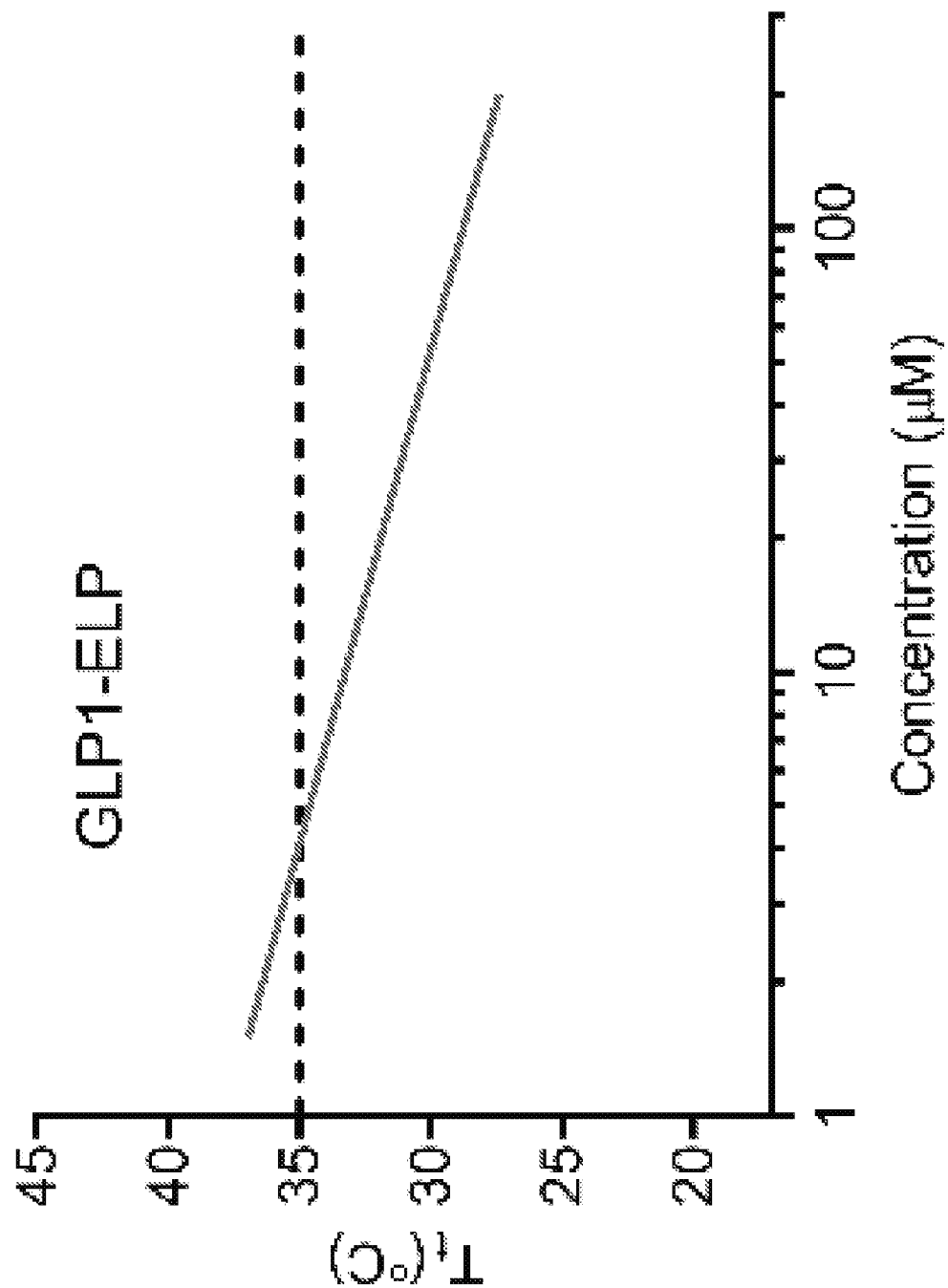
Figure 6E:
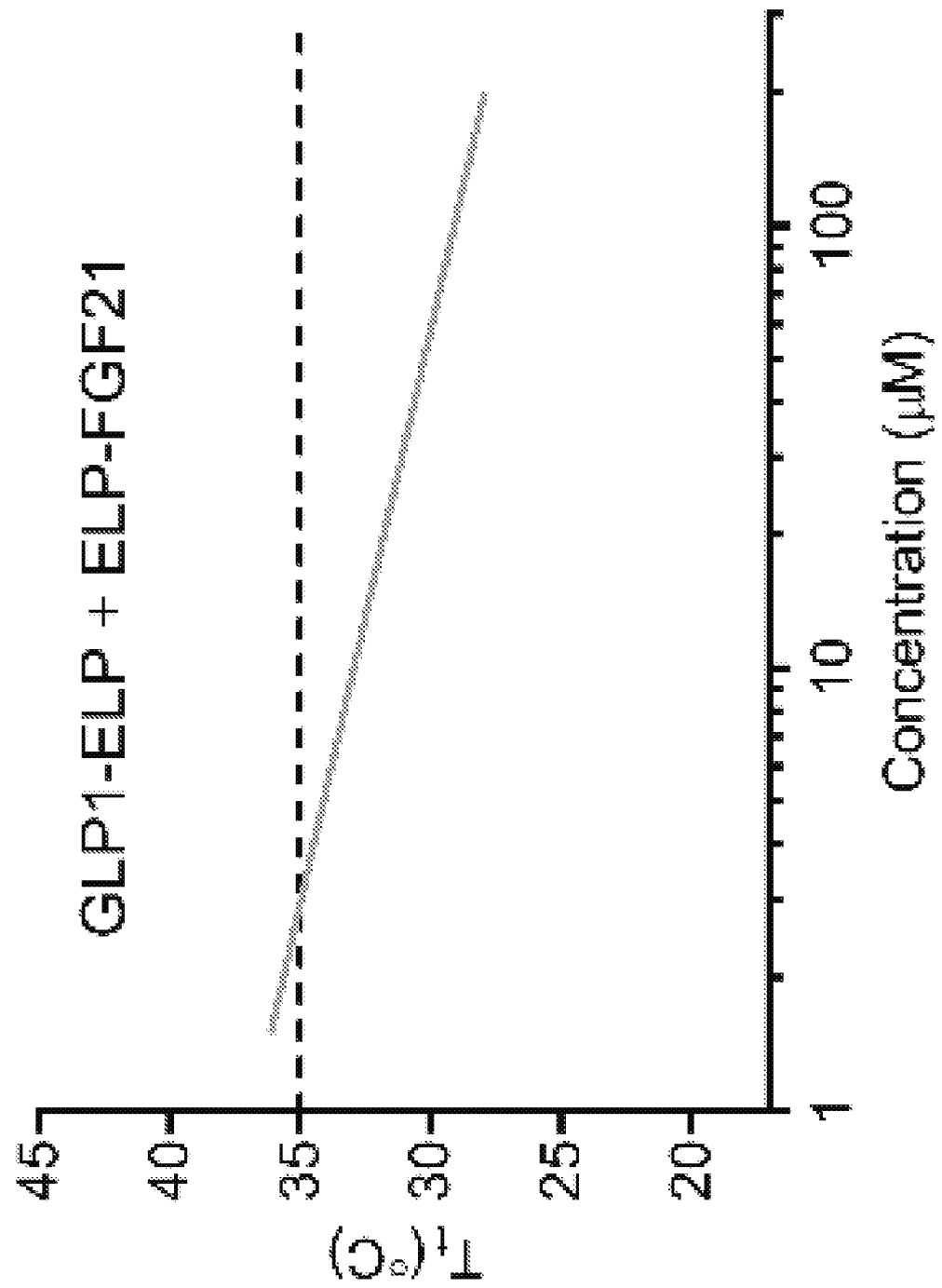
Figure 6F:
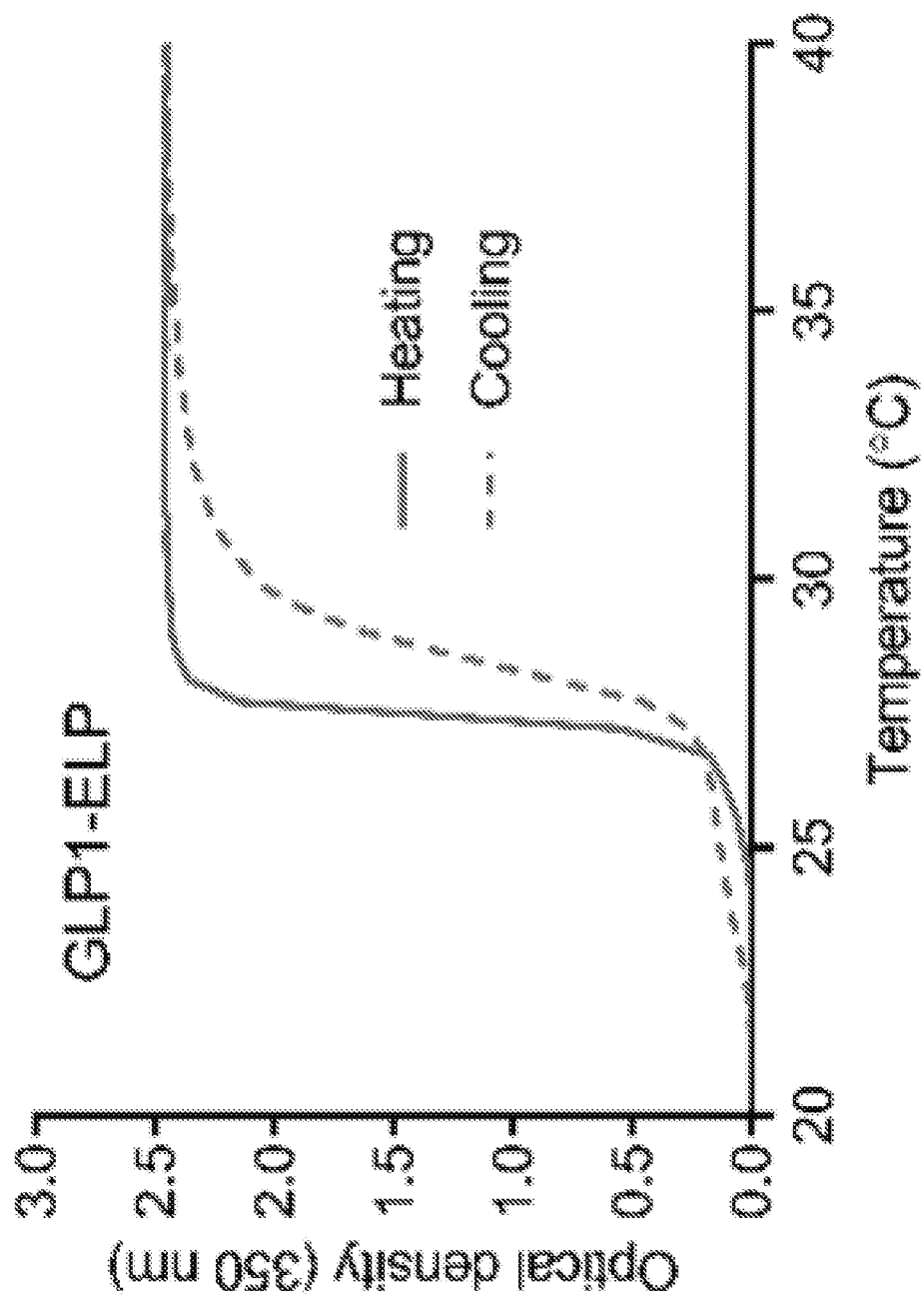
Figure 6G:
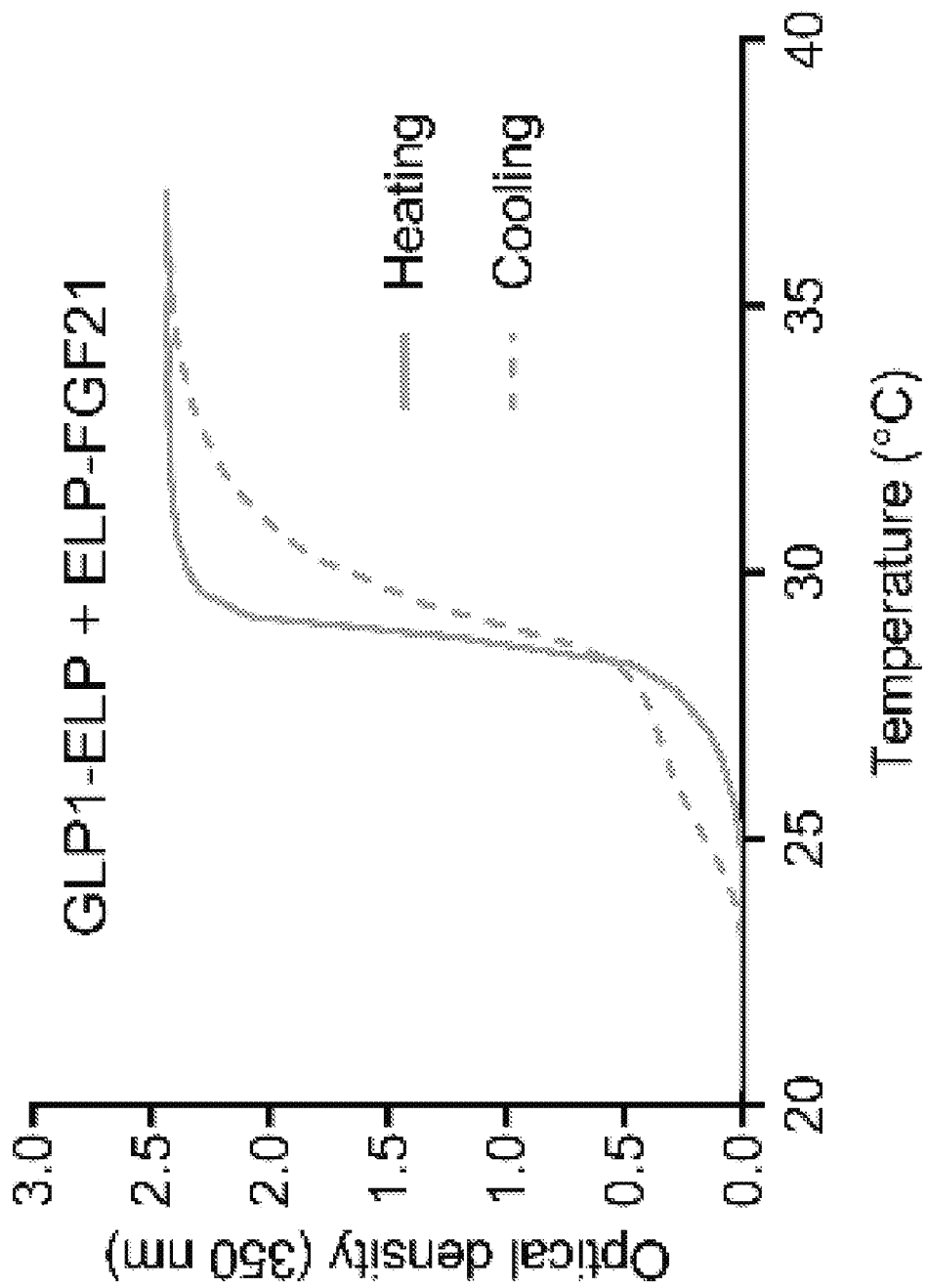

To ensure consistency across treatments, the same ELP sequence was employed in each drug formulation. To do so, a vector encoding GLP-1 fused at its C terminus to the ELP of interest ((VPGXG)$_{120}$ (SEQ ID NO:1) with a 4:1 valine:alanine ratio at the X residue position) was expressed in *E. coli* and purified by ITC. A 52 kDa band associated with the GLP1-ELP fusion was visible by SDS-PAGE following purification. The GLP1-ELP fusion was tested for GLP-1R agonism and exhibited a ten-fold increase in EC$_{50}$ compared to native GLP-1 (FIG. 6A). LCST phase transition behavior was evaluated for GLP1-ELP and an equimolar mixture of GLP1-ELP and ELP-FGF21, revealing T$_t$s of 27.5° C. and 28° C., respectively, at the injection-relevant concentration of 200 μM (FIG. 6B and FIG. 6C). The T$_t$s were concentration-dependent (FIG. 6D and FIG. 6E), and the phase change behavior of each fusion/fusion mixture was reversible (FIG. 6F and FIG. 6G)). Note that the LCST phase transition behavior of ELP-FGF21 has been characterized previously (Gilroy, C.A., S. Roberts, and A. Chilkoti, *Fusion of fibroblast growth factor 21 to a thermally responsive biopolymer forms an injectable depot with sustained anti-diabetic action*. Journal of Controlled Release, 2018. 277: p. 154-164, which is incorporated by reference herein in its entirety).

Figure 7A:
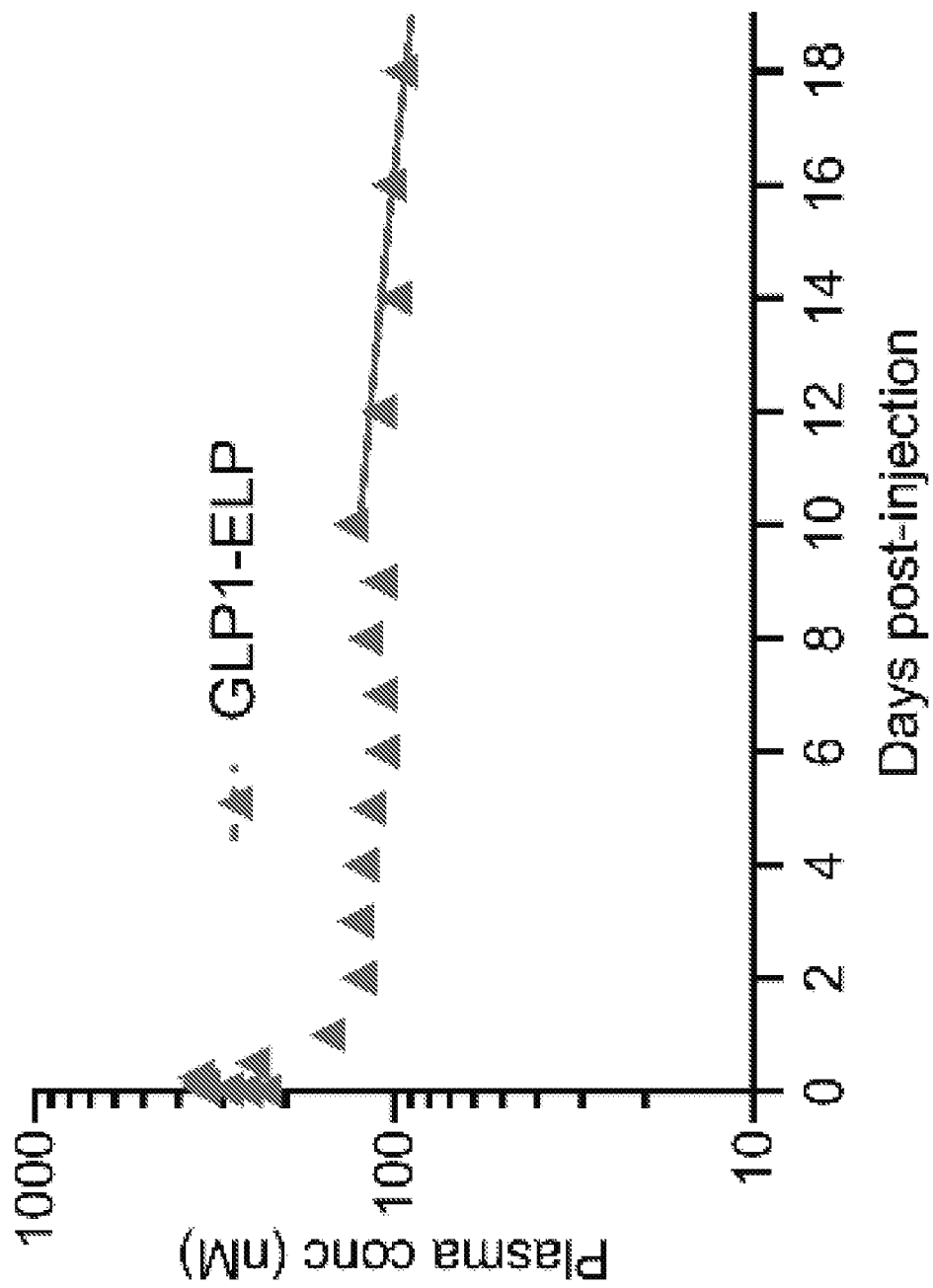
FIG. 7 is a set of plots showing single agonist ELP fusion control pharmacokinetic profiles. 6-week-old db/db mice (n=4-5) received a single s.c. injection of GLP1-ELP (FIG. 7A), or a 1:1 mixture of GLP1-ELP and ELP-FGF21 (FIG. 7B). GLP1-ELP was radiolabeled in (FIG. 7A), while the 1:1 mixture in (FIG. 7B) was tested once when GLP1-ELP was radiolabeled and once when ELP-FGF21 was radiolabeled. All fusions were injected at 200 μM and dosed at 1000 nmol/kg, with the 1:1 mixture consisting of 1000 nmol/kg each GLP1-ELP and ELP-FGF21. Blood samples were collected at indicated time points following injection, and plasma gamma counts were measured and correlated to fusion protein concentration. Lines represent regression curves fit to the terminal portion of each data set. Data can be described by both a first-order (dotted) or a zero-order (solid) elimination model. Data are presented as mean±SEM.
Figure 7B:
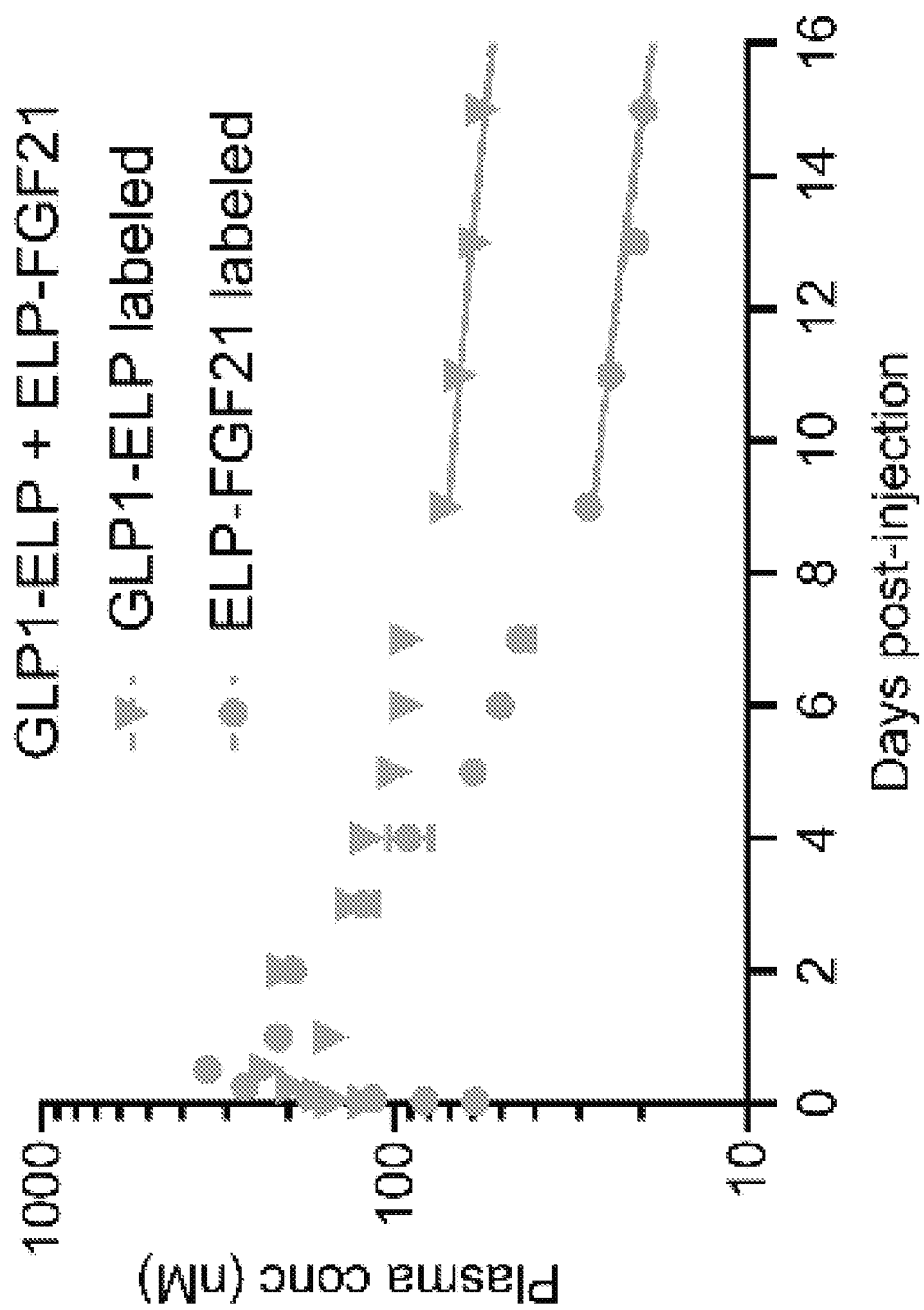

Next, pharmacokinetic profiles were evaluated for the GLP1-ELP fusion, as well as the equimolar mixture of GLP1-ELP and ELP-FGF21. Both GLP1-ELP and the mixture exhibited steady plasma drug levels consistent with sustained release from an s.c. depot. The GLP1-ELP monotherapy depot behaved similarly to that of the dual agonist, releasing fusion molecules into circulation at a rate that could be described by a zero-order elimination model (Table 2), and resulting in plasma drug levels hovering near 100 nM for at least 10 days (FIG. 7A). Interestingly, the 1:1 mixed depot released GLP1-ELP and ELP-FGF21 fusion unimers at different rates (FIG. 7B). The ELP-FGF21 component reached a higher $C_{max}$ than the GLP1-ELP component (Table 3), and ELP-FGF21 plasma levels dropped below 100 nM by day 4, while GLP1-ELP plasma levels hovered steadily around 100 nM for 7 days. Though absorption of each component of the mixture fit a zero-order release model (Table 2), neither GLP1-ELP nor ELP-FGF21 maintained steady plasma levels for as long as GLP1-ELP-FGF21, suggesting an advantage to delivering the two drugs as a single molecule.

Figure 12A:
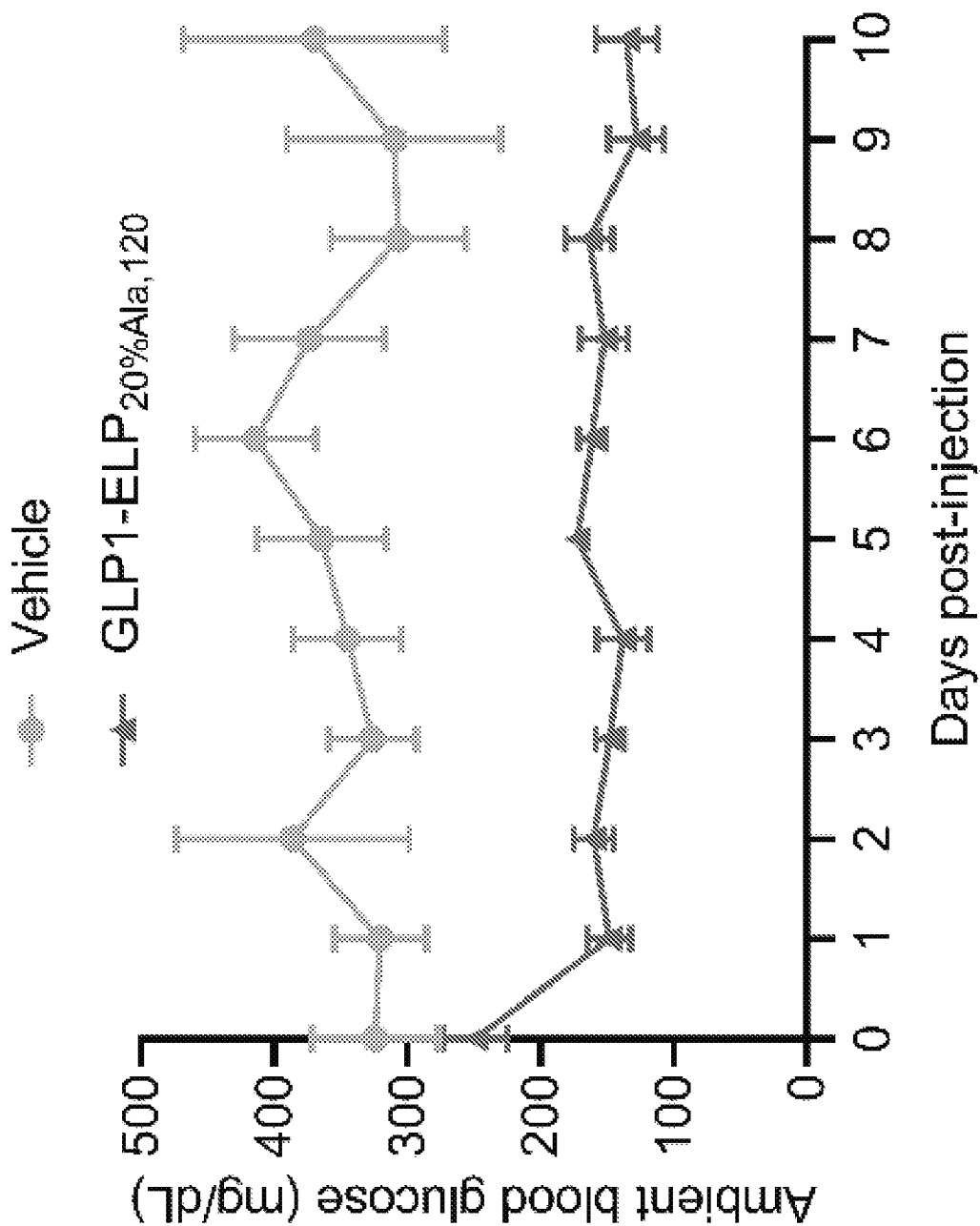
FIG. 12 is a set of plots showing GLP1-ELP effects on glycemia and body weight. 6-week-old db/db mice (n=3-4) received a single s.c. injection of 1000 nmol-kg GLP1-ELP$_{20\%Ala,120}$ or PBS vehicle. Ambient blood glucose levels (FIG. 12A) were measured every 24 h for 10 days, and body weights (FIG. 12B) were recorded daily and reported as a % change from pre-injection weight over time. Data are presented as means±SEM.
Figure 12B:
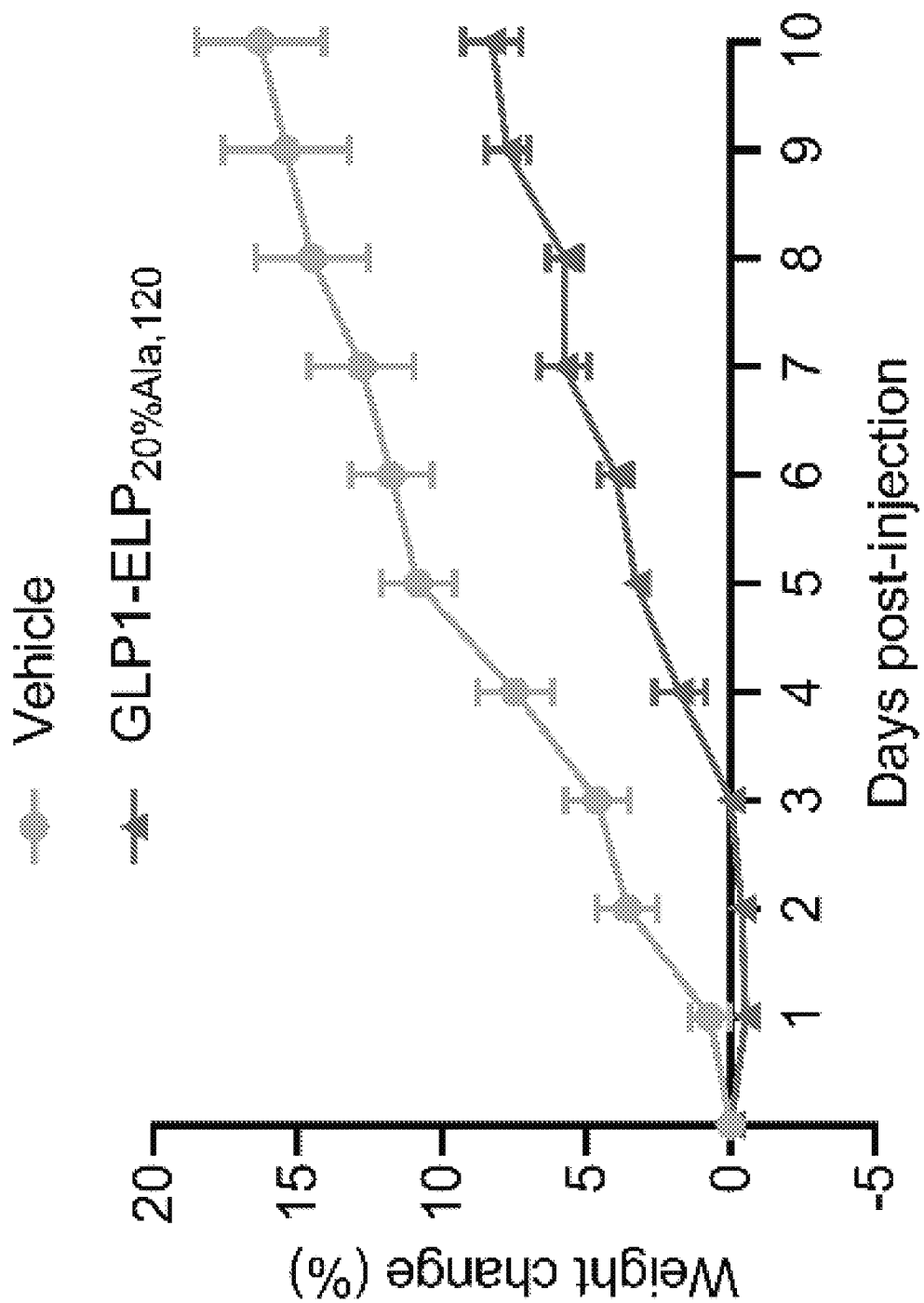

As a further analysis of the GLP1-ELP control, ambient blood glucose levels were measured daily for 10 days, and treatment with the GLP1-ELP fusion resulted in significant and sustained effects on glycemia, reducing levels from >300 mg/dL to <200 mg/dL for the duration of the study (FIG. 12A). Body weights were recorded daily and reported as a % change from pre-injection weight, and GLP1-ELP$_{20\%Ala,120}$ treatment significantly inhibited weight gain compared to control mice (FIG. 12B). Thus, GLP1-ELP fusion is fully functional—as should be the associated GLP1-ELP/ELP-FGF21 mixture.

Figure 8A:
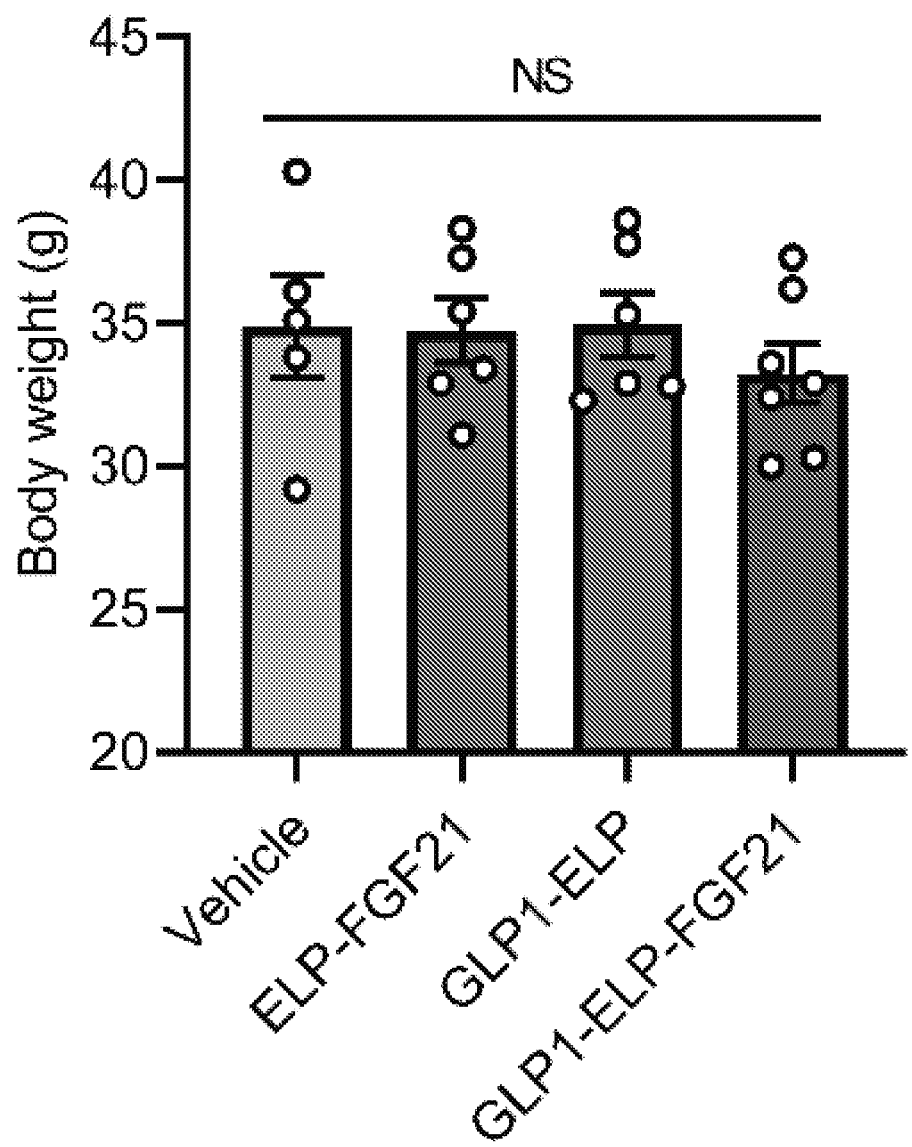
(FIG. 8A) Body weights are consistent between treatment groups at the glucose tolerance test (GTT) performed 3 days after the first injection (Day 3).
Figure 9A:
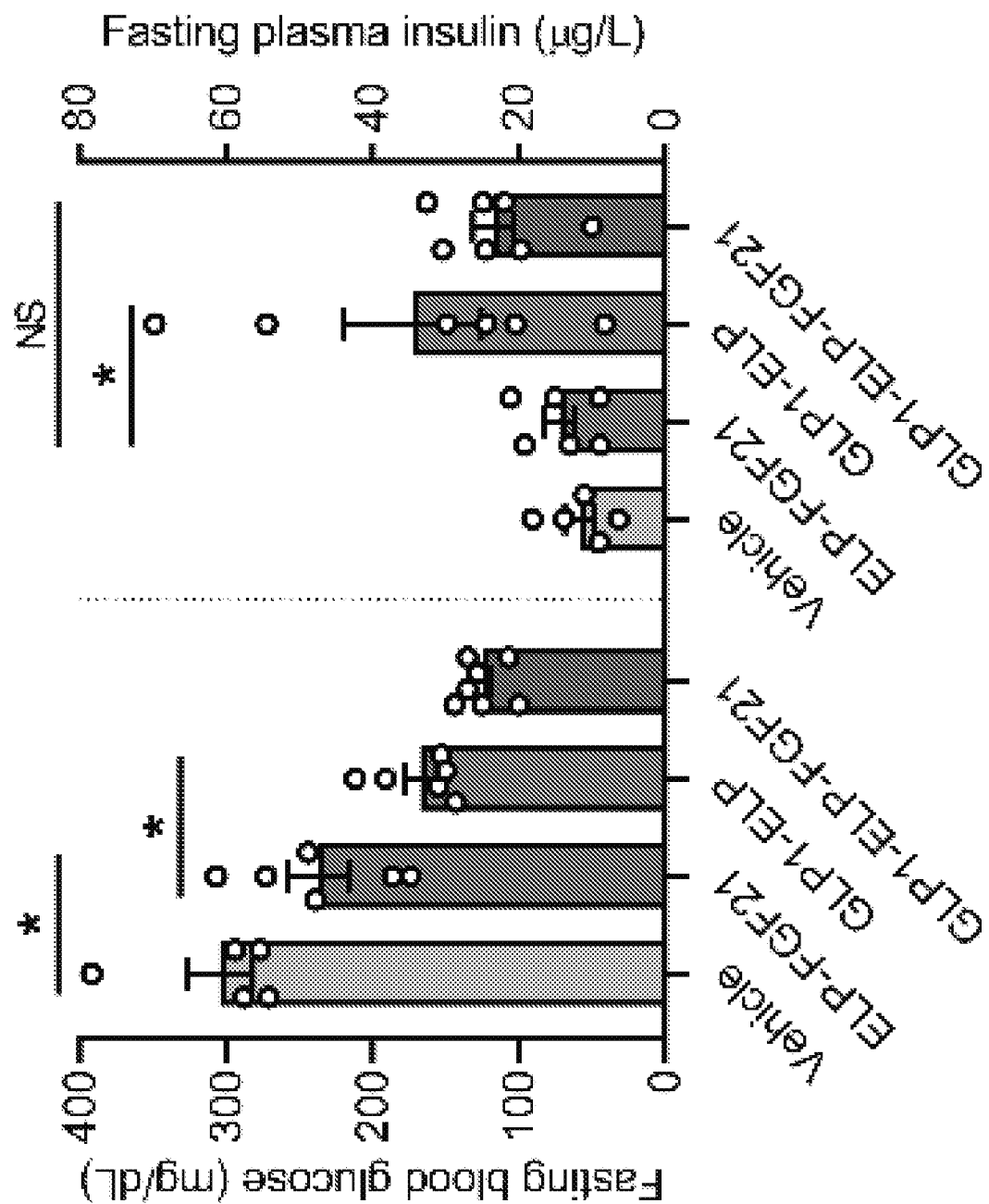
(FIG. 9A, FIG. 9B, and FIG. 9C) Glucose challenge. 72 h after the first treatment cycle, the dual agonist and single agonist control cohorts were fasted 5 h, baseline blood glucose and plasma insulin levels were measured (FIG. 9A), and mice were injected i.p. with 0.75 g/kg glucose. Blood glucose levels were measured at indicated time points (FIG. 9B), and blood glucose vs. time AUC values were calculated (FIG. 9C).
Figure 9B:
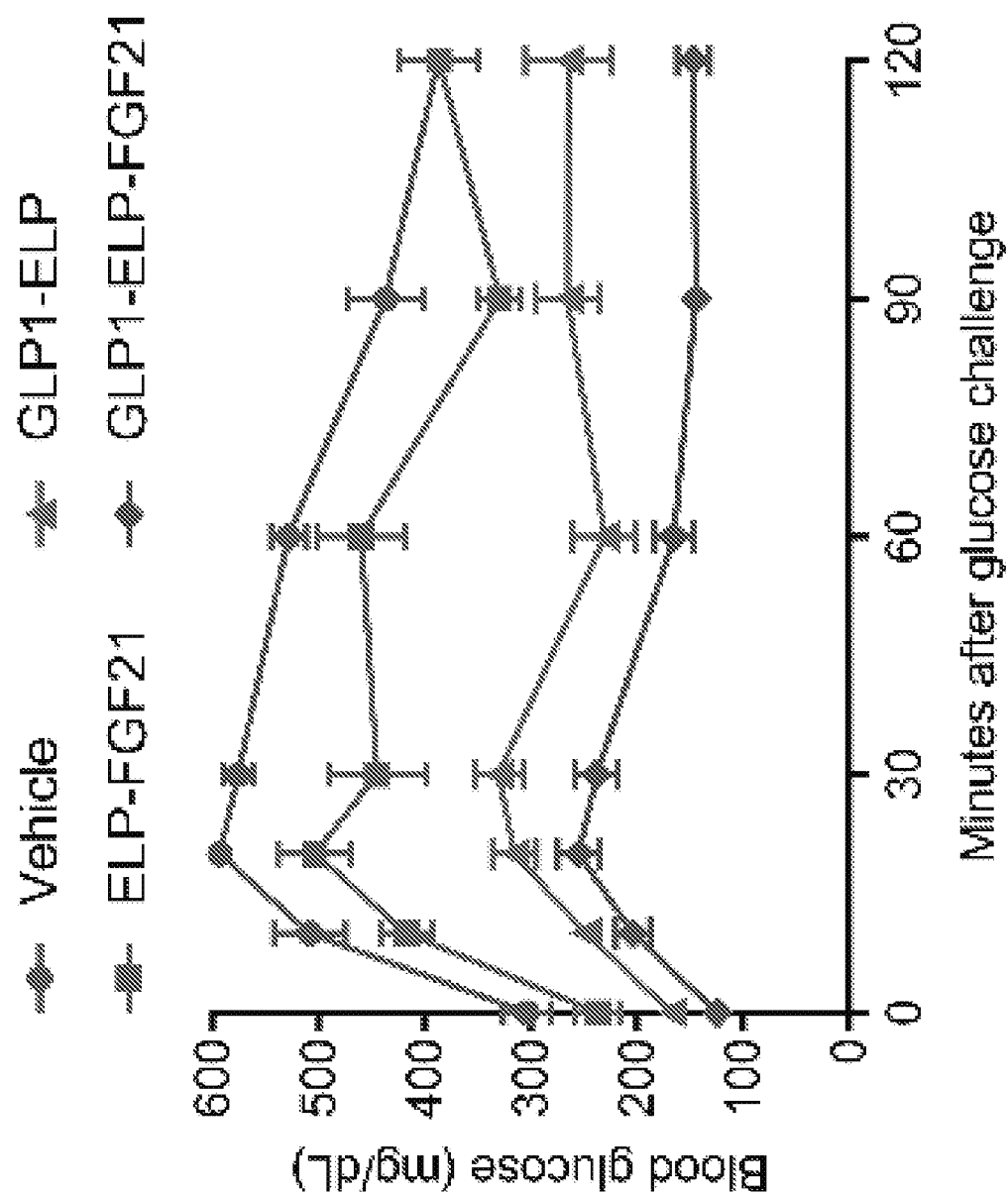
Figure 9C:
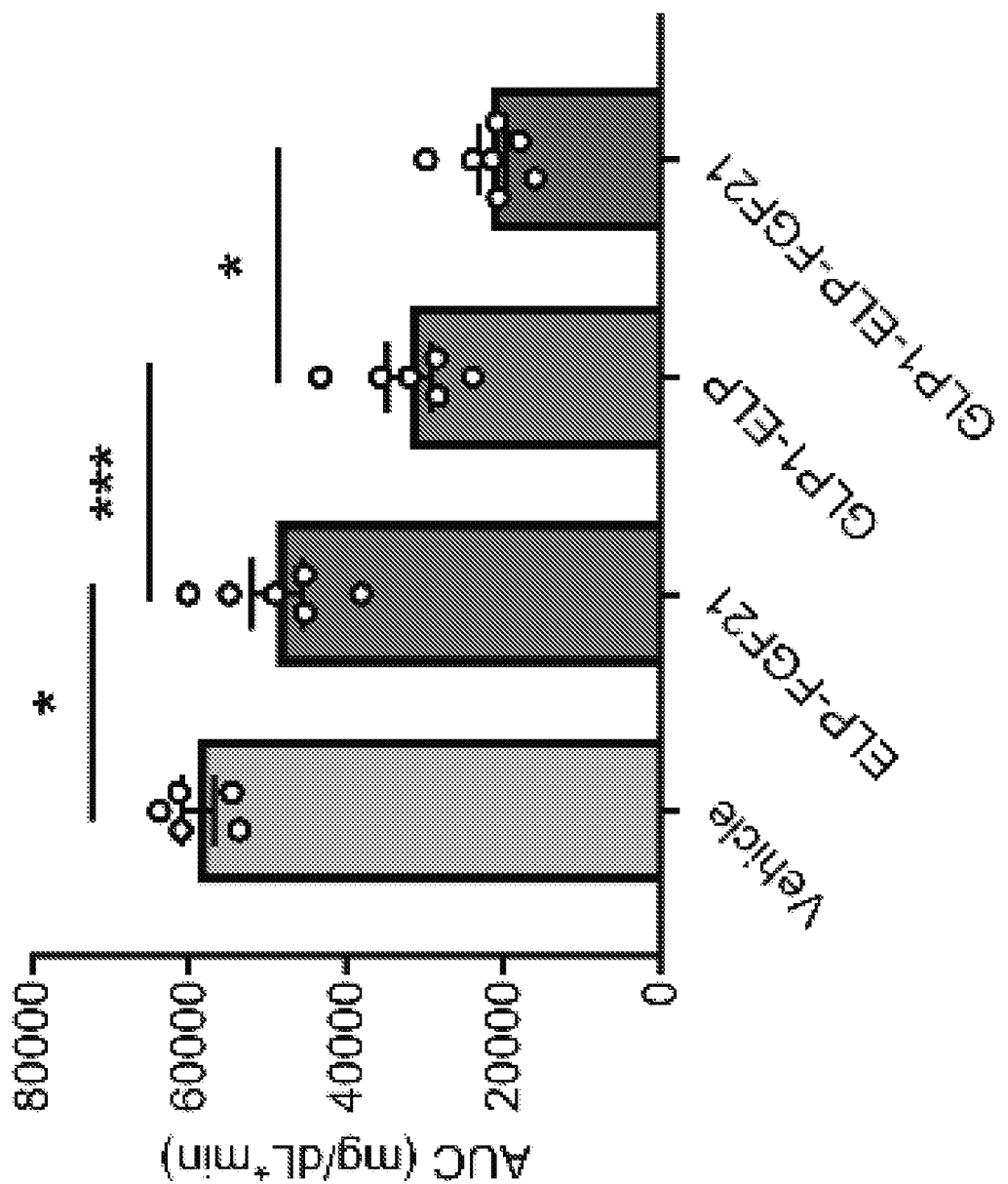

After establishing the optimal dosing parameters and appropriate controls, the dual agonist was assessed for its effects on glycemic control. Db/db mice were treated weekly for four weeks with 1000 nmol/kg GLP1-ELP-FGF21, GLP1-ELP monotherapy, ELP-FGF21 monotherapy, or vehicle. Acute glycemic effects were evaluated through an intraperitoneal (i.p.) glucose tolerance test (GTT) (0.75 mg/kg) performed 3 days after the first dosing cycle, when body weights were consistent across treatment groups (FIG. 8A). Fasting blood glucose and plasma insulin levels were measured prior to the glucose challenge (FIG. 9A). ELP-FGF21 monotherapy treatment significantly decreased GTT AUC compared to vehicle (FIG. 9B and FIG. 9C) with equivalent levels of fasting plasma insulin (FIG. 9A, right panel), suggesting increased insulin sensitivity upon FGF21 treatment. GLP1-ELP monotherapy outperformed ELP-FGF21 in improving glucose tolerance (FIG. 9B and FIG. 9C), and the GLP1-ELP-FGF21 treatment was superior to both single agonist monotherapies. Fasting blood glucose levels were lowest in the dual agonist cohort (125±6.0 mg/dL compared to 167±11 mg/dL for GLP1-ELP and 237±21 mg/dL for ELP-FGF21) (FIG. 9A, left panel), and GLP1-ELP-FGF21 treatment significantly decreased GTT AUC compared to GLP1-ELP or ELP-FGF21 (FIG. 9B and FIG. 9C). Whereas GLP1-ELP achieved its effects on glycemia with a concomitant significant increase in fasting plasma insulin, the dual agonist achieved robust glycemic control without a significant elevation in insulin, indicating increased insulin sensitivity mediated specifically by the FGF21 component. Insulin sensitization is believed to be the primary mechanism by which FGF21 alters glycemia, however other mechanisms may include increasing glucose uptake in adipose and muscle tissues, decreasing hepatic glucose output and inhibiting glucagon secretion.

TABLE 2

Regression fits for pharmacokinetic data.

| Labeled construct | Regression model | R-squared |
|---|---|---|
| GLP1-ELP-FGF21 | Log(y) = −0.04160x + 2.431 | 0.85 |
|  | y = −7.273x + 174.1 | 0.81 |
| GLP1-ELP | Log(y) = −0.01628x + 2.263 | 0.61 |
|  | y = −3.932x + 164.1 | 0.58 |
| GLP1-ELP AS PART OF 1:1 SINGLE AGONIST FUSION MIXTURE | Log(y) = −0.01803x + 2.013 | 0.87 |
|  | y = −2.584x + 93.91 | 0.86 |
| ELP-FGF21 AS PART OF 1:1 SINGLE AGONIST FUSION MIXTURE | Log(y) = −0.02515x + 1.671 | 0.63 |
|  | y = −1.264x + 38.80 | 0.60 |

Figure 8B:
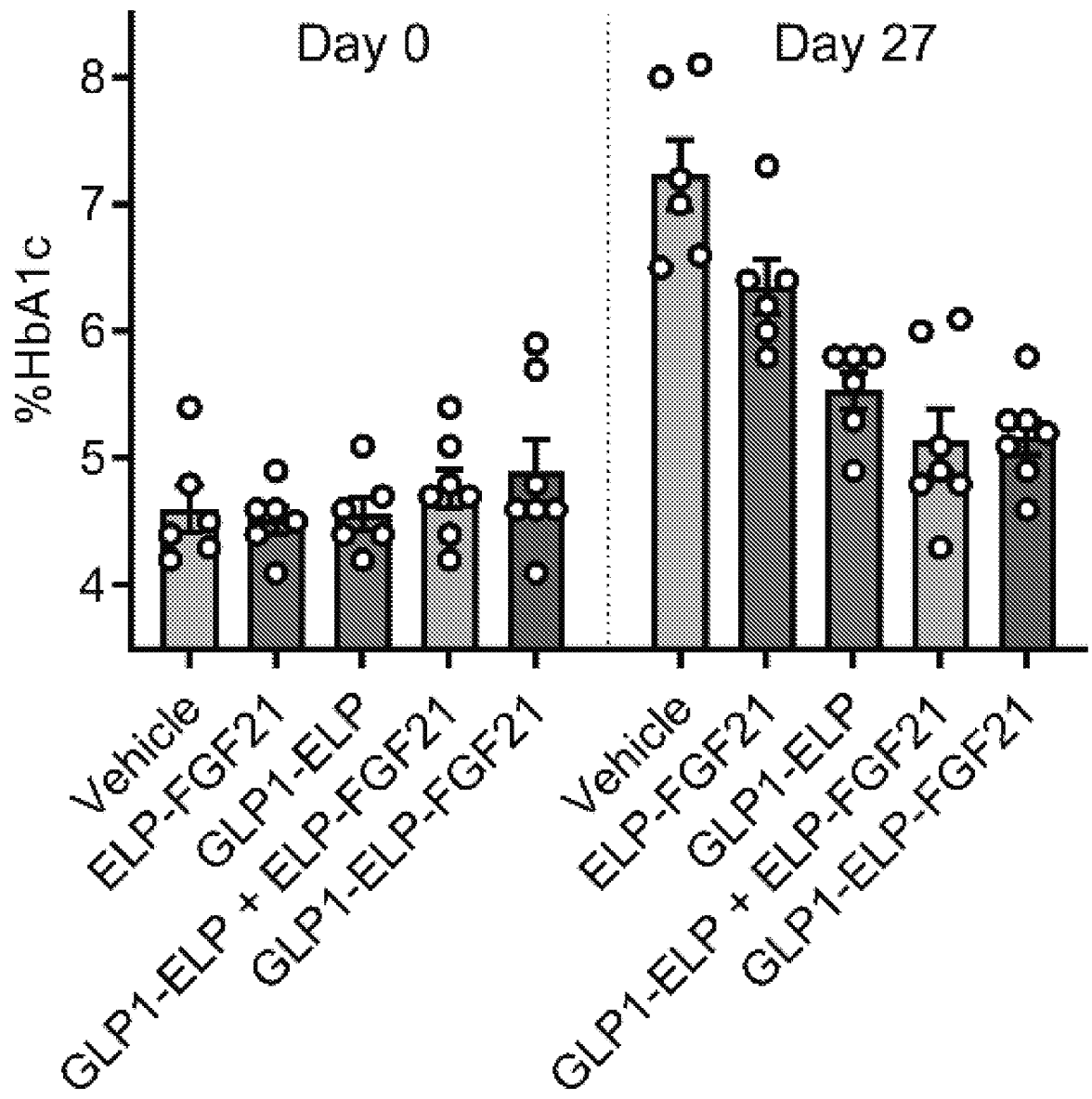
(FIG. 8B) Chronic treatment with GLP-1/FGF21 combination therapy protects from % HbA1c elevation. % HbA1c was measured prior to the first treatment (Day 0) and 6 days following the final treatment (Day 27).
Figure 9D:
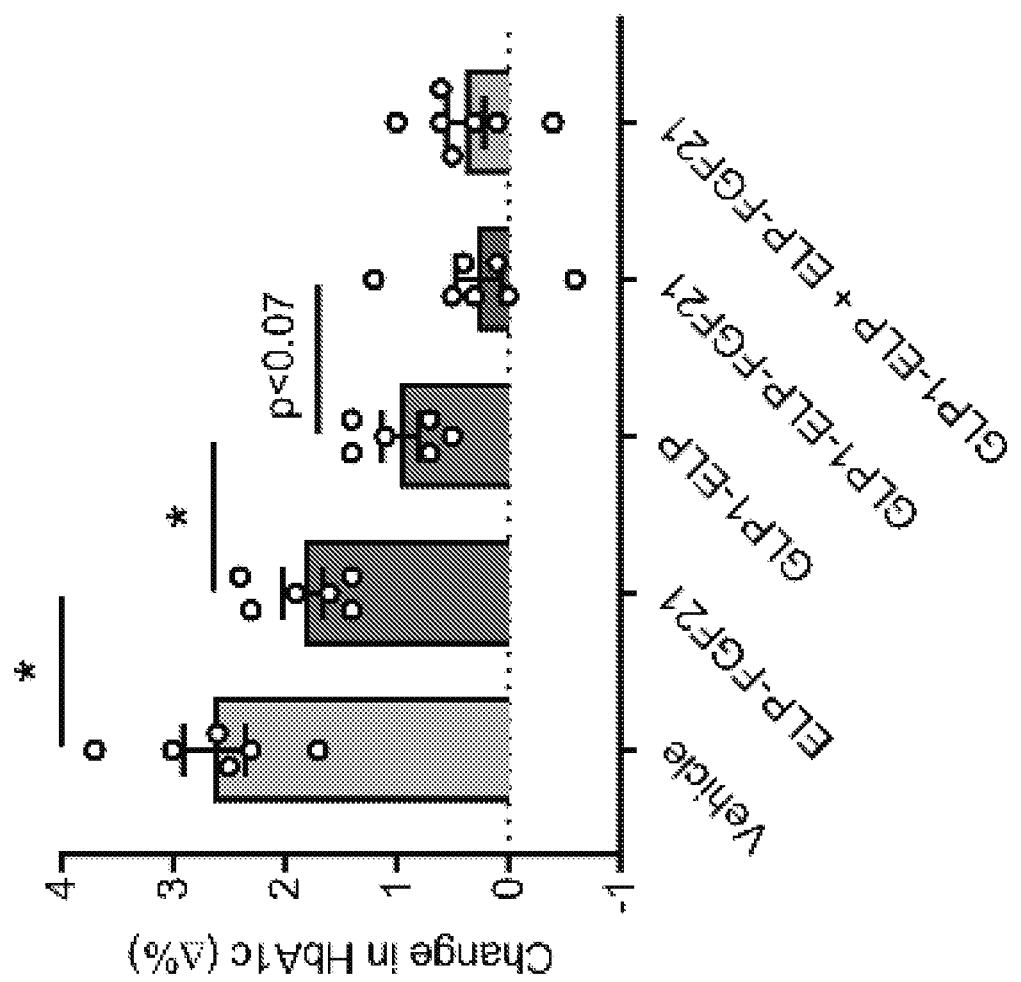
(FIG. 9D) Prior to the first treatment (Day 0) and 6 days following the final treatment (Day 27), % HbA1c was measured in all cohorts, and reported as a magnitude change from pre-study values.

To assess long-term glycemic control, percent glycated hemoglobin A1c (% HbA1c) was measured prior to initiation of treatment (day 0) and at the termination (day 27) of the chronic dosing study. Both ELP-FGF21 and GLP1-ELP monotherapies significantly reduced % HbA1c elevation relative to control over the four-week study, though chronic GLP1-ELP treatment induced a +1.0±0.2% rise from days 0 to 27 (FIG. 9D and FIG. 8B). The dual agonist cohort exhibited the greatest degree of long-term glycemic control, with a minimal +0.3±0.2% change in % HbA1c (p<0.07 compared to GLP1-ELP). Together these data demonstrate that treatment with the GLP1-ELP-FGF21 dual agonist drug affords superior glycemic control compared to equimolar dosing of a long-acting GLP-1RA. Furthermore, GLP-1 and FGF21 appear to act additively in improving glucose homeostasis through enhanced insulin secretion and insulin sensitivity associated with each respective component of the dual agonist.

TABLE 3

Pharmacokinetic parameters for ELP fusion protein depots following s.c. administration to mice.

| LABELED CONSTRUCT | $C_{MAX}$ (NM) | $T_{MAX}$ (H) | AUC (NM*D) | $T_{1/2, ABS}$ (D) |
|---|---|---|---|---|
| GLP1-ELP-FGF21 | 411 ± 51 | 10.5 ± 1.5 | 1961 ± 59 | 7.6 ± 1.1 |
| GLP1-ELP | 369 ± 14 | 4.8 ± 0.7 | 2023 ± 67 | 20.8 ± 3.2 |
| GLP1-ELP AS PART OF 1:1 SINGLE AGONIST FUSION MIXTURE | 233 ± 13 | 21 ± 9 | 1552 ± 66 | 17.0 ± 1.4 |
| ELP-FGF21 AS PART OF 1:1 SINGLE AGONIST FUSION MIXTURE | 338 ± 23 | 12 ± 0 | 1135 ± 59 | 13.2 ± 2.7 |

Data are reported as means ± SEM. $C_{max}$, observed maximum serum concentration; $t_{max}$, time to $C_{max}$; AUC, area under the curve; $t_{1/2, abs}$, absorption half-life.

Figure 9E:
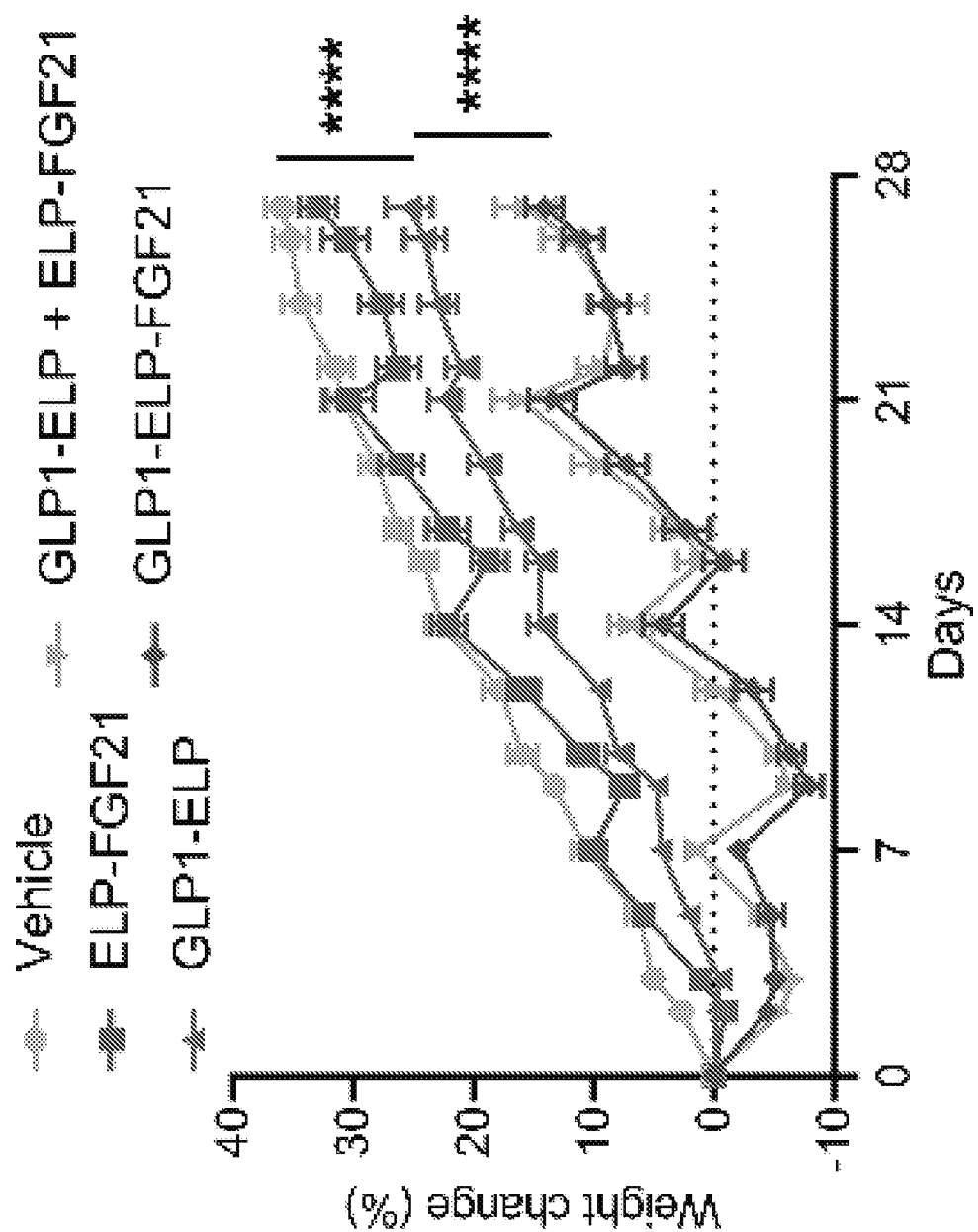
(FIG. 9E and FIG. 9F) Body weights and food consumption were measured every 1-2 days and are reported as % change from pre-injection weights (FIG. 9D) and cumulative food intake per mouse (FIG. 9E).

GLP-1 and FGF21 act in combination to inhibit weight gain: Chronic dosing with the GLP1-ELP monotherapy significantly inhibited weight gain over the four-week treatment period compared to vehicle. The reduced rate of weight gain was likely due in part to a significant reduction in food intake by the GLP1-ELP cohort (FIG. 9F)—which is consistent with the anorectic effect observed upon GLP-1RA therapy. The dual agonist treatment also inhibited weight gain, and each treatment cycle resulted in a potent weight loss effect, with negative net weight gain values persisting through day 12 (FIG. 9E). Chronic dual agonist treatment resulted in significantly reduced weight gain compared to GLP1-ELP monotherapy (14.1±1.6% vs. to 25.3±1.9/6), despite GLP1-ELP-FGF21-treated mice consuming chow at an equivalent rate to GLP1-ELP. Thus, the weight reducing effects of the dual agonist cannot be attributed to an enhanced anorectic effect, but instead point to a separate mechanism likely involving thermogenic action exclusive to the FGF21 component. It should be noted that ELP-FGF21 monotherapy did not induce a significant effect on body weight, indicating that cooperative action between FGF21 and GLP-1 may be necessary for realizing the full weight loss effect.

Figure 8C:
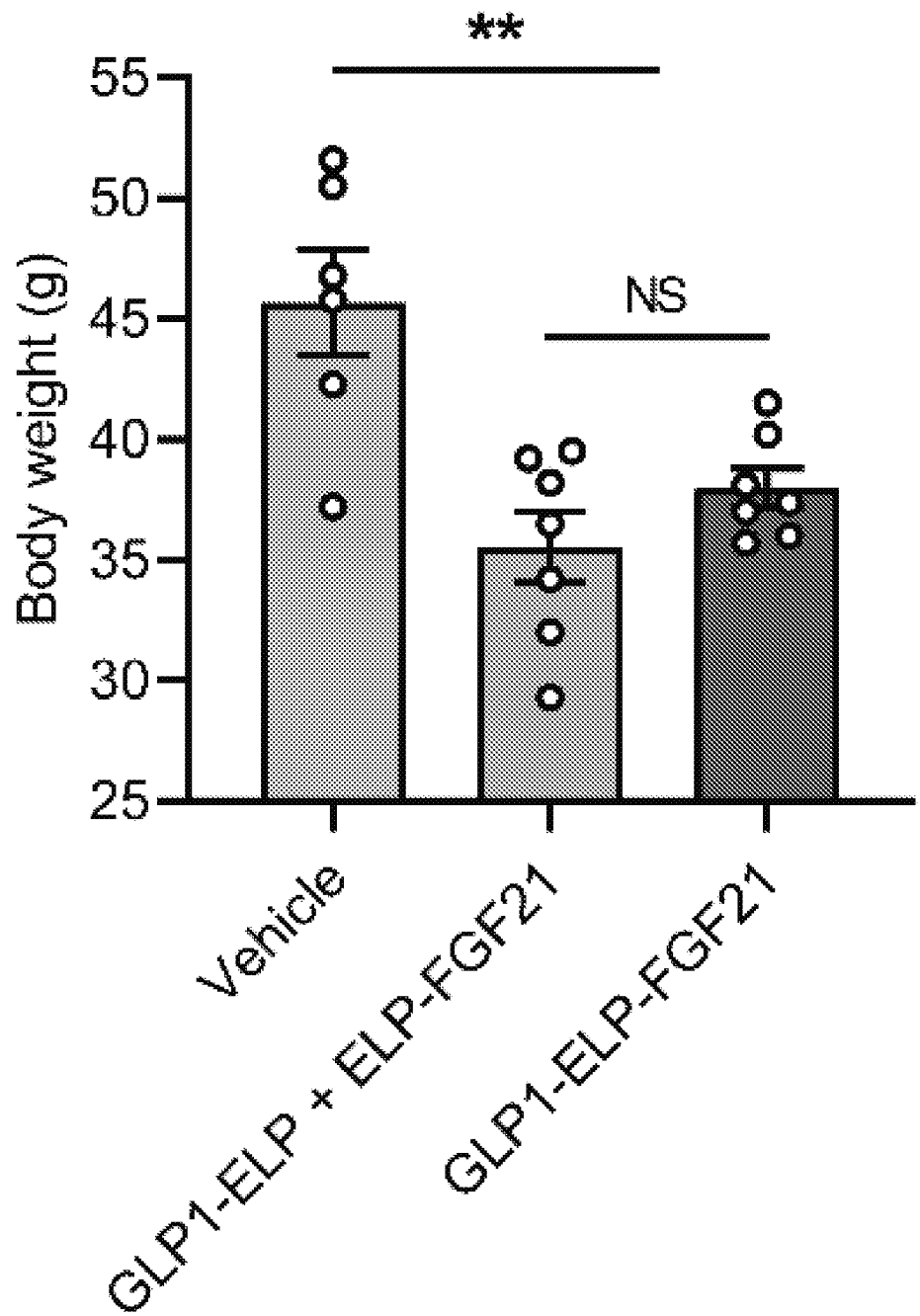
(FIG. 8C) Body weights are consistent between mice treated chronically with either a 1:1 mixture of GLP1-ELP and ELP-FGF21 or the GLP1-ELP-FGF21 dual agonist drug. Data are presented as mean±SEM, **=p<0.01, NS=not significant.
Figure 9F:
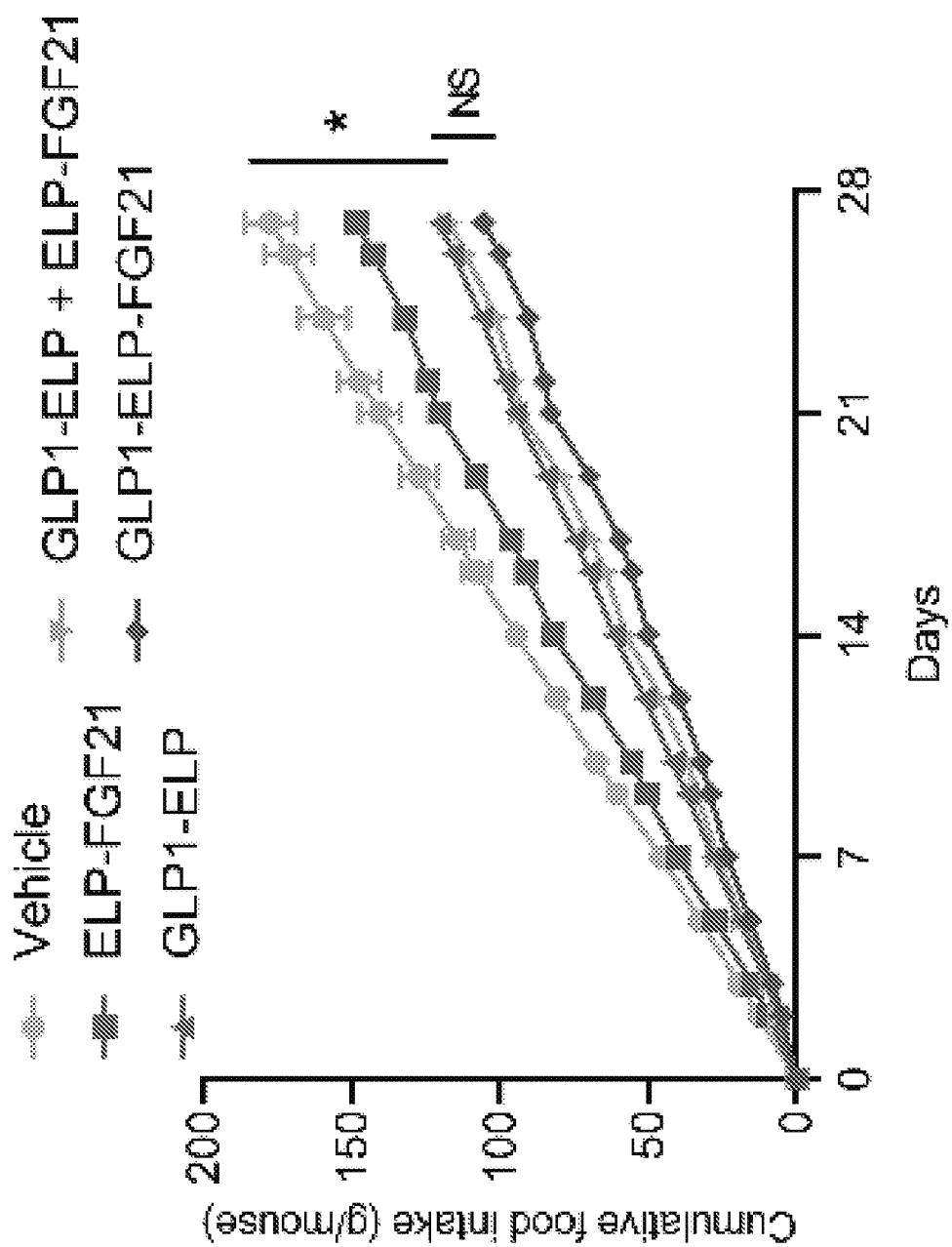
Figure 9G:
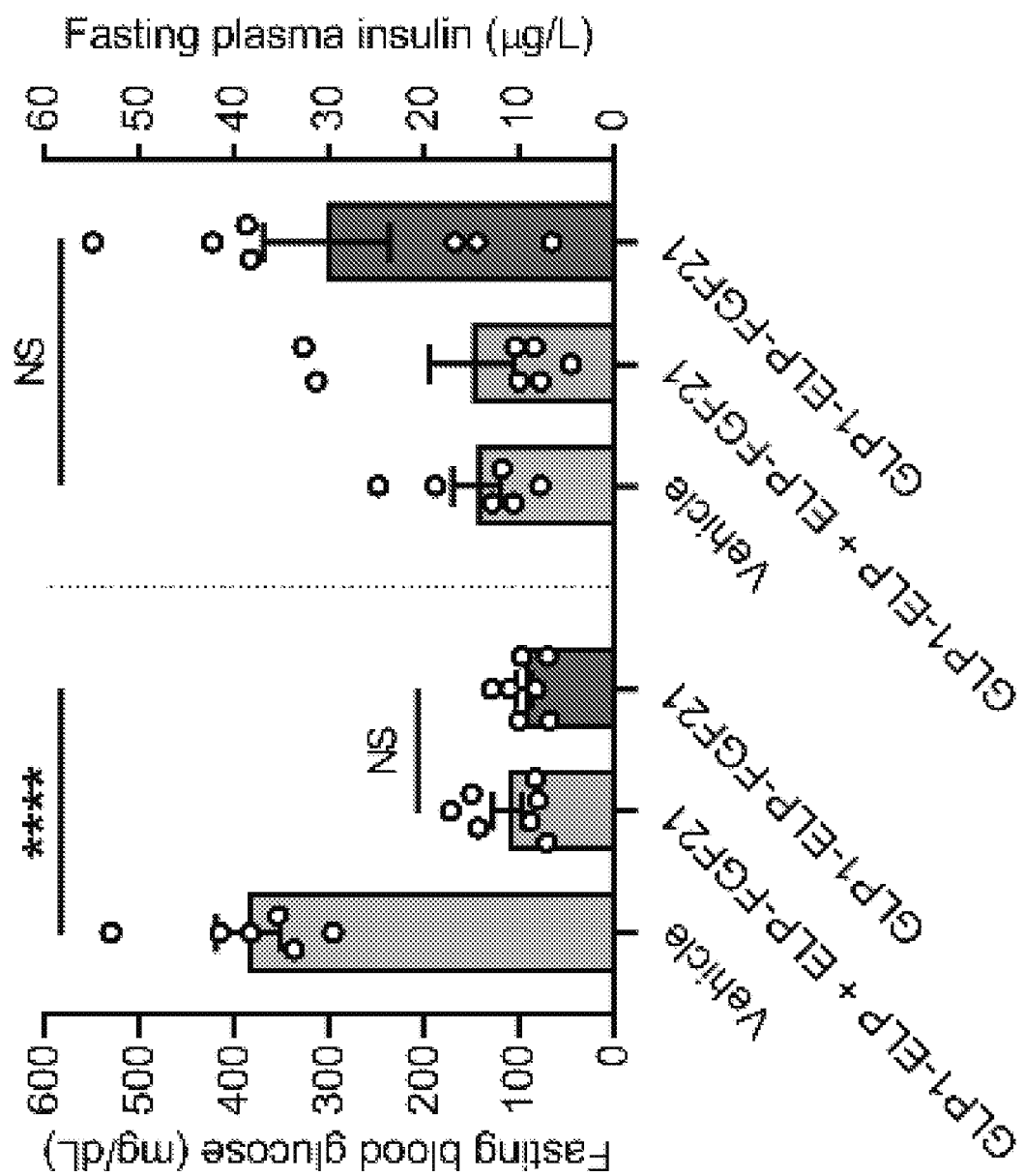
(FIG. 9G, FIG. 9H, and FIG. 9I) 72 h following the final treatment cycle, a GTT was repeated in the dual agonist and 1:1 mixture treatment cohort. Data are presented as mean±SEM; *=p<0.05; *=p<0.001; ****=p<0.0001; NS=not significant.
Figure 9H:
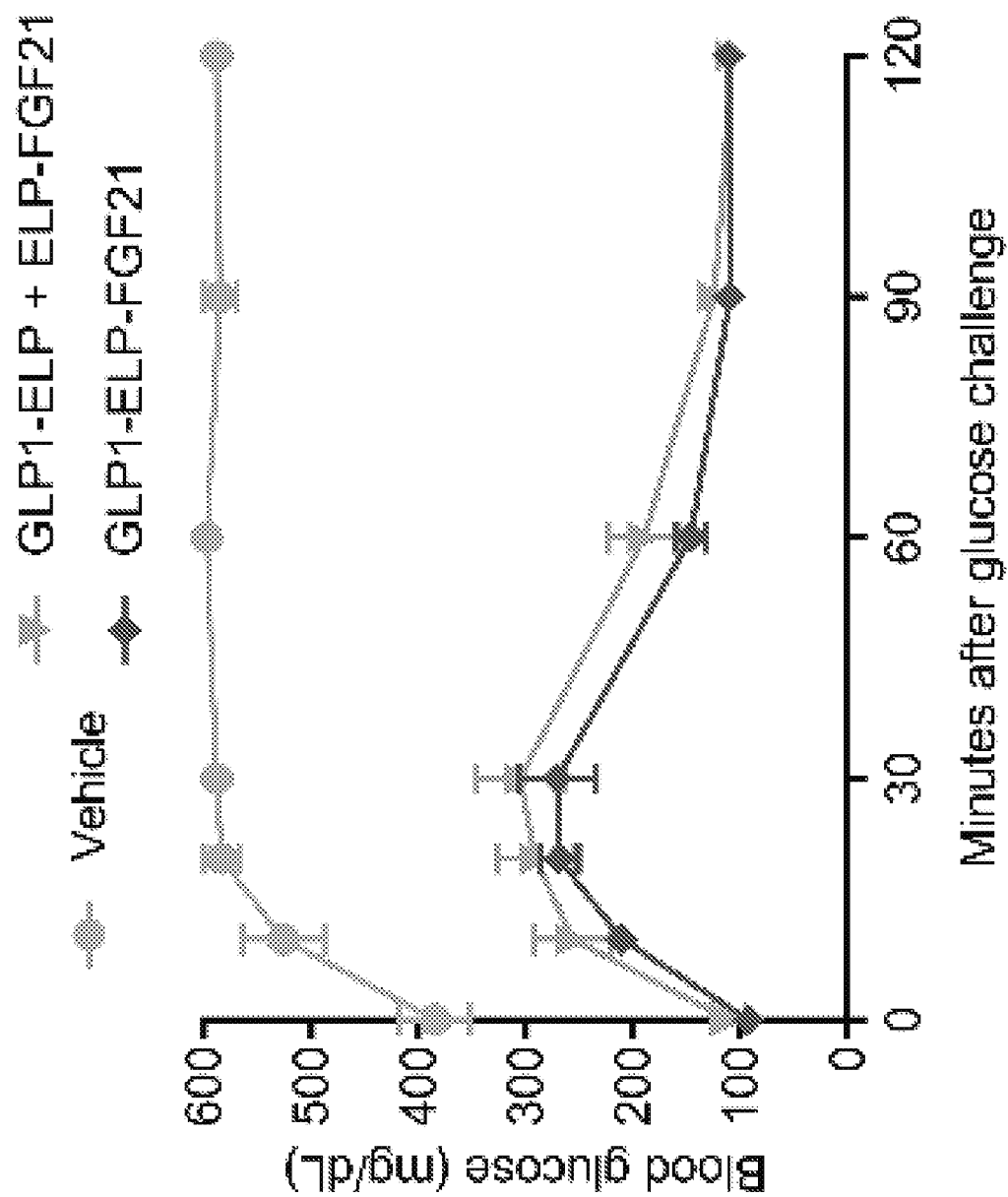
Figure 9I:
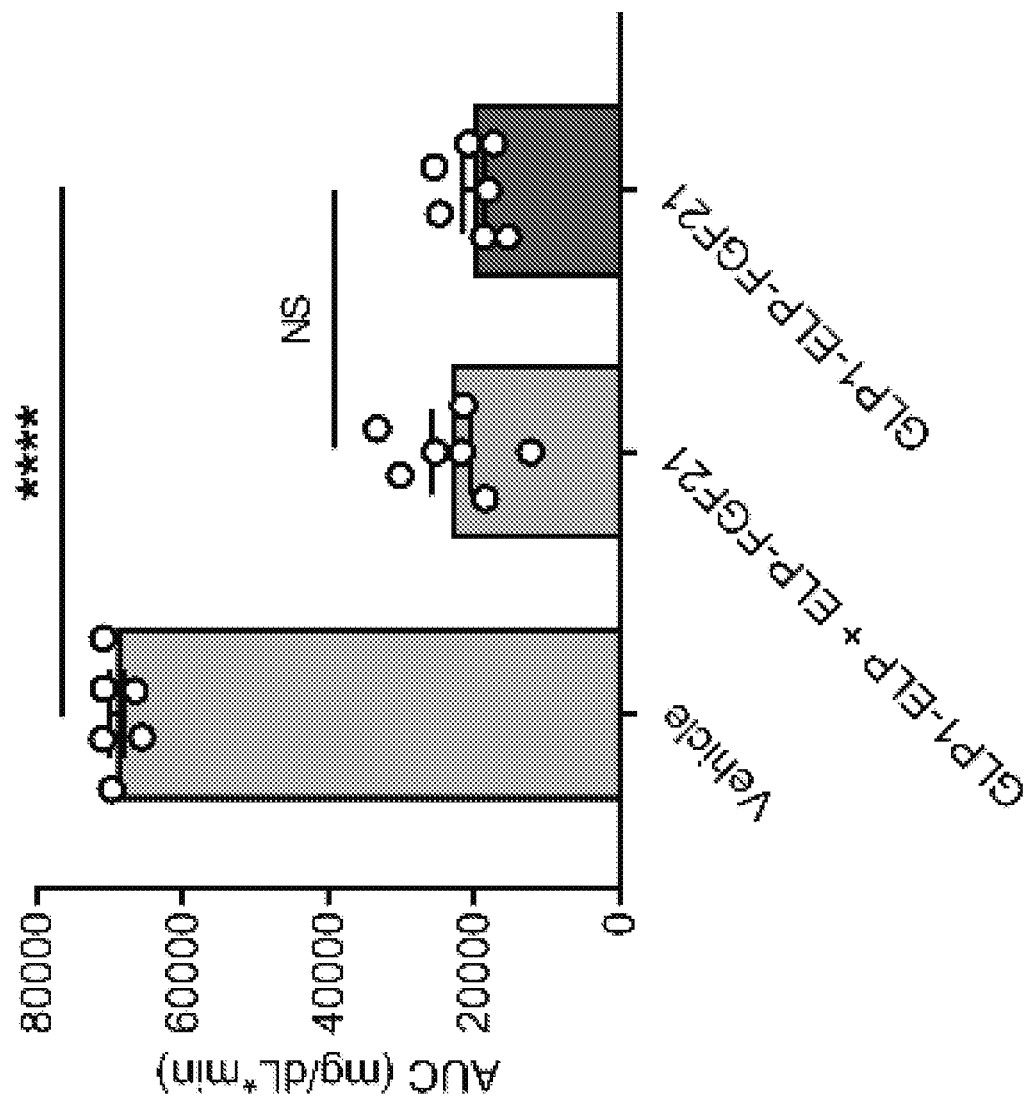

Metabolic effects observed between the GLP1-ELP-FGF21 dual agonist and a GLP-1/FGF21 single agonist mixture: To elucidate whether the metabolic effects of GLP-1/FGF21 combination therapy were impacted by the drug format, a mixture of GLP1-ELP and ELP-FGF21 was included in the chronic dosing study for direct comparison to GLP1-ELP-FGF21. Changes in % HbA1c were consistent between cohorts, however the mixture group trended slightly higher than the dual agonist (+0.4±0.2% compared to +0.3±0.2%). Glycemic control was further evaluated by a GTT performed 3 days following the final treatment. Fasting blood glucose levels were potently reduced upon GLP1-ELP-FGF21 treatment compared to vehicle (92.7±8.3 mg/dL vs. 384.8±33.2 mg/dL), while fasting levels in the co-therapy cohort trended slightly higher (111.4±15.5 mg/dL) (FIG. 9G, left panel). Both combination therapy formats resulted in greatly improved glucose tolerance (FIG. 9H and FIG. 9I), though the dual agonist cohort trended towards lower glucose peaks and faster recoveries to pre-injection baselines compared to a mixture of the two drugs. Body weight and food intake data for the co-therapy group nearly overlapped with those for the dual agonist (FIG. 9E, FIG. 9F, and FIG. 8C). Therefore, the dual agonist's more robust glucose response could not be attributed to the indirect effect of decreased body weight but might be a result of elevated fasting insulin levels (FIG. 9G, right panel).

Although differences between the dual agonist and the single agonist mixture were not statistically significant, GLP1-ELP-FG2F21 showed consistently superior pharmacological trends, effects that we hypothesize may prove to be significant in a larger cohort of animals, or when challenging with larger doses of glucose. These trends may be attributable to the dual agonist's more consistent pharmacokinetic profile compared to the mixed depot, resulting in fewer peaks and valleys and thus maintaining therapeutic levels of both GLP-1 and FGF21 for a larger portion of each dosing cycle.

Figure 10A:
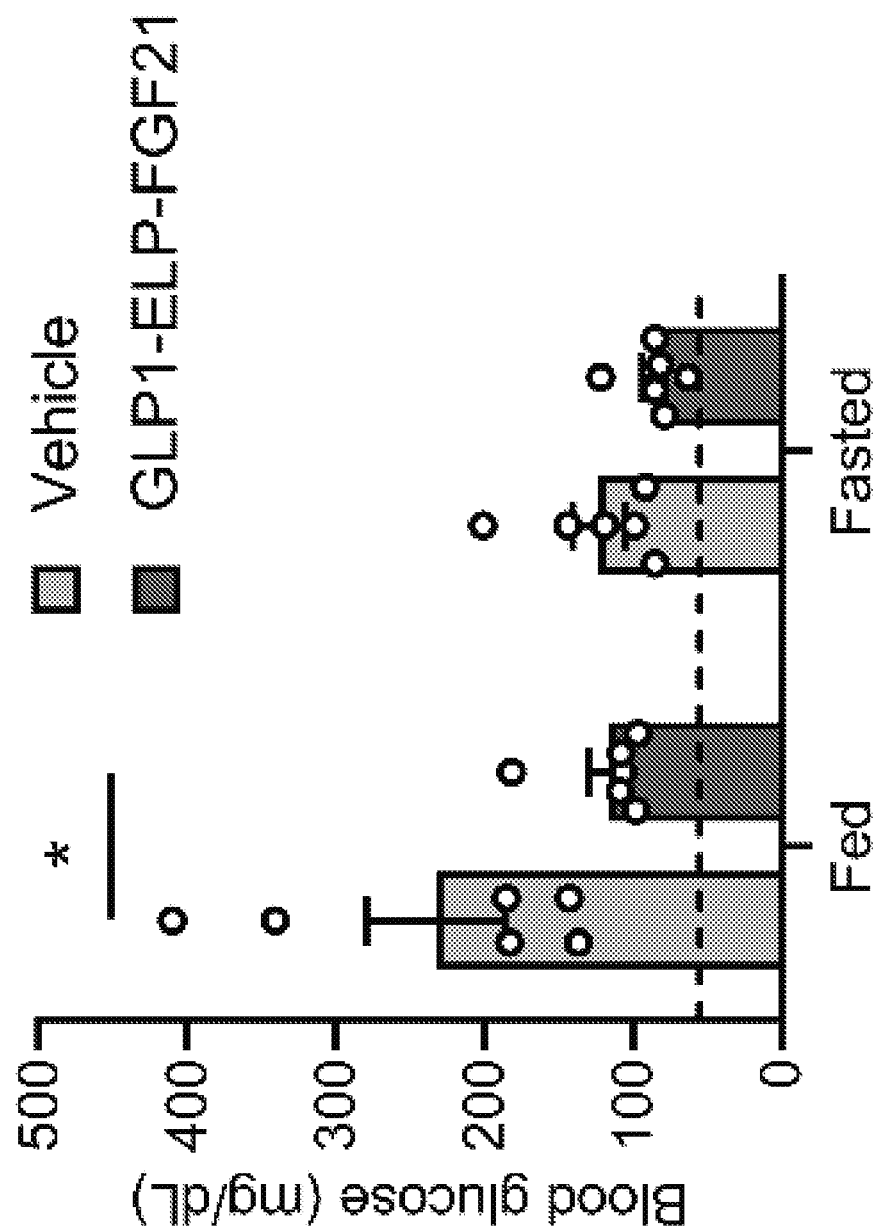
(FIG. 10A) 8-week-old db/db mice (n=6) were injected s.c. with 1000 nmol/kg GLP1-ELP-FGF21 or vehicle, and ad libitum-fed blood glucose levels were measured 48 h following treatment administration ("Fed"). Mice were then subjected to an overnight 16 h fast, after which blood glucose measurements were repeated ("Fasted"). The horizontal dashed line indicates the traditionally defined threshold of hypoglycemia, 55 mg/dL (FIG. 10B) 6-week-old db/db mice (n=6-7) were injected s.c. with 1000 nmol/kg dual agonist or vehicle, and subjected to a glucose tolerance test 72 h post-treatment. Animals were fasted 5 h, after which mice were injected i.p. with 0.75 g/kg glucose. Fasting plasma insulin levels were measured immediately before the glucose bolus, and glucose-stimulated insulin levels were measured 10 min following the bolus. Data are presented as mean±SEM, *=p<0.05. NS=not significant.
Figure 10B:
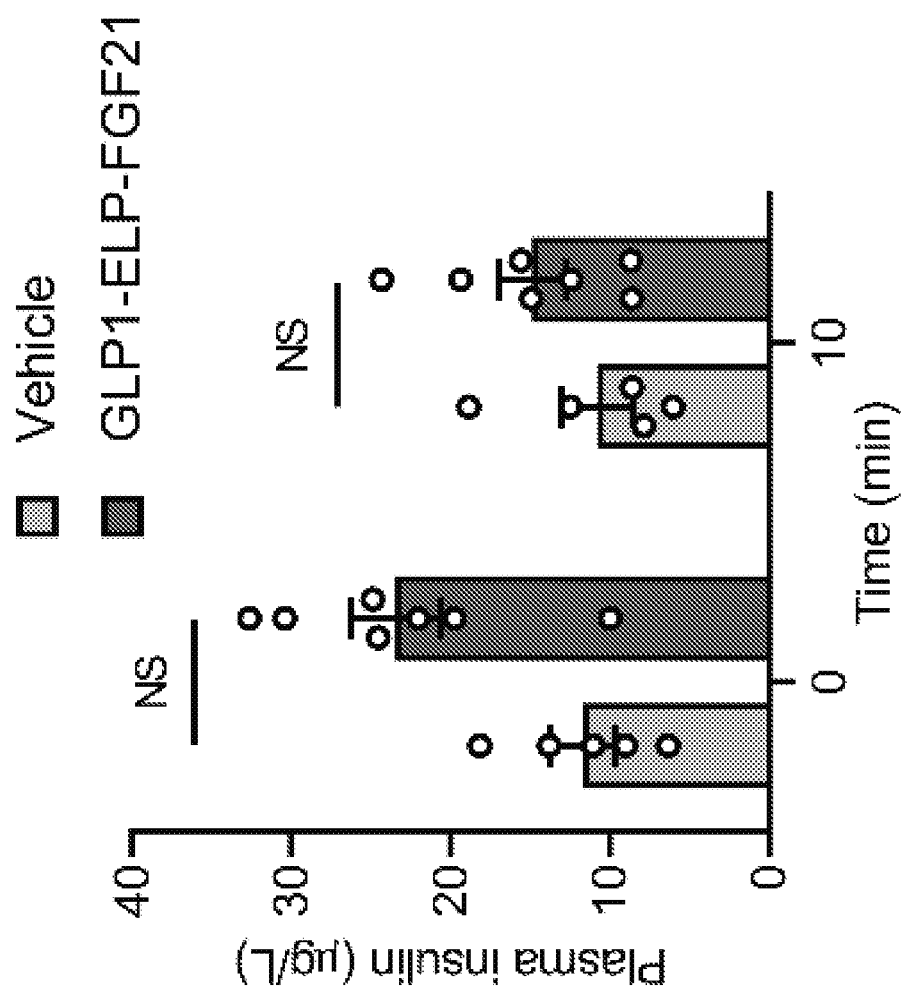
FIG. 10 is a set of plots showing that GLP1-ELP-FGF21 treatment does not predispose mice to nocturnal hypoglycemia or excessive glucose-stimulated insulin secretion.

A GLP1-ELP-FGF21 dual agonist does not increase risk of hypoglycemia: Administering GLP-1 and FGF21 in combination was not expected to pose a risk of hypoglycemia, as each respective agonist has been shown have protective effects: FGF21 lowers glucose levels primarily by increasing insulin sensitivity, while GLP-1 stimulates insulin secretion only in the presence of elevated glucose. However, as a safety check, the dual agonist was tested for increased risk of hypoglycemia during prolonged fasting (nocturnal hypoglycemia) and following recovery from a prandial glucose spike (reactive hypoglycemia). Db/db mice were treated with 1000 nmol/kg GLP1-ELP-FGF21 or vehicle, and ad libitum-fed blood glucose levels measured 48 h post-treatment showed significant reductions in the dual agonist cohort (FIG. 10A). Mice were then subjected to an overnight 16 h fast, after which both cohorts maintained blood glucose levels above the traditionally defined threshold of hypoglycemia, 50-55 mg/dL, indicating that dual agonist-treated mice tolerated the extended fast. Returning to the GTT, an additional plasma insulin measurement was incorporated at t=10 min to assess the glucose-stimulated insulin secretion capacity of dual agonist-treated mice. Plasma insulin levels during a glucose bolus were not significantly elevated in comparison to vehicle treatment (FIG. 10B), and during recovery from t=60 to t=120 min post-challenge, blood glucose levels in the GLP1-ELP-FGF21 cohort returned to the pre-injection baselines, ~100 mg/dL, without evidence of hypoglycemia. Thus, dual agonist treatment does not appear to increase susceptibility to reactive hypoglycemia due to excessive insulin secretion.

For reasons of completeness, various aspects of the invention are set out in the following numbered clauses:

Clause 1. A fusion protein comprising an elastin-like polypeptide (ELP) domain; a GLP-1 receptor agonist domain attached to a N-terminal end of the ELP domain; and a FGF21 receptor agonist domain attached to a C-terminal end of the ELP domain.

Clause 2. The fusion protein of clause 1, wherein the ELP domain comprises an amino acid sequence of $(VPGXG)_n$ (SEQ ID NO:1), wherein X is any amino acid except proline and n is 2 to 200.

Clause 3. The fusion protein of clause 2, wherein n is 80 to 160.

Clause 4. The fusion protein of clause 2 or clause 3, wherein X is valine, alanine, leucine, or a combination thereof.

Clause 5. The fusion protein of any of clauses 2-4, wherein X is a ratio of valine:alanine of 1:0 to 10:1.

Clause 6. The fusion protein of any of clauses 2-5, wherein n is 120 and X is a ratio of valine:alanine of 4:1.

Clause 7. The fusion protein of any of clauses 1-6, wherein the GLP-1 receptor agonist domain comprises an amino acid sequence selected from the group consisting of (SEQ ID NO:2), (SEQ ID NO:3), (SEQ ID NO:4), and variants thereof.

Clause 8. The fusion protein of any of clauses 1-7, wherein the FGF21 receptor agonist domain comprises an amino acid sequence selected from the group consisting of (SEQ ID NO:5), (SEQ ID NO:6), (SEQ ID NO:7), (SEQ ID NO:8), and variants thereof.

Clause 9. The fusion protein of any of clauses 1-8, wherein the fusion protein has a transition temperature ($T_t$) of about 25° C. to about 37° C.

Clause 10. The fusion protein of any of clauses 1-9, wherein the fusion protein has a molecular weight of about 50 kDa to about 100 kDa.

Clause 11. A composition comprising a plurality of fusion proteins according to any one of clauses 1-10, wherein the plurality of fusion proteins assemble into an aggregate above the $T_t$ of the fusion protein.

Clause 12. The composition of clause 11, further comprising a biologically active agent.

Clause 13. A method of treating a metabolic disease in a subject in need thereof, the method comprising administering to the subject an effective amount of the composition of clause 11 or clause 12.

Clause 14. The method of clause 13, wherein the metabolic disease is selected from the group consisting of obesity, type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, and a combination thereof.

Clause 15. The method of clause 13 or clause 14, wherein the composition releases the fusion protein following administration for greater than 3 days.

Clause 16. The method of any of clauses 13-15, wherein administration of the composition results in the subject having at least one of decreased blood glucose level, decreased body fat, increased insulin production, decreased hemoglobin A1c values, decreased circulating fatty acids, decreased liver fat content, decreased liver inflammation, and decreased liver fibrosis compared to a subject not receiving the administration of the composition.

Clause 17. A method of synthesizing a dual agonist fusion protein, the method comprising transforming a bacteria with a recombinant expression vector comprising a first polynucleotide encoding the fusion protein of any of clauses 1-10; and culturing the transformed bacteria to express the fusion protein.

Clause 18. The method of clause 17, wherein the expression vector further comprises a second polynucleotide encoding a translation initiation domain attached to the N-terminal end of the fusion protein.

Clause 19. The method of clause 18, wherein the translation initiation domain comprises a leader sequence and a protease cleavage site, the protease cleavage site located between the leader sequence and the fusion protein.

Clause 20. The method of any of clauses 17-19, wherein culturing is done at less than 37° C.

Sequences

| Description | Amino Acid Sequence | Molecular Weight (kDa)/SEQ ID NO |
|---|---|---|
| ELP Repeat | (VPGXG)$_n$ | (SEQ ID NO: 1) |
| GLP-1 | AAHGEGTFTSDVSSYLEEQAAKEFIAWLVKGA | (SEQ ID NO: 2) |
| Amended Leader GLP-1 | GAHGEGTFTSDVSSYLEEQAAKEFIAWLVKGA | (SEQ ID NO: 3) |
| No Leader GLP-1 | HGEGTFTSDVSSYLEEQAAKEFIAWLVKGA | (SEQ ID NO: 4) |
| Murine FGF21 with stabilizing mutations | AYPIPDSSPLLQFGGQVRQRYLYTDDDQDTEAH LEIREDGTVVGAAHRSPESLLELKALKPGVIQIL GVKASRFLCQQPDGALYGSPHFDPEACSFRERL LEDGYNVYQSEAHGLPLRLPQKDSPNQDATSW GPVRFLPMPGLLHEPQDQAGFLPPEPPDVGSSDP LSMVEGSQGRSPSYAS | (SEQ ID NO: 5) |
| Murine FGF21 without stabilizing mutations | AYPIPDSSPLLQFGGQVRQRYLYTDDDQDTEAH LEIREDGTVVGAAHRSPESLLELKALKPGVIQIL GVKASRFLCQQPDGALYGSPHFDPEACSFRELL LEDGYNVYQSEAHGLPLRLPQKDSPNQDATSW GPVRFLPMPGLLHEPQDQAGFLPPEPPDVGSSDP LSMVEPLQGRSPSYAS | (SEQ ID NO: 6) |
| Human FGF21 with stabilizing mutations | HPIPDSSPIIQFGGQVRQRYLYTDDAQQTEAHL EIREDGTVGGAADQSPESLLQLKALKPGVIQILG VKTSRFLCQRPDGALYGSLHFDPEACSFRERLL EDGYNVYQSEAHGLPLHLPGNKSPHRDPAPRGP ARFLPLPGLPPALPEPPGILAPQPPDVGSSDPLSM VGGSQGRSPSYAS | (SEQ ID NO: 7) |
| Human FGF21 without stabilizing mutations | HPIPDSSPLLQFGGQVRQRYLYTDDAQQTIAHL EIREDGTVGGAADQSPESLLQLKALKPGVIQILG VKTSRFLCQRPDGALYGSLHFDPEACSFRELLE DGYNVYQSEAHGLPLHLPGNKSPHRDPAPRGP ARFLPLPGLPPALPEPPGILAPQPPDVGSSDPLSM VGPSQGRSPSYAS | (SEQ ID NO: 8) |
| ELP$_{100\% Val,60}$-FGF21 | GVGVPGVGVPGVGVPGVGVPGVGVPGVGVPG VGVPGVGVPGVGVPGVGVPGVGVPGVGVPGV GVPGYGYPGYGVPGVGYPGYGVPGVGVPGYG VPGVGVPGVGVPGVGVPGVGVPGVGVPGVGV PGVGVPGVGVPGVGVPGVGVPGVGVPGVGVP GYGYPGVGVGYPGYGYPGYGYPGYGVPGYGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVPGAYPIPDSSPL LQFGGQVRQRYLYTDDDQDTEAHLEIREDG TVVGAAHRSPESLLELKALKPGVIQILGVKAS RFLCQQPDGALYGSPHFDPEACSFRERLLED GYNVYQSEAHGLPLRLPQKDSPNQDATSWG PVRFLPMPGLLHLPQDQAGFLPPEPPDVGSS DPLSMVEGSQGRSPSYASG | 44.6 (SEQ ID NO: 9) |
| ELP$_{100\% Val,60}$ | GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGYVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGYGYPGYGYPGYGYPGYGYPG | 24.6 (SEQ ID NO: 10) |
| ELP-tev-FGF21 | GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG | 45.5 (SEQ ID NO: 11) |

-continued

| Description | Amino Acid Sequence | Molecular Weight (kDa)/SEQ ID NO |
|---|---|---|
| | VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGYPGYGVPGVGVPGVGYPGVG VPGVGVPGVGVPGVGVPGVGVPGVGVPGVGV PGVGVPGVGVPGVGVPGVGVPG*ENLYFQ*AYP IPDSSPLLQFGGQVRQRYLYTDDDQDTEAHL EIREDGTVVGAAHRSPESLLELKALKPGVIQI LGVKASRFLCQQPDGALYGSPHFDPEACSFR ERLLEDGYNVYQSEAHGLPLRLPQKDSPNQD ATSWGPVRFLPMPGLLHEPQDQAGFLPPLPP DVGSSDPLSMVEGSQGRSPSYASG | |
| ELP-protease | GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVGVPGVGVPGVGYGVPGVGVPGVGVPGY GVPGVGVPGVGVPGVGVPGVGVPGVGVPGVG VPGVGVPGVGVPGVGVPGVGVPGVGVPGVGV PGVGVPGVGVPGVGVPGVGVPGGESLFKGPR DYNPISSTICHLTNESDGHTTSLYGIGFGPFIIT NKHLFRRNNGTLLVQSLHGVFKVKNTTTLQ QHLIDGRDMIIIRMPKDFPPFPQKLKFREPQR EERICLVTTNFQTKSMSSMVSDTSCTFPSSDGI FWKHWIQTKDGQCGSPLVSTRDGFIVGIHSA SNFTNTNNYFTSVPKNFMELLTNQEAQQWVS GWRLNADSVLWGGHKVFMVKPEEPFQPVK EATQLMNG | 51.5 (SEQ ID NO: 12) |
| ELP$_{100\%Val, 120}$-FGF21 | GVGVPGVGVPGVGVPGVGVPGVGVPGVGVPG VGVPGVGVPGVGVPGVGVPGVGVPGVGVPGY GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGAAYPIPDSSPLLQFGGQVRQR YLYTDDDQDTEAHLEIREDGTVVGAAHRSPE SLLELKALKPGVIQILGVKASRFLCQQPDGAL YGSPHFDPEACSFRERLLEDGYNVYQSEAHG LPLRLPQKDSPNQDATSWGPVRFLPMPGLLH EPQDQAGFLPPEPPDVGSSDPLSMVEGSQGRS PSYASG | 69.2 (SEQ ID NO: 13) |
| ELP$_{20\%Ala, 120}$-FGF21 | GVGVPGVGVPGAGVPGVGVPGVGVPGVGVPG VGVPGAGVPGVGVPGVGVPGVGVPGVGVPGA GVPGVGVPGVGVPGVGVPGVGVPGAGVPGVG VPGVGVPGVGVPGVGVPGAGVPGVGVPGVGV PGVGVPGVGVPGAGVPGVGVPGVGVPGVGVP GVGVPGAGVPGVGVPGVGVPGVGVPGVGVPG AGVPGVGVPGVGVPGVGVPGVGVPGAGVPGV GVPGVGVPGVGVPGVGVPGAGVPGVGVPGVG VPGVGVPGVGVPGAGVPGVGVPGVGVPGVGV PGVGVPGAGVPGVGVPGVGVPGVGVPGVGVP GAGVPGVGVPGVGVPGVGVPGVGVPGAGVPG VGVPGVGVPGVGVPGVGVPGAGVPGVGVPGV GVPGVGVPGVGVPGAGVPGVGVPGVGVPGVG VPGVGVPGAGVPGVGVPGVGVPGVGVPGVGV | 68.5 (SEQ ID NO: 14) |

-continued

| Description | Amino Acid Sequence | Molecular Weight (kDa)/SEQ ID NO |
|---|---|---|
| | PGAGVPGVGVPGVGVPGVGVPGVGVPGAGVP GVGVPGVGVPGVGVPGVGVPGAGVPGVGVPG VGVPGVGVPGVGVPGAGVPGVGVPGVGVPGV GVPGVGVPGAGVPGVGVPGVGVPGVGVPGVG VPGAGVPGVGVPGVGVPGVGVPGVGVPGAGV PGVGVPGVGVPGAYPIPDSSPLLQFGGQVRQR YLYTDDDQDTEAHLEIREDGTVVGAAHRSPE SLLELKALKPGVIQILGVKASRFLCQQPDGAL YGSPHFDPEACSFRERLLEDGYNVYQSEAHG LPLRLPQKDSPNQDATSWGPVRFLPMPGLLH EPQDQAGFLPPEPPDVGSSDPLSMVEGSQGRS PSYASG | |
| GLP1-ELP$_{20\%Ala,120}$-FGF21 | *AA*HGEGTFTSDVSSYLEEQAAKEFIAWLVKG AGVGVPGVGVPGAGVPGVGVPGVGVPGVGVP GVGVPGAGVPGVGVPGVGVPGVGVPGVGVPG AGVPGVGVPGVGVPGVGVPGVGVPGAGVPGV GVPGVGVPGVGVPGVGVPGAGVPGVGVPGVG VPGVGVPGVGVPGAGVPGVGVPGVGVPGVGV PGVGVPGAGVPGVGVPGVGVPGVGVPGVGVP GAGVPGVGVPGVGVPGVGVPGVGVPGAGVPG VGVPGVGVPGVGVPGAGVPGVGVPGVGVPGV GVPGVGVPGVGVPGAGVPGVGVPGVGVPGVG VPGVGVPGAGVPGVGVPGVGVPGVGVPGVGV PGAGVPGVGVPGVGVPGVGVPGVGVPGAGVP GVGVPGVGVPGVGVPGVGVPGAGVPGVGVPG VGVPGVGVPGVGVPGAGVPGVGVPGVGVPGV GVPGVGVPGAGVPGVGVPGVGVPGVGVPGVG VPGAGVPGVGVPGVGVPGVGVPGVGVPGAGV PGVGVPGVGVPGVGVPGAGVPGVGVPGVGVP GVGVPGVGVPGVGVPGAGVPGVGVPGVGVPG VGVPGVGVPGAGVPGVGVPGVGVPGVGVPGV GVPGAGVPGVGVPGVGVPGVGVPGVGVPGAG VPGVGVPGVGVPAYPIPDSSPLLQFGGQVRQ RYLYTDDDQDTEAHLEIREDGTVVGAAHRSP ESLLLLKALKPGVIQILGVKASRFLCQQPDGA LYGSPHFDPEACSFRERLLEDGYNVYQSEAH GLPLRLPQKDSPNQDATSWGPVRFLPMPGLL HEPQDQAGFLPPEPPDVGSSDPLSMVEGSQG RSPSYASG | 71.9 (SEQ ID NO: 15) |
| GLP1-ELP$_{20\%Ala,120}$ | *AA*HGEGTFTSDVSSYLELQAAKEFIAWLVKG AGVGVPGVGVPGAGVPGVGVPGVGVPGVGVP GVGVPGAGVPGVGVPGVGVPGVGVPGVGVPG AGVPGVGVPGVGVPGVGVPGVGVPGAGVPGV GVPGVGVPGVGVPGAGVPGVGVPGVGVPGVG VPGVGVPGVGVPGAGVPGVGVPGVGVPGVGV PGVGVPGAGVPGVGVPGVGVPGVGVPGVGVP GAGVPGVGVPGVGVPGVGVPGVGVPGAGVPG VGVPGVGVPGVGVPGAGVPGVGVPGVGVPGV GVPGVGVPGVGVPGAGVPGVGVPGVGVPGVG VPGVGVPGAGVPGVGVPGVGVPGVGVPGVGV PGAGVPGVGVPGVGVPGVGVPGVGVPGAGVP GVGVPGVGVPGVGVPGVGVPGAGVPGVGVPG VGVPGVGVPGVGVPGAGVPGVGVPGVGVPGY GVPGVGVPGAGVPGVGVPGVGVPGVGVPGVG VPGAGVPGVGVPGVGVPGVGVPGVGVPGAGV PGVGVPGVGVPGVGVPGVGVPGAGVPGVGVP GVGVPGVGVPGVGVPGAGVPGVGVPGVGVPG VGVPGVGVPGAGVPGVGVPGVGVPGVGVPGV GVPGAGVPGVGVPGVGVPGVGVPGVGVPGAG VPGVGVPGVGVPG | 51.9 (SEQ ID NO: 16) |
| Leader- GLP1-ELP$_{20\%Ala,120}$-FGF21 | *MSKGPGENLYFQGA*HGLGTFTSDVSSYLLEQA AKEFIAWLVKGAGVGVPGVGVPGAGVPGVGV PGVGVPGVGVPGVGVPGAGVPGVGVPGVGVP GVGVPGVGVPGAGVPGVGVPGVGVPGVGVPG VGVPGAGVPGVGVPGVGVPGVGVPGVGVPGA GVPGVGVPGVGVPGVGVPGVGVPGAGVPGVG VPGVGVPGVGVPGVGVPGAGVPGVGVPGVGV PGVGVPGVGVPGAGVPGVGVPGVGVPGVGVP GVGVPGAGVPGVGVPGVGVPGVGVPGVGVPG AGVPGVGVPGVGVPGVGVPGVGVPGAGVPGV GVPGVGVPGVGVPGVGVPGAGVPGVGVPGV | 73.2 (SEQ ID NO: 17) |

-continued

| Description | Amino Acid Sequence | Molecular Weight (kDa)/SEQ ID NO |
|---|---|---|
| | VPGVGVPGVGVPGAGVPGVGVPGVGVPGVGV<br>PGVGVPGAGVPGVGVPGVGVPGVGVPGVGVP<br>GAGVPGVGVPGVGVPGVGVPGVGVPGAGVPG<br>VGVPGVGVPGVGVPGVGVPGAGVPGVGVPGV<br>GVPGVGVPGVGVPGAGVPGVGVPGVGVPGVG<br>VPGVGVPGAGVPGVGVPGVGVPGVGVPGVGV<br>PGAGVPGVGVPGVGVPGVGVPGVGVPGAGVP<br>GVGVPGVGVPGVGVPGVGVPGAGVPGVGVPG<br>VGVPGVGVPGVGVPGAGVPGVGVPGVGVPGV<br>GVPGVGVPGAGVPGVGVPGVGVPGAYPIPDSS<br>PLLQFGGQVRQRYLYTDDDQDTEAHLEIRED<br>GTVVGAAHRSPESLLELKALKPGVIQILGVK<br>ASRFLCQQPDGALYGSPHFDPEACSFRERLLE<br>DGYNVYQSLAHGLPLRLPQKDSPNQDATSW<br>GPVRFLPMPGLLHEPQDQAGFLPPEPPDVGS<br>SDPLSMVEGSQGRSPSYASG | |
| GLP1-ELP$_{20\%Ala,120}$-FGF21<br>(no AA leader) | HGEGTFTSDVSSYLEEQAAKEFIAWLVKGAG<br>VGVPGVGVPGAGVPGVGVPGVGVPGVGVPGV<br>GVPGAGVPGVGVPGVGVPGVGVPGVGVPGAG<br>VPGVGVPGVGVPGVGVPGVGVPGAGVPGVGV<br>PGVGVPGVGVPGVGVPGAGVPGVGVPGVGVP<br>GVGVPGVGVPGAGVPGVGVPGVGVPGVGVPG<br>VGVPGAGVPGVGVPGVGVPGVGVPGVGVPGA<br>GVPGVGVPGVGVPGVGVPGVGVPGAGVPGVG<br>VPGVGVPGVGVPGVGVPGAGVPGVGVPGVGV<br>PGVGVPGVGVPGAGVPGVGVPGVGVPGVGVP<br>GVGVPGAGVPGVGVPGVGVPGVGVPGVGVPG<br>AGVPGVGVPGVGVPGVGVPGVGVPGAGVPGV<br>GVPGVGVPGVGVPGVGVPGAGVPGVGVPGVG<br>VPGVGVPGVGVPGAGVPGVGVPGVGVPGVGV<br>PGVGVPGAGVPGVGVPGVGVPGVGVPGVGVP<br>GAGVPGVGVPGVGVPGVGVPGVGVPGAGVPG<br>VGVPGVGVPGVGVPGVGVPGAGVPGVGVPGV<br>GVPGVGVPGVGVPGAGVPGVGVPGVGVPGVG<br>VPGVGVPGAGVPGVGVPGVGVPGVGVPGVGV<br>PGAGVPGVGVPGVGVPGVGVPGVGVPGAGVP<br>GVGVPGVGVPGAYPIPDSSPLLQFGGQVRQRY<br>LYTDDDQDTEAHLEIREDGTVVGAAHRSPLS<br>LLELKALKPGVIQILGVKASRFLCQQPDGAL<br>YGSPHFDPEACSFRERLLEDGYNVYQSEAHG<br>LPLRLPQKDSPNQDATSWGPVRFLPMPGLLH<br>EPQDQAGFLPPEPPDVGSSDPLSMVEGSQGRS<br>PSYASG** | (SEQ ID NO: 18) |
| ELP$_{20\%Ala,120}$ | GVGVPGVGVPGAGVPGVGVPGVGVPGVGVPG<br>VGVPGAGVPGVGVPGVGVPGVGVPGVGVPGA<br>GVPGVGVPGVGVPGVGVPGVGVPGAGVPGVG<br>VPGVGVPGVGVPGVGVPGAGVPGVGVPGVGV<br>PGVGVPGVGVPGAGVPGVGVPGVGVPGVGVP<br>GVGVPGAGVPGVGVPGVGVPGVGVPGVGVPG<br>AGVPGVGVPGVGVPGVGVPGVGVPGAGVPGV<br>GVPGVGVPGVGVPGVGVPGAGVPGVGVPGVG<br>VPGVGVPGVGVPGAGVPGVGVPGVGVPGVGV<br>PGVGVPGAGVPGVGVPGVGVPGVGVPGVGVP<br>GAGVPGVGVPGVGVPGVGVPGVGVPGAGVPG<br>VGVPGVGVPGVGVPGVGVPGAGVPGVGVPGV<br>GVPGVGVPGVGVPGAGVPGVGVPGVGVPGVG<br>VPGVGVPGAGVPGVGVPGVGVPGVGVPGVGV<br>PGAGVPGVGVPGVGVPGVGVPGVGVPGAGVP<br>GVGVPGVGVPGVGVPGVGVPGAGVPGVGVPG<br>VGVPGVGVPGVGVPGAGVPGVGVPGVGVPGV<br>GVPGVGVPGAGVPGVGVPGVGVPGVGVPGVG<br>VPGAGVPGVGVPGVGVPGVGVPGVGVPGAGV<br>PGVGVPGVGVPG | (SEQ ID NO: 19) |
| Leader Sequence | MSKGPGENLYFQGA | (SEQ ID NO: 20) |
| Expression-enhancing sequence | MSKGPG | (SEQ ID NO: 21) |
| TEV protease cleavage sequence | ENLYFQG | (SEQ ID NO: 22) |

-continued

| Description | Amino Acid Sequence | Molecular Weight (kDa)/SEQ ID NO |
|---|---|---|
| GLP1-ELP$_{100\%Val,120}$-FGF21 | AAHGEGTFTSDVSSYLEEQAAKEFIAWLVKG AGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGYGVPGVGVPGVGVPGYGVPG VGVPGVGVPGVGVPGVGVPGVGVPGVGVPGV GVPGVGVPGVGVPGVGVPGVGVPGVGVPGVG VPGVGVPGVGVPGAYPIPDSSPLLQFGGQVRQ RYLYTDDDQDTEAHLEIREDGTVVGAAHRSP ESLLELKALKPGVIQILGVKASRFLCQQPDGA LYGSPHFDPEACSFRERLLEDGYNVYQSEAH GLPLRLPQKDSPNQDATSWGPVRFLPMPGLL HEPQDQAGFLPPEPPDVGSSDPLSMVEGSQG RSPSYASG | (SEQ ID NO: 23) |
| GLP1-ELP$_{100\%Val,60}$-FGF21 | AAHGEGTFTSDVSSYLEEQAAKEFIAWLVKG AGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGVGVPGVGV PGVGVPGVGVPGVGVPGVGVPGVGVPGVGVP GVGVPGVGVPGVGVPGVGVPGVGVPGVGVPG VGVPGVGVPGVGVPGVGVPGVGVPGVGVPGV GVPGVGVPGVGVPGVGVPGVGVPGVGVPGVG VPGVGVPGVGVPGVGVPGVGVPGAYPIPDSSP LLQFGGQVRQRYLYTDDDQDTEAHLEIRED GTVVGAAHRSPESLLELKALKPGVIQILGVK ASRFLCQQPDGALYGSPHFDPEACSFRERLLE DGYNVYQSEAHGLPLRLPQKDSPNQDATSW GPVRFLPMPGLLHEPQDQAGFLPPEPPDVGS SDPLSMVEGSQGRSPSYASG | (SEQ ID NO: 24) |

Underlined text designates residues associated with ELPs; bold text designates functional proteins/peptides (FGF21, TEV protease, GLP1); italicized text designates residues associated with linkers or leaders.

What is claimed is:

1. A fusion protein comprising:
   an elastin-like polypeptide (ELP) domain, wherein the ELP domain comprises the amino acid sequence of SEQ ID NO: 19);
   a GLP-1 receptor agonist domain attached to the N-terminal end of the ELP domain, wherein the GLP-1 receptor agonist domain comprises the amino acid sequence selected from the group consisting of (SEQ ID NO:2), (SEQ ID NO:3), and (SEQ ID NO:4); and
   a FGF21 receptor agonist domain attached to the C-terminal end of the ELP domain, wherein the FGF21 receptor agonist domain comprises the amino acid sequence selected from the group consisting of (SEQ ID NO:5), (SEQ ID NO:6), (SEQ ID NO:7), and (SEQ ID NO:8).

2. The fusion protein of claim 1, wherein the fusion protein has a transition temperature ($T_t$) of about 25° C. to about 37° C.

3. A composition comprising:
   a plurality of fusion proteins according to claim 1, wherein the plurality of fusion proteins assemble into an aggregate above the $T_t$ of the fusion protein.

4. The composition of claim 3, further comprising a biologically active agent.

5. A method of treating a metabolic disease in a subject in need thereof, the method comprising administering to the subject an effective amount of the composition of claim 3, wherein the metabolic disease is selected from the group consisting of type 1 diabetes mellitus, type 2 diabetes mellitus, postprandial hyperglycemia, overweight, obesity, metabolic syndrome, gestational diabetes, pancreatitis, dyslipidemia, nonalcoholic fatty liver disease (NAFLD), nonalcoholic steatohepatitis (NASH), insulin resistance, hyperinsulinemia, glucose intolerance, and hyperglycemia, and a combination thereof.

6. The method of claim 5, wherein the metabolic disease is selected from the group consisting of obesity, type 2 diabetes mellitus, pancreatitis, dyslipidemia, nonalcoholic fatty liver disease (NAFLD), nonalcoholic steatohepatitis (NASH), insulin resistance, hyperinsulinemia, glucose intolerance, hyperglycemia, and a combination thereof.

7. The method of claim 5, wherein the composition releases the fusion protein following administration for greater than 3 days.

8. The method of claim 5, wherein administration of the composition results in the subject having at least one of decreased blood glucose level, decreased body fat, increased insulin production, decreased hemoglobin A1c values, decreased circulating fatty acids, decreased liver fat content, decreased liver inflammation, and decreased liver fibrosis compared to a subject not receiving the administration of the composition.

9. A method of synthesizing a dual agonist fusion protein, the method comprising:
   transforming a bacteria with a recombinant expression vector comprising a first polynucleotide encoding the fusion protein of claim 1; and
   culturing the transformed bacteria at less than 37° C. to express the fusion protein.

10. The method of claim 9, wherein the expression vector further comprises a second polynucleotide encoding a translation initiation domain attached to the N-terminal end of the fusion protein.

11. The method of claim 10, wherein the translation initiation domain comprises a leader sequence and a protease cleavage site, the protease cleavage site located between the leader sequence and the fusion protein.

* * * * *

SEQUENCE LISTING

<160> NUMBER OF SEQ ID NOS: 24

<210> SEQ ID NO 1
<211> LENGTH: 5
<212> TYPE: PRT
<213> ORGANISM: Artificial Sequence
<220> FEATURE:
<223> OTHER INFORMATION: Synthetic
<220> FEATURE:
<221> NAME/KEY: REPEAT
<222> LOCATION: (1)..(5)
<223> OTHER INFORMATION: Repeat unit: repeating one or more times
<220> FEATURE:
<221> NAME/KEY: MISC-FEATURE
<222> LOCATION: (4)..(4)
<223> OTHER INFORMATION: Xaa is any amino acid except proline

<400> SEQUENCE: 1

Val Pro Gly Xaa Gly
1               5

<210> SEQ ID NO 2
<211> LENGTH: 32
<212> TYPE: PRT
<213> ORGANISM: Artificial Sequence
<220> FEATURE:
<223> OTHER INFORMATION: Synthetic

<400> SEQUENCE: 2

Ala Ala His Gly Glu Gly Thr Phe Thr Ser Asp Val Ser Ser Tyr Leu
1               5                   10                  15
Glu Glu Gln Ala Ala Lys Glu Phe Ile Ala Trp Leu Val Lys Gly Ala
            20                  25                  30

<210> SEQ ID NO 3
<211> LENGTH: 32
<212> TYPE: PRT
<213> ORGANISM: Artificial Sequence
<220> FEATURE:
<223> OTHER INFORMATION: Synthetic

<400> SEQUENCE: 3

Gly Ala His Gly Glu Gly Thr Phe Thr Ser Asp Val Ser Ser Tyr Leu
1               5                   10                  15
Glu Glu Gln Ala Ala Lys Glu Phe Ile Ala Trp Leu Val Lys Gly Ala
            20                  25                  30

<210> SEQ ID NO 4
<211> LENGTH: 30
<212> TYPE: PRT
<213> ORGANISM: Artificial Sequence
<220> FEATURE:
<223> OTHER INFORMATION: Synthetic

<400> SEQUENCE: 4

His Gly Glu Gly Thr Phe Thr Ser Asp Val Ser Ser Tyr Leu Glu Glu
1               5                   10                  15
Gln Ala Ala Lys Glu Phe Ile Ala Trp Leu Val Lys Gly Ala
            20                  25                  30

<210> SEQ ID NO 5
<211> LENGTH: 182
<212> TYPE: PRT
<213> ORGANISM: Artificial Sequence
<220> FEATURE:
<223> OTHER INFORMATION: Synthetic

<400> SEQUENCE: 5

Ala Tyr Pro Ile Pro Asp Ser Ser Pro Leu Leu Gln Phe Gly Gly Gln
1               5                   10                  15
Val Arg Gln Arg Tyr Leu Tyr Thr Asp Asp Gln Asp Thr Glu Ala
            20                  25                  30
His Leu Glu Ile Arg Glu Asp Gly Thr Val Val Gly Ala Ala His Arg
        35                  40                  45
Ser Pro Glu Ser Leu Leu Glu Leu Lys Ala Leu Lys Pro Gly Val Ile
    50                  55                  60
Gln Ile Leu Gly Val Lys Ala Ser Arg Phe Leu Cys Gln Gln Pro Asp
65                  70                  75                  80
Gly Ala Leu Tyr Gly Ser Pro His Phe Asp Pro Glu Ala Cys Ser Phe
                85                  90                  95
Arg Glu Arg Leu Leu Glu Asp Gly Tyr Asn Val Tyr Gln Ser Glu Ala
            100                 105                 110

His Gly Leu Pro Leu Arg Leu Pro Gln Lys Asp Ser Pro Asn Gln Asp
        115                 120                 125

Ala Thr Ser Trp Gly Pro Val Arg Phe Leu Pro Met Pro Gly Leu Leu
130                 135                 140

His Glu Pro Gln Asp Gln Ala Gly Phe Leu Pro Pro Glu Pro Pro Asp
145                 150                 155                 160

Val Gly Ser Ser Asp Pro Leu Ser Met Val Glu Gly Ser Gln Gly Arg
                165                 170                 175

Ser Pro Ser Tyr Ala Ser
        180

<210> SEQ ID NO 6
<211> LENGTH: 182
<212> TYPE: PRT
<213> ORGANISM: Murine adenovirus

<400> SEQUENCE: 6

Ala Tyr Pro Ile Pro Asp Ser Ser Pro Leu Leu Gln Phe Gly Gly Gln
1               5                   10                  15

Val Arg Gln Arg Tyr Leu Tyr Thr Asp Asp Gln Asp Thr Glu Ala
        20                  25                  30

His Leu Glu Ile Arg Glu Asp Gly Thr Val Val Gly Ala Ala His Arg
        35                  40                  45

Ser Pro Glu Ser Leu Leu Glu Leu Lys Ala Leu Lys Pro Gly Val Ile
    50                  55                  60

Gln Ile Leu Gly Val Lys Ala Ser Arg Phe Leu Cys Gln Gln Pro Asp
65                  70                  75                  80

Gly Ala Leu Tyr Gly Ser Pro His Phe Asp Pro Glu Ala Cys Ser Phe
                85                  90                  95

Arg Glu Leu Leu Leu Glu Asp Gly Tyr Asn Val Tyr Gln Ser Glu Ala
            100                 105                 110

His Gly Leu Pro Leu Arg Leu Pro Gln Lys Asp Ser Pro Asn Gln Asp
        115                 120                 125

Ala Thr Ser Trp Gly Pro Val Arg Phe Leu Pro Met Pro Gly Leu Leu
130                 135                 140

His Glu Pro Gln Asp Gln Ala Gly Phe Leu Pro Pro Glu Pro Pro Asp
145                 150                 155                 160

Val Gly Ser Ser Asp Pro Leu Ser Met Val Glu Pro Leu Gln Gly Arg
                165                 170                 175

Ser Pro Ser Tyr Ala Ser
        180

<210> SEQ ID NO 7
<211> LENGTH: 181
<212> TYPE: PRT
<213> ORGANISM: Artificial Sequence
<220> FEATURE:
<223> OTHER INFORMATION: Synthetic

<400> SEQUENCE: 7

His Pro Ile Pro Asp Ser Ser Pro Leu Leu Gln Phe Gly Gly Gln Val
1               5                   10                  15

Arg Gln Arg Tyr Leu Tyr Thr Asp Ala Gln Gln Thr Glu Ala His
        20                  25                  30

Leu Glu Ile Arg Glu Asp Gly Thr Val Gly Gly Ala Ala Asp Gln Ser
        35                  40                  45

-continued

Pro Glu Ser Leu Leu Gln Leu Lys Ala Leu Lys Pro Gly Val Ile Gln
         50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Arg Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Ser Gln Gly Arg Ser
                165                 170                 175

Pro Ser Tyr Ala Ser
            180

<210> SEQ ID NO 8
<211> LENGTH: 181
<212> TYPE: PRT
<213> ORGANISM: Homo sapiens

<400> SEQUENCE: 8

His Pro Ile Pro Asp Ser Ser Pro Leu Leu Gln Phe Gly Gly Gln Val
 1               5                  10                  15

Arg Gln Arg Tyr Leu Tyr Thr Asp Asp Ala Gln Gln Thr Glu Ala His
            20                  25                  30

Leu Glu Ile Arg Glu Asp Gly Thr Val Gly Gly Ala Ala Asp Gln Ser
        35                  40                  45

Pro Glu Ser Leu Leu Gln Leu Lys Ala Leu Lys Pro Gly Val Ile Gln
    50                  55                  60

Ile Leu Gly Val Lys Thr Ser Arg Phe Leu Cys Gln Arg Pro Asp Gly
 65                  70                  75                  80

Ala Leu Tyr Gly Ser Leu His Phe Asp Pro Glu Ala Cys Ser Phe Arg
                 85                  90                  95

Glu Leu Leu Leu Glu Asp Gly Tyr Asn Val Tyr Gln Ser Glu Ala His
            100                 105                 110

Gly Leu Pro Leu His Leu Pro Gly Asn Lys Ser Pro His Arg Asp Pro
        115                 120                 125

Ala Pro Arg Gly Pro Ala Arg Phe Leu Pro Leu Pro Gly Leu Pro Pro
    130                 135                 140

Ala Leu Pro Glu Pro Pro Gly Ile Leu Ala Pro Gln Pro Pro Asp Val
145                 150                 155                 160

Gly Ser Ser Asp Pro Leu Ser Met Val Gly Pro Ser Gln Gly Arg Ser
                165                 170                 175

Pro Ser Tyr Ala Ser
            180

<210> SEQ ID NO 9
<211> LENGTH: 484
<212> TYPE: PRT
<213> ORGANISM: Artificial Sequence
<220> FEATURE:
<223> OTHER INFORMATION: Synthetic

<400> SEQUENCE: 9

```
Gly Val Gly Val Pro Gly Val Gly Val Pro Gly Val Gly Val Pro Gly
1               5                   10                  15
Val Gly Val Pro Gly Val Gly Val Pro Gly Val Gly Val Pro Gly Val
                20                  25                  30
Gly Val Pro Gly Val Gly Val Pro Gly Val Gly Val Pro Gly Val Gly
            35                  40                  45
Val Pro Gly Val Gly Val Pro Gly Val Gly Val Pro Gly Val Gly Val
        50                  55                  60
Pro Gly Val Gly Val Pro Gly Val Gly Val Pro Gly Val Gly Val Pro
65                  70                  75                  80
Gly Val Gly Val Pro Gly Val Gly Val Pro Gly Val Gly Val Pro Gly
                85                  90                  95
Val Gly Val Pro Gly Val Gly Val Pro Gly Val Gly Val Pro Gly Val
                100                 105                 110
Gly Val Pro Gly Val Gly Val Pro Gly Val Gly Val Pro Gly Val Gly
            115                 120                 125
Val Pro Gly Val Gly Val Pro Gly Val Gly Val Pro Gly Val Gly Val
        130                 135                 140
Pro Gly Val Gly Val Pro Gly Val Gly Val Pro Gly Val Gly Val Pro
145                 150                 155                 160
Gly Val Gly Val Pro Gly Val Gly Val Pro Gly Val Gly Val Pro Gly
                165                 170                 175
Val Gly Val Pro Gly Val Gly Val Pro Gly Val Gly Val Pro Gly Val
                180                 185                 190
Gly Val Pro Gly Val Gly Val Pro Gly Val Gly Val Pro Gly Val Gly
            195                 200                 205
Val Pro Gly Val Gly Val Pro Gly Val Gly Val Pro Gly Val Gly Val
        210                 215                 220
Pro Gly Val Gly Val Pro Gly Val Gly Val Pro Gly Val Gly Val Pro
225                 230                 235                 240
Gly Val Gly Val Pro Gly Val Gly Val Pro Gly Val Gly Val Pro Gly
                245                 250                 255
Val Gly Val Pro Gly Val Gly Val Pro Gly Val Gly Val Pro Gly Val
                260                 265                 270
Gly Val Pro Gly Val Gly Val Pro Gly Val Gly Val Pro Gly Val Gly
            275                 280                 285
Val Pro Gly Val Gly Val Pro Gly Val Gly Val Pro Gly Ala Tyr Pro
        290                 295                 300
Ile Pro Asp Ser Ser Pro Leu Leu Gln Phe Gly Gln Val Arg Gln
305                 310                 315                 320
Arg Tyr Leu Tyr Thr Asp Asp Gln Asp Thr Glu Ala His Leu Glu
                325                 330                 335
Ile Arg Glu Asp Gly Thr Val Val Gly Ala Ala His Arg Ser Pro Glu
                340                 345                 350
Ser Leu Leu Glu Leu Lys Ala Leu Lys Pro Gly Val Ile Gln Ile Leu
            355                 360                 365
Gly Val Lys Ala Ser Arg Phe Leu Cys Gln Gln Pro Asp Gly Ala Leu
        370                 375                 380
Tyr Gly Ser Pro His Phe Asp Pro Glu Ala Cys Ser Phe Arg Glu Arg
385                 390                 395                 400
Leu Leu Glu Asp Gly Tyr Asn Val Tyr Gln Ser Glu Ala His Gly Leu
                405                 410                 415
```

```
Pro Leu Arg Leu Pro Gln Lys Asp Ser Pro Asn Gln Asp Ala Thr Ser
            420                 425                 430

Trp Gly Pro Val Arg Phe Leu Pro Met Pro Gly Leu Leu His Glu Pro
        435                 440                 445

Gln Asp Gln Ala Gly Phe Leu Pro Pro Glu Pro Pro Asp Val Gly Ser
    450                 455                 460

Ser Asp Pro Leu Ser Met Val Glu Gly Ser Gln Gly Arg Ser Pro Ser
465                 470                 475                 480

Tyr Ala Ser Gly

<210> SEQ ID NO 10
<211> LENGTH: 301
<212> TYPE: PRT
<213> ORGANISM: Artificial Sequence
<220> FEATURE:
<223> OTHER INFORMATION: Synthetic

<400> SEQUENCE: 10

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285
```

Val Pro Gly Val Gly Val Pro Gly Val Gly Val Pro Gly
    290                 295                 300

<210> SEQ ID NO 11
<211> LENGTH: 491
<212> TYPE: PRT
<213> ORGANISM: Artificial Sequence
<220> FEATURE:
<223> OTHER INFORMATION: Synthetic

<400> SEQUENCE: 11

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
                85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
                165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
                245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
        275                 280                 285

Val Pro Gly Val Gly Val Pro Gly Val Gly Val Pro Gly Glu Asn Leu
    290                 295                 300

Tyr Phe Gln Gly Ala Tyr Pro Ile Pro Asp Ser Ser Pro Leu Leu Gln
305                 310                 315                 320

Phe Gly Gly Gln Val Arg Gln Arg Tyr Leu Tyr Thr Asp Asp Asp Gln
                325                 330                 335

Asp Thr Glu Ala His Leu Glu Ile Arg Glu Asp Gly Thr Val Val Gly
            340                 345                 350

```
Ala Ala His Arg Ser Pro Glu Ser Leu Glu Leu Lys Ala Leu Lys
            355                 360                 365

Pro Gly Val Ile Gln Ile Leu Gly Val Lys Ala Ser Arg Phe Leu Cys
    370                 375                 380

Gln Gln Pro Asp Gly Ala Leu Tyr Gly Ser Pro His Phe Asp Pro Glu
385                 390                 395                 400

Ala Cys Ser Phe Arg Glu Arg Leu Leu Glu Asp Gly Tyr Asn Val Tyr
                405                 410                 415

Gln Ser Glu Ala His Gly Leu Pro Leu Arg Leu Pro Gln Lys Asp Ser
            420                 425                 430

Pro Asn Gln Asp Ala Thr Ser Trp Gly Pro Val Arg Phe Leu Pro Met
    435                 440                 445

Pro Gly Leu Leu His Glu Pro Gln Asp Gln Ala Gly Phe Leu Pro Pro
    450                 455                 460

Glu Pro Pro Asp Val Gly Ser Ser Asp Pro Leu Ser Met Val Glu Gly
465                 470                 475                 480

Ser Gln Gly Arg Ser Pro Ser Tyr Ala Ser Gly
            485                 490

<210> SEQ ID NO 12
<211> LENGTH: 538
<212> TYPE: PRT
<213> ORGANISM: Artificial Sequence
<220> FEATURE:
<223> OTHER INFORMATION: Synthetic

<400> SEQUENCE: 12

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
    50                  55                  60

Pro Gly Val Gly Val Pro Gly Val Gly Val Pro Gly Val Gly Val Pro
65                  70                  75                  80

Gly Val Gly Val Pro Gly Val Gly Val Pro Gly Val Gly Val Pro Gly
            85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
        115                 120                 125

Val Pro Gly Val Gly Val Pro Gly Val Gly Val Pro Gly Val Gly Val
    130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
        195                 200                 205

Val Pro Gly Val Gly Val Pro Gly Val Gly Val Pro Gly Val Gly Val
    210                 215                 220
```

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
            245                 250                 255

Val Gly Val Pro Gly Val Gly Val Pro Gly Val Gly Val Pro Gly Val
        260                 265                 270

Gly Val Pro Gly Val Gly Val Pro Gly Val Gly Val Pro Gly Val Gly
    275                 280                 285

Val Pro Gly Val Gly Val Pro Gly Val Gly Val Pro Gly Gly Glu Ser
290                 295                 300

Leu Phe Lys Gly Pro Arg Asp Tyr Asn Pro Ile Ser Ser Thr Ile Cys
305                 310                 315                 320

His Leu Thr Asn Glu Ser Asp Gly His Thr Thr Ser Leu Tyr Gly Ile
            325                 330                 335

Gly Phe Gly Pro Phe Ile Ile Thr Asn Lys His Leu Phe Arg Arg Asn
        340                 345                 350

Asn Gly Thr Leu Leu Val Gln Ser Leu His Gly Val Phe Lys Val Lys
    355                 360                 365

Asn Thr Thr Thr Leu Gln Gln His Leu Ile Asp Gly Arg Asp Met Ile
370                 375                 380

Ile Ile Arg Met Pro Lys Asp Phe Pro Phe Pro Gln Lys Leu Lys
385                 390                 395                 400

Phe Arg Glu Pro Gln Arg Glu Glu Arg Ile Cys Leu Val Thr Thr Asn
            405                 410                 415

Phe Gln Thr Lys Ser Met Ser Ser Met Val Ser Asp Thr Ser Cys Thr
        420                 425                 430

Phe Pro Ser Ser Asp Gly Ile Phe Trp Lys His Trp Ile Gln Thr Lys
    435                 440                 445

Asp Gly Gln Cys Gly Ser Pro Leu Val Ser Thr Arg Asp Gly Phe Ile
450                 455                 460

Val Gly Ile His Ser Ala Ser Asn Phe Thr Asn Thr Asn Asn Tyr Phe
465                 470                 475                 480

Thr Ser Val Pro Lys Asn Phe Met Glu Leu Leu Thr Asn Gln Glu Ala
            485                 490                 495

Gln Gln Trp Val Ser Gly Trp Arg Leu Asn Ala Asp Ser Val Leu Trp
        500                 505                 510

Gly Gly His Lys Val Phe Met Val Lys Pro Glu Glu Pro Phe Gln Pro
    515                 520                 525

Val Lys Glu Ala Thr Gln Leu Met Asn Gly
530                 535

<210> SEQ ID NO 13
<211> LENGTH: 784
<212> TYPE: PRT
<213> ORGANISM: Artificial Sequence
<220> FEATURE:
<223> OTHER INFORMATION: Synthetic

<400> SEQUENCE: 13

Gly Val Gly Val Pro Gly Val Gly Val Pro Gly Val Gly Val Pro Gly
1               5                   10                  15

Val Gly Val Pro Gly Val Gly Val Pro Gly Val Gly Val Pro Gly Val
            20                  25                  30

Gly Val Pro Gly Val Gly Val Pro Gly Val Gly Val Pro Gly Val Gly
        35                  40                  45

Val Pro Gly Val Gly Val Pro Gly Val Gly Val Pro Gly Val Gly Val
 50                  55                  60

Pro Gly Val Gly Val Pro Gly Val Gly Val Pro Gly Val Gly Val Pro
 65                  70                  75                  80

Gly Val Gly Val Pro Gly Val Gly Val Pro Gly Val Gly Val Pro Gly
             85                  90                  95

Val Gly Val Pro Gly Val Gly Val Pro Gly Val Gly Val Pro Gly Val
            100                 105                 110

Gly Val Pro Gly Val Gly Val Pro Gly Val Gly Val Pro Gly Val Gly
            115                 120                 125

Val Pro Gly Val Gly Val Pro Gly Val Gly Val Pro Gly Val Gly Val
        130                 135                 140

Pro Gly Val Gly Val Pro Gly Val Gly Val Pro Gly Val Gly Val Pro
145                 150                 155                 160

Gly Val Gly Val Pro Gly Val Gly Val Pro Gly Val Gly Val Pro Gly
            165                 170                 175

Val Gly Val Pro Gly Val Gly Val Pro Gly Val Gly Val Pro Gly Val
            180                 185                 190

Gly Val Pro Gly Val Gly Val Pro Gly Val Gly Val Pro Gly Val Gly
            195                 200                 205

Val Pro Gly Val Gly Val Pro Gly Val Gly Val Pro Gly Val Gly Val
        210                 215                 220

Pro Gly Val Gly Val Pro Gly Val Gly Val Pro Gly Val Gly Val Pro
225                 230                 235                 240

Gly Val Gly Val Pro Gly Val Gly Val Pro Gly Val Gly Val Pro Gly
            245                 250                 255

Val Gly Val Pro Gly Val Gly Val Pro Gly Val Gly Val Pro Gly Val
            260                 265                 270

Gly Val Pro Gly Val Gly Val Pro Gly Val Gly Val Pro Gly Val Gly
            275                 280                 285

Val Pro Gly Val Gly Val Pro Gly Val Gly Val Pro Gly Val Gly Val
        290                 295                 300

Pro Gly Val Gly Val Pro Gly Val Gly Val Pro Gly Val Gly Val Pro
305                 310                 315                 320

Gly Val Gly Val Pro Gly Val Gly Val Pro Gly Val Gly Val Pro Gly
            325                 330                 335

Val Gly Val Pro Gly Val Gly Val Pro Gly Val Gly Val Pro Gly Val
            340                 345                 350

Gly Val Pro Gly Val Gly Val Pro Gly Val Gly Val Pro Gly Val Gly
            355                 360                 365

Val Pro Gly Val Gly Val Pro Gly Val Gly Val Pro Gly Val Gly Val
        370                 375                 380

Pro Gly Val Gly Val Pro Gly Val Gly Val Pro Gly Val Gly Val Pro
385                 390                 395                 400

Gly Val Gly Val Pro Gly Val Gly Val Pro Gly Val Gly Val Pro Gly
            405                 410                 415

Val Gly Val Pro Gly Val Gly Val Pro Gly Val Gly Val Pro Gly Val
            420                 425                 430

Gly Val Pro Gly Val Gly Val Pro Gly Val Gly Val Pro Gly Val Gly
            435                 440                 445

Val Pro Gly Val Gly Val Pro Gly Val Gly Val Pro Gly Val Gly Val
        450                 455                 460

Pro Gly Val Gly Val Pro Gly Val Gly Val Pro Gly Val Gly Val Pro

```
            465                 470                 475                 480
Gly Val Gly Val Pro Gly Val Gly Val Pro Gly Val Gly Val Pro Gly
                485                 490                 495
Val Gly Val Pro Gly Val Gly Val Pro Gly Val Gly Val Pro Gly Val
            500                 505                 510
Gly Val Pro Gly Val Gly Val Pro Gly Val Gly Val Pro Gly Val Gly
        515                 520                 525
Val Pro Gly Val Gly Val Pro Gly Val Gly Val Pro Gly Val Gly Val
    530                 535                 540
Pro Gly Val Gly Val Pro Gly Val Gly Val Pro Gly Val Gly Val Pro
545                 550                 555                 560
Gly Val Gly Val Pro Gly Val Gly Val Pro Gly Val Gly Val Pro Gly
                565                 570                 575
Val Gly Val Pro Gly Val Gly Val Pro Gly Val Gly Val Pro Gly Val
            580                 585                 590
Gly Val Pro Gly Val Gly Val Pro Gly Ala Tyr Pro Ile Pro Asp Ser
        595                 600                 605
Ser Pro Leu Leu Gln Phe Gly Gly Gln Val Arg Gln Arg Tyr Leu Tyr
    610                 615                 620
Thr Asp Asp Gln Asp Thr Glu Ala His Leu Glu Ile Arg Glu Asp
625                 630                 635                 640
Gly Thr Val Val Gly Ala Ala His Arg Ser Pro Glu Ser Leu Leu Glu
                645                 650                 655
Leu Lys Ala Leu Lys Pro Gly Val Ile Gln Ile Leu Gly Val Lys Ala
            660                 665                 670
Ser Arg Phe Leu Cys Gln Gln Pro Asp Gly Ala Leu Tyr Gly Ser Pro
        675                 680                 685
His Phe Asp Pro Glu Ala Cys Ser Phe Arg Glu Arg Leu Leu Glu Asp
    690                 695                 700
Gly Tyr Asn Val Tyr Gln Ser Glu Ala His Gly Leu Pro Leu Arg Leu
705                 710                 715                 720
Pro Gln Lys Asp Ser Pro Asn Gln Asp Ala Thr Ser Trp Gly Pro Val
                725                 730                 735
Arg Phe Leu Pro Met Pro Gly Leu Leu His Glu Pro Gln Asp Gln Ala
            740                 745                 750
Gly Phe Leu Pro Pro Glu Pro Pro Asp Val Gly Ser Ser Asp Pro Leu
        755                 760                 765
Ser Met Val Glu Gly Ser Gln Gly Arg Ser Pro Ser Tyr Ala Ser Gly
    770                 775                 780

<210> SEQ ID NO 14
<211> LENGTH: 784
<212> TYPE: PRT
<213> ORGANISM: Artificial Sequence
<220> FEATURE:
<223> OTHER INFORMATION: Synthetic

<400> SEQUENCE: 14

Gly Val Gly Val Pro Gly Val Gly Val Pro Gly Ala Gly Val Pro Gly
1               5                   10                  15
Val Gly Val Pro Gly Val Gly Val Pro Gly Val Gly Val Pro Gly Val
            20                  25                  30
Gly Val Pro Gly Ala Gly Val Pro Gly Val Gly Val Pro Gly Val Gly
        35                  40                  45
Val Pro Gly Val Gly Val Pro Gly Val Gly Val Pro Gly Ala Gly Val
```

```
            50                  55                  60
Pro Gly Val Gly Val Pro Gly Val Gly Val Pro Gly Val Gly Val Pro
65                  70                  75                  80

Gly Val Gly Val Pro Gly Ala Gly Val Pro Gly Val Gly Val Pro Gly
                    85                  90                  95

Val Gly Val Pro Gly Val Gly Val Pro Gly Val Gly Val Pro Gly Ala
                100                 105                 110

Gly Val Pro Gly Val Gly Val Pro Gly Val Gly Val Pro Gly Val Gly
            115                 120                 125

Val Pro Gly Val Gly Val Pro Gly Ala Gly Val Pro Gly Val Gly Val
130                 135                 140

Pro Gly Val Gly Val Pro Gly Val Gly Val Pro Gly Val Gly Val Pro
145                 150                 155                 160

Gly Ala Gly Val Pro Gly Val Gly Val Pro Gly Val Gly Val Pro Gly
                165                 170                 175

Val Gly Val Pro Gly Val Gly Val Pro Gly Ala Gly Val Pro Gly Val
                180                 185                 190

Gly Val Pro Gly Val Gly Val Pro Gly Val Gly Val Pro Gly Val Gly
            195                 200                 205

Val Pro Gly Ala Gly Val Pro Gly Val Gly Val Pro Gly Val Gly Val
210                 215                 220

Pro Gly Val Gly Val Pro Gly Val Gly Val Pro Gly Ala Gly Val Pro
225                 230                 235                 240

Gly Val Gly Val Pro Gly Val Gly Val Pro Gly Val Gly Val Pro Gly
                245                 250                 255

Val Gly Val Pro Gly Ala Gly Val Pro Gly Val Gly Val Pro Gly Val
                260                 265                 270

Gly Val Pro Gly Val Gly Val Pro Gly Val Gly Val Pro Gly Ala Gly
            275                 280                 285

Val Pro Gly Val Gly Val Pro Gly Val Gly Val Pro Gly Val Gly Val
290                 295                 300

Pro Gly Val Gly Val Pro Gly Ala Gly Val Pro Gly Val Gly Val Pro
305                 310                 315                 320

Gly Val Gly Val Pro Gly Val Gly Val Pro Gly Val Gly Val Pro Gly
                325                 330                 335

Ala Gly Val Pro Gly Val Gly Val Pro Gly Val Gly Val Pro Gly Val
                340                 345                 350

Gly Val Pro Gly Val Gly Val Pro Gly Ala Gly Val Pro Gly Val Gly
            355                 360                 365

Val Pro Gly Val Gly Val Pro Gly Val Gly Val Pro Gly Val Gly Val
370                 375                 380

Pro Gly Ala Gly Val Pro Gly Val Gly Val Pro Gly Val Gly Val Pro
385                 390                 395                 400

Gly Val Gly Val Pro Gly Val Gly Val Pro Gly Ala Gly Val Pro Gly
                405                 410                 415

Val Gly Val Pro Gly Val Gly Val Pro Gly Val Gly Val Pro Gly Val
                420                 425                 430

Gly Val Pro Gly Ala Gly Val Pro Gly Val Gly Val Pro Gly Val Gly
            435                 440                 445

Val Pro Gly Val Gly Val Pro Gly Val Gly Val Pro Gly Ala Gly Val
450                 455                 460

Pro Gly Val Gly Val Pro Gly Val Gly Val Pro Gly Val Gly Val Pro
465                 470                 475                 480
```

```
Gly Val Gly Val Pro Gly Ala Gly Val Pro Gly Val Gly Val Pro Gly
            485                 490                 495

Val Gly Val Pro Gly Val Gly Val Pro Gly Val Gly Val Pro Gly Ala
        500                 505                 510

Gly Val Pro Gly Val Gly Val Pro Gly Val Gly Val Pro Gly Val Gly
    515                 520                 525

Val Pro Gly Val Gly Val Pro Gly Ala Gly Val Pro Gly Val Gly Val
530                 535                 540

Pro Gly Val Gly Val Pro Gly Val Gly Val Pro Gly Val Gly Val Pro
545                 550                 555                 560

Gly Ala Gly Val Pro Gly Val Gly Val Pro Gly Val Gly Val Pro Gly
            565                 570                 575

Val Gly Val Pro Gly Val Gly Val Pro Gly Ala Gly Val Pro Gly Val
        580                 585                 590

Gly Val Pro Gly Val Gly Val Pro Gly Ala Tyr Pro Ile Pro Asp Ser
    595                 600                 605

Ser Pro Leu Leu Gln Phe Gly Gly Gln Val Arg Gln Arg Tyr Leu Tyr
            610                 615                 620

Thr Asp Asp Gln Asp Thr Glu Ala His Leu Glu Ile Arg Glu Asp
625                 630                 635                 640

Gly Thr Val Val Gly Ala Ala His Arg Ser Pro Glu Ser Leu Leu Glu
            645                 650                 655

Leu Lys Ala Leu Lys Pro Gly Val Ile Gln Ile Leu Gly Val Lys Ala
        660                 665                 670

Ser Arg Phe Leu Cys Gln Gln Pro Asp Gly Ala Leu Tyr Gly Ser Pro
    675                 680                 685

His Phe Asp Pro Glu Ala Cys Ser Phe Arg Glu Arg Leu Leu Glu Asp
690                 695                 700

Gly Tyr Asn Val Tyr Gln Ser Glu Ala His Gly Leu Pro Leu Arg Leu
705                 710                 715                 720

Pro Gln Lys Asp Ser Pro Asn Gln Asp Ala Thr Ser Trp Gly Pro Val
            725                 730                 735

Arg Phe Leu Pro Met Pro Gly Leu Leu His Glu Pro Gln Asp Gln Ala
        740                 745                 750

Gly Phe Leu Pro Pro Glu Pro Pro Asp Val Gly Ser Ser Asp Pro Leu
    755                 760                 765

Ser Met Val Glu Gly Ser Gln Gly Arg Ser Pro Ser Tyr Ala Ser Gly
770                 775                 780

<210> SEQ ID NO 15
<211> LENGTH: 816
<212> TYPE: PRT
<213> ORGANISM: Artificial Sequence
<220> FEATURE:
<223> OTHER INFORMATION: Synthetic

<400> SEQUENCE: 15

Ala Ala His Gly Glu Gly Thr Phe Thr Ser Asp Val Ser Ser Tyr Leu
1               5                   10                  15

Glu Glu Gln Ala Ala Lys Glu Phe Ile Ala Trp Leu Val Lys Gly Ala
            20                  25                  30

Gly Val Gly Val Pro Gly Val Gly Val Pro Gly Ala Gly Val Pro Gly
        35                  40                  45

Val Gly Val Pro Gly Val Gly Val Pro Gly Val Gly Val Pro Gly Val
    50                  55                  60
```

-continued

Gly Val Pro Gly Ala Gly Val Pro Gly Val Gly Val Pro Gly Val Gly
65                  70                  75                  80

Val Pro Gly Val Gly Val Pro Gly Val Gly Val Pro Gly Ala Gly Val
            85                  90                  95

Pro Gly Val Gly Val Pro Gly Val Gly Val Pro Gly Val Gly Val Pro
                100                 105                 110

Gly Val Gly Val Pro Gly Ala Gly Val Pro Gly Val Gly Val Pro Gly
            115                 120                 125

Val Gly Val Pro Gly Val Gly Val Pro Gly Val Gly Val Pro Gly Ala
            130                 135                 140

Gly Val Pro Gly Val Gly Val Pro Gly Val Gly Val Pro Gly Val Gly
145                 150                 155                 160

Val Pro Gly Val Gly Val Pro Gly Ala Gly Val Pro Gly Val Gly Val
            165                 170                 175

Pro Gly Val Gly Val Pro Gly Val Gly Val Pro Gly Val Gly Val Pro
            180                 185                 190

Gly Ala Gly Val Pro Gly Val Gly Val Pro Gly Val Gly Val Pro Gly
            195                 200                 205

Val Gly Val Pro Gly Val Gly Val Pro Gly Ala Gly Val Pro Gly Val
            210                 215                 220

Gly Val Pro Gly Val Gly Val Pro Gly Val Gly Val Pro Gly Val Gly
225                 230                 235                 240

Val Pro Gly Ala Gly Val Pro Gly Val Gly Val Pro Gly Val Gly Val
            245                 250                 255

Pro Gly Val Gly Val Pro Gly Val Gly Val Pro Gly Ala Gly Val Pro
            260                 265                 270

Gly Val Gly Val Pro Gly Val Gly Val Pro Gly Val Gly Val Pro Gly
            275                 280                 285

Val Gly Val Pro Gly Ala Gly Val Pro Gly Val Gly Val Pro Gly Val
            290                 295                 300

Gly Val Pro Gly Val Gly Val Pro Gly Val Gly Val Pro Gly Ala Gly
305                 310                 315                 320

Val Pro Gly Val Gly Val Pro Gly Val Gly Val Pro Gly Val Gly Val
            325                 330                 335

Pro Gly Val Gly Val Pro Gly Ala Gly Val Pro Gly Val Gly Val Pro
            340                 345                 350

Gly Val Gly Val Pro Gly Val Gly Val Pro Gly Val Gly Val Pro Gly
            355                 360                 365

Ala Gly Val Pro Gly Val Gly Val Pro Gly Val Gly Val Pro Gly Val
            370                 375                 380

Gly Val Pro Gly Val Gly Val Pro Gly Ala Gly Val Pro Gly Val Gly
385                 390                 395                 400

Val Pro Gly Val Gly Val Pro Gly Val Gly Val Pro Gly Val Gly Val
            405                 410                 415

Pro Gly Ala Gly Val Pro Gly Val Gly Val Pro Gly Val Gly Val Pro
            420                 425                 430

Gly Val Gly Val Pro Gly Val Gly Val Pro Gly Ala Gly Val Pro Gly
            435                 440                 445

Val Gly Val Pro Gly Val Gly Val Pro Gly Val Gly Val Pro Gly Val
            450                 455                 460

Gly Val Pro Gly Ala Gly Val Pro Gly Val Gly Val Pro Gly Val Gly
465                 470                 475                 480

Val Pro Gly Val Gly Val Pro Gly Val Gly Val Pro Gly Ala Gly Val
            485                 490                 495

Pro Gly Val Gly Val Pro Gly Val Gly Val Pro Gly Val Gly Val Pro
            500                 505                 510

Gly Val Gly Val Pro Gly Ala Gly Val Pro Gly Val Gly Val Pro Gly
            515                 520                 525

Val Gly Val Pro Gly Val Gly Val Pro Gly Val Gly Val Pro Gly Ala
            530                 535                 540

Gly Val Pro Gly Val Gly Val Pro Gly Val Gly Val Pro Gly Val Gly
545                 550                 555                 560

Val Pro Gly Val Gly Val Pro Gly Ala Gly Val Pro Gly Val Gly Val
            565                 570                 575

Pro Gly Val Gly Val Pro Gly Val Gly Val Pro Gly Val Gly Val Pro
            580                 585                 590

Gly Ala Gly Val Pro Gly Val Gly Val Pro Gly Val Gly Val Pro Gly
            595                 600                 605

Val Gly Val Pro Gly Val Gly Val Pro Gly Ala Gly Val Pro Gly Val
            610                 615                 620

Gly Val Pro Gly Val Gly Val Pro Gly Ala Tyr Pro Ile Pro Asp Ser
625                 630                 635                 640

Ser Pro Leu Leu Gln Phe Gly Gly Gln Val Arg Gln Arg Tyr Leu Tyr
            645                 650                 655

Thr Asp Asp Gln Asp Thr Glu Ala His Leu Glu Ile Arg Glu Asp
            660                 665                 670

Gly Thr Val Val Gly Ala Ala His Arg Ser Pro Glu Ser Leu Leu Glu
            675                 680                 685

Leu Lys Ala Leu Lys Pro Gly Val Ile Gln Ile Leu Gly Val Lys Ala
690                 695                 700

Ser Arg Phe Leu Cys Gln Gln Pro Asp Gly Ala Leu Tyr Gly Ser Pro
705                 710                 715                 720

His Phe Asp Pro Glu Ala Cys Ser Phe Arg Glu Arg Leu Leu Glu Asp
            725                 730                 735

Gly Tyr Asn Val Tyr Gln Ser Glu Ala His Gly Leu Pro Leu Arg Leu
            740                 745                 750

Pro Gln Lys Asp Ser Pro Asn Gln Asp Ala Thr Ser Trp Gly Pro Val
            755                 760                 765

Arg Phe Leu Pro Met Pro Gly Leu Leu His Glu Pro Gln Asp Gln Ala
770                 775                 780

Gly Phe Leu Pro Glu Pro Pro Asp Val Gly Ser Ser Asp Pro Leu
785                 790                 795                 800

Ser Met Val Glu Gly Ser Gln Gly Arg Ser Pro Ser Tyr Ala Ser Gly
            805                 810                 815

<210> SEQ ID NO 16
<211> LENGTH: 633
<212> TYPE: PRT
<213> ORGANISM: Artificial Sequence
<220> FEATURE:
<223> OTHER INFORMATION: Synthetic

<400> SEQUENCE: 16

Ala Ala His Gly Glu Gly Thr Phe Thr Ser Asp Val Ser Ser Tyr Leu
1               5                   10                  15

Glu Glu Gln Ala Ala Lys Glu Phe Ile Ala Trp Leu Val Lys Gly Ala
            20                  25                  30

-continued

Gly Val Gly Val Pro Gly Val Gly Val Pro Gly Ala Gly Val Pro Gly
                35                  40                  45
Val Gly Val Pro Gly Val Gly Val Pro Gly Val Gly Val Pro Gly Val
            50                  55                  60
Gly Val Pro Gly Ala Gly Val Pro Gly Val Gly Val Pro Gly Val Gly
65                  70                  75                  80
Val Pro Gly Val Gly Val Pro Gly Val Gly Val Pro Gly Ala Gly Val
                85                  90                  95
Pro Gly Val Gly Val Pro Gly Val Gly Val Pro Gly Val Gly Val Pro
            100                 105                 110
Gly Val Gly Val Pro Gly Ala Gly Val Pro Gly Val Gly Val Pro Gly
            115                 120                 125
Val Gly Val Pro Gly Val Gly Val Pro Gly Val Gly Val Pro Gly Ala
            130                 135                 140
Gly Val Pro Gly Val Gly Val Pro Gly Val Gly Val Pro Gly Val Gly
145                 150                 155                 160
Val Pro Gly Val Gly Val Pro Gly Ala Gly Val Pro Gly Val Gly Val
                165                 170                 175
Pro Gly Val Gly Val Pro Gly Val Gly Val Pro Gly Val Gly Val Pro
            180                 185                 190
Gly Ala Gly Val Pro Gly Val Gly Val Pro Gly Val Gly Val Pro Gly
            195                 200                 205
Val Gly Val Pro Gly Val Gly Val Pro Gly Ala Gly Val Pro Gly Val
            210                 215                 220
Gly Val Pro Gly Val Gly Val Pro Gly Val Gly Val Pro Gly Val Gly
225                 230                 235                 240
Val Pro Gly Ala Gly Val Pro Gly Val Gly Val Pro Gly Val Gly Val
                245                 250                 255
Pro Gly Val Gly Val Pro Gly Val Gly Val Pro Gly Ala Gly Val Pro
            260                 265                 270
Gly Val Gly Val Pro Gly Val Gly Val Pro Gly Val Gly Val Pro Gly
            275                 280                 285
Val Gly Val Pro Gly Ala Gly Val Pro Gly Val Gly Val Pro Gly Val
            290                 295                 300
Gly Val Pro Gly Val Gly Val Pro Gly Val Gly Val Pro Gly Ala Gly
305                 310                 315                 320
Val Pro Gly Val Gly Val Pro Gly Val Gly Val Pro Gly Val Gly Val
                325                 330                 335
Pro Gly Val Gly Val Pro Gly Ala Gly Val Pro Gly Val Gly Val Pro
            340                 345                 350
Gly Val Gly Val Pro Gly Val Gly Val Pro Gly Val Gly Val Pro Gly
            355                 360                 365
Ala Gly Val Pro Gly Val Gly Val Pro Gly Val Gly Val Pro Gly Val
            370                 375                 380
Gly Val Pro Gly Val Gly Val Pro Gly Ala Gly Val Pro Gly Val Gly
385                 390                 395                 400
Val Pro Gly Val Gly Val Pro Gly Val Gly Val Pro Gly Val Gly Val
                405                 410                 415
Pro Gly Ala Gly Val Pro Gly Val Gly Val Pro Gly Val Gly Val Pro
            420                 425                 430
Gly Val Gly Val Pro Gly Val Gly Val Pro Gly Ala Gly Val Pro Gly
            435                 440                 445
Val Gly Val Pro Gly Val Gly Val Pro Gly Val Gly Val Pro Gly Val

```
            450                 455                 460
Gly Val Pro Gly Ala Gly Val Pro Gly Val Gly Val Pro Gly Val Gly
465                 470                 475                 480

Val Pro Gly Val Gly Val Pro Gly Val Gly Val Pro Gly Ala Gly Val
                485                 490                 495

Pro Gly Val Gly Val Pro Gly Val Gly Val Pro Gly Val Gly Val Pro
            500                 505                 510

Gly Val Gly Val Pro Gly Ala Gly Val Pro Gly Val Gly Val Pro Gly
        515                 520                 525

Val Gly Val Pro Gly Val Gly Val Pro Gly Val Gly Val Pro Gly Ala
    530                 535                 540

Gly Val Pro Gly Val Gly Val Pro Gly Val Gly Val Pro Gly Val Gly
545                 550                 555                 560

Val Pro Gly Val Gly Val Pro Gly Ala Gly Val Pro Gly Val Gly Val
                565                 570                 575

Pro Gly Val Gly Val Pro Gly Val Gly Val Pro Gly Val Gly Val Pro
            580                 585                 590

Gly Ala Gly Val Pro Gly Val Gly Val Pro Gly Val Gly Val Pro Gly
        595                 600                 605

Val Gly Val Pro Gly Val Gly Val Pro Gly Ala Gly Val Pro Gly Val
    610                 615                 620

Gly Val Pro Gly Val Gly Val Pro Gly
625                 630

<210> SEQ ID NO 17
<211> LENGTH: 828
<212> TYPE: PRT
<213> ORGANISM: Artificial Sequence
<220> FEATURE:
<223> OTHER INFORMATION: Synthetic

<400> SEQUENCE: 17

Met Ser Lys Gly Pro Gly Glu Asn Leu Tyr Phe Gln Gly Ala His Gly
1               5                   10                  15

Glu Gly Thr Phe Thr Ser Asp Val Ser Ser Tyr Leu Glu Glu Gln Ala
            20                  25                  30

Ala Lys Glu Phe Ile Ala Trp Leu Val Lys Gly Ala Gly Val Gly Val
        35                  40                  45

Pro Gly Val Gly Val Pro Gly Ala Gly Val Pro Gly Val Gly Val Pro
    50                  55                  60

Gly Val Gly Val Pro Gly Val Gly Val Pro Gly Val Gly Val Pro Gly
65                  70                  75                  80

Ala Gly Val Pro Gly Val Gly Val Pro Gly Val Gly Val Pro Gly Val
                85                  90                  95

Gly Val Pro Gly Val Gly Val Pro Gly Ala Gly Val Pro Gly Val Gly
            100                 105                 110

Val Pro Gly Val Gly Val Pro Gly Val Gly Val Pro Gly Val Gly Val
        115                 120                 125

Pro Gly Ala Gly Val Pro Gly Val Gly Val Pro Gly Val Gly Val Pro
    130                 135                 140

Gly Val Gly Val Pro Gly Val Gly Val Pro Gly Ala Gly Val Pro Gly
145                 150                 155                 160

Val Gly Val Pro Gly Val Gly Val Pro Gly Val Gly Val Pro Gly Val
                165                 170                 175

Gly Val Pro Gly Ala Gly Val Pro Gly Val Gly Val Pro Gly Val Gly
```

-continued

```
                180                 185                 190
Val Pro Gly Val Gly Val Pro Gly Val Gly Val Pro Gly Ala Gly Val
            195                 200                 205
Pro Gly Val Gly Val Pro Gly Val Gly Val Pro Gly Val Gly Val Pro
            210                 215                 220
Gly Val Gly Val Pro Gly Ala Gly Val Pro Gly Val Gly Val Pro Gly
225                 230                 235                 240
Val Gly Val Pro Gly Val Gly Val Pro Gly Val Gly Val Pro Gly Ala
            245                 250                 255
Gly Val Pro Gly Val Gly Val Pro Gly Val Gly Val Pro Gly Val Gly
            260                 265                 270
Val Pro Gly Val Gly Val Pro Gly Ala Gly Val Pro Gly Val Gly Val
            275                 280                 285
Pro Gly Val Gly Val Pro Gly Val Gly Val Pro Gly Val Gly Val Pro
            290                 295                 300
Gly Ala Gly Val Pro Gly Val Gly Val Pro Gly Val Gly Val Pro Gly
305                 310                 315                 320
Val Gly Val Pro Gly Val Gly Val Pro Gly Ala Gly Val Pro Gly Val
            325                 330                 335
Gly Val Pro Gly Val Gly Val Pro Gly Val Gly Val Pro Gly Val Gly
            340                 345                 350
Val Pro Gly Ala Gly Val Pro Gly Val Gly Val Pro Gly Val Gly Val
            355                 360                 365
Pro Gly Val Gly Val Pro Gly Val Gly Val Pro Gly Ala Gly Val Pro
            370                 375                 380
Gly Val Gly Val Pro Gly Val Gly Val Pro Gly Val Gly Val Pro Gly
385                 390                 395                 400
Val Gly Val Pro Gly Ala Gly Val Pro Gly Val Gly Val Pro Gly Val
            405                 410                 415
Gly Val Pro Gly Val Gly Val Pro Gly Val Gly Val Pro Gly Ala Gly
            420                 425                 430
Val Pro Gly Val Gly Val Pro Gly Val Gly Val Pro Gly Val Gly Val
            435                 440                 445
Pro Gly Val Gly Val Pro Gly Ala Gly Val Pro Gly Val Gly Val Pro
            450                 455                 460
Gly Val Gly Val Pro Gly Val Gly Val Pro Gly Val Gly Val Pro Gly
465                 470                 475                 480
Ala Gly Val Pro Gly Val Gly Val Pro Gly Val Gly Val Pro Gly Val
            485                 490                 495
Gly Val Pro Gly Val Gly Val Pro Gly Ala Gly Val Pro Gly Val Gly
            500                 505                 510
Val Pro Gly Val Gly Val Pro Gly Val Gly Val Pro Gly Val Gly Val
            515                 520                 525
Pro Gly Ala Gly Val Pro Gly Val Gly Val Pro Gly Val Gly Val Pro
            530                 535                 540
Gly Val Gly Val Pro Gly Val Gly Val Pro Gly Ala Gly Val Pro Gly
545                 550                 555                 560
Val Gly Val Pro Gly Val Gly Val Pro Gly Val Gly Val Pro Gly Val
            565                 570                 575
Gly Val Pro Gly Ala Gly Val Pro Gly Val Gly Val Pro Gly Val Gly
            580                 585                 590
Val Pro Gly Val Gly Val Pro Gly Val Gly Val Pro Gly Ala Gly Val
            595                 600                 605
```

-continued

Pro Gly Val Gly Val Pro Gly Val Gly Val Pro
    610                 615                 620

Gly Val Gly Val Pro Gly Ala Gly Val Pro Gly Val Gly Val Pro Gly
625                 630                 635                 640

Val Gly Val Pro Gly Ala Tyr Pro Ile Pro Asp Ser Ser Pro Leu Leu
                645                 650                 655

Gln Phe Gly Gly Gln Val Arg Gln Arg Tyr Leu Tyr Thr Asp Asp Asp
                660                 665                 670

Gln Asp Thr Glu Ala His Leu Glu Ile Arg Glu Asp Gly Thr Val Val
            675                 680                 685

Gly Ala Ala His Arg Ser Pro Glu Ser Leu Leu Glu Leu Lys Ala Leu
            690                 695                 700

Lys Pro Gly Val Ile Gln Ile Leu Gly Val Lys Ala Ser Arg Phe Leu
705                 710                 715                 720

Cys Gln Gln Pro Asp Gly Ala Leu Tyr Gly Ser Pro His Phe Asp Pro
                725                 730                 735

Glu Ala Cys Ser Phe Arg Glu Arg Leu Leu Glu Asp Gly Tyr Asn Val
            740                 745                 750

Tyr Gln Ser Glu Ala His Gly Leu Pro Leu Arg Leu Pro Gln Lys Asp
            755                 760                 765

Ser Pro Asn Gln Asp Ala Thr Ser Trp Gly Pro Val Arg Phe Leu Pro
770                 775                 780

Met Pro Gly Leu Leu His Glu Pro Gln Asp Gln Ala Gly Phe Leu Pro
785                 790                 795                 800

Pro Glu Pro Pro Asp Val Gly Ser Ser Asp Pro Leu Ser Met Val Glu
                805                 810                 815

Gly Ser Gln Gly Arg Ser Pro Ser Tyr Ala Ser Gly
            820                 825

<210> SEQ ID NO 18
<211> LENGTH: 814
<212> TYPE: PRT
<213> ORGANISM: Artificial Sequence
<220> FEATURE:
<223> OTHER INFORMATION: Synthetic

<400> SEQUENCE: 18

His Gly Glu Gly Thr Phe Thr Ser Asp Val Ser Ser Tyr Leu Glu Glu
1               5                   10                  15

Gln Ala Ala Lys Glu Phe Ile Ala Trp Leu Val Lys Gly Ala Gly Val
            20                  25                  30

Gly Val Pro Gly Val Gly Val Pro Gly Ala Gly Val Pro Gly Val Gly
            35                  40                  45

Val Pro Gly Val Gly Val Pro Gly Val Gly Val Pro Gly Val Gly Val
        50                  55                  60

Pro Gly Ala Gly Val Pro Gly Val Gly Val Pro Gly Val Gly Val Pro
65                  70                  75                  80

Gly Val Gly Val Pro Gly Val Gly Val Pro Gly Ala Gly Val Pro Gly
                85                  90                  95

Val Gly Val Pro Gly Val Gly Val Pro Gly Val Gly Val Pro Gly Val
                100                 105                 110

Gly Val Pro Gly Ala Gly Val Pro Gly Val Gly Val Pro Gly Val Gly
            115                 120                 125

Val Pro Gly Val Gly Val Pro Gly Val Gly Val Pro Gly Ala Gly Val
        130                 135                 140

```
Pro Gly Val Gly Val Pro Gly Val Gly Val Pro Gly Val Gly Val Pro
145                 150                 155                 160
Gly Val Gly Val Pro Gly Ala Gly Val Pro Gly Val Gly Val Pro Gly
                165                 170                 175
Val Gly Val Pro Gly Val Gly Val Pro Gly Val Gly Val Pro Gly Ala
            180                 185                 190
Gly Val Pro Gly Val Gly Val Pro Gly Val Gly Val Pro Gly Val Gly
            195                 200                 205
Val Pro Gly Val Gly Val Pro Gly Ala Gly Val Pro Gly Val Gly Val
210                 215                 220
Pro Gly Val Gly Val Pro Gly Val Gly Val Pro Gly Val Gly Val Pro
225                 230                 235                 240
Gly Ala Gly Val Pro Gly Val Gly Val Pro Gly Val Gly Val Pro Gly
            245                 250                 255
Val Gly Val Pro Gly Val Gly Val Pro Gly Ala Gly Val Pro Gly Val
            260                 265                 270
Gly Val Pro Gly Val Gly Val Pro Gly Val Gly Val Pro Gly Val Gly
            275                 280                 285
Val Pro Gly Ala Gly Val Pro Gly Val Gly Val Pro Gly Val Gly Val
290                 295                 300
Pro Gly Val Gly Val Pro Gly Val Gly Val Pro Gly Ala Gly Val Pro
305                 310                 315                 320
Gly Val Gly Val Pro Gly Val Gly Val Pro Gly Val Gly Val Pro Gly
            325                 330                 335
Val Gly Val Pro Gly Ala Gly Val Pro Gly Val Gly Val Pro Gly Val
            340                 345                 350
Gly Val Pro Gly Val Gly Val Pro Gly Val Gly Val Pro Gly Ala Gly
            355                 360                 365
Val Pro Gly Val Gly Val Pro Gly Val Gly Val Pro Gly Val Gly Val
370                 375                 380
Pro Gly Val Gly Val Pro Gly Ala Gly Val Pro Gly Val Gly Val Pro
385                 390                 395                 400
Gly Val Gly Val Pro Gly Val Gly Val Pro Gly Val Gly Val Pro Gly
            405                 410                 415
Ala Gly Val Pro Gly Val Gly Val Pro Gly Val Gly Val Pro Gly Val
            420                 425                 430
Gly Val Pro Gly Val Gly Val Pro Gly Ala Gly Val Pro Gly Val Gly
            435                 440                 445
Val Pro Gly Val Gly Val Pro Gly Val Gly Val Pro Gly Val Gly Val
            450                 455                 460
Pro Gly Ala Gly Val Pro Gly Val Gly Val Pro Gly Val Gly Val Pro
465                 470                 475                 480
Gly Val Gly Val Pro Gly Val Gly Val Pro Gly Ala Gly Val Pro Gly
            485                 490                 495
Val Gly Val Pro Gly Val Gly Val Pro Gly Val Gly Val Pro Gly Val
            500                 505                 510
Gly Val Pro Gly Ala Gly Val Pro Gly Val Gly Val Pro Gly Val Gly
            515                 520                 525
Val Pro Gly Val Gly Val Pro Gly Val Gly Val Pro Gly Ala Gly Val
            530                 535                 540
Pro Gly Val Gly Val Pro Gly Val Gly Val Pro Gly Val Gly Val Pro
545                 550                 555                 560
```

Gly Val Gly Val Pro Gly Ala Gly Val Pro Gly Val Gly Val Pro Gly
            565                 570                 575

Val Gly Val Pro Gly Val Gly Val Pro Gly Val Gly Val Pro Gly Ala
        580                 585                 590

Gly Val Pro Gly Val Gly Val Pro Gly Val Gly Val Pro Gly Val Gly
            595                 600                 605

Val Pro Gly Val Gly Val Pro Gly Ala Gly Val Pro Gly Val Gly Val
        610                 615                 620

Pro Gly Val Gly Val Pro Gly Ala Tyr Pro Ile Pro Asp Ser Ser Pro
625                 630                 635                 640

Leu Leu Gln Phe Gly Gly Gln Val Arg Gln Arg Tyr Leu Tyr Thr Asp
                645                 650                 655

Asp Asp Gln Asp Thr Glu Ala His Leu Glu Ile Arg Glu Asp Gly Thr
            660                 665                 670

Val Val Gly Ala Ala His Arg Ser Pro Glu Ser Leu Leu Glu Leu Lys
        675                 680                 685

Ala Leu Lys Pro Gly Val Ile Gln Ile Leu Gly Val Lys Ala Ser Arg
    690                 695                 700

Phe Leu Cys Gln Gln Pro Asp Gly Ala Leu Tyr Gly Ser Pro His Phe
705                 710                 715                 720

Asp Pro Glu Ala Cys Ser Phe Arg Glu Arg Leu Leu Glu Asp Gly Tyr
                725                 730                 735

Asn Val Tyr Gln Ser Glu Ala His Gly Leu Pro Leu Arg Leu Pro Gln
            740                 745                 750

Lys Asp Ser Pro Asn Gln Asp Ala Thr Ser Trp Gly Pro Val Arg Phe
        755                 760                 765

Leu Pro Met Pro Gly Leu Leu His Glu Pro Gln Asp Gln Ala Gly Phe
    770                 775                 780

Leu Pro Pro Glu Pro Pro Asp Val Gly Ser Ser Asp Pro Leu Ser Met
785                 790                 795                 800

Val Glu Gly Ser Gln Gly Arg Ser Pro Ser Tyr Ala Ser Gly
                805                 810

<210> SEQ ID NO 19
<211> LENGTH: 601
<212> TYPE: PRT
<213> ORGANISM: Artificial Sequence
<220> FEATURE:
<223> OTHER INFORMATION: Synthetic

<400> SEQUENCE: 19

Gly Val Gly Val Pro Gly Val Gly Val Pro Gly Ala Gly Val Pro Gly
1               5                   10                  15

Val Gly Val Pro Gly Val Gly Val Pro Gly Val Gly Val Pro Gly Val
            20                  25                  30

Gly Val Pro Gly Ala Gly Val Pro Gly Val Gly Val Pro Gly Val Gly
        35                  40                  45

Val Pro Gly Val Gly Val Pro Gly Val Gly Val Pro Gly Ala Gly Val
    50                  55                  60

Pro Gly Val Gly Val Pro Gly Val Gly Val Pro Gly Val Gly Val Pro
65                  70                  75                  80

Gly Val Gly Val Pro Gly Ala Gly Val Pro Gly Val Gly Val Pro Gly
                85                  90                  95

Val Gly Val Pro Gly Val Gly Val Pro Gly Val Gly Val Pro Gly Ala
            100                 105                 110

```
Gly Val Pro Gly Val Gly Val Pro Gly Val Gly Val Pro Gly Val Gly
            115                 120                 125
Val Pro Gly Val Gly Val Pro Gly Ala Gly Val Pro Gly Val Gly Val
        130                 135                 140
Pro Gly Val Gly Val Pro Gly Val Gly Val Pro Gly Val Gly Val Pro
145                 150                 155                 160
Gly Ala Gly Val Pro Gly Val Gly Val Pro Gly Val Gly Val Pro Gly
                165                 170                 175
Val Gly Val Pro Gly Val Gly Val Pro Gly Ala Gly Val Pro Gly Val
            180                 185                 190
Gly Val Pro Gly Val Gly Val Pro Gly Val Gly Val Pro Gly Val Gly
        195                 200                 205
Val Pro Gly Ala Gly Val Pro Gly Val Gly Val Pro Gly Val Gly Val
210                 215                 220
Pro Gly Val Gly Val Pro Gly Val Gly Val Pro Gly Ala Gly Val Pro
225                 230                 235                 240
Gly Val Gly Val Pro Gly Val Gly Val Pro Gly Val Gly Val Pro Gly
                245                 250                 255
Val Gly Val Pro Gly Ala Gly Val Pro Gly Val Gly Val Pro Gly Val
            260                 265                 270
Gly Val Pro Gly Val Gly Val Pro Gly Val Gly Val Pro Gly Ala Gly
        275                 280                 285
Val Pro Gly Val Gly Val Pro Gly Val Gly Val Pro Gly Val Gly Val
290                 295                 300
Pro Gly Val Gly Val Pro Gly Ala Gly Val Pro Gly Val Gly Val Pro
305                 310                 315                 320
Gly Val Gly Val Pro Gly Val Gly Val Pro Gly Val Gly Val Pro Gly
                325                 330                 335
Ala Gly Val Pro Gly Val Gly Val Pro Gly Val Gly Val Pro Gly Val
            340                 345                 350
Gly Val Pro Gly Val Gly Val Pro Gly Ala Gly Val Pro Gly Val Gly
        355                 360                 365
Val Pro Gly Val Gly Val Pro Gly Val Gly Val Pro Gly Val Gly Val
370                 375                 380
Pro Gly Ala Gly Val Pro Gly Val Gly Val Pro Gly Val Gly Val Pro
385                 390                 395                 400
Gly Val Gly Val Pro Gly Val Gly Val Pro Gly Ala Gly Val Pro Gly
                405                 410                 415
Val Gly Val Pro Gly Val Gly Val Pro Gly Val Gly Val Pro Gly Val
            420                 425                 430
Gly Val Pro Gly Ala Gly Val Pro Gly Val Gly Val Pro Gly Val Gly
        435                 440                 445
Val Pro Gly Val Gly Val Pro Gly Val Gly Val Pro Gly Ala Gly Val
450                 455                 460
Pro Gly Val Gly Val Pro Gly Val Gly Val Pro Gly Val Gly Val Pro
465                 470                 475                 480
Gly Val Gly Val Pro Gly Ala Gly Val Pro Gly Val Gly Val Pro Gly
                485                 490                 495
Val Gly Val Pro Gly Val Gly Val Pro Gly Val Gly Val Pro Gly Ala
            500                 505                 510
Gly Val Pro Gly Val Gly Val Pro Gly Val Gly Val Pro Gly Val Gly
        515                 520                 525
Val Pro Gly Val Gly Val Pro Gly Ala Gly Val Pro Gly Val Gly Val
```

-continued

```
            530                 535                 540
Pro Gly Val Gly Val Pro Gly Val Gly Val Pro Gly Val Gly Val Pro
545                 550                 555                 560

Gly Ala Gly Val Pro Gly Val Gly Val Pro Gly Val Gly Val Pro Gly
                565                 570                 575

Val Gly Val Pro Gly Val Gly Val Pro Gly Ala Gly Val Pro Gly Val
            580                 585                 590

Gly Val Pro Gly Val Gly Val Pro Gly
        595                 600
```

<210> SEQ ID NO 20
<211> LENGTH: 14
<212> TYPE: PRT
<213> ORGANISM: Artificial Sequence
<220> FEATURE:
<223> OTHER INFORMATION: Synthetic

<400> SEQUENCE: 20

```
Met Ser Lys Gly Pro Gly Glu Asn Leu Tyr Phe Gln Gly Ala
1               5                   10
```

<210> SEQ ID NO 21
<211> LENGTH: 6
<212> TYPE: PRT
<213> ORGANISM: Artificial Sequence
<220> FEATURE:
<223> OTHER INFORMATION: Synthetic

<400> SEQUENCE: 21

```
Met Ser Lys Gly Pro Gly
1               5
```

<210> SEQ ID NO 22
<211> LENGTH: 7
<212> TYPE: PRT
<213> ORGANISM: Artificial Sequence
<220> FEATURE:
<223> OTHER INFORMATION: Synthetic

<400> SEQUENCE: 22

```
Glu Asn Leu Tyr Phe Gln Gly
1               5
```

<210> SEQ ID NO 23
<211> LENGTH: 816
<212> TYPE: PRT
<213> ORGANISM: Artificial Sequence
<220> FEATURE:
<223> OTHER INFORMATION: Synthetic

<400> SEQUENCE: 23

```
Ala Ala His Gly Glu Gly Thr Phe Thr Ser Asp Val Ser Ser Tyr Leu
1               5                   10                  15

Glu Glu Gln Ala Ala Lys Glu Phe Ile Ala Trp Leu Val Lys Gly Ala
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

Gly Val Pro Gly Val Gly Val Pro Gly Val Gly Val Pro Gly Val Gly
65                  70                  75                  80

Val Pro Gly Val Gly Val Pro Gly Val Gly Val Pro Gly Val Gly Val
```

```
                 85                  90                  95
Pro Gly Val Gly Val Pro Gly Val Gly Val Pro Gly Val Gly Val Pro
            100                 105                 110
Gly Val Gly Val Pro Gly Val Gly Val Pro Gly Val Gly Val Pro Gly
            115                 120                 125
Val Gly Val Pro Gly Val Gly Val Pro Gly Val Gly Val Pro Gly Val
            130                 135                 140
Gly Val Pro Gly Val Gly Val Pro Gly Val Gly Val Pro Gly Val Gly
145                 150                 155                 160
Val Pro Gly Val Gly Val Pro Gly Val Gly Val Pro Gly Val Gly Val
                165                 170                 175
Pro Gly Val Gly Val Pro Gly Val Gly Val Pro Gly Val Gly Val Pro
            180                 185                 190
Gly Val Gly Val Pro Gly Val Gly Val Pro Gly Val Gly Val Pro Gly
            195                 200                 205
Val Gly Val Pro Gly Val Gly Val Pro Gly Val Gly Val Pro Gly Val
            210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Val Gly Val Pro Gly Val Gly Val Pro Gly Val Gly Val Pro
            260                 265                 270
Gly Val Gly Val Pro Gly Val Gly Val Pro Gly Val Gly Val Pro Gly
            275                 280                 285
Val Gly Val Pro Gly Val Gly Val Pro Gly Val Gly Val Pro Gly Val
            290                 295                 300
Gly Val Pro Gly Val Gly Val Pro Gly Val Gly Val Pro Gly Val Gly
305                 310                 315                 320
Val Pro Gly Val Gly Val Pro Gly Val Gly Val Pro Gly Val Gly Val
                325                 330                 335
Pro Gly Val Gly Val Pro Gly Val Gly Val Pro Gly Val Gly Val Pro
            340                 345                 350
Gly Val Gly Val Pro Gly Val Gly Val Pro Gly Val Gly Val Pro Gly
            355                 360                 365
Val Gly Val Pro Gly Val Gly Val Pro Gly Val Gly Val Pro Gly Val
            370                 375                 380
Gly Val Pro Gly Val Gly Val Pro Gly Val Gly Val Pro Gly Val Gly
385                 390                 395                 400
Val Pro Gly Val Gly Val Pro Gly Val Gly Val Pro Gly Val Gly Val
                405                 410                 415
Pro Gly Val Gly Val Pro Gly Val Gly Val Pro Gly Val Gly Val Pro
            420                 425                 430
Gly Val Gly Val Pro Gly Val Gly Val Pro Gly Val Gly Val Pro Gly
            435                 440                 445
Val Gly Val Pro Gly Val Gly Val Pro Gly Val Gly Val Pro Gly Val
            450                 455                 460
Gly Val Pro Gly Val Gly Val Pro Gly Val Gly Val Pro Gly Val Gly
465                 470                 475                 480
Val Pro Gly Val Gly Val Pro Gly Val Gly Val Pro Gly Val Gly Val
                485                 490                 495
Pro Gly Val Gly Val Pro Gly Val Gly Val Pro Gly Val Gly Val Pro
            500                 505                 510
```

Gly Val Gly Val Pro Gly Val Gly Val Pro Gly Val Gly Val Pro Gly
            515                 520                 525

Val Gly Val Pro Gly Val Gly Val Pro Gly Val Gly Val Pro Gly Val
        530                 535                 540

Gly Val Pro Gly Val Gly Val Pro Gly Val Gly Val Pro Gly Val Gly
545                 550                 555                 560

Val Pro Gly Val Gly Val Pro Gly Val Gly Val Pro Gly Val Gly Val
                565                 570                 575

Pro Gly Val Gly Val Pro Gly Val Gly Val Pro Gly Val Gly Val Pro
            580                 585                 590

Gly Val Gly Val Pro Gly Val Gly Val Pro Gly Val Gly Val Pro Gly
        595                 600                 605

Val Gly Val Pro Gly Val Gly Val Pro Gly Val Gly Val Pro Gly Val
    610                 615                 620

Gly Val Pro Gly Val Gly Val Pro Gly Ala Tyr Pro Ile Pro Asp Ser
625                 630                 635                 640

Ser Pro Leu Leu Gln Phe Gly Gln Val Arg Gln Arg Tyr Leu Tyr
                645                 650                 655

Thr Asp Asp Gln Asp Thr Glu Ala His Leu Glu Ile Arg Glu Asp
            660                 665                 670

Gly Thr Val Val Gly Ala Ala His Arg Ser Pro Glu Ser Leu Leu Glu
        675                 680                 685

Leu Lys Ala Leu Lys Pro Gly Val Ile Gln Ile Leu Gly Val Lys Ala
690                 695                 700

Ser Arg Phe Leu Cys Gln Gln Pro Asp Gly Ala Leu Tyr Gly Ser Pro
705                 710                 715                 720

His Phe Asp Pro Glu Ala Cys Ser Phe Arg Glu Arg Leu Leu Glu Asp
                725                 730                 735

Gly Tyr Asn Val Tyr Gln Ser Glu Ala His Gly Leu Pro Leu Arg Leu
            740                 745                 750

Pro Gln Lys Asp Ser Pro Asn Gln Asp Ala Thr Ser Trp Gly Pro Val
        755                 760                 765

Arg Phe Leu Pro Met Pro Gly Leu Leu His Glu Pro Gln Asp Gln Ala
    770                 775                 780

Gly Phe Leu Pro Pro Glu Pro Pro Asp Val Gly Ser Ser Asp Pro Leu
785                 790                 795                 800

Ser Met Val Glu Gly Ser Gln Gly Arg Ser Pro Ser Tyr Ala Ser Gly
                805                 810                 815

<210> SEQ ID NO 24
<211> LENGTH: 516
<212> TYPE: PRT
<213> ORGANISM: Artificial Sequence
<220> FEATURE:
<223> OTHER INFORMATION: Synthetic

<400> SEQUENCE: 24

Ala Ala His Gly Glu Gly Thr Phe Thr Ser Asp Val Ser Ser Tyr Leu
1               5                   10                  15

Glu Glu Gln Ala Ala Lys Glu Phe Ile Ala Trp Leu Val Lys Gly Ala
            20                  25                  30

Gly Val Gly Val Pro Gly Val Gly Val Pro Gly Val Gly Val Pro Gly
        35                  40                  45

Val Gly Val Pro Gly Val Gly Val Pro Gly Val Gly Val Pro Gly Val
    50                  55                  60

```
Gly Val Pro Gly Val Gly Val Pro Gly Val Gly Val Pro Gly Val Gly
 65                  70                  75                  80
Val Pro Gly Val Gly Val Pro Gly Val Gly Val Pro Gly Val Gly Val
                 85                  90                  95
Pro Gly Val Gly Val Pro Gly Val Gly Val Pro Gly Val Gly Val Pro
            100                 105                 110
Gly Val Gly Val Pro Gly Val Gly Val Pro Gly Val Gly Val Pro Gly
        115                 120                 125
Val Gly Val Pro Gly Val Gly Val Pro Gly Val Gly Val Pro Gly Val
    130                 135                 140
Gly Val Pro Gly Val Gly Val Pro Gly Val Gly Val Pro Gly Val Gly
145                 150                 155                 160
Val Pro Gly Val Gly Val Pro Gly Val Gly Val Pro Gly Val Gly Val
                165                 170                 175
Pro Gly Val Gly Val Pro Gly Val Gly Val Pro Gly Val Gly Val Pro
            180                 185                 190
Gly Val Gly Val Pro Gly Val Gly Val Pro Gly Val Gly Val Pro Gly
        195                 200                 205
Val Gly Val Pro Gly Val Gly Val Pro Gly Val Gly Val Pro Gly Val
    210                 215                 220
Gly Val Pro Gly Val Gly Val Pro Gly Val Gly Val Pro Gly Val Gly
225                 230                 235                 240
Val Pro Gly Val Gly Val Pro Gly Val Gly Val Pro Gly Val Gly Val
                245                 250                 255
Pro Gly Val Gly Val Pro Gly Val Gly Val Pro Gly Val Gly Val Pro
            260                 265                 270
Gly Val Gly Val Pro Gly Val Gly Val Pro Gly Val Gly Val Pro Gly
        275                 280                 285
Val Gly Val Pro Gly Val Gly Val Pro Gly Val Gly Val Pro Gly Val
    290                 295                 300
Gly Val Pro Gly Val Gly Val Pro Gly Val Gly Val Pro Gly Val Gly
305                 310                 315                 320
Val Pro Gly Val Gly Val Pro Gly Val Gly Val Pro Gly Ala Tyr Pro
                325                 330                 335
Ile Pro Asp Ser Ser Pro Leu Leu Gln Phe Gly Gly Gln Val Arg Gln
            340                 345                 350
Arg Tyr Leu Tyr Thr Asp Asp Gln Asp Thr Glu Ala His Leu Glu
        355                 360                 365
Ile Arg Glu Asp Gly Thr Val Val Gly Ala Ala His Arg Ser Pro Glu
    370                 375                 380
Ser Leu Leu Glu Leu Lys Ala Leu Lys Pro Gly Val Ile Gln Ile Leu
385                 390                 395                 400
Gly Val Lys Ala Ser Arg Phe Leu Cys Gln Gln Pro Asp Gly Ala Leu
                405                 410                 415
Tyr Gly Ser Pro His Phe Asp Pro Glu Ala Cys Ser Phe Arg Glu Arg
            420                 425                 430
Leu Leu Glu Asp Gly Tyr Asn Val Tyr Gln Ser Glu Ala His Gly Leu
        435                 440                 445
Pro Leu Arg Leu Pro Gln Lys Asp Ser Pro Asn Gln Asp Ala Thr Ser
    450                 455                 460
Trp Gly Pro Val Arg Phe Leu Pro Met Pro Gly Leu Leu His Glu Pro
465                 470                 475                 480
```

-continued

```
Gln Asp Gln Ala Gly Phe Leu Pro Pro Glu Pro Pro Asp Val Gly Ser
                485                 490                 495

Ser Asp Pro Leu Ser Met Val Glu Gly Ser Gln Gly Arg Ser Pro Ser
            500                 505                 510

Tyr Ala Ser Gly
        515
```